(12) United States Patent
Yao et al.

(10) Patent No.: US 12,173,002 B2
(45) Date of Patent: Dec. 24, 2024

(54) PRMT5 INHIBITORS AND METHODS OF USE

(71) Applicant: SHANGHAI APEIRON THERAPEUTICS COMPANY LIMITED, Shanghai (CN)

(72) Inventors: Bing Yao, Shanghai (CN); Xiaohui Gu, Shanghai (CN)

(73) Assignee: SHANGHAI APEIRON THERAPEUTICS COMPANY LIMITED, Shanghai (CN)

( * ) Notice: Subject to any disclaimer, the term of this patent is extended or adjusted under 35 U.S.C. 154(b) by 0 days.

(21) Appl. No.: 18/437,335

(22) Filed: Feb. 9, 2024

(65) Prior Publication Data

US 2024/0294528 A1    Sep. 5, 2024

Related U.S. Application Data

(63) Continuation of application No. PCT/CN2023/120923, filed on Sep. 25, 2023.

(30) Foreign Application Priority Data

| Sep. 26, 2022 | (CN) | ............... 202211173943.5 |
| Nov. 22, 2022 | (CN) | ............... 202211473887.7 |
| Jan. 17, 2023 | (CN) | ............... 202310080068.4 |
| Apr. 14, 2023 | (CN) | ............... 202310402301.6 |
| Sep. 1, 2023 | (CN) | ............... 202311142241.5 |

(51) Int. Cl.
*C07D 471/14* (2006.01)
*C07D 487/04* (2006.01)

(52) U.S. Cl.
CPC ......... *C07D 471/14* (2013.01); *C07D 487/04* (2013.01)

(58) Field of Classification Search
CPC ........................... C07D 471/14; C07D 487/04
See application file for complete search history.

(56) References Cited

FOREIGN PATENT DOCUMENTS

| CN | 102388044 A | 3/2012 | |
| CN | 113234079 A | 8/2021 | |
| WO | 2004085439 A1 | 10/2004 | |
| WO | WO2004/085439 | * 10/2004 | ........... C07D 487/04 |
| WO | 2021254493 A1 | 12/2021 | |
| WO | 2021254529 A1 | 12/2021 | |
| WO | 2022048631 A1 | 3/2022 | |
| WO | 2022169948 A1 | 8/2022 | |

* cited by examiner

*Primary Examiner* — Erich A Leeser
(74) *Attorney, Agent, or Firm* — Bayramoglu Law Offices LLC

(57) ABSTRACT

Compounds that inhibit Protein Arginine N-Methyl Transferase 5(PRMT5) activity, as well as method for their preparation and use are provided. Specifically, compounds of Formula (I) and pharmaceutically acceptable salts, hydrates and solvates, as well as method for their preparation and use are provided.

16 Claims, No Drawings

PRMT5 INHIBITORS AND METHODS OF USE

CROSS REFERENCE TO THE RELATED APPLICATIONS

This application is the continuation application of International Application No. PCT/CN2023/120923, filed on Sep. 25, 2023, which is based upon and claims priority to Chinese Patent Applications No. 202211173943.5, filed on Sep. 26, 2022; 202211473887.7, filed on Nov. 22, 2022; 202310080068.4, filed on Jan. 17, 2023; 202310402301.6, filed on Apr. 14, 2023; 202311142241.5, filed on, Sep. 1, 2023; the entire contents of which are incorporated herein by reference.

TECHNICAL FIELD

The present invention relates to drug synthesis field. In particular, the present invention relates to PRMT5 inhibitors and methods for use thereof.

BACKGROUND

Epigenetic changes play a crucial role in driving and sustaining the malignant phenotype of tumors. Processes such as DNA methylation, histone acetylation and methylation, non-coding RNA, and post-translational modifications are epigenetic drivers of cancer, independent of DNA sequence changes. Arginine methylation is a significant post-translational modification that, by regulating transcription and post-transcriptional RNA processing, affects cell growth, proliferation, apoptosis, angiogenesis, and metastasis. Methylated arginines include three types: ω-NG, N'G-asymmetric dimethylarginine (ADMA), and ω-NG, N'G-symmetric dimethylarginine (SDMA). This modification is catalyzed by the protein arginine methyltransferase (PRMT) family, transferring methyl groups from S-adenosyl methionine (AdoMet) to arginine side chains in both histone and non-histone proteins. The human genome annotates nine PRMT genes, categorized into Type I (PRMT1, 2, 3, 4, 6, and 8), Type II (PRMT5 and PRMT9), and Type III enzymes (PRMT7). PRMT5, primarily a Type II enzyme, is responsible for catalyzing symmetric dimethylation of arginine. It was initially discovered through a yeast two-hybrid experiment screening for proteins interacting with Janus kinase 2 (Jak2).

PRMT5 serves as a versatile transcriptional repressor, forming complexes with various transcription factors like BRG1, Hbrm, Blimp1, and Snail. Engaging in diverse cellular processes, PRMT5 methylates substrates in both the cytoplasm and nucleus, including histone H4 residue Arg3 (H4R3) and histone H3 residue Arg8 (H3R8). H4R3 methylation is linked to transcriptional repression, while H3R8 methylation is associated with both transcriptional activation and repression. Beyond inducing repressive histone marks directly, PRMT5's role in gene silencing involves the formation of multi-repressive protein complexes, incorporating NuRD components, HDACs, MDB proteins, and DNA methyltransferases. PRMT5 influences substrate specificity through interactions with binding proteins within these complexes. At the core of this protein complex is MEP50, crucial for PRMT5's enzymatic activity. Studies reveal PRMT5's ability to methylate proteins involved in RNA splicing, such as SmD3, providing insight into monitoring PRMT5's chemical activity in cellular biology.

PRMT5 plays a crucial role in tumorigenesis. Studies have shown upregulation of PRMT5 expression in various cancers, including lymphoma, lung cancer, breast cancer, and colorectal cancer. Additionally, PRMT5 expression is elevated in Mantle Cell Lymphoma (MCL) patient samples, and PRMT5 depletion inhibits MCL cell proliferation, highlighting its significance in MCL. PRMT5 overexpression promotes cell proliferation, while PRMT5 knockout inhibits proliferation in melanoma, breast cancer, and lung cancer cell lines. Therefore, PRMT5 stands as a potential target for cancer therapy.

The loss of Methylthioadenosine Phosphorylase (MTAP) imparts selective dependence on PRMT5 and its binding protein WDR77. MTAP is often lost due to its proximity to the frequently deleted tumor suppressor gene CDKN2A. Cells with MTAP loss exhibit increased intracellular Methylthioadenosine (MTA, a metabolite cleaved by MTAP). As MTA shares a similar structure with S-adenosyl methionine (SAM), an inherent selective inhibitor, elevated MTA concentration inhibits the binding of SAM to PRMT5, consequently suppressing PRMT5's methyltransferase activity.

The structural divergence between cancer cells with MTAP loss and those with wild-type MTAP primarily manifests in the PRMT5-MTA complex due to the accumulation of MTA in MTAP-deficient cells. Inhibitors designed to target the PRMT5-MTA complex demonstrate selective efficacy against cancer cells with MTAP loss, minimizing impact on normal cells and substantially enhancing the therapeutic index.

Hence, the identification and development of small molecules inhibiting PRMT5 activity stand as methods for treating various PRMT5-associated diseases or conditions, particularly cancer.

SUMMARY

To address the technical issues of the present invention, the invention provides a class of compounds with novel structures having potent inhibitory activity against PRMT5.

Specifically, in one embodiment, the invention provides a compound of Formula (I), or pharmaceutically acceptable salt thereof, the ester thereof, the prodrug thereof, the stereoisomer thereof and isotopic derivative thereof.

Formula (I)

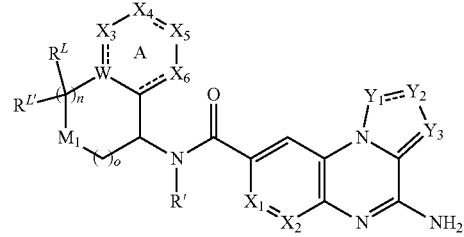

Wherein, W is C;

Wherein, $X_3$ is N or $CR^{X3}$; $X_4$ is N or $CR^{X4}$; $X_5$ is N or $CR^{X5}$; $X_6$ is N or $CR^{X6}$;

Wherein, when $X_3$ is $CR^{X3}$, $R^{X3}$ is hydrogen, deuterium, $C_1$-$C_6$ alkyl, deuterated $C_1$-$C_6$ alkyl, halogen, —$OR^a$, —$SR^a$, —$P(O)R^aR^b$, —CN, —$S(O)2R^a$, —$S(O)R^a$, —$SF_5$, —$NR^aR^b$, $C_1$-$C_6$ haloalkyl, $C_1$-$C_6$ haloalkoxy, $C_1$-$C_6$ haloalkylthio, hydroxy($C_1$-$C_6$ alkyl) or $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl, wherein each ring of $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl is optionally substituted with 0-4 deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$ or —$CONR^aR^b$;

Wherein, when $X_4$ is $CR^{X4}$, $R^{X4}$ is hydrogen, deuterium, $C_1$-$C_6$ alkyl, deuterated $C_1$-$C_6$ alkyl, halogen, —$OR^a$, —$SR^a$, —$P(O)R^aR^b$, —CN, —$S(O)_2R^a$, —$S(O)R^a$, —$SF_5$, —$NR^aR^b$, $C_1$-$C_6$ haloalkyl, $C_1$-$C_6$ haloalkoxy, $C_1$-$C_6$ haloalkylthio, hydroxy($C_1$-$C_6$ alkyl) or $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl, wherein each ring of $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl is optionally substituted with 0-4 deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$ or —$CONR^aR^b$.

Wherein, when $X_5$ is $CR^{X5}$, $R^{X5}$ is hydrogen, deuterium, $C_1$-$C_6$ alkyl, deuterated $C_1$-$C_6$ alkyl, halogen, —$OR^a$, —$SR^a$, —$P(O)R^aR^b$, —CN, —$S(O)_2R^a$, —$S(O)R^a$, —$SF_5$, —$NR^aR^b$, $C_1$-$C_6$ haloalkyl, $C_1$-$C_6$ haloalkoxy, $C_1$-$C_6$ haloalkylthio, hydroxy($C_1$-$C_6$ alkyl) or $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl, wherein each ring of $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl is optionally substituted with 0-4 deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$ or —$CONR^aR^b$;

Wherein, when $X_6$ is $CR^{X6}$, $R^{X6}$ is hydrogen, deuterium, $C_1$-$C_6$ alkyl, deuterated $C_1$-$C_6$ alkyl, halogen, —$OR^a$, —$SR^a$, —$P(O)R^aR^b$, —CN, —$S(O)_2R^a$, —$S(O)R^a$, —$SF_5$, —$NR^aR^b$, $C_1$-$C_6$ haloalkyl, $C_1$-$C_6$ haloalkoxy, $C_1$-$C_6$ haloalkylthio, hydroxy($C_1$-$C_6$ alkyl) or $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl, wherein each ring of $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl is optionally substituted with 0-4 deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$ or —$CONR^aR^b$.

Wherein, the ring A can optionally fuse at the chemical bond between $X_3$ and $X_4$ with a 5-6 membered saturated or unsaturated ring, which can contain 0-3 heteroatoms selected from O, N, S;

Wherein, the ring A can optionally fuse at the chemical bond between $X_4$ and $X_5$ with a 5-6 membered saturated or unsaturated ring, which can contain 0-3 heteroatoms selected from O, N, S;

Wherein, the ring A can optionally fuse at the chemical bond between $X_5$ and $X_6$ with a 5-6 membered saturated or unsaturated ring, which can contain 0-3 heteroatoms selected from O, N, S;

Wherein, the ring A also can be optionally substituted with 0, 1, 2, 3 groups selected from deuterium, $C_1$-$C_6$ alkyl, deuterated $C_1$-$C_6$ alkyl, halogen, —$OR^a$, —$SR^a$, —$P(O)R^aR^b$, —CN, —$S(O)_2R^a$, —$S(O)R^a$, —$SF_5$, —$NR^aR^b$, $C_1$-$C_6$ haloalkyl, $C_1$-$C_6$ haloalkoxy, hydroxy($C_1$-$C_6$) alkyl or substituted groups which is optionally substituted with 0-4 substituted groups selected from deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxy ($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$, or —$CONR^aR^b$.

Wherein, R' is $C_1$-$C_6$ alkyl, $C_3$-$C_{10}$ cycloalkyl, 4-10 membered heterocyclyl, $C_6$-$C_{10}$ aryl, 5-10 membered heteroaryl, which are independently optionally substituted with 0-3 groups selected from deuterium, halogen, $C_1$-$C_6$ alkyl, $C_2$-$C_6$ alkenyl, $C_2$-$C_6$ alkynyl, $C_3$-$C_6$ cycloalkyl, 3-6 membered saturated or unsaturated monocyclic heterocyclyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$S(O)_2R^a$, —$S(O)R^a$, —$SF_5$, —$C(O)R^a$, —$C(O)OR^a$, —$OC(O)R^a$, —$OC(O)NR^aR^b$, —$NR^aCOR^b$ or —$CONR^aR^b$.

Preferably, R' is —$CHR^2R^3$ or —$CDR^2R^3$;

Wherein, $R^2$ and $R^3$ are independently hydrogen, deuterium, —$OR^a$, halogen, —CN, —$C_1$-$C_6$ alkyl, $C_1$-$C_6$ haloalkyl, $C_1$-$C_6$ haloalkoxy, hydroxy($C_1$-$C_6$ alkyl), —$C_3$-$C_{10}$ cycloalkyl or 4-10 membered heterocyclyl, $C_6$-$C_{10}$ aryl and 5-10 membered heteroaryl, the 4-10 membered heterocyclyl, $C_6$-$C_{10}$ aryl and 5-10 membered heteroaryl can be optionally substituted with 0-3 groups selected from deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$S(O)_2R^a$, —$S(O)R^a$, —$SF_5$, —$C(O)R^a$, —$C(O)OR^a$, —$OC(O)R^a$, —$OC(O)NR^aR^b$, —$NR^aCOR^b$ or —$CONR^aR^b$.

Wherein, $M^1$ is $CR^aR^b$, $NR^a$, O, S or Se;

Wherein, $R^L$ and $R^{L'}$ are independently hydrogen, deuterium, $C_1$-$C_6$ alkyl, or $R^L$ and $R^{L'}$ can be taken together with the atoms to which they are attached to form a $C_3$-$C_6$ carbocyclyl or heterocyclyl.

Wherein, n and o are independently 0, 1 or 2.

Wherein, $X_1$ is N or $CR^{X1}$;

Wherein, $X_2$ is N or $CR^{X2}$;

Wherein, $Y_1$ is $CR^{Y1}R^{Y1'}$, $NR^{Y1}$, O, S, Se;

Wherein, $Y_2$ is $CR^{Y2}R^{Y2'}$, $NR^{Y2}$, O, S, Se;

Wherein, $Y_3$ is $CR^{Y3}R^{Y3'}$, $NR^{Y3}$, O, S, Se;

Wherein, $R^{X1}$ and $R^{X2}$ are independently hydrogen, deuterium, $C_1$-$C_6$ alkyl, deuterated $C_1$-$C_6$ alkyl, $C_1$-$C_6$ haloalkyl, $C_1$-$C_6$ haloalkoxy, hydroxy($C_1$-$C_6$) alkyl, $C_2$-$C_6$ alkenyl, $C_2$-$C_6$ alkynl, —$OR^a$, —$SR^a$, —$S(O)_2R^a$, —$S(O)R^a$, —CN, —$OC(O)R^a$, —$OCONR^aR^b$, halogen, —$OSO_3R^a$, —$NR^aR^b$, —$SF_5$. Wherein, $R^{Y1}$, $R^{Y1'}$, $R^{Y2}$, $R^{Y2'}$, $R^{Y3}$ and $R^{Y3'}$ are independently absent, hydrogen, deuterium, $C_1$-$C_6$ alkyl, deuterated $C_1$-$C_6$ alkyl, $C_1$-$C_6$ haloalkyl, $C_1$-$C_6$ haloalkoxy, hydroxyl($C_1$-$C_6$) alkyl, $C_2$-$C_6$ alkenyl, $C_2$-$C_6$ alkynyl, $C_3$-$C_6$ cycloalkyl, —$OR^a$, —$SR^a$, —$S(O)_2R^a$, —$S(O)R^a$, —CN, —$OC(O)R^a$, —$OCONR^aR^b$, halogen, —$OSO_3R^a$, —$NR^aR^b$, —$SF_5$.

Wherein, $=\!=\!=$ is single bond or double bond.

Wherein, $R^a$ and $R^b$ are independently hydrogen, deuterium, halogen, $C_1$-$C_6$ alkyl, $C_3$-$C_6$ cyclopropyl, $C_1$-$C_6$ haloalkyl, or $R^a$ and $R^b$ can be taken together with the atoms to which they are attached to form a 3-14 membered saturated or unsaturated cycle, which can optionally contain 0-2 heteroatoms selected from O, S and N.

In another embodiment, the invention provides a compound of Formula (II), the pharmaceutical salt thereof, the ester thereof, the prodrug thereof, the stereoisomer thereof or isotopic derivative thereof:

Formula (II)

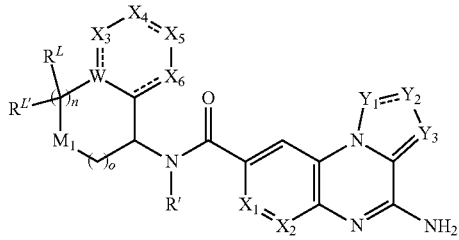

Wherein, W is C;

Wherein, $X_3$ is N or $CR^{X3}$; $X_4$ is N or $CR^{X4}$; $X_5$ is N or $CR^{X5}$; $X_6$ is N or $CR^{X6}$;

Wherein, when $X_3$ is $CR^{X3}$, $R^{X3}$ is hydrogen, deuterium, $C_1$-$C_6$ alkyl, deuterated $C_1$-$C_6$ alkyl, halogen, —$OR^a$, —$SR^a$, —$P(O)R^aR^b$, —CN, —$S(O)_2R^a$, —$S(O)R^a$, —$SF_5$, —$NR^aR^b$, $C_1$-$C_6$ haloalkyl, $C_1$-$C_6$ haloalkoxy, $C_1$-$C_6$ haloalkylthio, hydroxy($C_1$-$C_6$ alkyl) or $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl, wherein each ring of $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl is optionally substituted with 0-4 deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$ or —$CONR^aR^b$;

Wherein, when $X_4$ is $CR^{X4}$, $R^{X4}$ is hydrogen, deuterium, $C_1$-$C_6$ alkyl, deuterated $C_1$-$C_6$ alkyl, halogen, —$OR^a$, —$SR^a$, —$P(O)R^aR^b$, —CN, —$S(O)_2R^a$, —$S(O)R^a$, —$SF_5$, —$NR^aR^b$, $C_1$-$C_6$ haloalkyl, $C_1$-$C_6$ haloalkoxy, $C_1$-$C_6$ haloalkylthio, hydroxy($C_1$-$C_6$ alkyl) or $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl, wherein each ring of $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl is optionally substituted with 0-4 deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$ or —$CONR^aR^b$;

Wherein, when $X_5$ is $CR^{X5}$, $R^{X5}$ is hydrogen, deuterium, $C_1$-$C_6$ alkyl, deuterated $C_1$-$C_6$ alkyl, halogen, —$OR^a$, —$SR^a$, —$P(O)R^aR^b$, —CN, —$S(O)_2R^a$, —$S(O)R^a$, —$SF_5$, —$NR^aR^b$, $C_1$-$C_6$ haloalkyl, $C_1$-$C_6$ haloalkoxy, $C_1$-$C_6$ haloalkylthio, hydroxy($C_1$-$C_6$ alkyl) or $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl, wherein each ring of $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl is optionally substituted with 0-4 deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$ or —$CONR^aR^b$;

Wherein, when $X_6$ is $CR^{X6}$, $R^{X6}$ is hydrogen, deuterium, $C_1$-$C_6$ alkyl, deuterated $C_1$-$C_6$ alkyl, halogen, —$OR^a$, —$SR^a$, —$P(O)R^aR^b$, —CN, —$S(O)_2R^a$, —$S(O)R^a$, —$SF_5$, —$NR^aR^b$, $C_1$-$C_6$ haloalkyl, $C_1$-$C_6$ haloalkoxy, $C_1$-$C_6$ haloalkylthio, hydroxy($C_1$-$C_6$ alkyl) or $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl, wherein each ring of $C_3$-$C_{10}$ cycloalkyl, $C_6$-$C_{10}$ cycloalkenyl, 4-10 membered heterocyclyl, 6-10 membered heterocycloalkenyl, $C_6$-$C_{10}$ aryl, 5-10 membered heteroaryl is optionally substituted with 0-4 deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$SF_5$, —$C(O)R^a$, —$C(O)OR^a$, —$OC(O)R^a$, —$OC(O)NR^aR^b$, —$NR^aCOR^b$ or —$CONR^aR^b$;

Wherein, R' is $C_1$-$C_6$ alkyl, $C_3$-$C_{10}$ cycloalkyl, 4-10 membered heterocyclyl, $C_6$-$C_{10}$ aryl, 5-10 membered heteroaryl, which are independently optionally substituted with 0-3 groups selected from deuterium, halogen, $C_1$-$C_6$ alkyl, $C_2$-$C_6$ alkenyl, $C_2$-$C_6$ alkynyl, $C_3$-$C_6$ cycloalkyl, 3-6 membered saturated or unsaturated monocyclic heterocyclyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$S(O)_2R^a$, —$S(O)R^a$, —$SF_5$, —$C(O)R^a$, —$C(O)OR^a$, —$OC(O)R^a$, —$OC(O)NR^aR^b$, —$NR^aCOR^b$ or —$CONR^aR^b$.

Preferably, R' is —$CHR^2R^3$ or —$CDR^2R^3$;

Wherein, $R^2$ and $R^3$ are independently hydrogen, deuterium, —$OR^a$, halogen, —CN, —$C_1$-$C_6$ alkyl, $C_1$-$C_6$ haloalkyl, $C_1$-$C_6$ haloalkoxy, hydroxy($C_1$-$C_6$ alkyl), —$C_3$-$C_{10}$ cycloalkyl or 4-10 membered heterocyclyl, $C_6$-$C_{10}$ aryl and 5-10 membered heteroaryl, the 4-10 membered heterocyclyl, $C_6$-$C_{10}$ aryl and 5-10 membered heteroaryl can be optionally substituted with 0-3 groups selected from deuterium, halogen, $C_1$-$C_6$ alkyl, $C_2$-$C_6$ alkenyl, $C_2$-$C_6$ alkynyl, $C_3$-$C_6$ cycloalkyl, —$OR^a$, oxo, hydroxyl($C_1$-$C_6$ alkyl), $NR^aR^b$, —CN, $C_1$-$C_6$ haloalkyl, $C_1$-$C_6$ haloalkoxy, —$SO_3R^a$, —$SR^a$, —$S(O)_2R^a$, —$S(O)R^a$, —$SF_5$, —$C(O)R^a$, —$C(O)OR^a$, —$OC(O)R^a$, —$OC(O)NR^aR^b$, —$NR^aCOR^b$ or —$CONR^aR^b$.

Wherein, $M^1$ is $CR^aR^b$, $NR^a$, O, S or Se;

Wherein, $R^L$ and $R^{L'}$ are independently hydrogen, deuterium, $C_1$-$C_6$ alkyl, or $R^L$ and $R^{L'}$ can be taken together with the atoms to which they are attached to form a 3-6 membered carbocyclyl or heterocyclyl.

Wherein, n and o are independently 0, 1 or 2.

Wherein, $X_1$ is N or $CR^{X1}$;

Wherein, $X_2$ is N or $CR^{X2}$;

Wherein, $Y_1$ is $CR^{Y1}R^{Y1'}$, $NR^{Y1}$, O, S, Se;

Wherein, $Y_2$ is $CR^{Y2}R^{Y2'}$, $NR^{Y2}$, O, S, Se;

Wherein, $Y_3$ is $CR^{Y3}R^{Y3'}$, $NR^{Y3}$, O, S, Se;

Wherein, $R^{X1}$ and $R^{X2}$ are independently hydrogen, deuterium, $C_1$-$C_6$ alkyl, deuterated $C_1$-$C_6$ alkyl, $C_1$-$C_6$ haloalkyl, $C_1$-$C_6$ haloalkoxy, hydroxy($C_1$-$C_6$) alkyl, $C_2$-$C_6$ alkenyl, $C_2$-$C_6$ alkynl, —$OR^a$, —$SR^a$, —$S(O)_2R^a$, —$S(O)R^a$, —CN, —$OC(O)R^a$, —$OCONR^aR^b$, halogen, —$OSO_3R^a$, —$NR^aR^b$, —$SF_5$. Wherein, $R^{Y1}$, $R^{Y1'}$, $R^{Y2}$, $R^{Y2'}$, $R^{Y3}$ and $R^{Y3'}$ are independently absent, hydrogen, deuterium, $C_1$-$C_6$ alkyl, deuterated $C_1$-$C_6$ alkyl, $C_1$-$C_6$ haloalkyl, $C_1$-$C_6$ haloalkoxy, hydroxyl($C_1$-$C_6$) alkyl, $C_2$-$C_6$ alkenyl, $C_2$-$C_6$ alkynyl, $C_3$-$C_6$ cycloalkyl, —$OR^a$, —$SR^a$, —$S(O)_2R^a$, —S(O)R$^a$, —CN, —OC(O)R$^a$, —OCONR$^a$R$^b$, halogen, —OSO$_3$R$^a$, —NR$^a$R$^b$, —SF$_5$;

Wherein, $=\!=\!=$ is single bond or double bond.

Wherein, R$^a$ and R$^b$ are independently hydrogen, deuterium, halogen, C$_1$-C$_6$ alkyl, C$_3$-C$_6$ cyclopropyl, C$_1$-C$_6$ haloalkyl, or R$^a$ and R$^b$ can be taken together with the atoms to which they are attached to form a 3-14 membered saturated or unsaturated cycle, which can optionally contain 0-2 heteroatoms selected from O, S and N.

In a preferred embodiment of the invention, wherein, $=\!=\!=$ is double bond.

In a preferred embodiment of the invention, wherein, X$_1$ is CR$^{X1}$ or N, wherein, R$^{X1}$ is hydrogen, deuterium, halogen, —CN, C$_1$-C$_6$ alkyl, deuterated C$_1$-C$_6$ alkyl, C$_1$-C$_6$ alkoxy, C$_1$-C$_6$ haloalkyl.

In a preferred embodiment of the invention, wherein, X$_1$ is CH, CF or N.

In a preferred embodiment of the invention, wherein, X$_2$ is CH or CD.

In a preferred embodiment of the invention, wherein, X$_2$ is CH.

In a preferred embodiment of the invention, wherein, X$_3$ is CH, CD or N.

In a preferred embodiment of the invention, wherein, X$_3$ is CH.

In a preferred embodiment of the invention, wherein, X$_4$ is CR$^{X4}$ or N, wherein, R$^{X4}$ is hydrogen, deuterium, C$_1$-C$_6$ alkyl, deuterated C$_1$-C$_6$ alkyl, C$_1$-C$_6$ alkoxy, C$_1$-C$_6$ alkylthio, C$_1$-C$_6$ haloalkyl, C$_1$-C$_6$ haloalkoxy, C$_1$-C$_6$ haloalkylthio, halogen, SF$_5$, —S(O)$_2$R$^a$, —P(O) R$^a$R$^b$, CN or C$_3$-C$_{10}$ cycloalkyl, C$_6$-C$_{10}$ cycloalkenyl, 4-10 membered heterocyclyl, C$_6$-C$_{10}$ aryl and 5-10 membered heteroaryl, wherein, each ring of C$_3$-C$_{10}$ cycloalkyl, C$_6$-C$_{10}$ cycloalkenyl, 4-10 membered heterocyclyl, C$_6$-C$_{10}$ aryl and 5-10 membered heteroaryl is optionally substituted with 0-4 groups independently selected from deuterium, halogen, C$_1$-C$_6$ alkyl, C$_2$-C$_6$ alkenyl, C$_2$-C$_6$ alkynyl, C$_3$-C$_6$ cycloalkyl, —OR$^a$, oxo, hydroxy(C$_1$-C$_6$) alkyl, NR$^a$R$^b$, —CN, C$_1$-C$_6$ haloalkyl, C$_1$-C$_6$ haloalkoxy, —S(O)$_2$R$^a$, —SR$^a$, —SF$_5$, —C(O)R$^a$, —C(O)OR$^a$, —OC(O)R$^a$, —OC(O)NR$^a$R$^b$, —NR$^a$COR$^b$ or —CONR$^a$R$^b$.

In a preferred embodiment of the invention, wherein, X$_4$ is CR$^{X4}$; wherein, R$^{X4}$ is C$_1$-C$_6$ alkoxy, C$_1$-C$_6$ alkylthio, C$_1$-C$_6$ haloalkoxy, C$_1$-C$_6$ haloalkylthio, C$_1$-C$_6$ haloalkyl, —SF$_5$.

In a preferred embodiment of the invention, wherein, X$_4$ is CR$^{X4}$; wherein, R$^{X4}$ is C$_1$-C$_6$ haloalkoxy, C$_1$-C$_6$ haloalkylthio, C$_1$-C$_6$ haloalkyl, —SF$_5$.

In a preferred embodiment of the invention, wherein, X$_5$ is CR$^{X5}$ or N, wherein, R$^{X5}$ is hydrogen, deuterium, C$_1$-C$_6$ alkyl, C$_1$-C$_6$ alkoxy, C$_1$-C$_6$ haloalkyl, C$_1$-C$_6$ haloalkoxy, halogen, —SF$_5$ or CN.

In a preferred embodiment of the invention, wherein, X$_5$ is CH.

In a preferred embodiment of the invention, wherein, X$_6$ is CH, CD or N.

In a preferred embodiment of the invention, wherein, X$_6$ is CH.

In a preferred embodiment of the invention, wherein, the chemical bond between Y$_1$ and Y$_2$ is double bond.

In a preferred embodiment of the invention, wherein, Y$_1$ is CH, CD or CCH$_3$.

In a preferred embodiment of the invention, wherein, Y$_2$ is N.

In a preferred embodiment of the invention, wherein, Y$_3$ is CH, CD, CCH$_3$ or CCH$_2$OH.

In a preferred embodiment of the invention, wherein, R' is —CHR$^2$R$^3$ or —CDR$^2$R$^3$, wherein, R$^2$ and R$^3$ are independently hydrogen, deuterium, C$_1$-C$_6$ alkyl or C$_3$-C$_{10}$ cycloalkyl, 4-10 membered heterocyclyl, C$_6$-C$_{10}$ aryl, 5-10 membered heteroaryl, wherein, each ring of C$_3$-C$_{10}$ cycloalkyl, 4-10 membered heterocyclyl, C$_6$-C$_{10}$ aryl, 5-10 membered heteroaryl is independently optionally substituted with 0-3 groups selected from halogen, C$_1$-C$_6$ alkyl, C$_2$-C$_6$ alkenyl, C$_2$-C$_6$ alkynyl, C$_3$-C$_6$ cycloalkyl, —OR$^a$, oxo, hydroxy(C$_1$-C$_6$) alkyl, NR$^a$R$^b$, —CN, C$_1$-C$_6$ haloalkyl, C$_1$-C$_6$ haloalkoxy, —SO$_3$R$^a$, —SR$^a$, —S(O)$_2$R$^a$, —S(O)R$^a$, —SF$_5$, —C(O)R$^a$, —C(O)OR$^a$, —OC(O)R$^a$, —OC(O)NR$^a$R$^b$, —NR$^a$COR$^b$ or —CONR$^a$R$^b$.

In a preferred embodiment of the invention, wherein, R' is —CHR$^2$R$^3$ or —CDR$^2$R$^3$, wherein, R$^2$ is hydrogen, deuterium, C$_1$-C$_6$ alkyl; R$^3$ is hydrogen, deuterium, C$_1$-C$_6$ alkyl or C$_3$-C$_{10}$ cycloalkyl, 4-10 membered heterocyclyl, C$_6$-C$_{10}$ aryl, 5-10 membered heteroaryl, wherein, each ring of C$_3$-C$_{10}$ cycloalkyl, 4-10 membered heterocyclyl, C$_6$-C$_{10}$ aryl, 5-10 membered heteroaryl is independently optionally substituted with 0-3 groups selected from halogen, C$_1$-C$_6$ alkyl, C$_2$-C$_6$ alkenyl, C$_2$-C$_6$ alkynyl, C$_3$-C$_6$ cycloalkyl, —OR$^a$, oxo, hydroxy(C$_1$-C$_6$) alkyl, NR$^a$R$^b$, —CN, C$_1$-C$_6$ haloalkyl, C$_1$-C$_6$haloalkoxy, —SO$_3$R$^a$, —SR$^a$, —S(O)$_2$R$^a$, —S(O)R$^a$, —SF$_5$, —C(O)R$^a$, —C(O)OR$^a$, —OC(O)R$^a$, —OC(O)NR$^a$R$^b$, —NR$^a$COR$^b$ or —CONR$^a$R$^b$.

In a preferred embodiment of the invention, wherein, R' is C$_3$-C$_{10}$ cycloalkyl which is optionally substituted with 0-3 groups independently selected from deuterium, halogen, C$_1$-C$_6$ alkyl, hydroxy(C$_1$-C$_6$) alkyl, —OR$^a$, —CN, NR$^a$R$^b$, C$_1$-C$_6$ haloalkyl, C$_1$-C$_6$ haloalkoxy. In a preferred embodiment of the invention, wherein, R' is C$_1$-C$_6$ alkyl (preferably methyl, ethyl) or deuterated C$_1$-C$_6$ alkyl (preferably deuterated methyl, deuterated ethyl) or C$_3$-C$_6$ cycloalkyl (preferably cyclopropyl).

In a preferred embodiment of the invention, wherein, M$_1$ is O or S.

In a preferred embodiment of the invention, wherein, o is 1 or 2.

In a preferred embodiment of the invention, wherein, o is 1.

In a preferred embodiment of the invention, wherein, n is 0 or 1.

In a preferred embodiment of the invention, wherein, n is 0.

In a preferred embodiment of the invention, wherein, n is 1.

In a preferred embodiment of the invention, wherein, R$^L$ and R$^{L'}$ are independently hydrogen or C$_1$-C$_6$ alkyl.

Specifically, in an embodiment, the present invention provides following compounds:

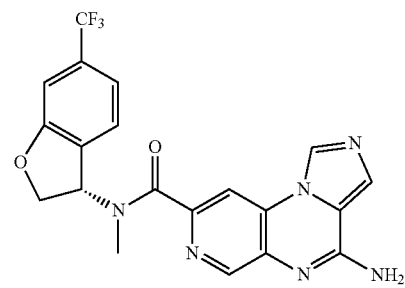

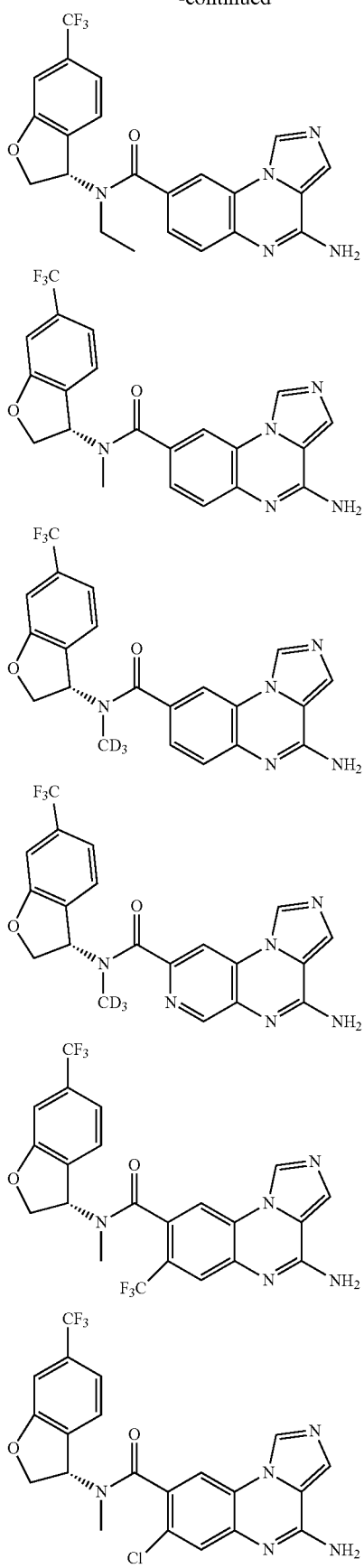
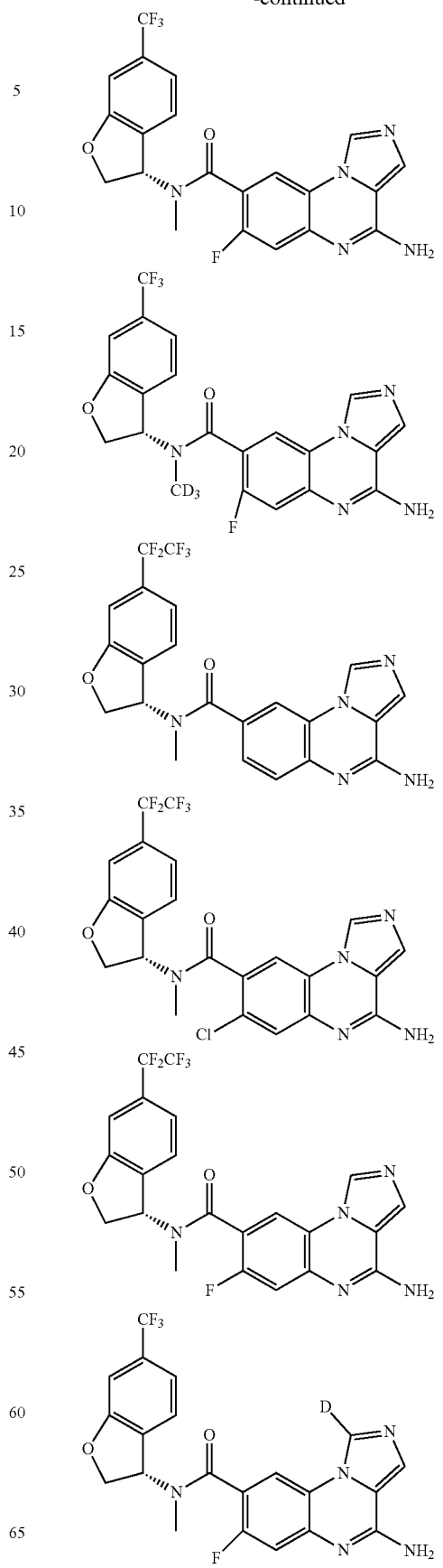

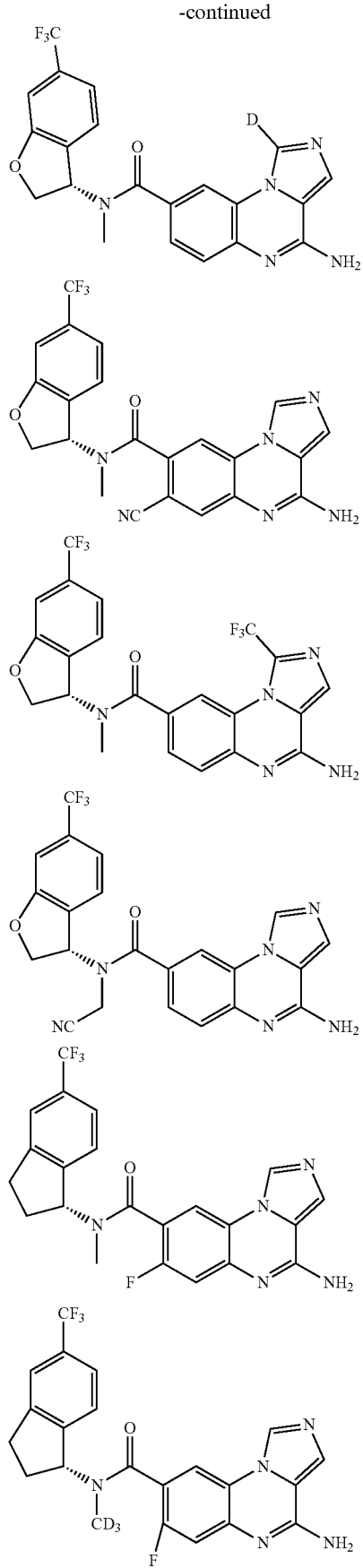
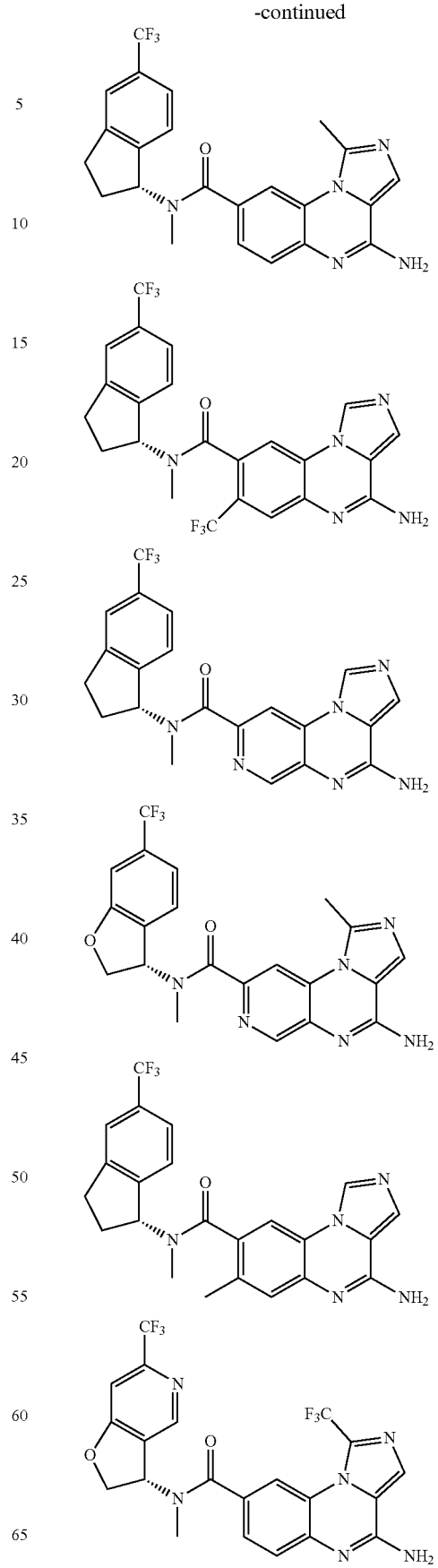

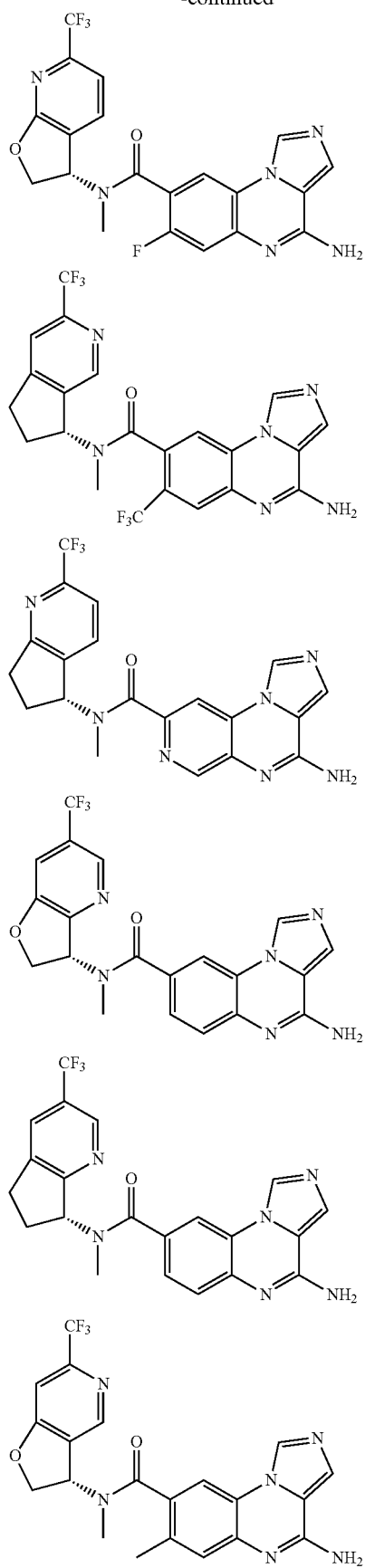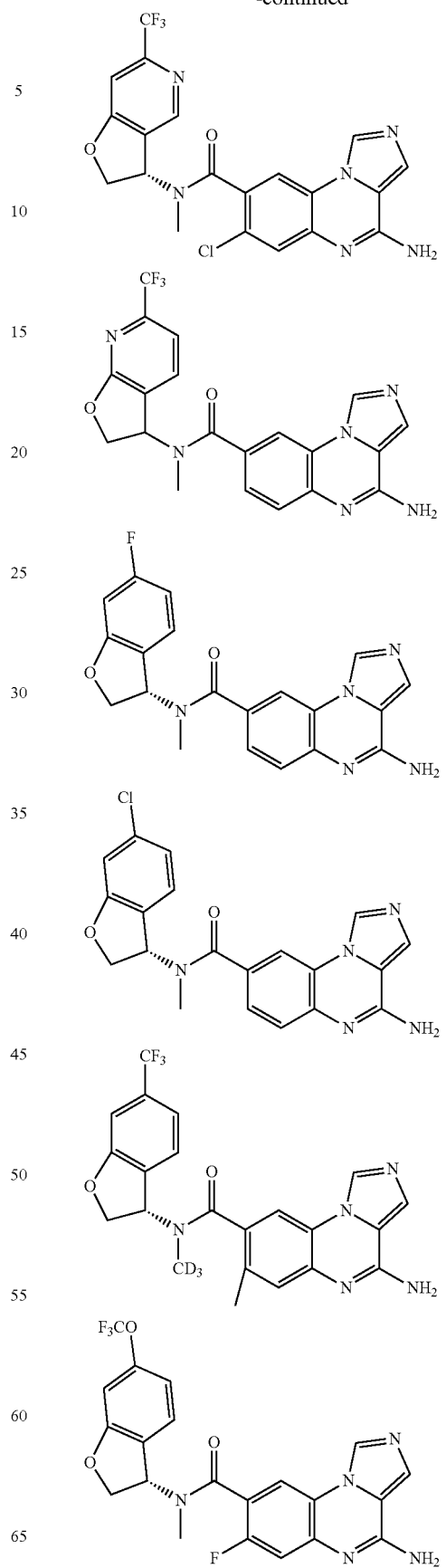

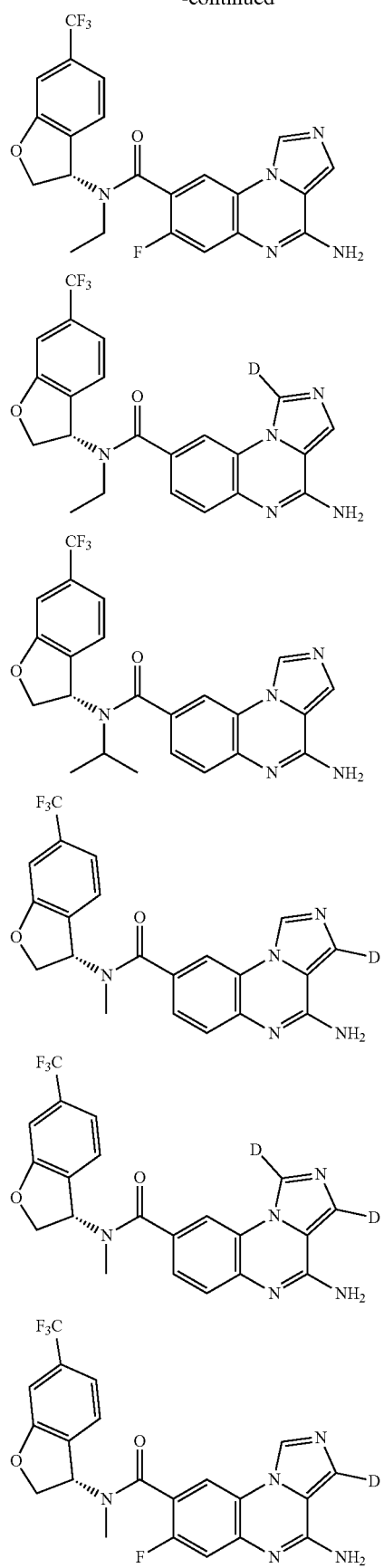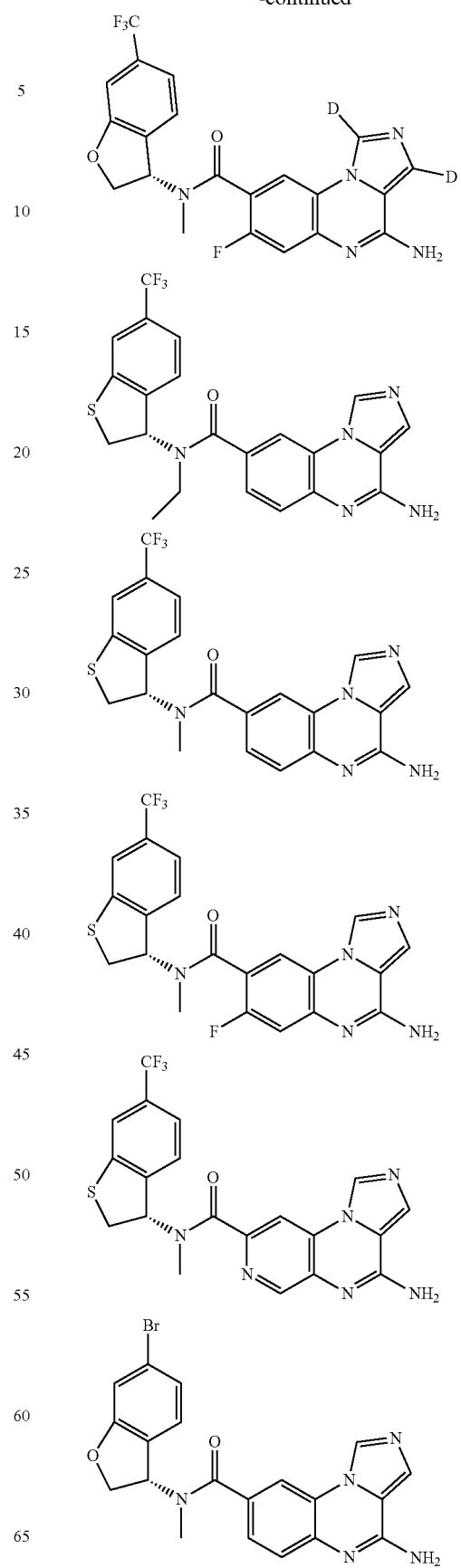

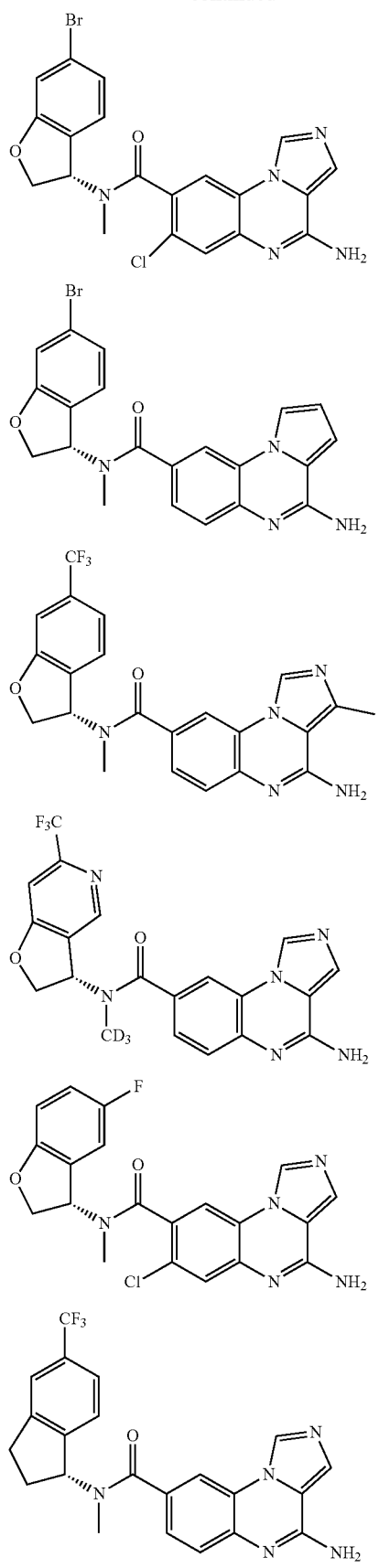
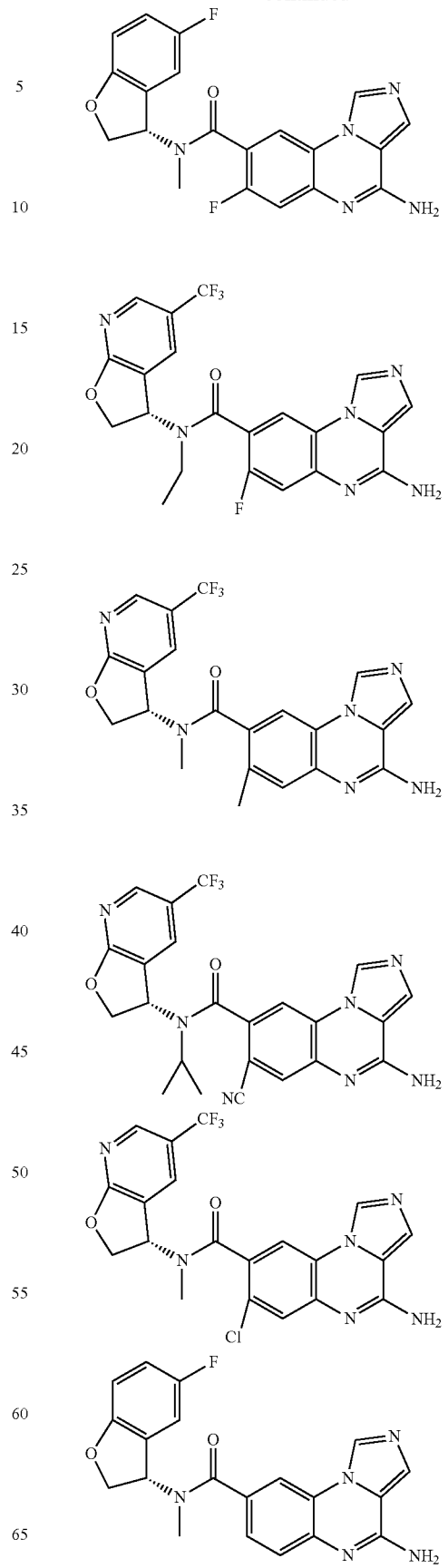

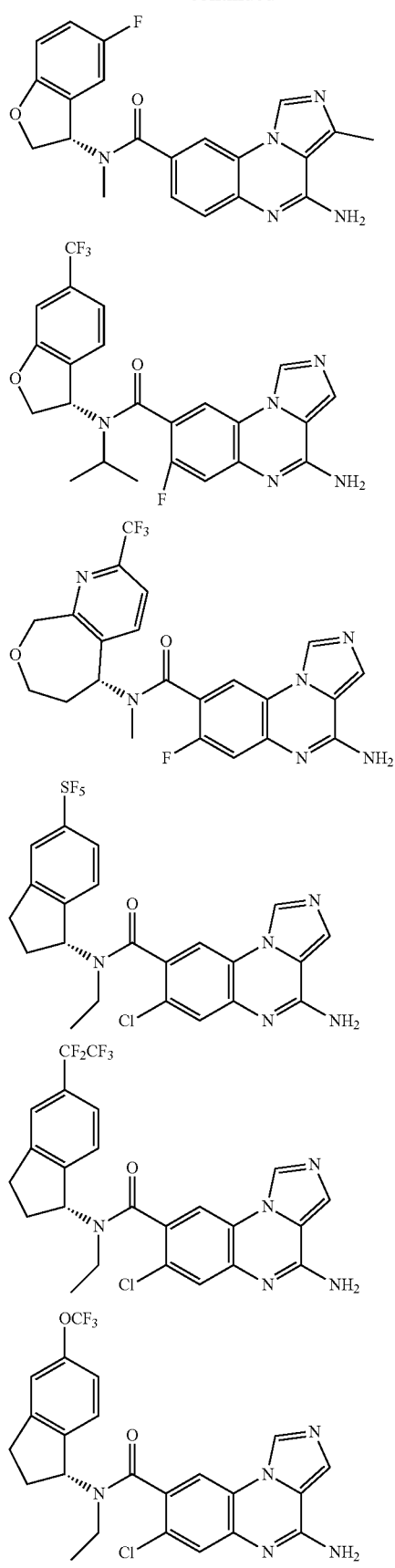
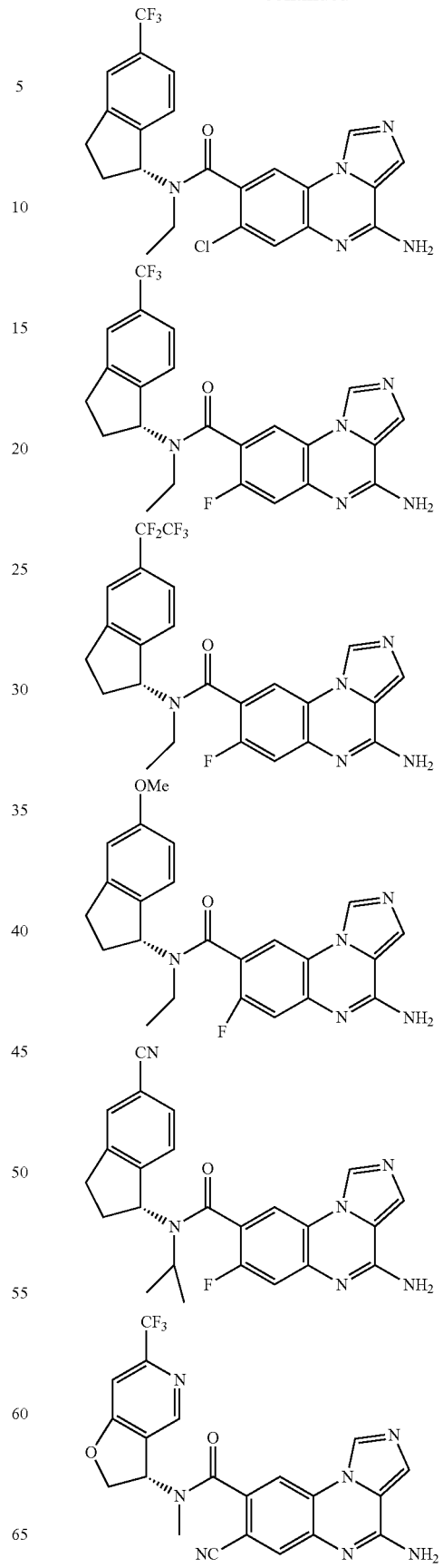

-continued
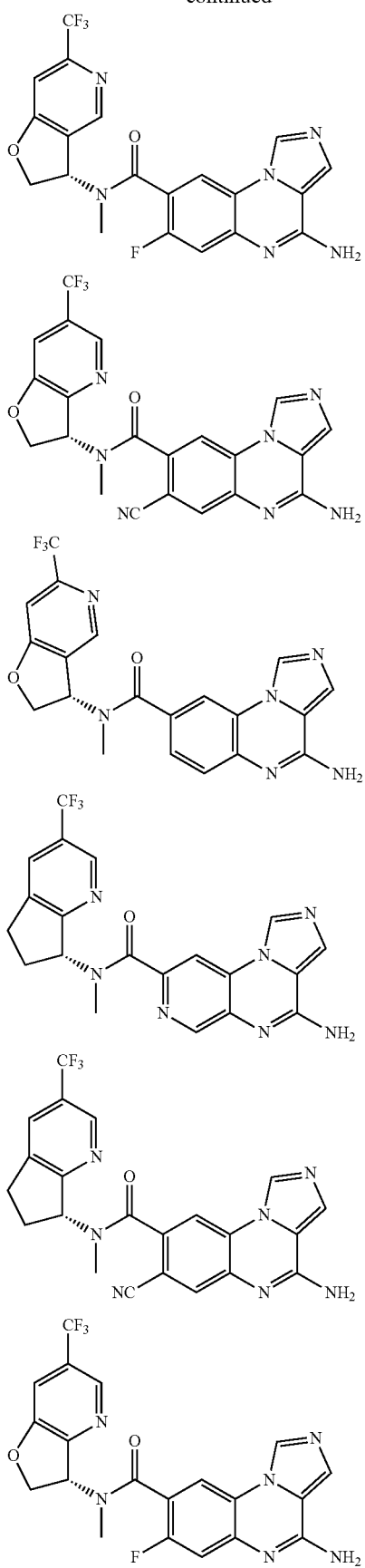
-continued
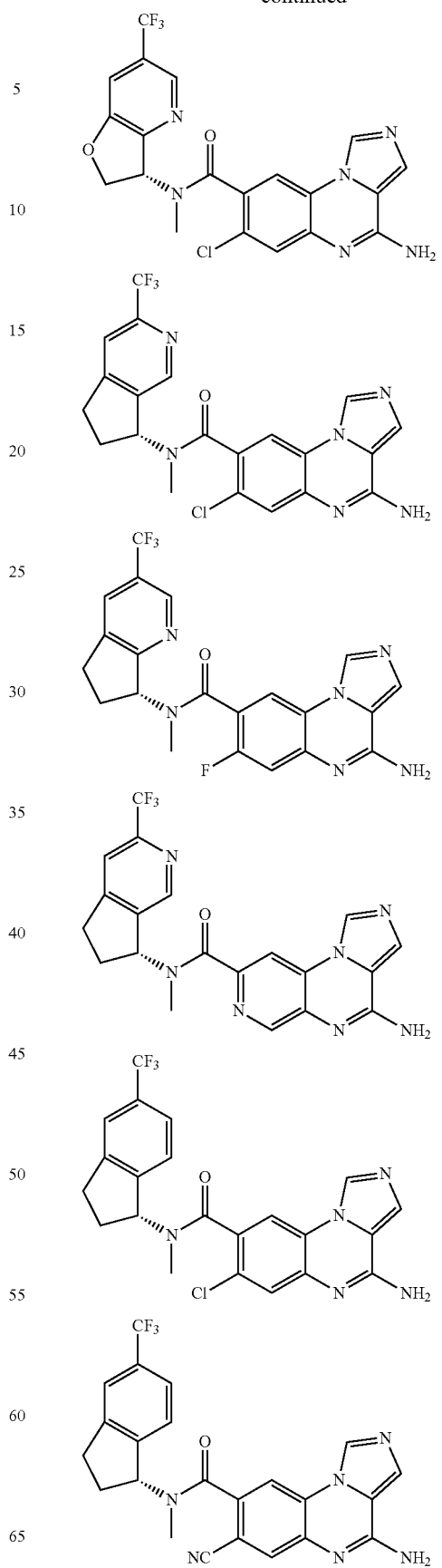

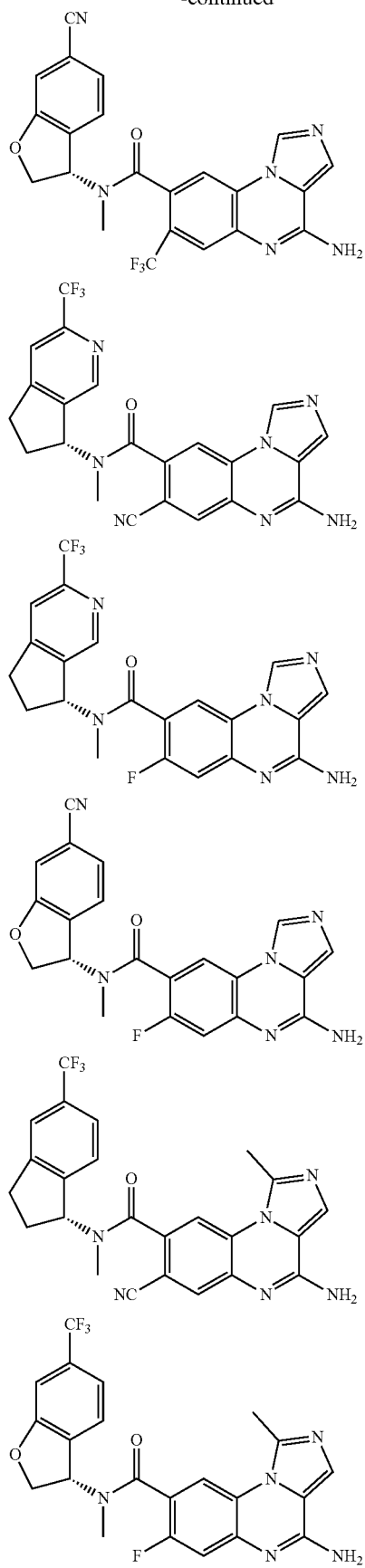
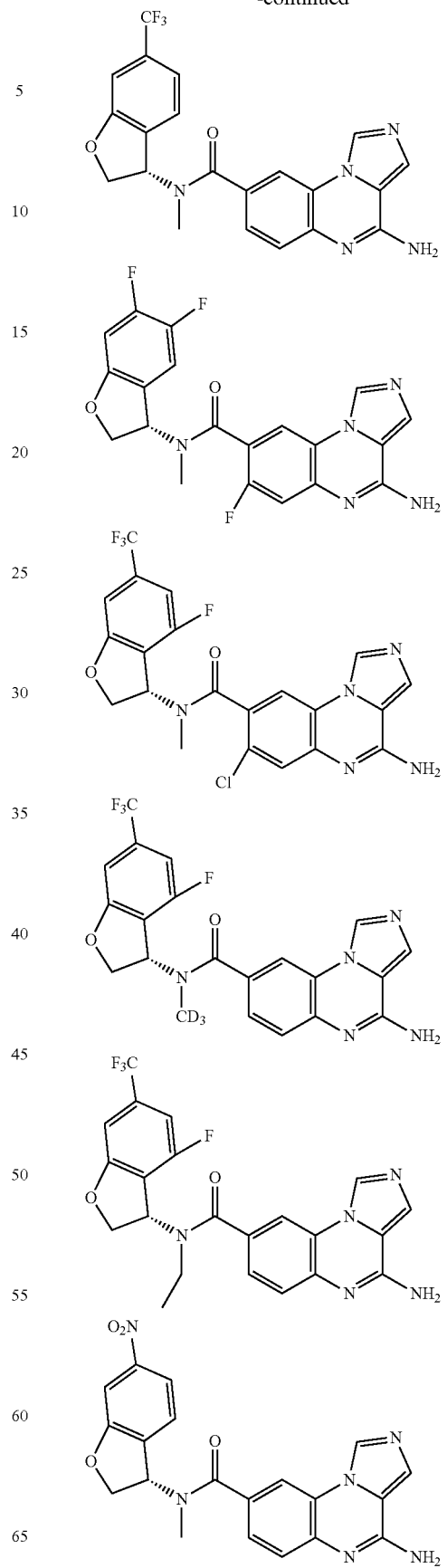

25
-continued
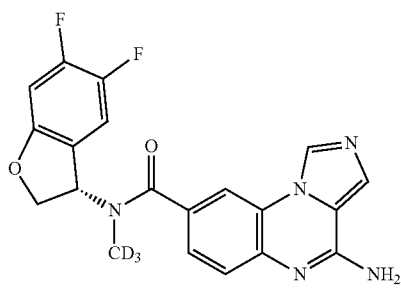
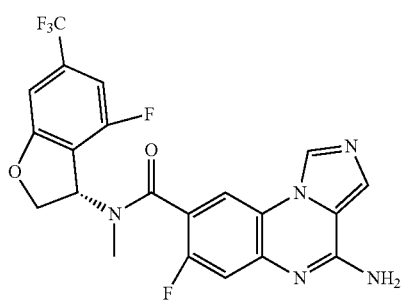
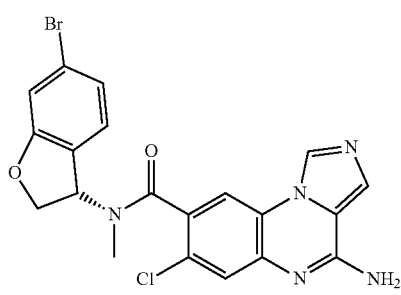
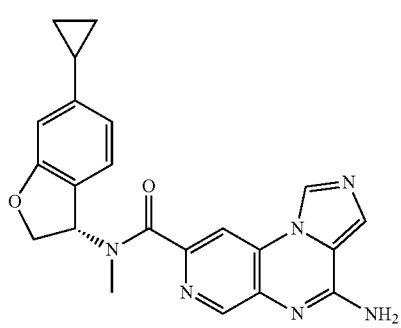
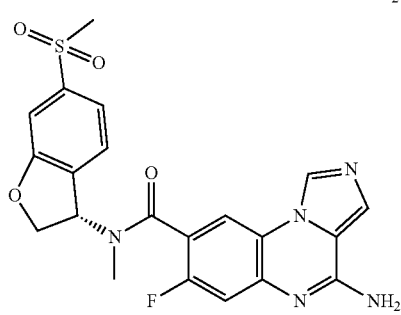
26
-continued
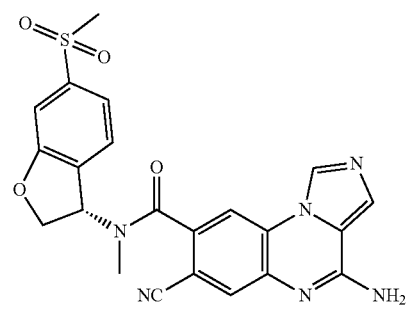
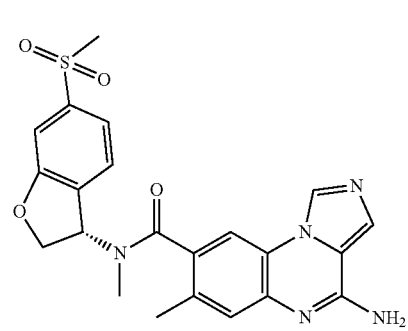
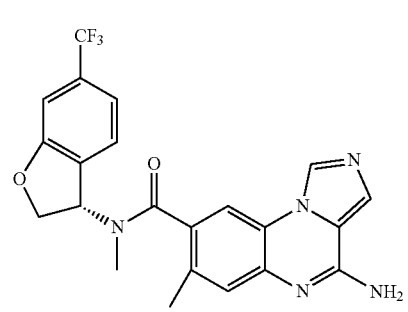
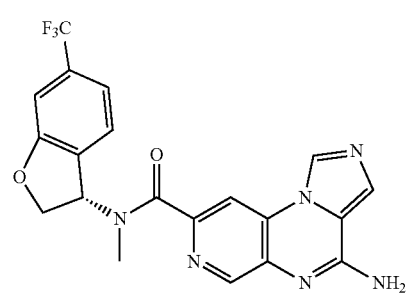
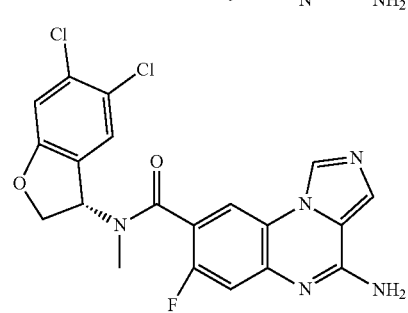

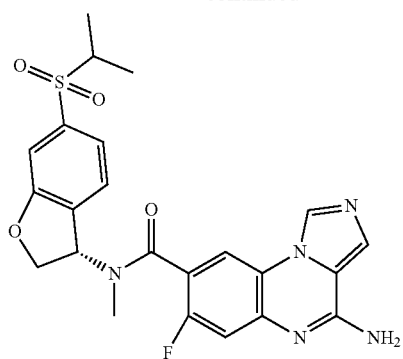
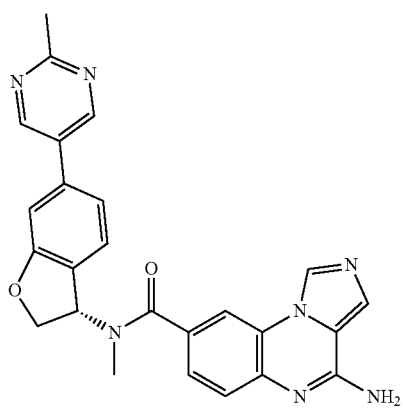
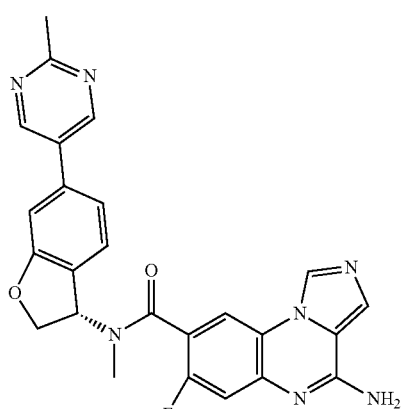
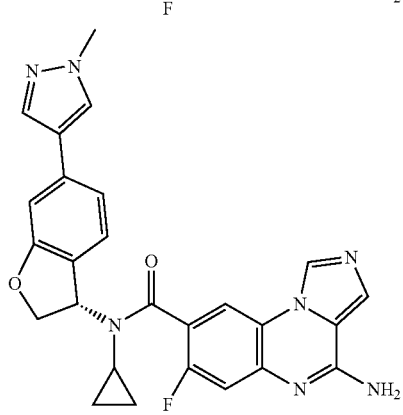
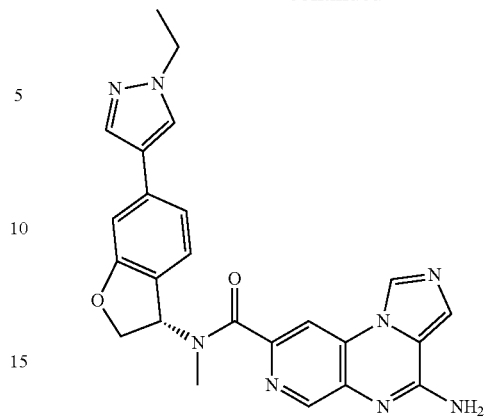
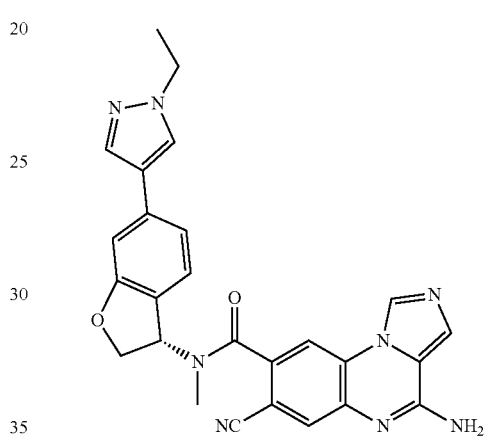
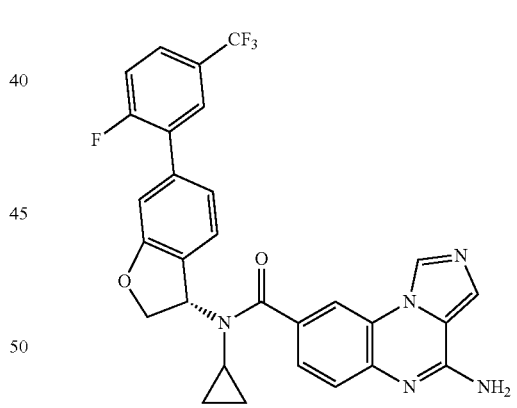
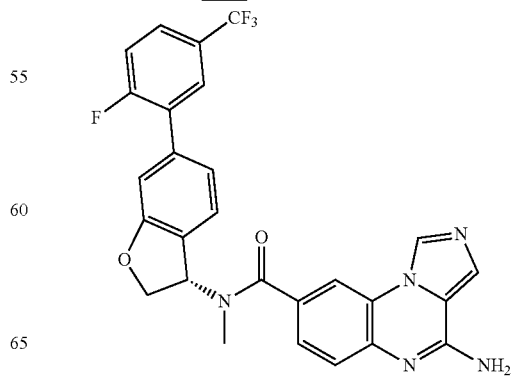

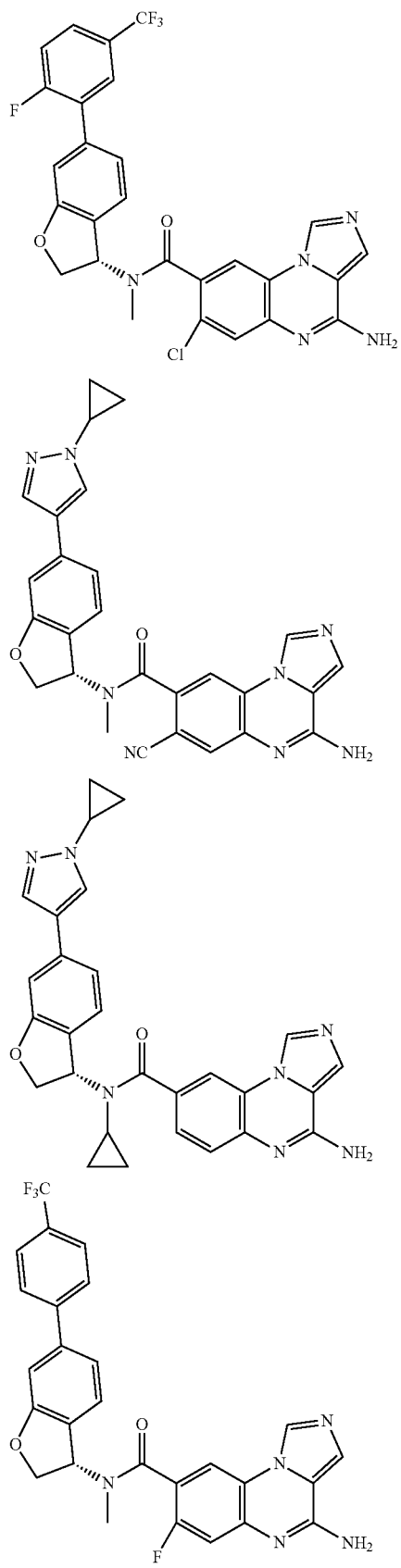
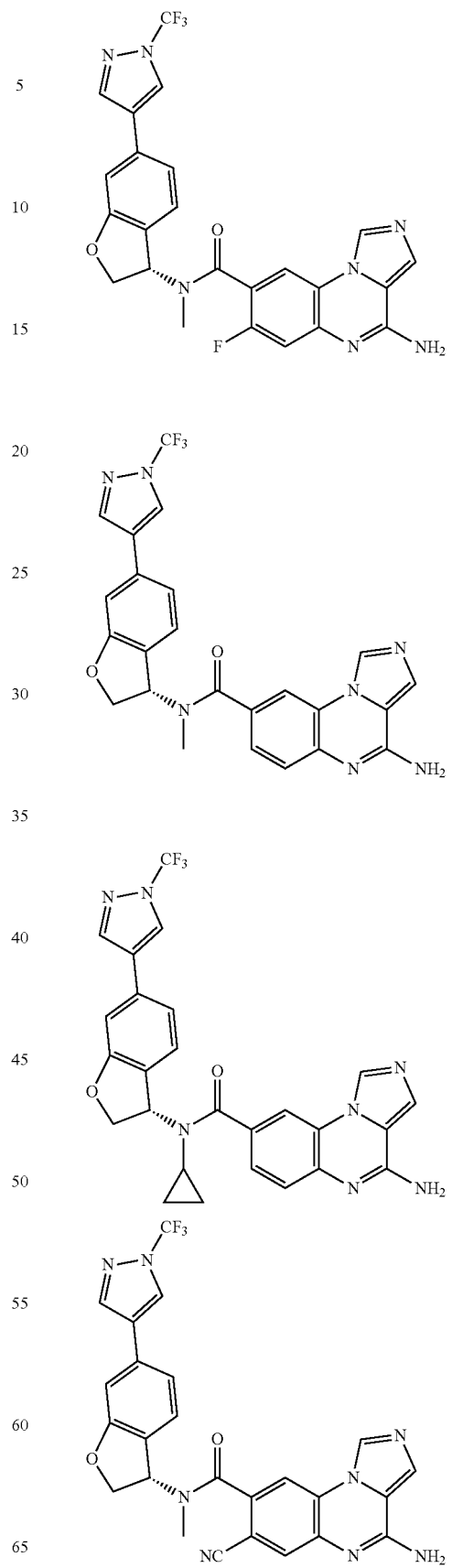

31
-continued
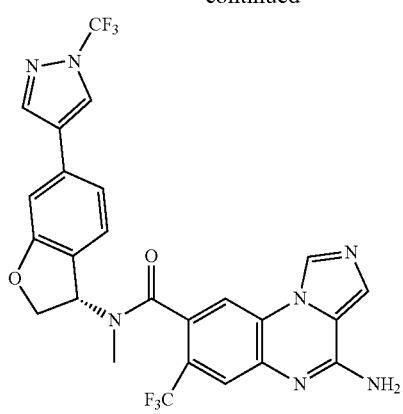
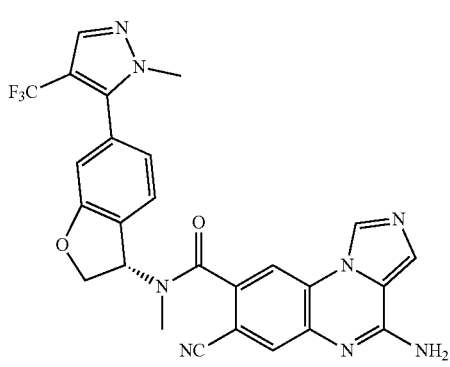
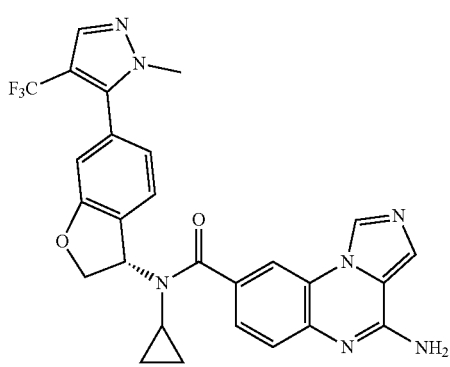
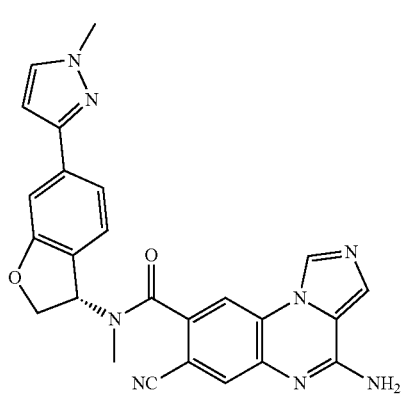
32
-continued
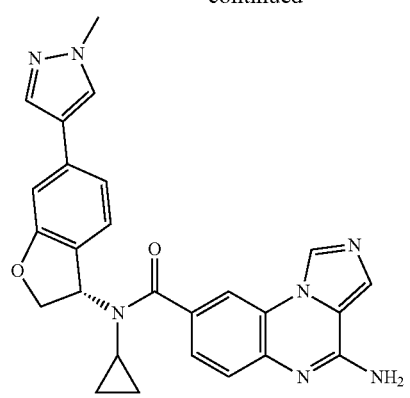
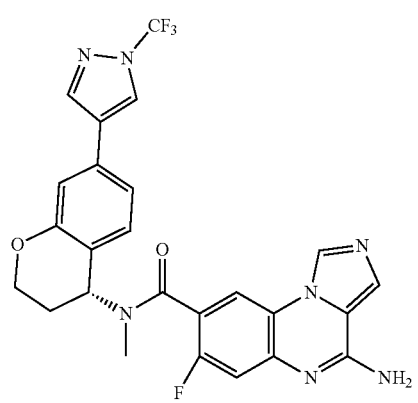
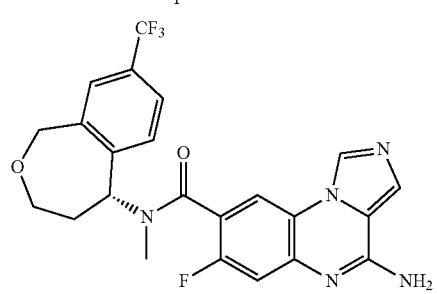
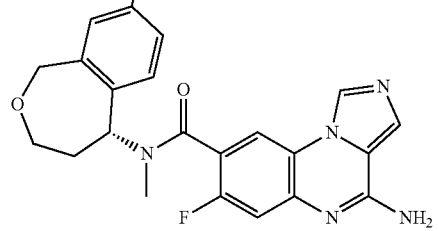
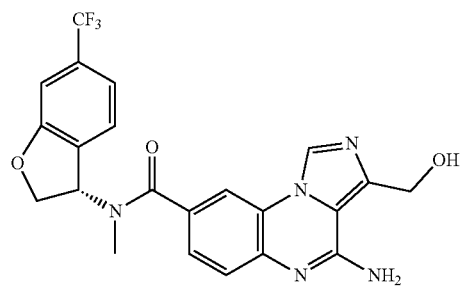

33
-continued
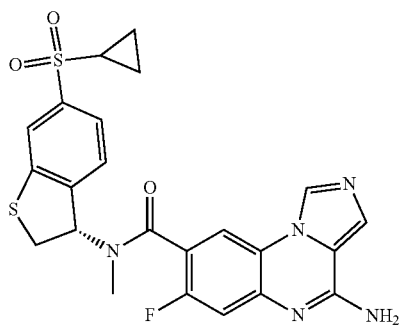
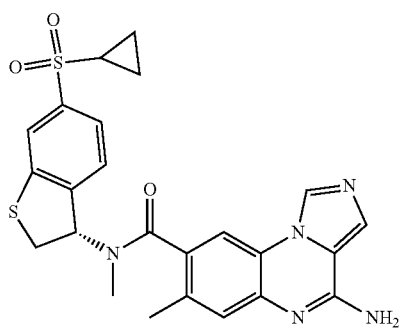
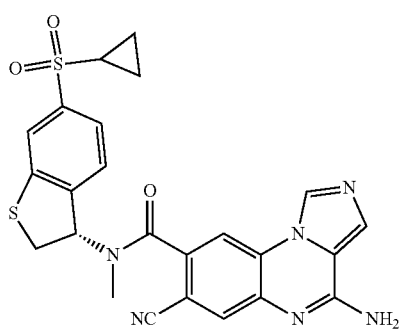
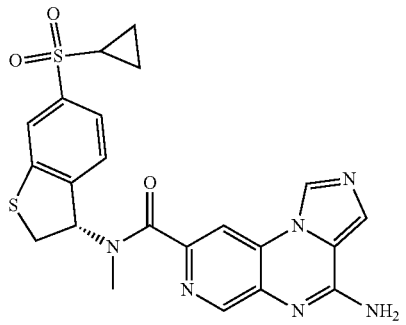
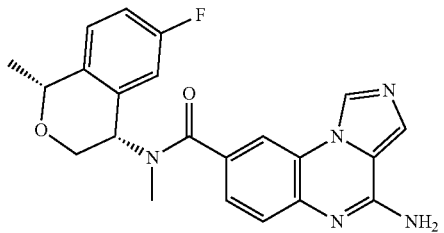
34
-continued
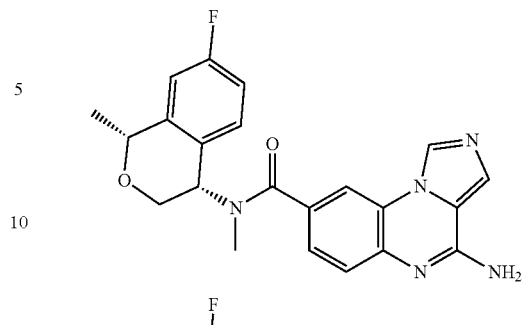
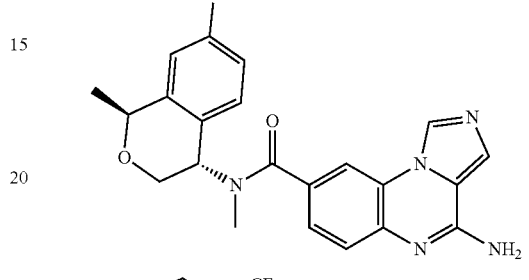
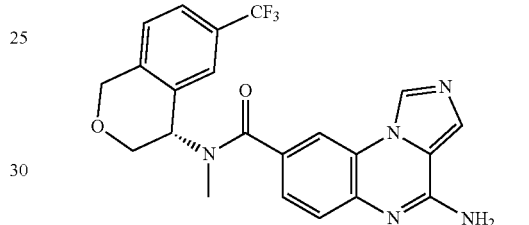
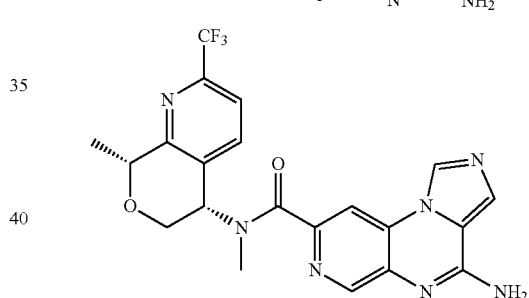
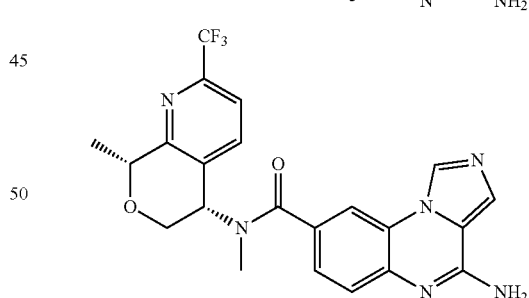
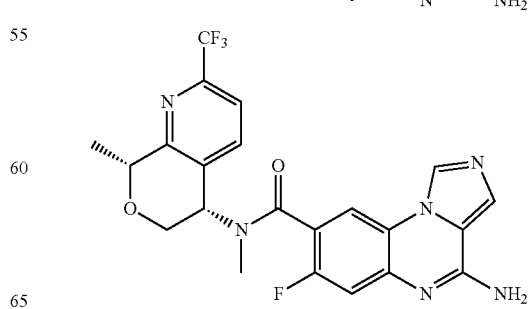

35
-continued
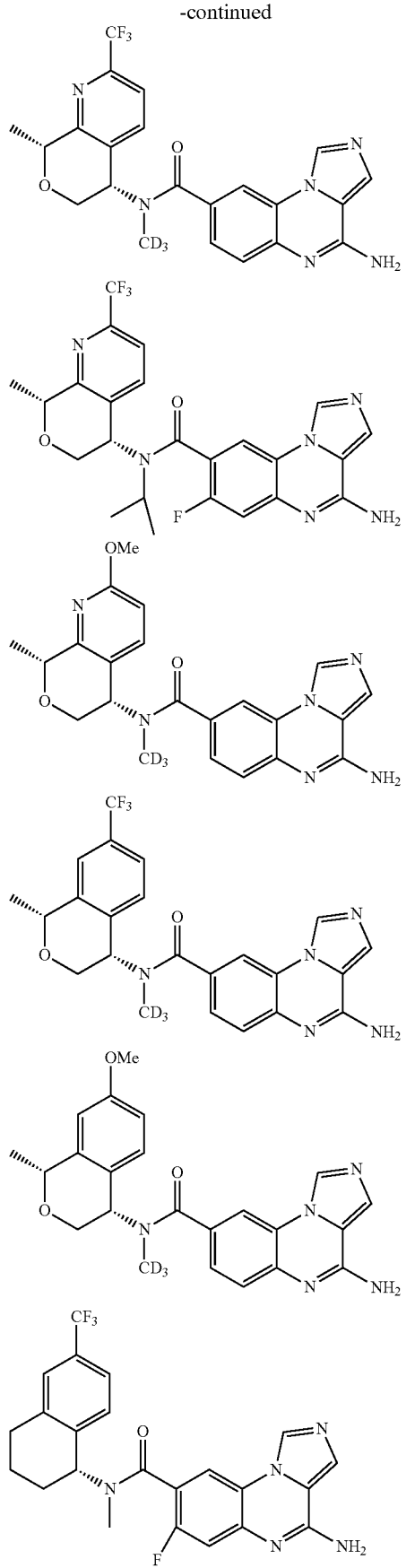
36
-continued
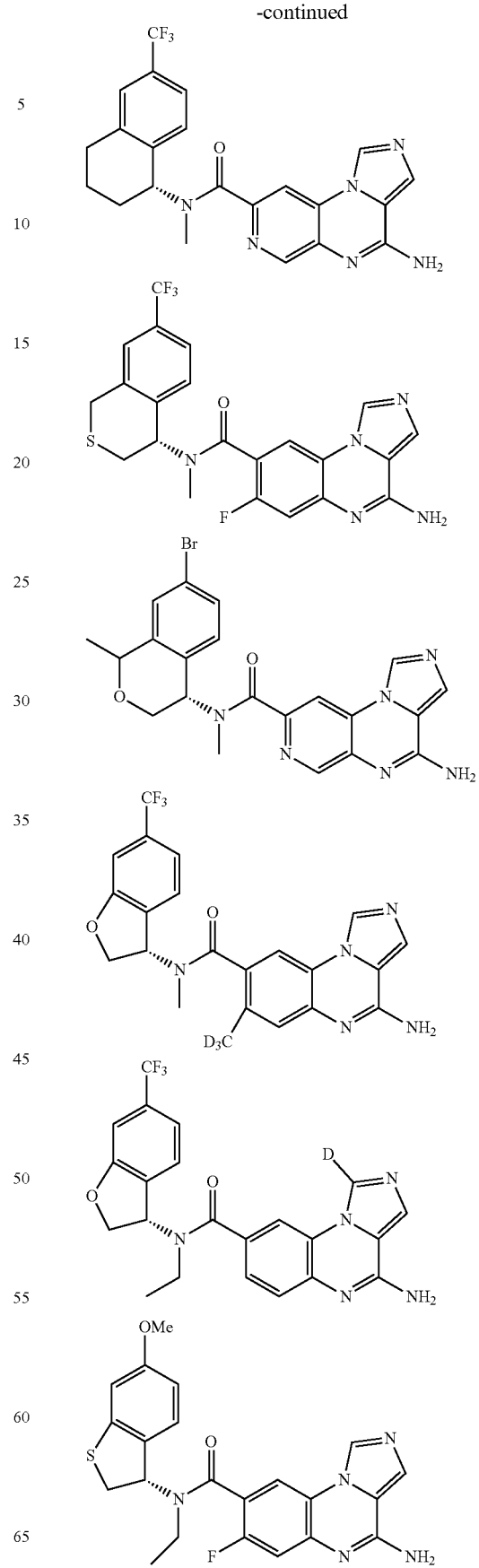

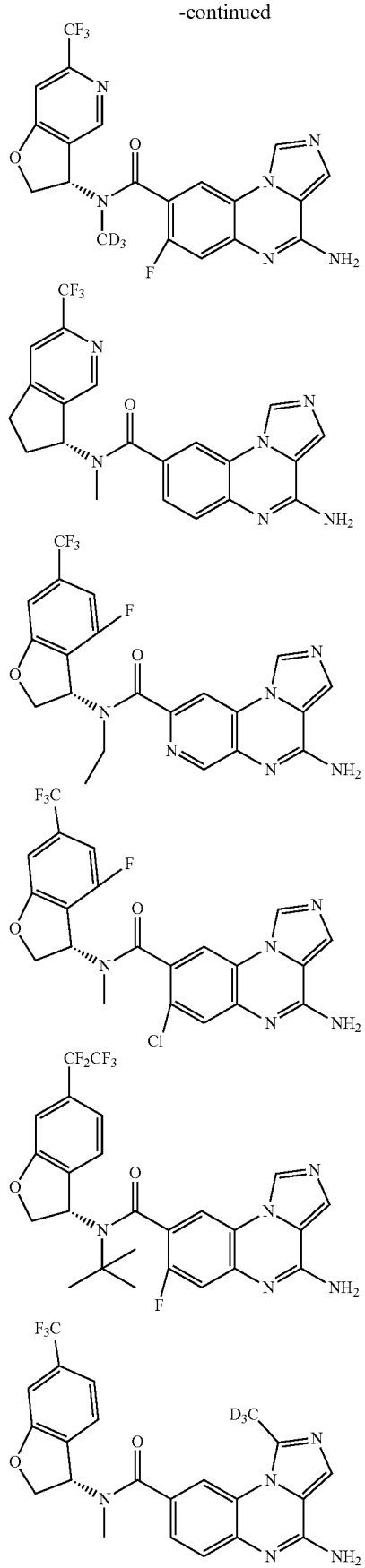
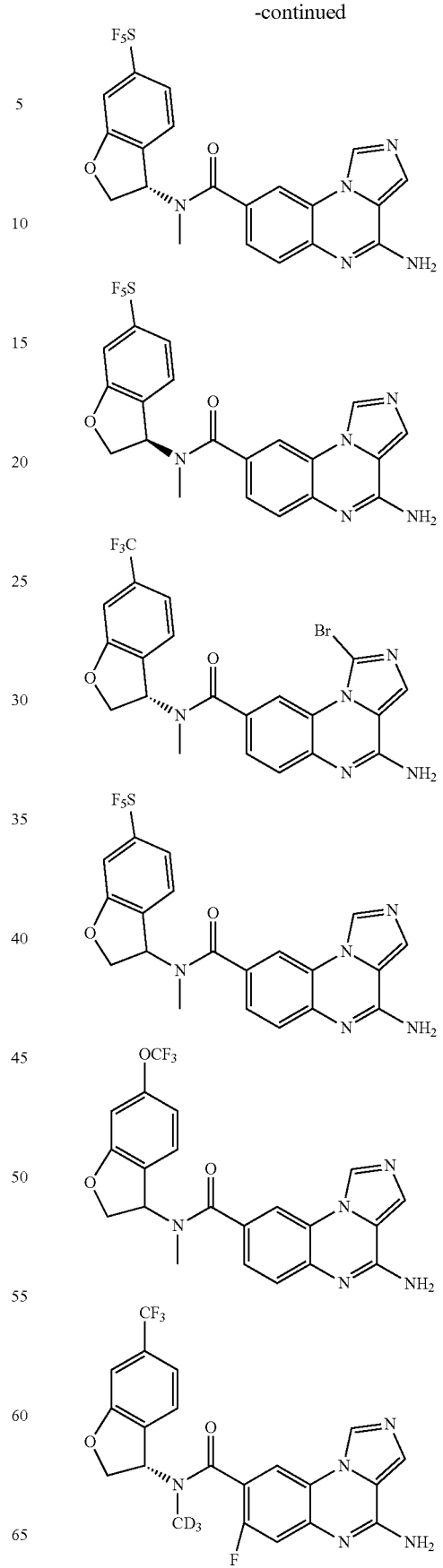

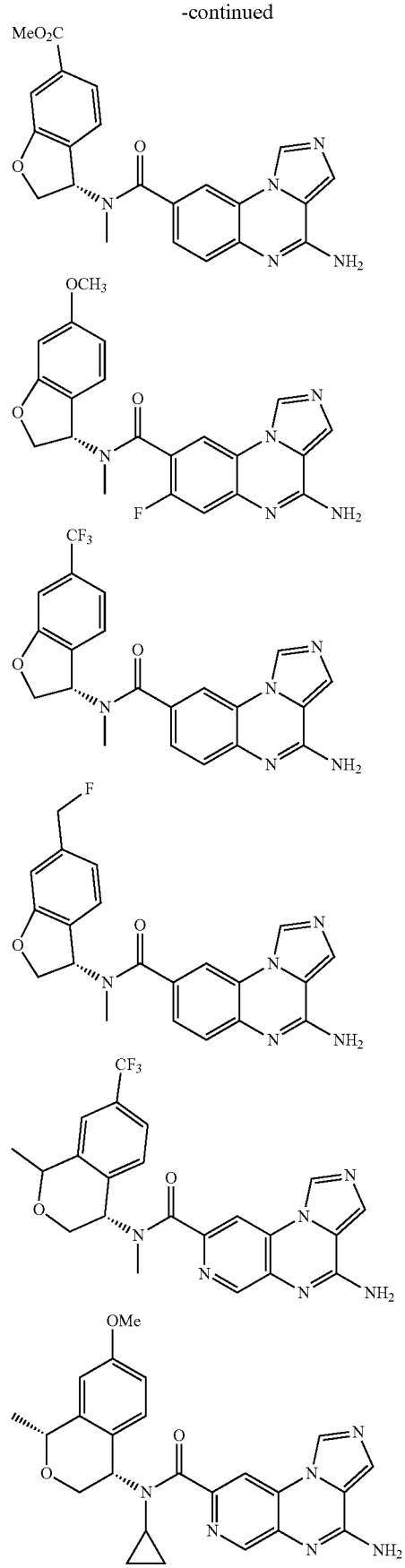
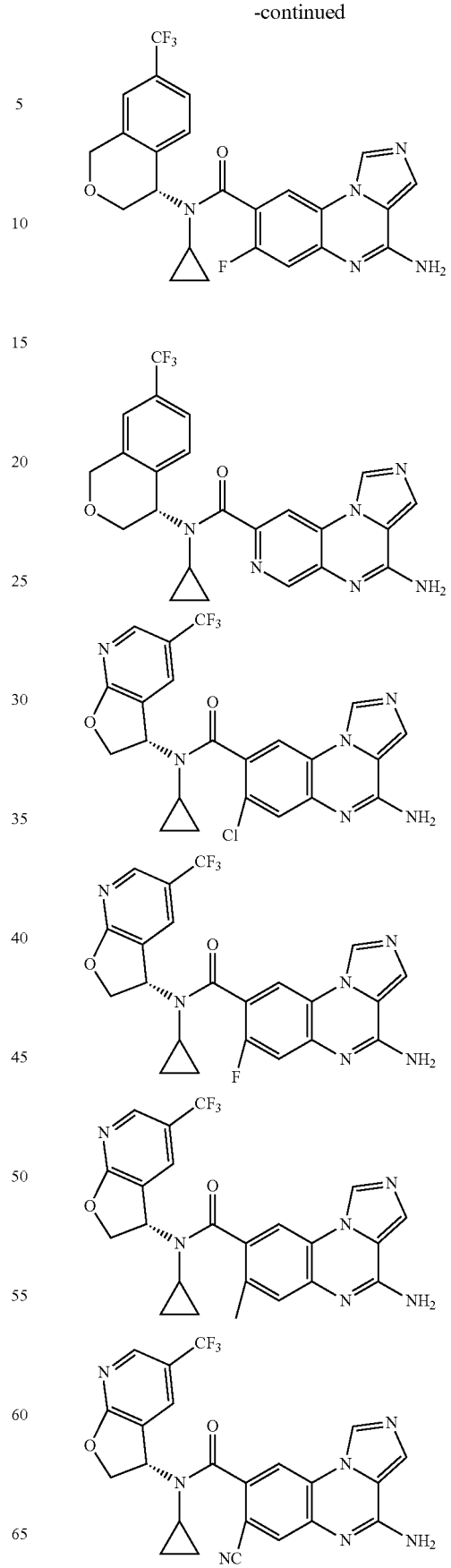

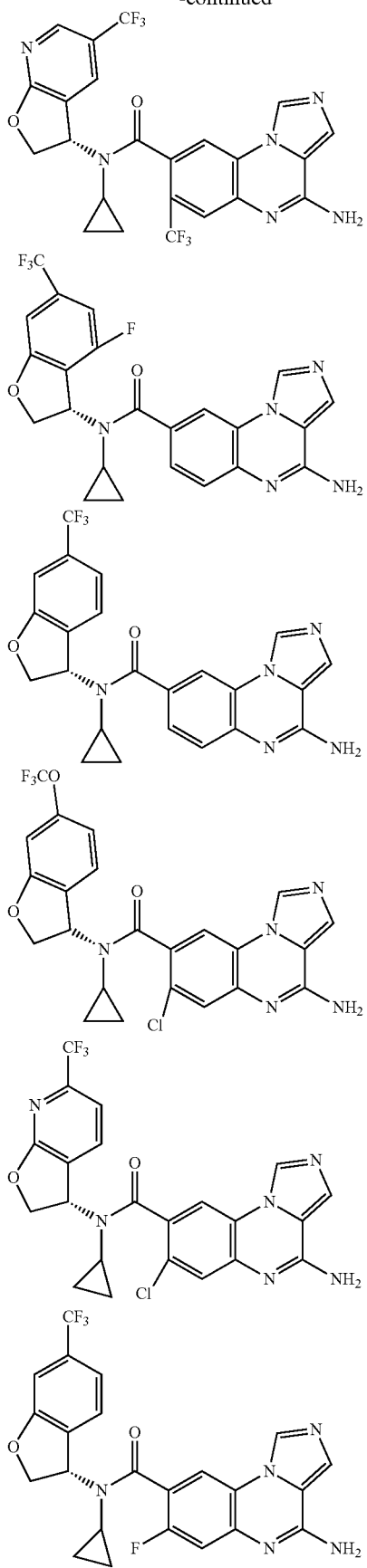
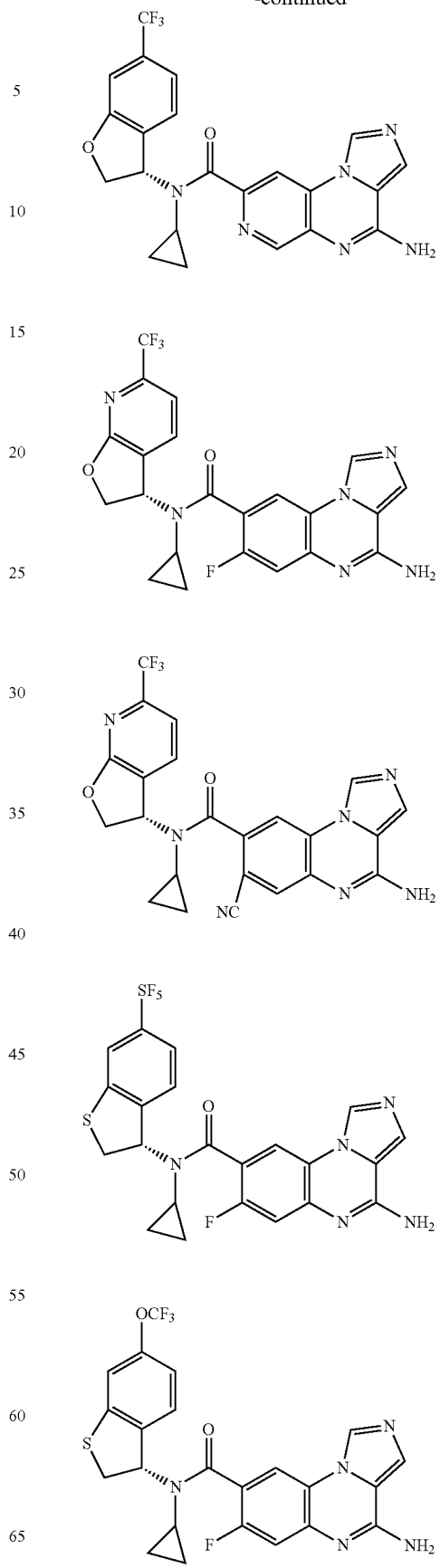

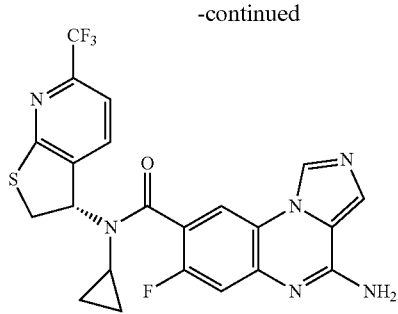
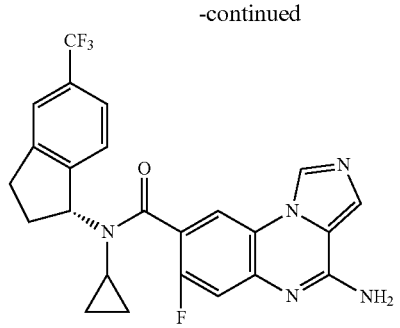
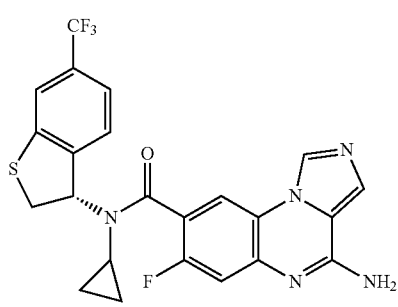
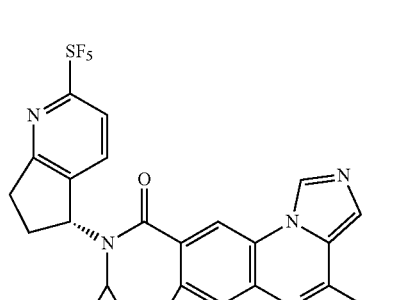
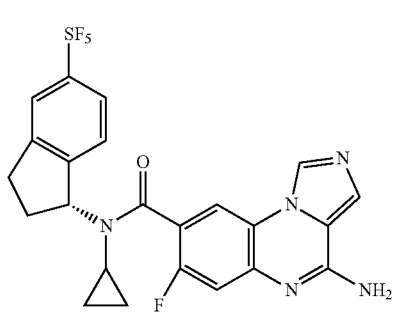
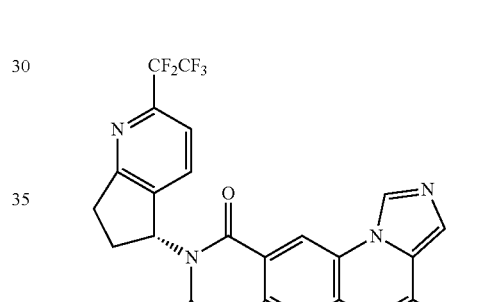
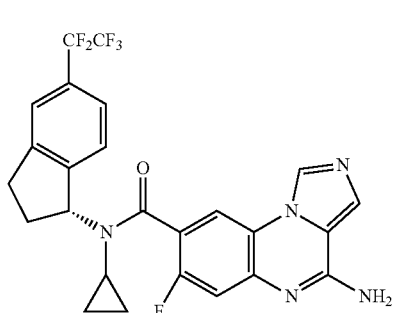
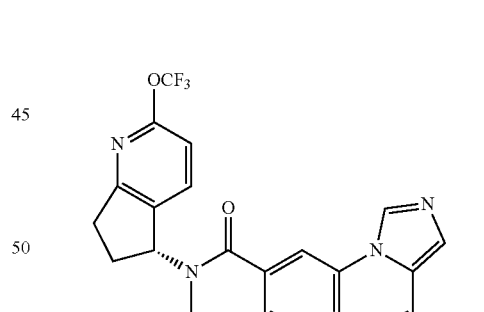
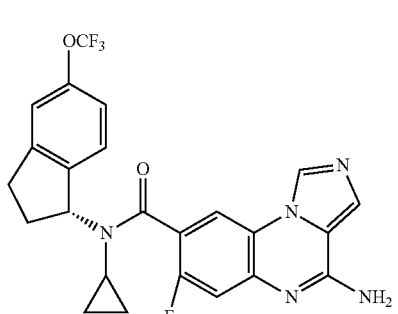
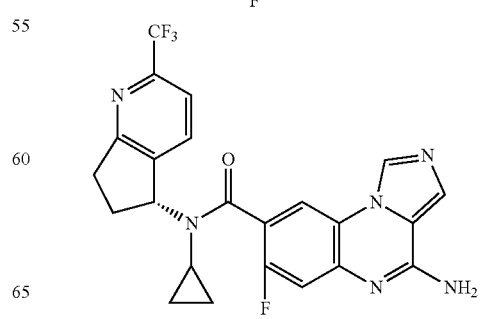

-continued
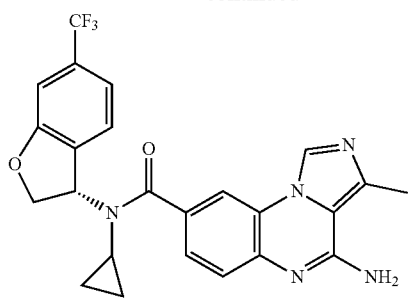
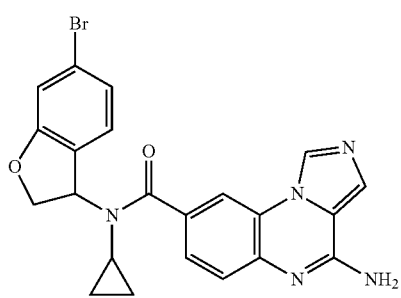
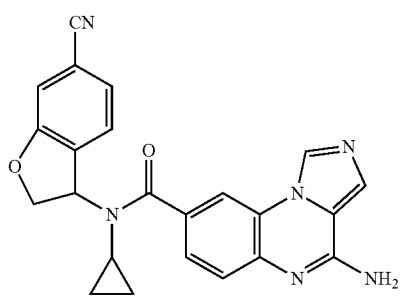
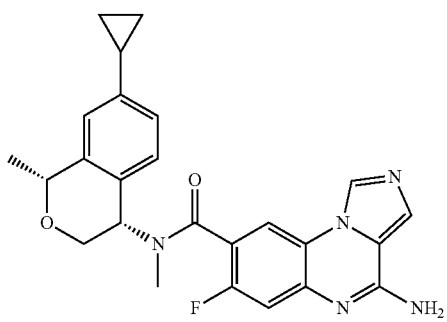
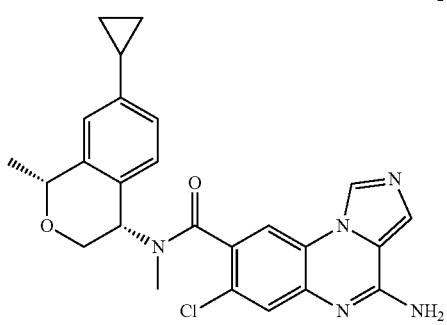
-continued
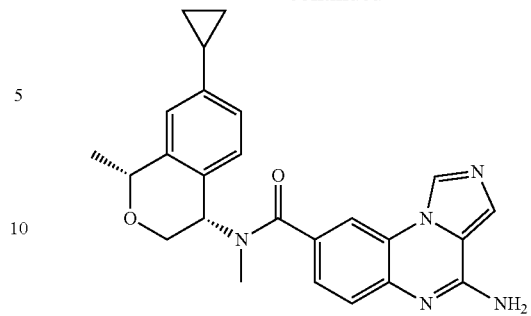
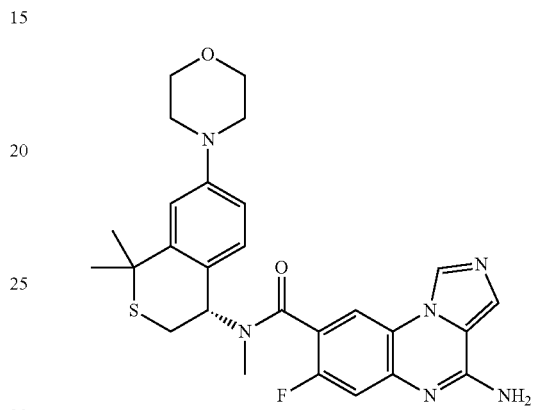
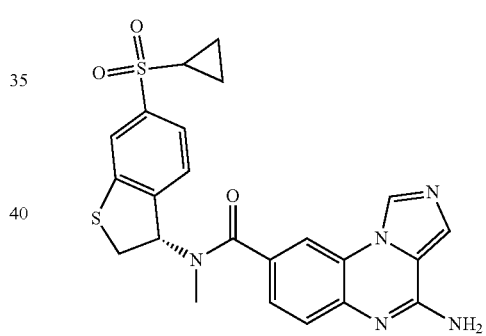
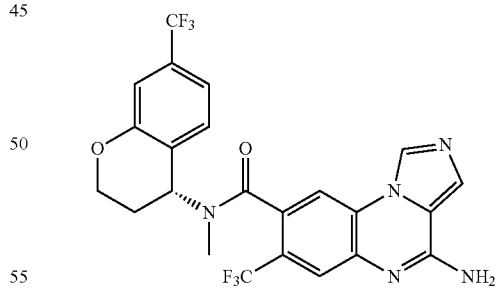
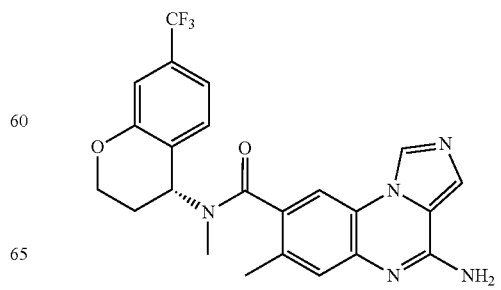

47
-continued
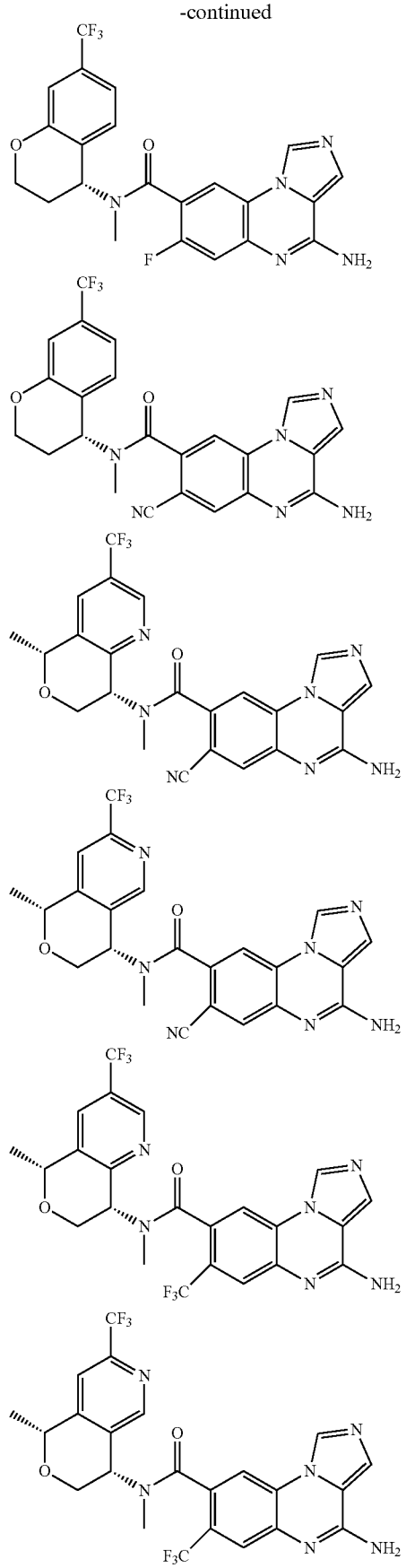
48
-continued
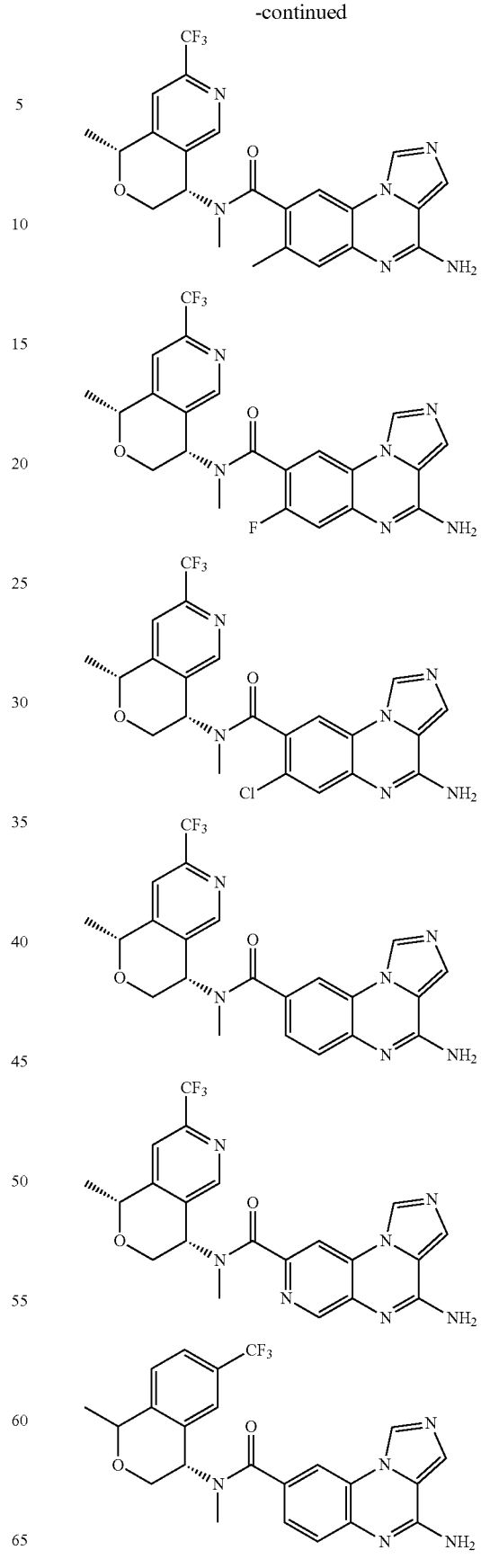

49
-continued
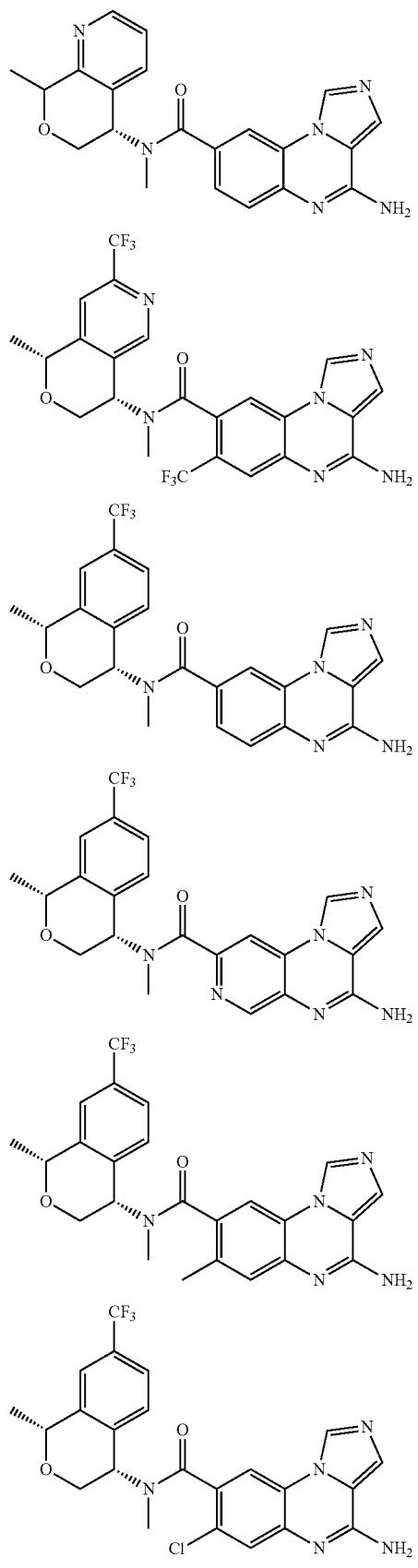
50
-continued
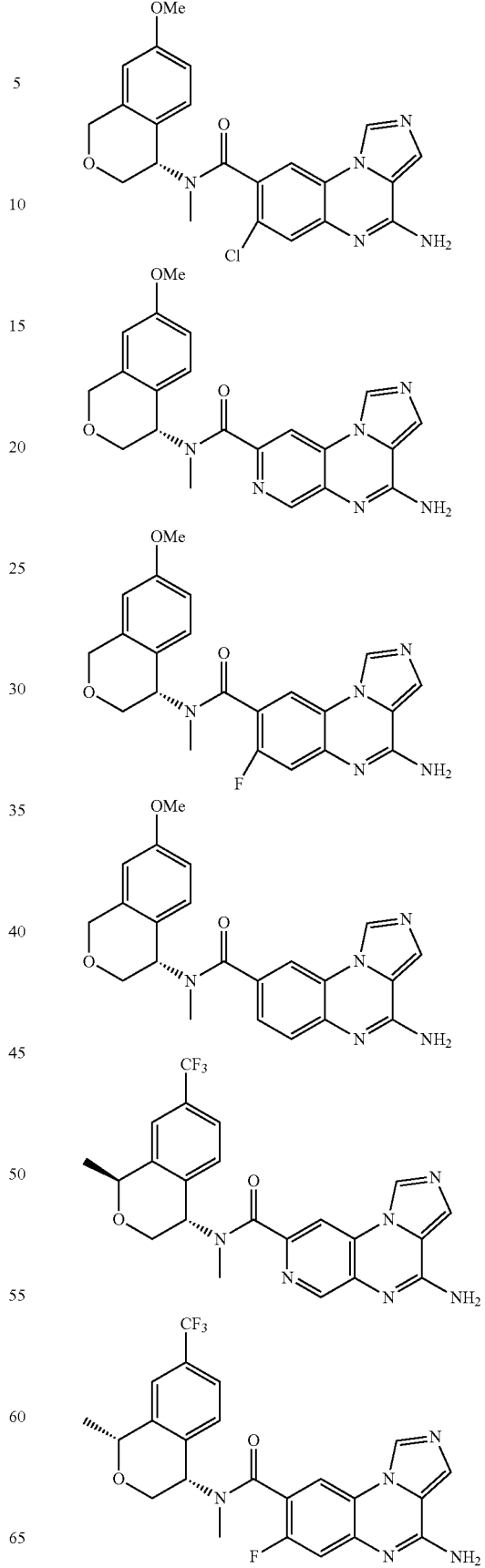

51
-continued
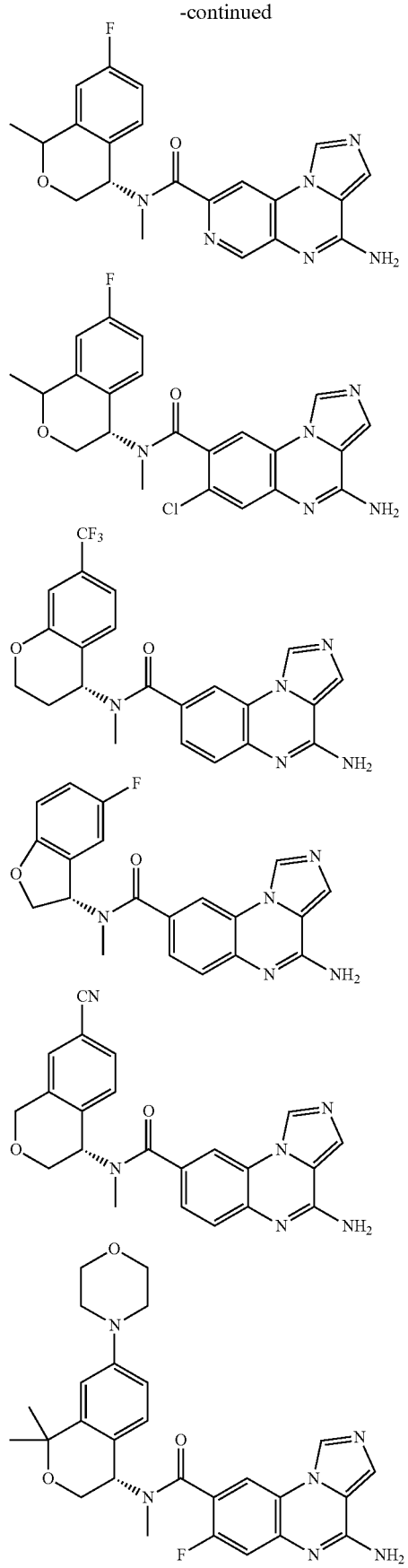
52
-continued
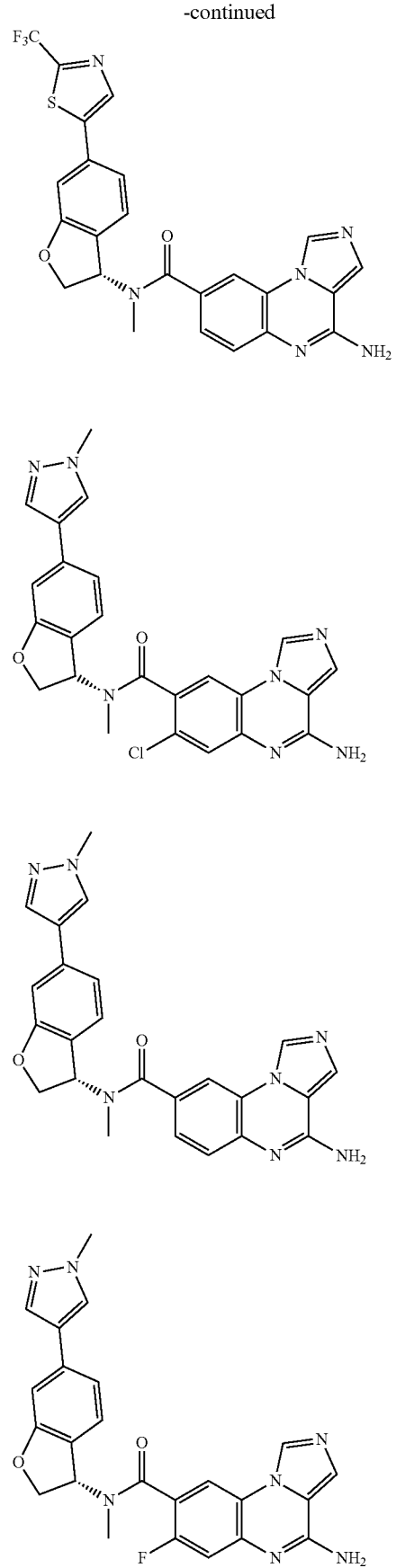

53
-continued
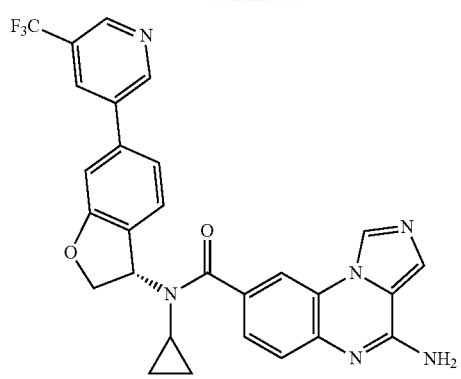
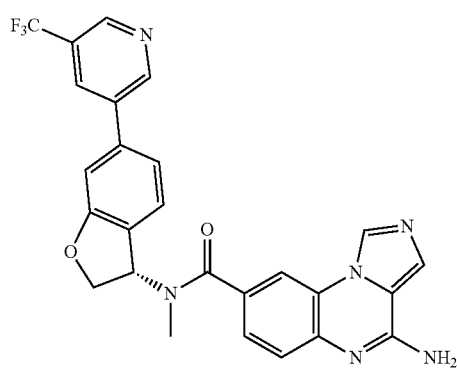
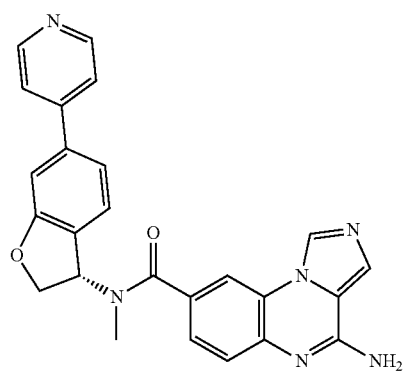
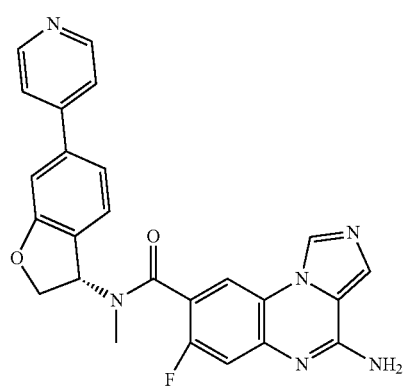
54
-continued
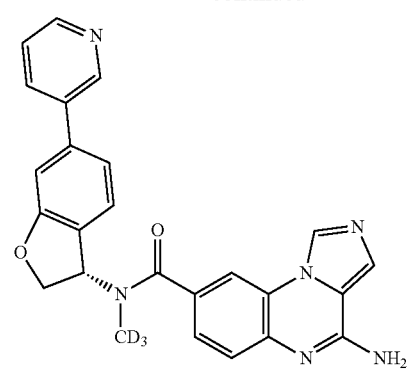
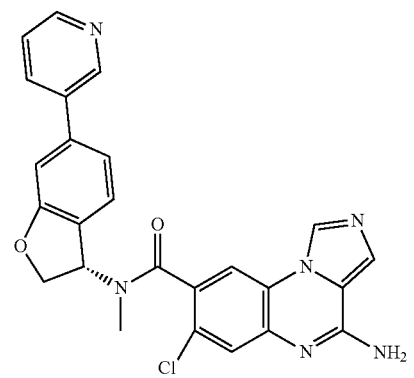
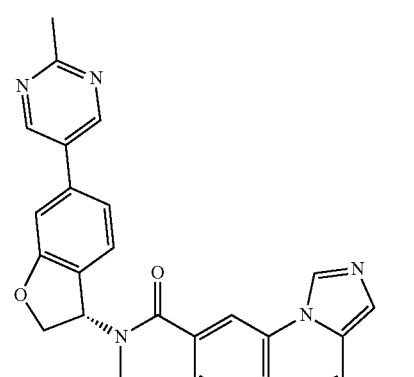
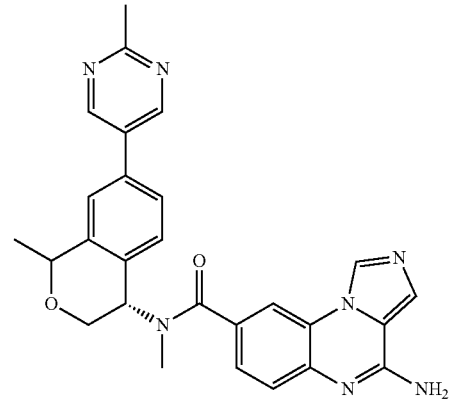

55
-continued
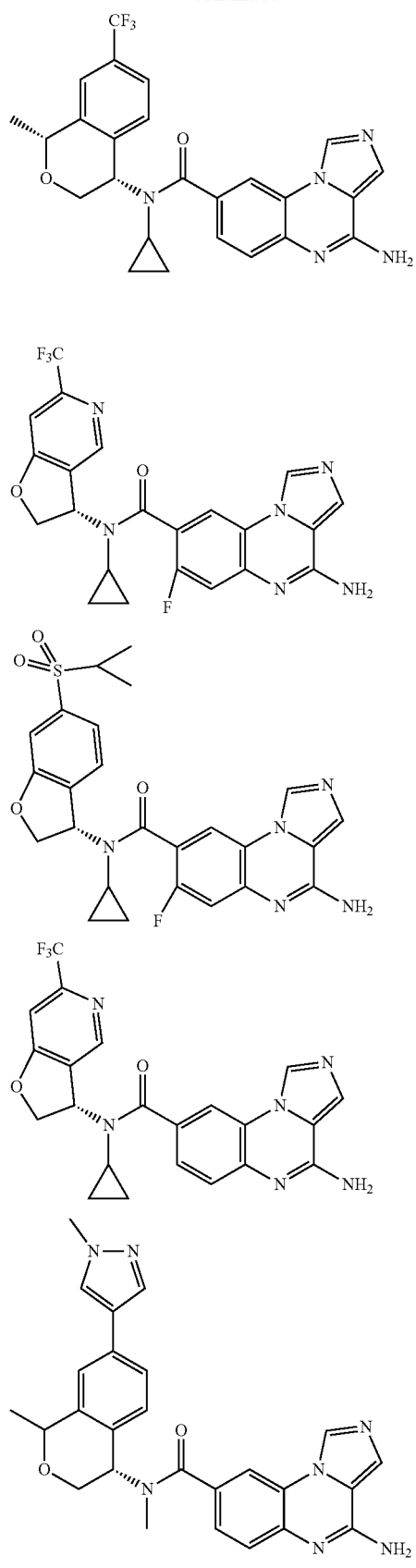
56
-continued
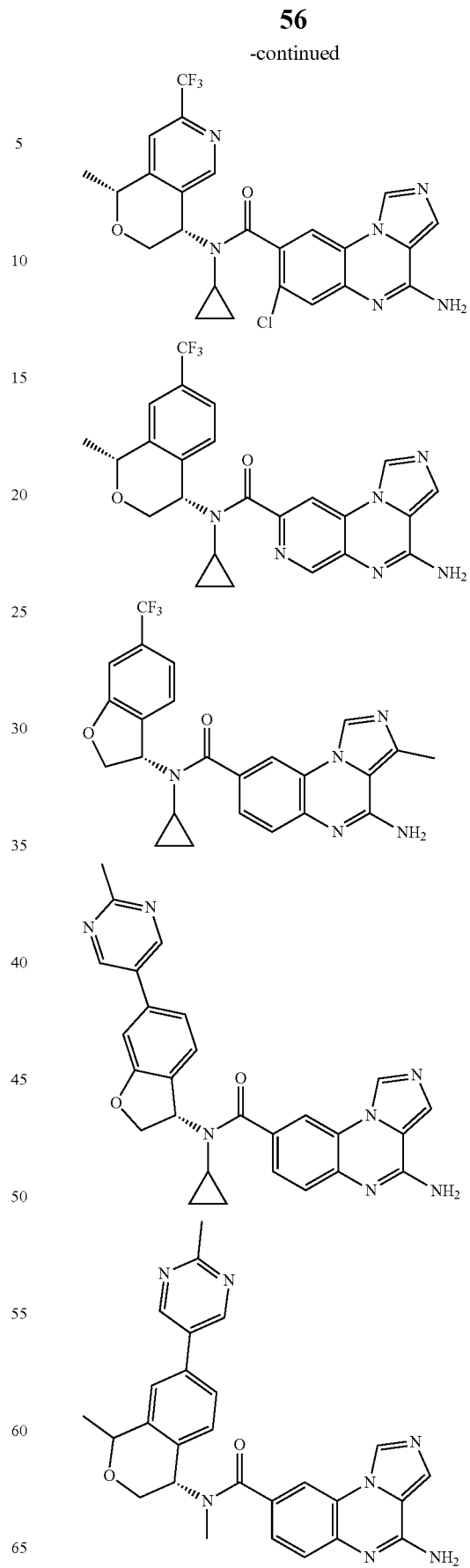

57
-continued
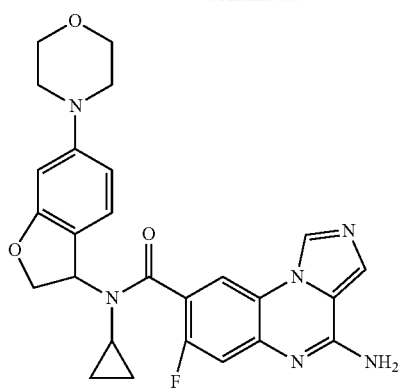
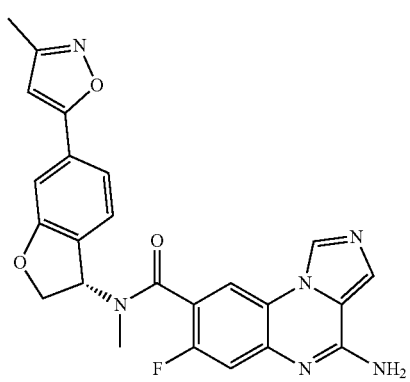
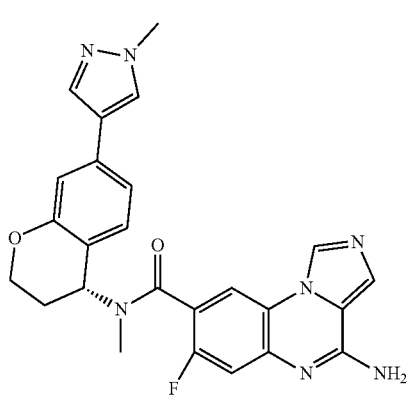
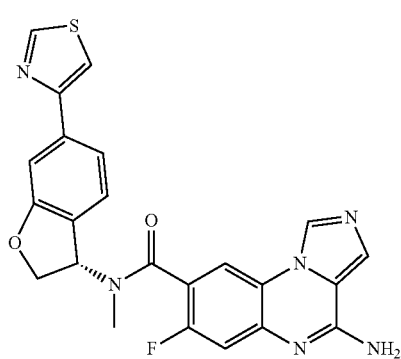
58
-continued
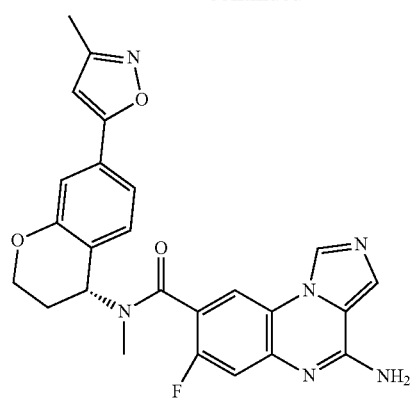
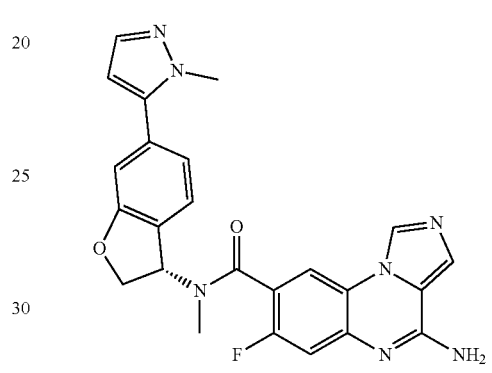
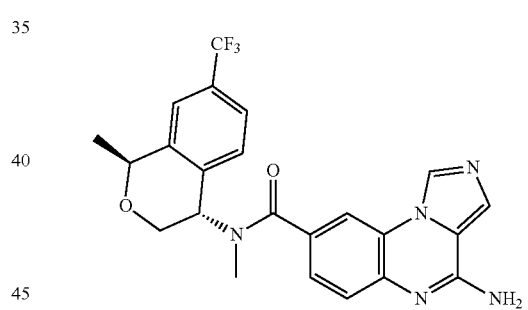
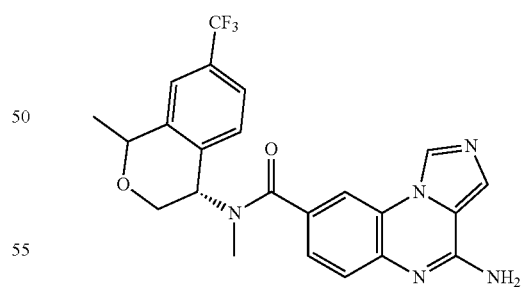
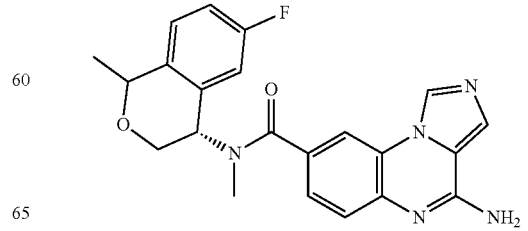

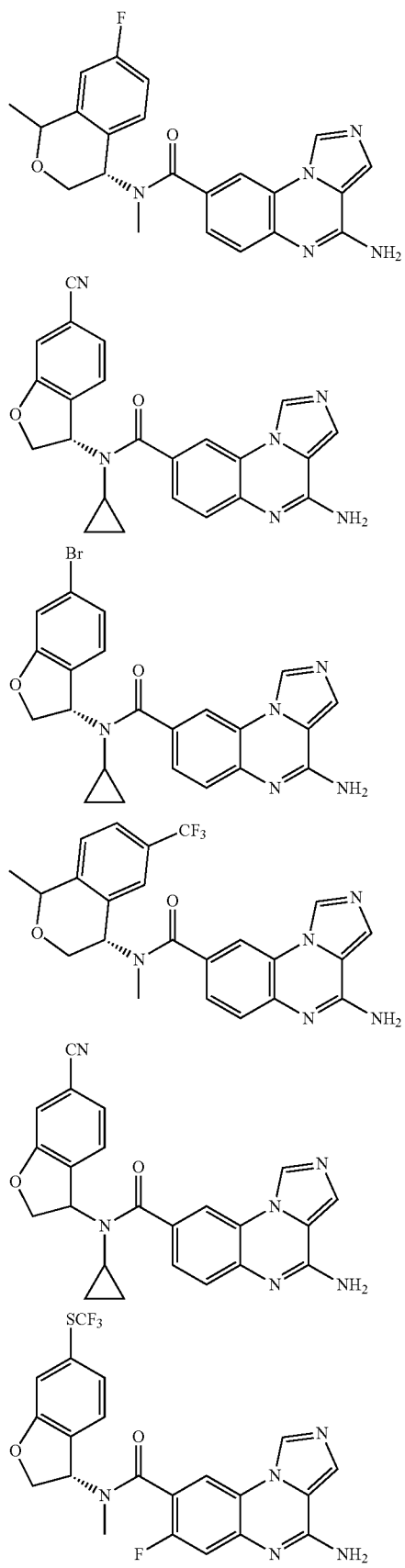
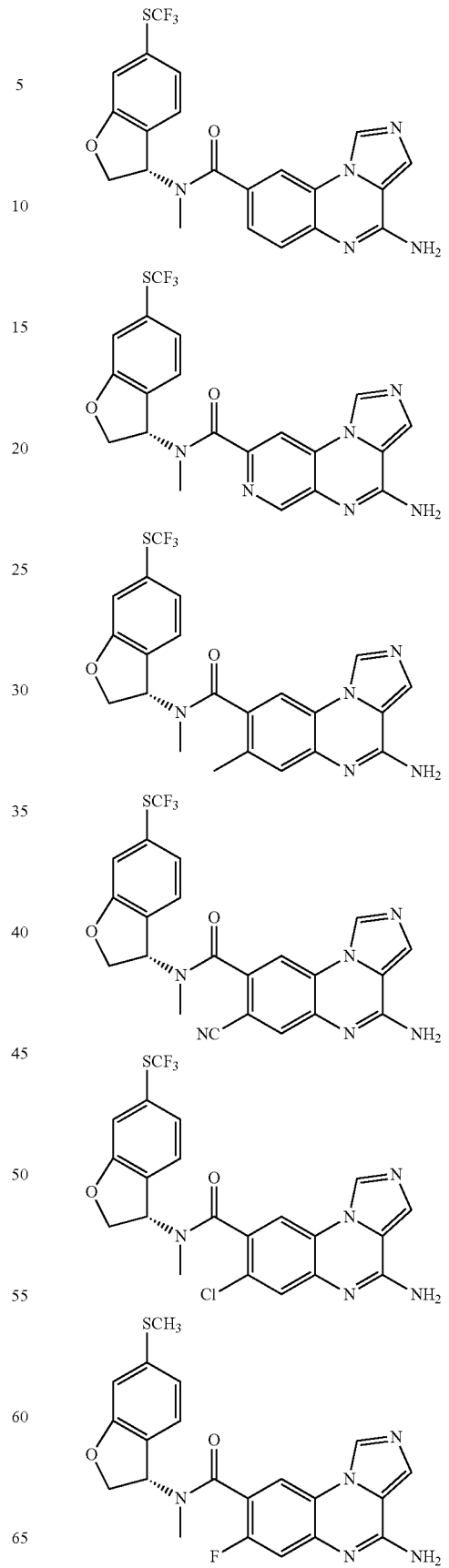

61
-continued
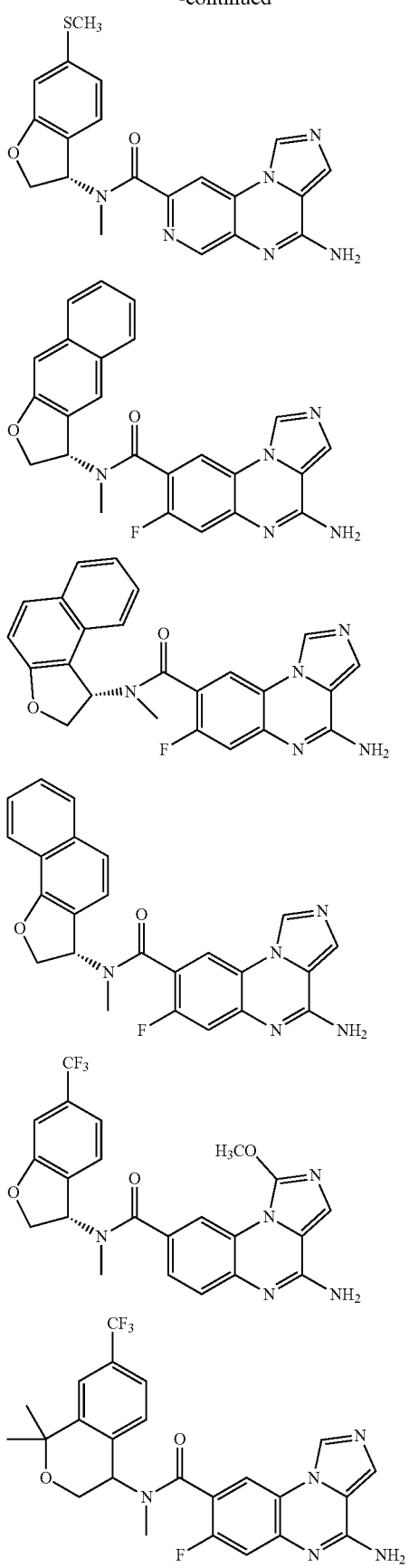
62
-continued
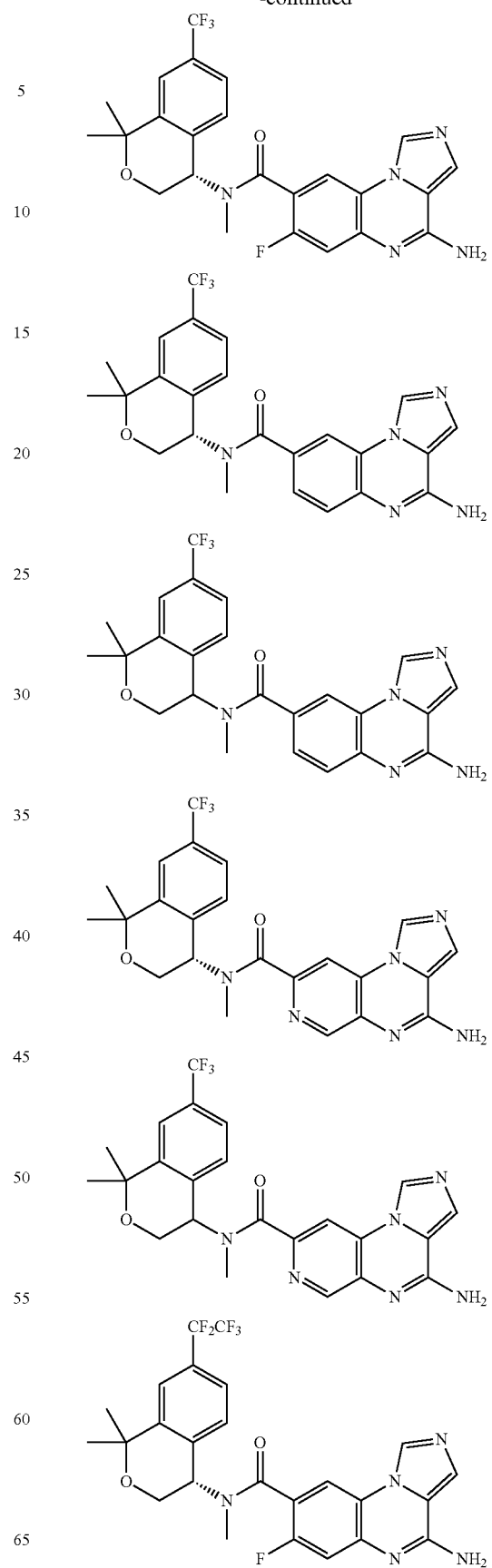

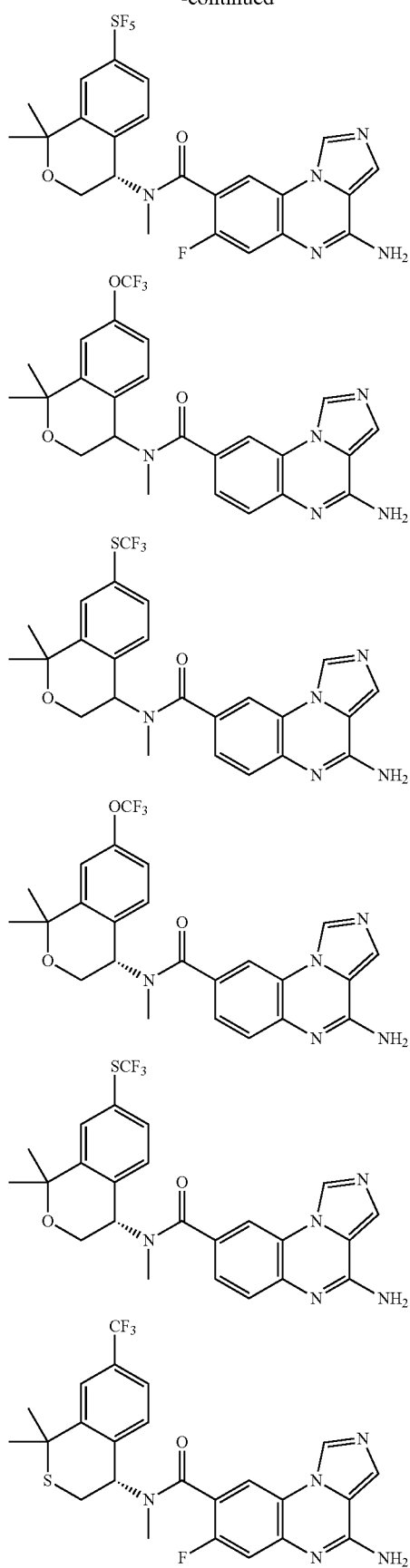
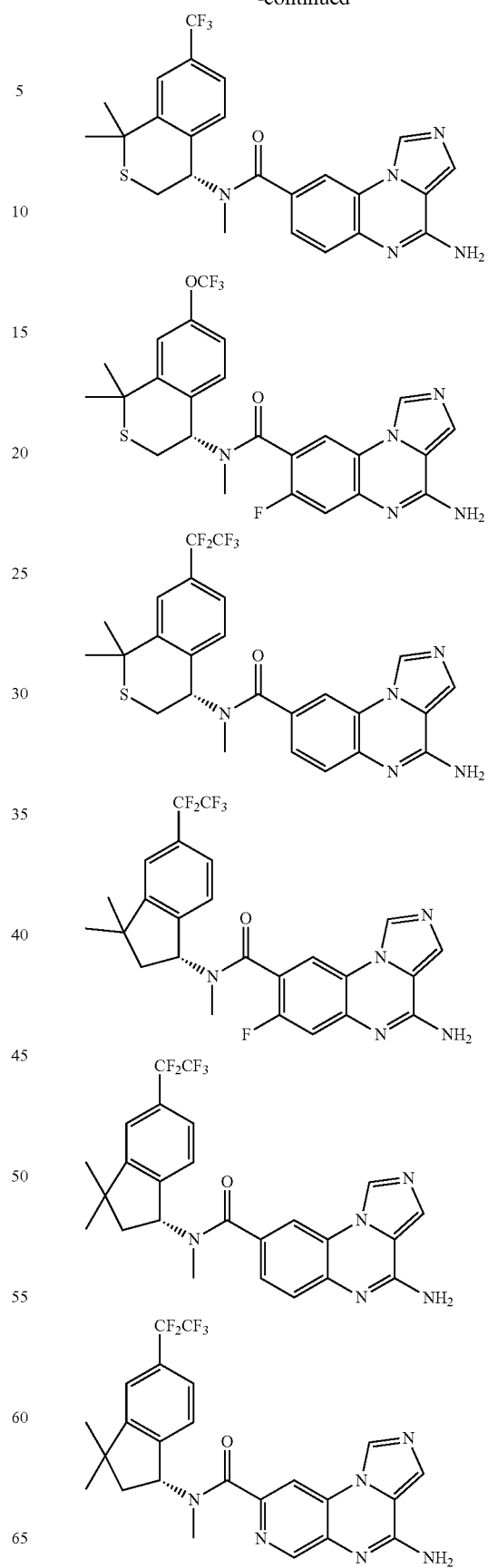

65
-continued
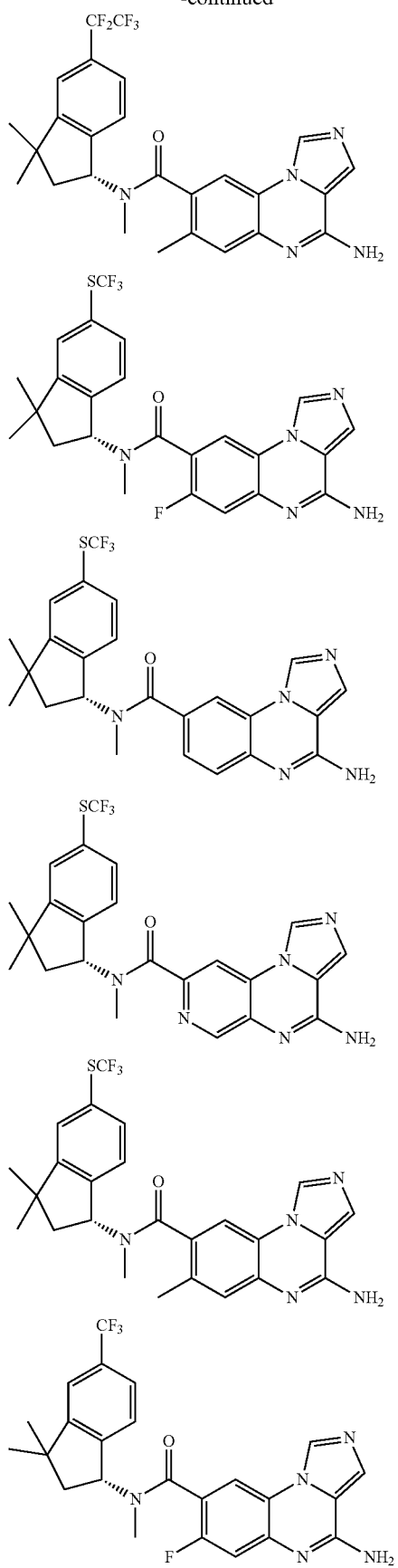
66
-continued
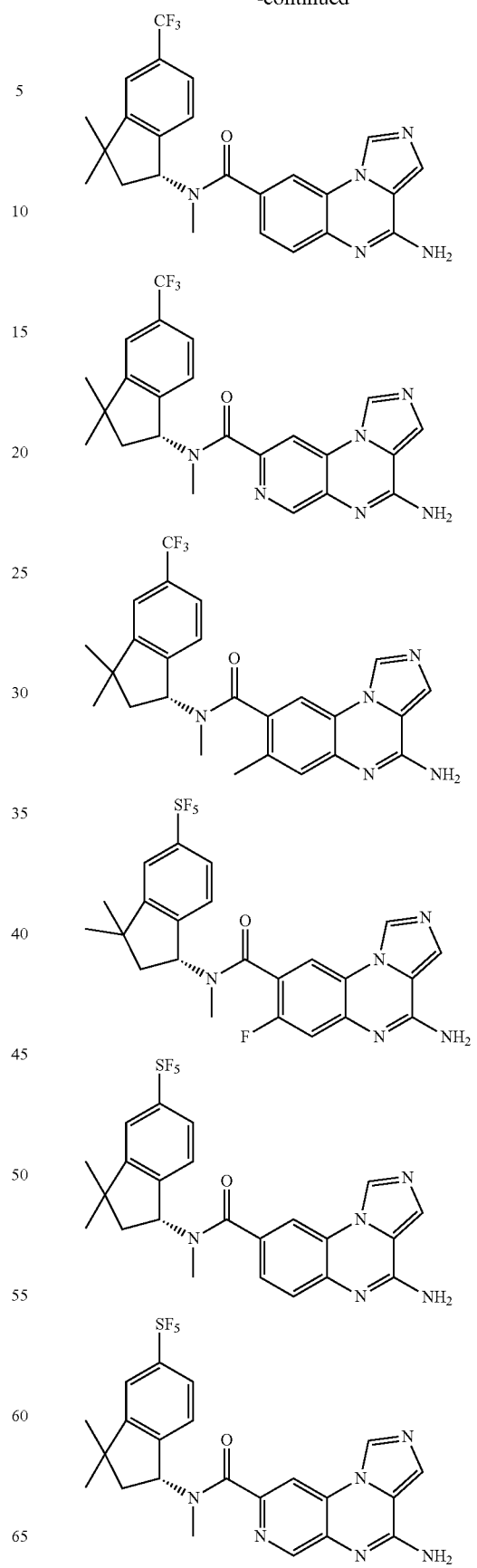

67
-continued
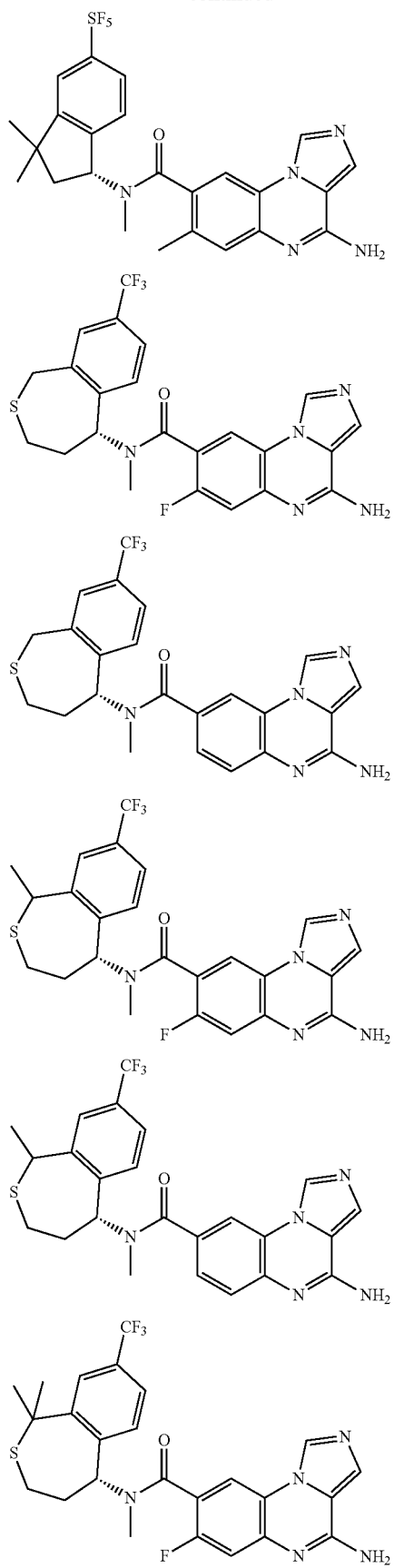
68
-continued
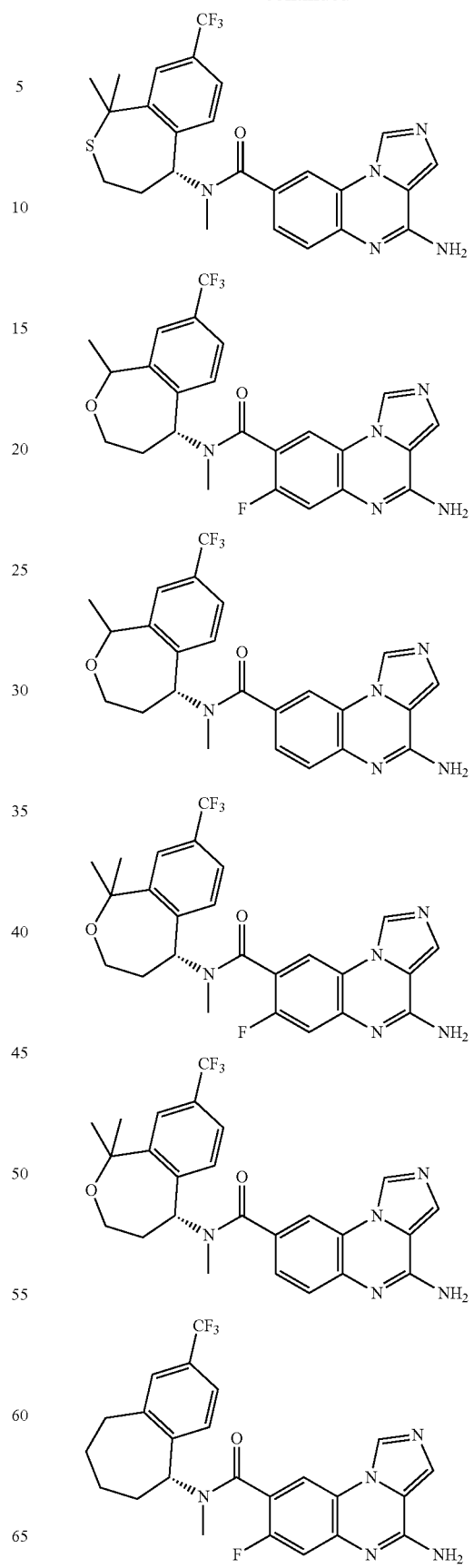

69
-continued
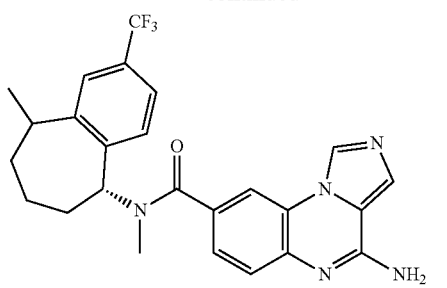
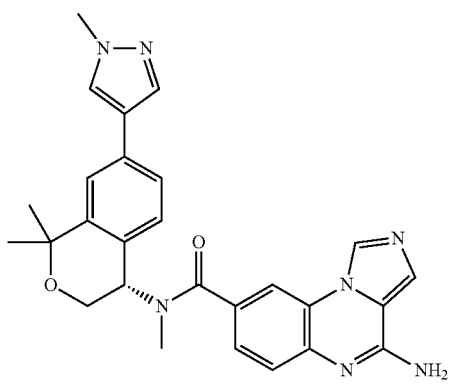
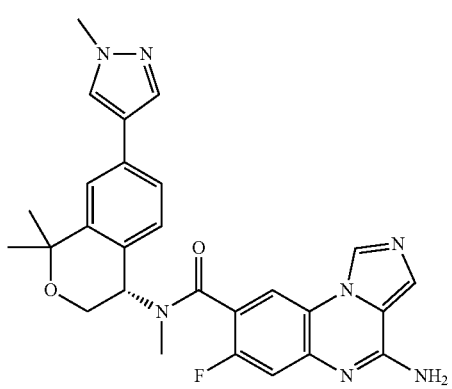
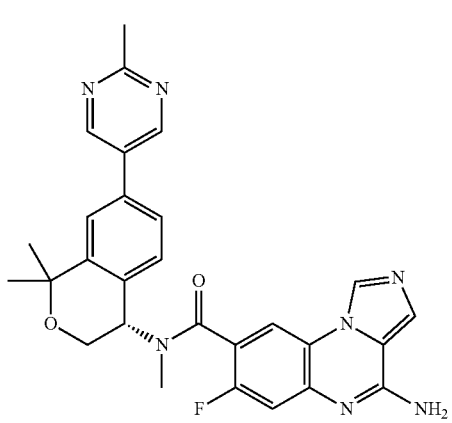
70
-continued
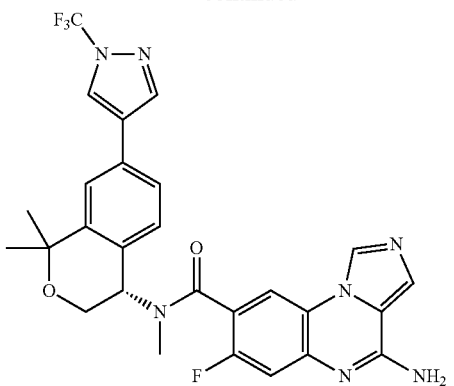
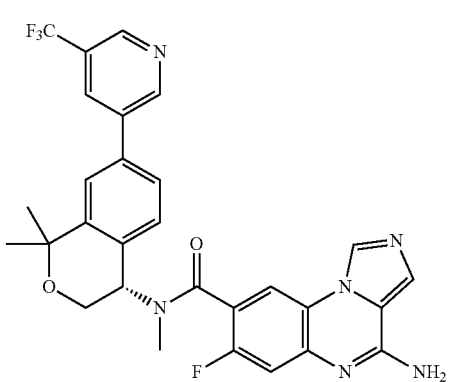
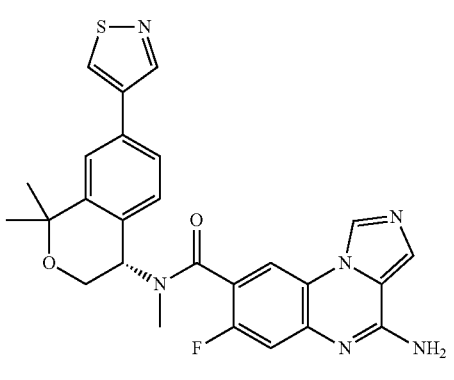
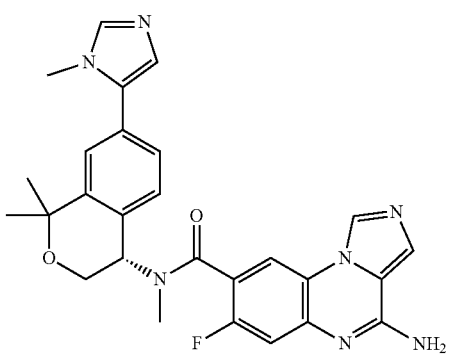

71
-continued
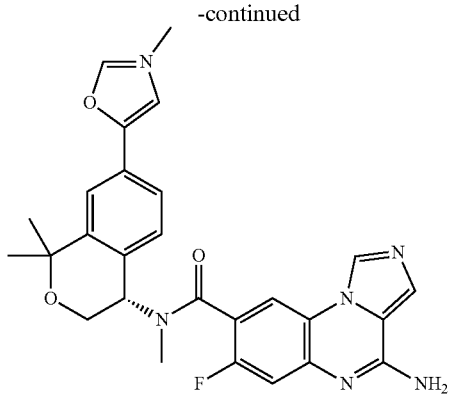
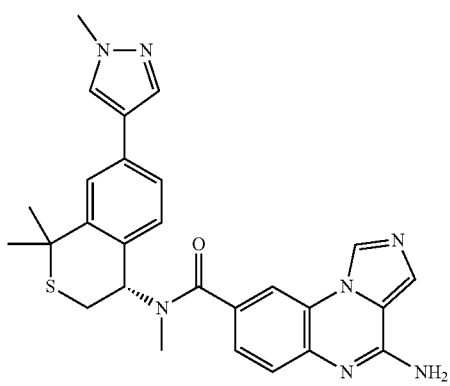
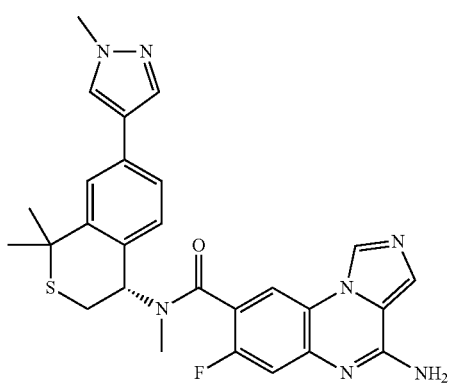
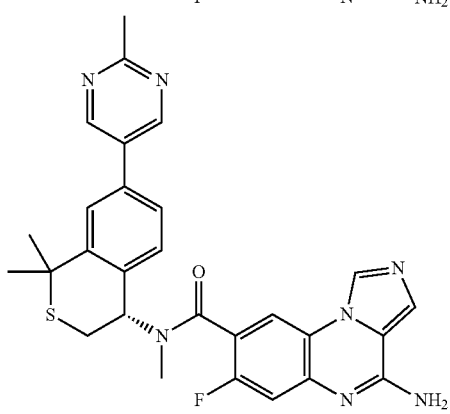
72
-continued
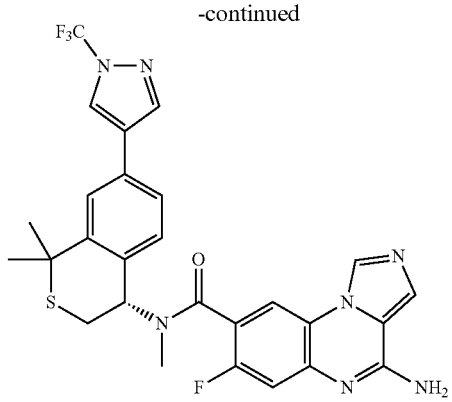
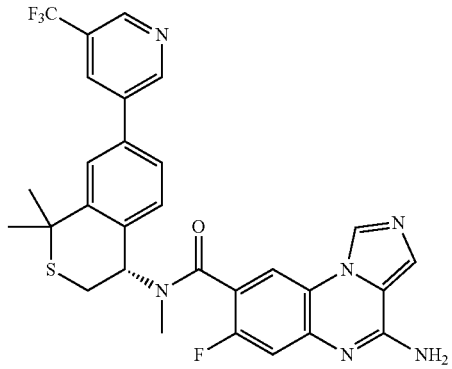
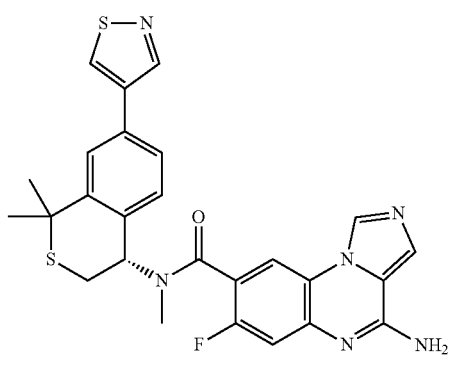
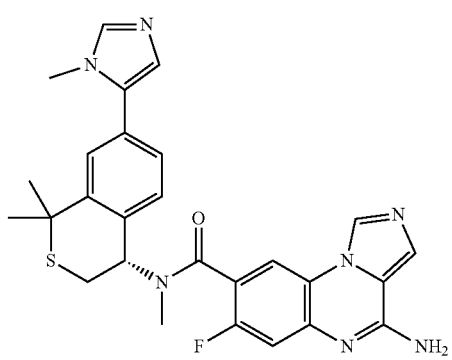

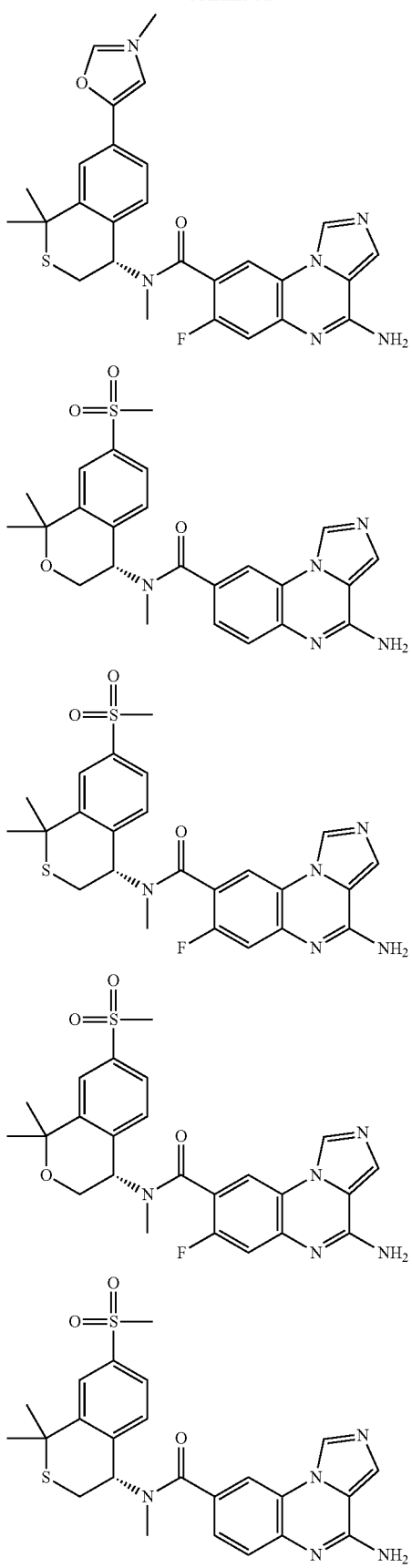
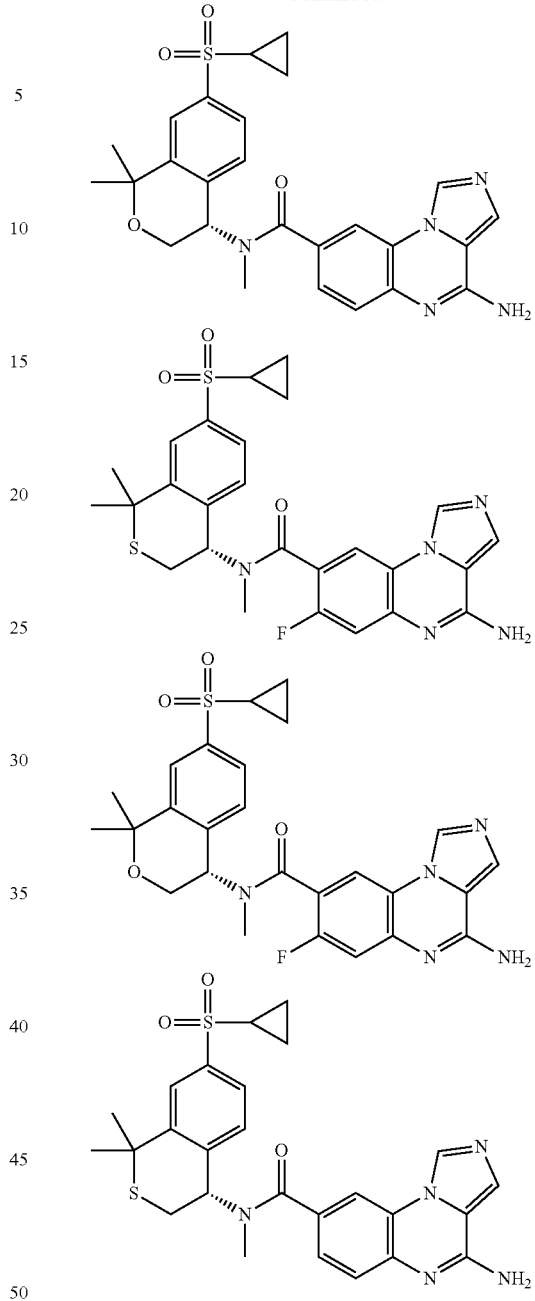

Unless explicitly stated otherwise, the compounds in this invention, apart from their specific structures, are expansively interpreted to include pharmaceutically acceptable salts, stereoisomers, isotopic variants (such as deuterated compounds), solvates, hydrates, prodrugs, and metabolites. Namely, the pharmaceutically acceptable salts, stereoisomers, isotopic variants (such as deuterated compounds), solvates, hydrates, prodrugs, and metabolites of the compound are also encompassed within the protective scope of the compound.

Preferably, the pharmaceutical composition of the present invention may further comprise a second active substance, wherein the second active substance is an anticancer agent, and the anticancer agent includes chemotherapeutic drugs, tumor-targeted treatment drugs, tumor treatment antibody drugs, or a combination thereof.

Furthermore, the present invention provides a compound of the invention, its pharmaceutically acceptable salts, esters, prodrugs, stereoisomers, or isotopic derivatives, and methods of treating diseases, preferably tumors, by inhibiting the action of PRMT5.

Definition

Unless specified otherwise, the term 'alkyl,' either independently or as part of another substituent, denotes a hydrocarbon group that can be straight-chain (unbranched) or branched, cyclic, or a combination thereof. It may be saturated, mono- or polyunsaturated, and can include divalent or multivalent moieties, with a specified carbon atom count (e.g., $C_1$-$C_{10}$ indicating one to ten carbon atoms). Examples of unsaturated alkyl groups include, but are not limited to, ethenyl, 2-propenyl, crotonyl, 2-(buta-1,3-dienyl), 2-isopentenyl, 2,4-pentadienyl, 3-(1,4-pentadienyl), ethynyl, 1-propynyl and 3-propynyl, 3-butynyl, as well as higher homologs and isomers. Alkyl groups limited to hydrocarbons are referred to as 'homoalkyl.' The alkyl groups may optionally be substituted with one or more halogen atoms.

The term 'haloalkyl' refers to the alkyl groups as defined above, in which one or more hydrogen atoms are replaced by halogen atoms.

The term 'alkylene' by itself or as part of another substituent refers to a divalent group derived from an alkyl, such as, but not limited to, —$CH_2CH_2CH_2CH_2$—, —$CH_2CH$=$CHCH_2$—, —$CH_2C$≡$CCH_2$—, —$CH_2CH_2CH$($CH_2CH_2CH_3$)$CH_2$—. Alkyl (or alkylene) groups typically have 1 to 24 carbon atoms, and the present invention preferably encompasses groups with 10 or fewer carbon atoms. 'Lower alkyl' or 'lower alkylene' refers to shorter chain alkyl or alkylene groups, usually with eight or fewer carbon atoms. The alkylene groups may optionally be substituted with one or more halogen atoms.

The term 'alkynyl' denotes a carbon chain containing at least one carbon-carbon triple bond, which may be linear, branched, or a combination thereof. Examples of alkynyl include ethynyl, propynyl, 3-methyl-1-pentynyl, 2-heptynyl, etc. The alkynyl groups may optionally be substituted with one or more halogen atoms.

The term 'cycloalkyl' refers to a monocyclic or bicyclic saturated carbon ring, each having 3 to 10 carbon atoms. 'Fused analogs' of cycloalkyl groups refer to mono-cycle fuse with aryl or heteroaryl, where the connecting point is in the non-aromatic portion. Examples of cycloalkyl and its fused analogs include cyclopropyl, cyclobutyl, cyclopentyl, cyclohexyl, tetrahydronaphthyl, decahydronaphthyl, dihydroindanyl, etc. The cycloalkyl groups may optionally be substituted with one or more halogen atoms. Furthermore, in the context of the present invention, the term 'cycloalkyl' encompasses bridged and spirocyclic systems.

The term 'alkoxy' refers to linear or branched alkoxyl groups indicating the number of carbon atoms. For example, $C_{1-6}$ alkoxy, includes methoxy, ethoxy, propoxy, isopropoxy, etc.

Unless specified otherwise, the term 'heteroalkyl,' either alone or in combination with other terms, refers to stable linear or branched hydrocarbon groups, or cyclic hydrocarbon groups, or their combination, incorporating at least one carbon atom and at least one heteroatom chosen from O, N, P, Si, and S. Optional oxidation of nitrogen, phosphorus, or sulfur atoms, and potential quaternization of nitrogen atoms are permitted. The heteroatoms O, N, P, S, and Si can be positioned at any location within the heteroalkyl or location at which the alkyl connected to the rest part of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three contiguous heteroatoms are allowed. For instance, —$CH_2$—NH—$OCH_3$ and —$CH_2$—O—Si($CH_3$)$_3$. Similarly, the term 'heteroalkylidene,' alone or in combination, designates divalent groups derived from heteroalkyl, including but not limited to —$CH_2$—$CH_2$—S—$CH_2$—$CH_2$— and —$CH_2$—S—$CH_2$—$CH_2$—NH—$CH_2$—. Heteroatoms in heteroalkylidene can be positioned at either end or both ends of the chain (e.g., alkylenoxy, alkylendioxy, alkylenamino, alkylendiamino, etc.). Additionally, for alkoxy and heteroalkoxy linking groups, the molecular formula is written without indicating the orientation of the linking group (e.g., —C(O)OR'— represents both —C(O)OR'— and —R'OC(O)—). As stated above, the term 'heteroalkyl' encompasses groups connected to the rest of the molecule through heteroatoms, such as —C(O)R', —C(O)NR', —NR'R", —OR', —SR', and/or —$SO_2R'$. When 'heteroalkyl' is mentioned and specific heteroalkyls like —NR'R" are subsequently cited, it should be understood that the term 'heteroalkyl' and —NR'R" are distinct and not mutually exclusive. The inclusion of specific heteroalkyls is for clarification and does not preclude others like —NR'R"."

The term 'cycloalkyloxy' refers to the cyclic alkyl groups as defined above, bound to an oxygen atom, such as cyclopropyloxy.

The term 'haloalkoxy' refers to an alkoxyl group as defined above with one or more hydrogen atoms substituted by halogen The term 'aryl' refers to a monocyclic or bicyclic aryl group consisting exclusively of carbon atoms. The 'fused analogs' of aryl are those in which aryl is combined with a monocyclic cycloalkyl or monocyclic heterocyclyl, with the connection point located in the aryl portion. Examples of aryl and its fused analogs include phenyl, naphthyl, indanyl, indenyl, tetrahydronaphthyl, 2,3-dihydrobenzofuranyl, 1,4-benzodioxanyl, etc.

The term 'heteroaryl' refers to a monocyclic or bicyclic aryl group containing at least one heteroatom selected from N, O, and S. The 'fused analogs' of heteroaryl are those in which heteroaryl is combined with a monocyclic cycloalkyl or monocyclic heterocyclyl, with the connection point located in the heteroaryl portion. Examples of heteroaryl include pyrrolyl, isoxazolyl, isothiazolyl, pyrazolyl, pyridinyl, oxazolyl, oxadiazolyl, thiadiazolyl, thiazolyl, imidazolyl, triazolyl, tetrazolyl, furanyl, triazine, thiophenyl, pyrimidinyl, quinazolinyl, pyrazinyl, quinoxalinyl, benzoxazolyl, benzothiazolyl, benzimidazolyl, benzofuranyl, benzothiophenyl, furan[2,3-b]pyridinyl, quinolinyl, indolyl, isoquinolinyl, etc.

"Substituted or unsubstituted": The defined alkyl, aryl, and heteroaryl groups can be unsubstituted or substituted with at least one substituent selected from the group consisting of halogen atoms, alkyl groups with 1 to 6 carbon atoms, alkoxy groups with 1 to 6 carbon atoms, haloalkyl groups with 1 to 6 carbon atoms, halogenated alkoxy groups with 1 to 6 carbon atoms, —CN, alkynyl groups with 2 to 6 carbon atoms, acyl groups with 1 to 6 carbon atoms, cycloalkyl groups with 3 to 7 ring atoms, heteroaryl groups, aryl groups, arylalkoxy groups with 7-10 carbon atoms, aryloxycarbonyl groups, aminocarbonyl groups, vinyl groups with 2 to 5 carbon atoms, alkylthio groups with 1 to 6 carbon atoms, amino sulfonyl groups, sulfonyl amino groups, hydroxy groups, —$SF_5$, hydroxyalkyl groups with 1 to 4 carbon atoms, nitro groups, amino groups, carboxyl groups, alkoxy carbonyl groups with 2 to 5 carbon atoms, alkoxyalkyl groups with 1 to 4 carbon atoms, alkylsulfonyl groups with 1 to 4 carbon atoms, acylamino groups with 1 to 4 carbon atoms, acyl(amino)amino groups with 1 to 6 carbon atoms, acyl(amino)aminoalkyl groups with 1 to 6 carbon atoms in both acyl and alkyl parts, sulfonylamino groups with 1 to 4 carbon atoms, single alkylamino groups with 1 to 6 carbon atoms or double alkylamino groups with 1 to 6 carbon atoms, single alkylaminoalkyl groups with 1 to 6 carbon atoms or double alkylaminoalkyl groups with 1 to 6 carbon atoms, aminoalkyl groups with 1 to 4 carbon atoms, single alkylamino groups with 1 to 6 carbon atoms or double alkylamino groups with 1 to 6 carbon atoms in both alkyl parts, arylalkyl groups with 7 to 10 carbon atoms, heteroarylalkyl groups with 1 to 4 carbon atoms in alkyl parts, heteroaryloxyalkyl groups with 1 to 4 carbon atoms in alkoxy parts, and alkylsulfonylamino groups with 1 to 4 carbon atoms.

As used herein, the term "heterocycle" or "heterocyclic" or "heterocycloalkyl" or "heterocyclo" refers to a saturated, partially saturated, or unsaturated group (but not aromatic) with a single ring or fused rings (including bridged and spiro systems), having 1 to 10 carbon atoms and 1 to 4 heteroatoms selected from nitrogen, sulfur, or oxygen. In fused systems, one or more rings can be cycloalkyl, aryl, or heteroaryl, as long as the connection points are through non-aromatic rings. In one embodiment, nitrogen and/or sulfur atoms of heterocyclic groups may optionally be oxidized to provide N-oxides, sulfinyl, and sulfonyl portions. Examples of "heterocyclic" and its fused analogs include pyrrolidinyl, piperidinyl, pyrazinyl, imidazolidinyl, 2,3-dihydrofuran(2,3-b)pyridinyl, quinazolinyl, tetrahydroquinoline, tetrahydroisoquinoline, dihydroindole, etc. The term also encompasses non-aromatic, partially unsaturated monocycles, such as 2- or 4-pyridones or N-substituted-(1H, 3H)-pyrimidin-2,4-diones (N-substituted uracils).

As used herein, the term "substituted heterocycloalkyl" or "substituted heterocyclo" refers to a heterocycloalkyl group substituted with 1 to 5 (such as 1 to 3) substituents, wherein the substituents are the same as those defined for substituted cycloalkyl.

Unless otherwise specified, the term "halogenated" or "halo" refers to fluorine, chlorine, bromine, or iodine atoms, either by themselves or as part of another substituent. Additionally, the term "halogenated alkyl" refers to both mono-halogenated alkyl and poly-halogenated alkyl. For example, the term "halogenated ($C_1$-$C_6$) alkyl" includes, but is not limited to, trifluoromethyl, 2,2,2-trifluoroethyl, pentafluoroethyl, 4-chlorobutyl, 3-bromopropyl, and so on.

"Prodrug" refers to a substance that, when administered into the body, undergoes a conversion to the parent drug. In certain situations, prodrugs are frequently used because they might be more easily administered than the parent drug. For instance, a prodrug administered orally may be more bioavailable than the parent drug. In drug combinations, prodrugs can also exhibit higher solubility than the parent drug. Examples of prodrugs include, but are not limited to, any compound from compound of formula (I) administered in the form of an ester (prodrug) to facilitate transmembrane transport. This aids in overcoming barriers posed by cell membranes, as the water solubility of the prodrug is detrimental to migration across the membrane. Once inside the beneficial aqueous environment of the cell, the ester is metabolized and hydrolyzed to the active carboxylic acid substance. Another example of a prodrug can be short peptide (polyamino acid) conjugated with an acid moiety, where the peptide undergoes metabolism to release the active portion.

The compound of Formula (I) contains one or more asymmetric centers, and thus, it can exist as a racemate and racemic mixtures, individual enantiomers, diastereomers, and individual diastereomers. The present invention encompasses all these stereoisomeric forms of the compound of Formula (I).

Some compounds described in this disclosure contain olefinic double bonds, which, unless otherwise specified, refers to both E and Z geometric isomers. Certain compounds of the present invention may comprise one or more ring systems, giving rise to cis- and trans-isomers. The invention is intended to encompass all these cis- and trans-isomers.

Certain compounds described herein may exist with different points of hydrogen attachment, known as tautomerism. An example is keto-enol tautomerism, where a keto form and its enol form are involved. Individual tautomers and their mixtures are included in the compounds of the present invention.

The compounds of the present invention can be separated into diastereoisomeric pairs of enantiomers, for example, by fractional crystallization from suitable solvents such as methanol or ethyl acetate or mixtures thereof. Enantiomeric pairs thus obtained can be separated into individual stereoisomers through conventional methods, including using optically active amines or acids as resolving agents or by separation on a chiral HPLC column.

Alternatively, any diastereoisomer of the compounds of the present invention can be stereoselectively synthesized using optically pure starting materials or reagents of known configuration.

Salt and Dosage Form

The compounds mentioned in this disclosure, as used herein, are understood to include pharmaceutically acceptable salts.

Application

These compounds can be employed for the treatment of PRMT5-related diseases.

The compounds of the present invention can be prepared through the following reaction scheme:

Method A:

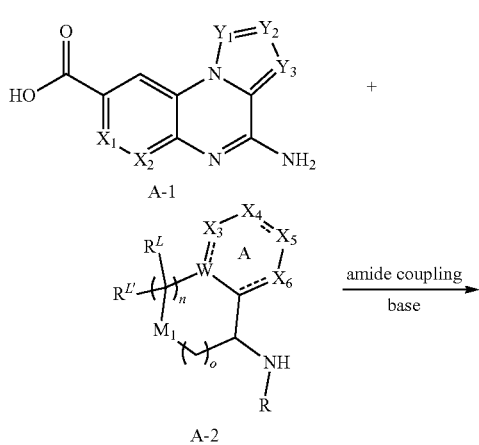

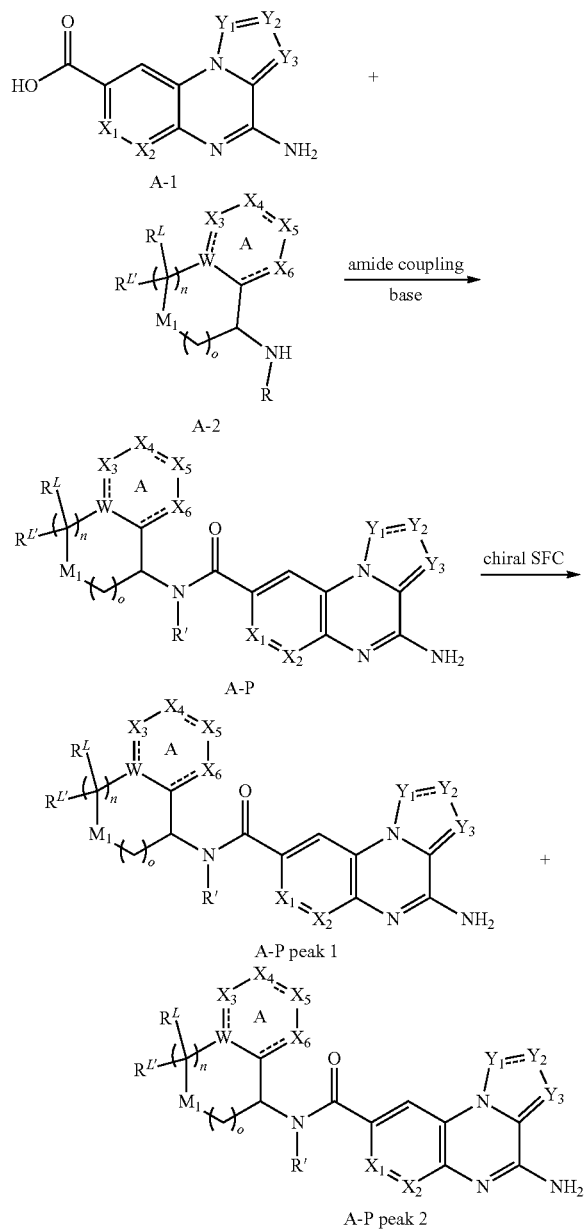

Method A-SFC

Wherein, $R^L$, $R^{L'}$, R', ring A, W, n, o, $M_1$, $X_1$, $X_2$, $X_3$, $X_4$, $X_5$, $X_6$, $Y_1$, $Y_2$, $Y_3$ and ═══ as defined in claim 1.

Method A: Compound A-P can be obtained through the condensation reaction of carboxylic acid A-1 and amine A-2, using HATU or PyBrOP as the condensing agent and DIPEA or TEA as the base, with DMF or DMAc as the solvent. If the used amine is a racemate, chiral SFC will be employed for resolution, and the stereochemistry of the resulting isomer will be arbitrarily assigned as R or S.

Analytical HPLC:
 Instrument: Agilent 1260;
 Column specifications: Agilent Poroshell HPH-C18 (3.0× 50 mm, 2.7 μm);
 Binary solvent system, mobile phase A: water (0.1% v/v ammonium bicarbonate), mobile phase B: acetonitrile;
 Flow rate: 1 milliliter/minute;
 Gradient: from 10% B to 90% B;
 Duration: 12 minutes;
 Detector: DAD detector;
 Wavelength: 254/220 nanometers.

Preparative HPLC:
 HPLC equipment: Waters 2489;
 Column specifications: Ultimate μ XB-C18 (130A, 5 um, 30 mm×150 mm);
 Binary solvent system, mobile phase A: water (0.1% v/v ammonium bicarbonate), mobile phase B: acetonitrile;
 Flow rate: 60-100 milliliters/minute;
 Gradient: from 10% B to 90% B;
 Detector: DAD detector;
 Wavelength: 254/220 nanometers;
 Mass spectrometer: Agilent G6125B.

The compounds of the present invention can be prepared through chemical synthesis, as illustrated in the following examples. It should be understood that the order of steps in the process can be altered, specific mentioned reagents, solvents, and reaction conditions can be substituted, and, if necessary, reactive sites can be protected and deprotected.

The abbreviations below have the following meanings:
 ACN: acetonitrile
 EA: ethyl acetate
 CDI: N, N'-carbonyldiimidazole
 DBU: 1,8-diazabicyclo[5.4.0]undec-7-ene
 DIBAL-H: diisobutylaluminum hydride
 DIEA: diisopropylethylamine
 DMAP: N, N-dimethylaminopyridine
 DME: 1,2-dimethoxyethane
 DMF: N, N-dimethylformamide
 DMA and DMAc: N, N-dimethylacetamide
 DMPE: 1,2-bis(dimethylphosphino)ethane
 DMSO: dimethyl sulfoxide
 DPPB: 1,4-bis(diphenylphosphino)butane
 dppe: 1,2-bis(diphenylphosphino)ethane
 dppf: 1,1'-bis(diphenylphosphino)ferrocene
 dppm: 1,1'-bis(diphenylphosphino)methane
 DIAD: diisopropyl azodicarboxylate
 EDCJ: 1-(3-dimethylaminopropyl)-3-ethylcarbodiimide
 HATU: 2-(7-aza-1H-benzotriazol-1-yl)-1,1,3,3-tetramethyluronium hexafluorophosphate
 HMPA: hexamethylphosphoramide
 IPA: isopropanol
 LDA: lithium diisopropylamide
 LHMDS: lithium bis(trimethylsilyl)amide
 LAH: lithium aluminum hydride
 NCS: N-chlorosuccinimide
 NaHMDS: sodium bis(trimethylsilyl)amide
 PyBOP: benzotriazol-1-yloxytripyrrolidinophosphonium hexafluorophosphate
 PyBrOP: tripyrrolidinophosphonium bromide hexafluorophosphate
 TDA-J: tri(2-(2-methoxyethoxy)ethyl)amine
 DCM: dichloromethane TEA: triethylamine
TFA: trifluoroacetic acid
THF: tetrahydrofuran
NMM: N-methylmorpholine
NMP: N-methyl-2-pyrrolidone
PPh3: triphenylphosphine
r.t.: room temperature
PMB: para-methoxybenzyl
Tosmic: p-toluenesulfonylmethyl isocyanide
(Boc)$_2$O: di-tert-butyl dicarbonate
PE: petroleum ether
o/n: overnight reaction.

The following preparation and implementation examples illustrate the present invention but do not limit it in any way.

A detailed description of selected embodiments will provide a clearer understanding of the features and advantages of the subject matter of the present invention. As one skilled in the art would appreciate, the disclosed and claimed subject matter can be modified in various aspects, and all such modifications are within the scope of the claims. Therefore, the description should be considered as explanatory rather than restrictive in nature. The full scope of the subject matter of the present invention is defined in the claims.

For a better understanding of the present invention, reference may be made to the following examples, which are provided for illustrative purposes and not to limit the scope of the invention.

Intermediates

The intermediate raw materials were purchased from different suppliers:

| Int. No. | structure | name | CAS |
|---|---|---|---|
| 1 | F-substituted dihydrobenzofuran-amine | (S)-6-fluoro-2,3-dihydrobenzofuran-3-amine | 1228559-33-8 |
| 2 | Cl-substituted dihydrobenzofuran-amine | (S)-6-chloro-2,3-dihydrobenzofuran-3-amine | 1228561-83-8 |
| 3 | Br-substituted dihydrobenzofuran-amine | (S)-6-bromo-2,3-dihydrobenzofuran-3-amine | 1228568-69-1 |
| 4 | F$_3$C-substituted dihydrobenzofuran-amine | (S)-6-(trifluoromethyl)-2,3-dihydrobenzofuran-3-amine | 1272724-36-3 |
| 5 | F$_3$C-substituted dihydrobenzofuran-amine | (R)-6-(trifluoromethyl)-2,3-dihydrobenzofuran-3-amine | 1272732-77-0 |

-continued

| Int. No. | structure | name | CAS |
|---|---|---|---|
| 6 | 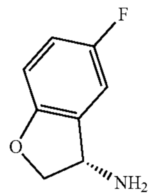 | (S)-5-fluoro-2,3-dihydrobenzofuran-3-amine | 1228571-72-9 |
| 7 | 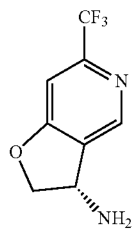 | (S)-6-(trifluoromethyl)-2,3-dihydrofuro[3,2-c]pyridin-3-amine | |
| 8 | 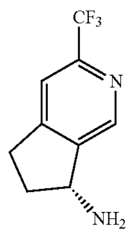 [SMILES: N[C@@H]1CCc2cc(C(F)(F)F)ncc21] | (R)-3-(trifluoromethyl)-6,7-dihydro-5H-cyclopenta[c]pyridin-7-amine | |
| 9 | 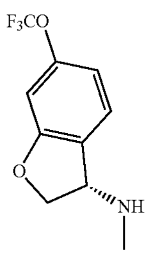 | (S)-N-methyl-6-(trifluoromethoxy)-2,3-dihydrobenzofuran-3-amine | 2814522-50-2 |
| 10 | 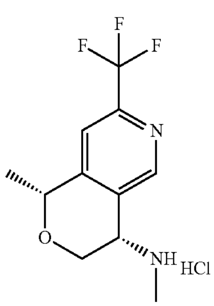 [SMILES: CN[C@@H]1CO[C@H](C)c2cc(C(F)(F)F)ncc21 ; Cl] | (1R,4S)-N,1-dimethyl-7-(trifluoromethyl)-3,4-dihydro-1H-pyrano[4,3-c]pyridin-4-amine hydrochloride | |
| 11 | 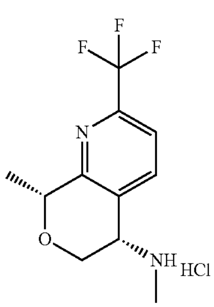 [SMILES: CN[C@@H]1CO[C@H](C)c2nc(C(F)(F)F)ccc21 ; Cl] | (5S,8R)-N,8-dimethyl-2-(trifluoromethyl)-5,8-dihydro-6H-pyrano[3,4-b]pyridin-5-amine hydrochloride | |

| Int. No. | structure | name | CAS |
|---|---|---|---|
| 99 | 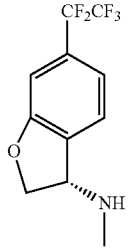 | (S)-N-methyl-6-(perfluoroethyl)-2,3-dihydrobenzofuran-3-amine | |

Int. 12: (S)—N-methyl-6-(trifluoromethyl)-2,3-dihydrobenzofuran-3-amine

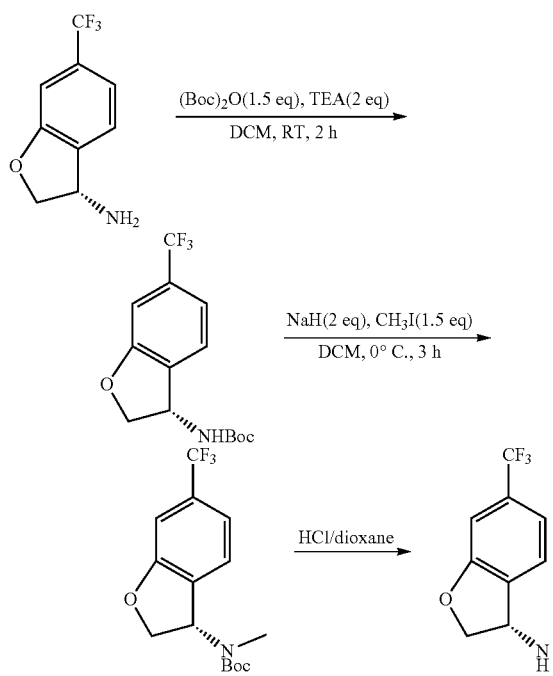

Step 1: Synthesis of tert-butyl (S)-(6-(trifluoromethyl)-2,3-dihydrobenzofuran-3-yl)carbamate (S)-6-(trifluoromethyl)-2,3-dihydrobenzofuran-3-amine (200 mg, 0.99 mmol) was dissolved in 2 ml DCM, then di-tert-butyl dicarbonate (325 mg, 1.49 mmol) and triethylamine (200 mg, 1.98 mmol) were added. The mixture was stirred at room temperature for 2 hours. The reaction was monitored by LCMS. Residues were purified by rapid column chromatography (20 g silica gel column, 20% ethyl acetate/petroleum ether) to yield a yellow liquid: tert-butyl (S)-(6-(trifluoromethyl)-2,3-dihydrobenzofuran-3-yl)carbamate (300 mg, yield: 99%).

LCMS (ESI) m/z: 304 [M+H]$^+$

Step 2: synthesis of tert-butyl (S)-methyl(6-(trifluoromethyl)-2,3-dihydrobenzofuran-3-yl)carbamate At 0° C., (S)-(6-(trifluoromethyl)-2,3-dihydrobenzofuran-3-yl)carbamate (300 mg, 0.99 mmol) was dissolved in DMF (5.00 mL), followed by the addition of sodium hydride (48 mg, 2.00 mmol). The mixture was stirred at 0° C. for 1 hour. Methyl iodide (211 mg, 1.49 mmol) was then added. The mixture was stirred at room temperature for 2 hours. The reaction progress was monitored by LCMS. Residues were purified by rapid column chromatography (20 g silica gel column, 15% ethyl acetate/petroleum ether) to yield a yellow liquid of tert-butyl (S)-methyl(6-(trifluoromethyl)-2,3-dihydrobenzofuran-3-yl)carbamate (200.0 mg, 64% yield).

LCMS (ESI) m/z: 318 [M+H]$^+$

Step 3: synthesis of (S)—N-methyl-6-(trifluoromethyl)-2,3-dihydrobenzofuran-3-amine At room temperature, (S)-methyl(6-(trifluoromethyl)-2,3-dihydrobenzofuran-3-yl)carbamate (200.0 mg, 0.63 mmol) was dissolved in a solution of hydrogen chloride in 1,4-dioxane (5.00 mL). The mixture was stirred at room temperature for 0.5 hours. The reaction progress was monitored by LCMS. The mixture was concentrated to yield a yellow liquid of (S)—N-methyl-6-(trifluoromethyl)-2,3-dihydrobenzofuran-3-amine (130.0 mg, 95% yield).

LCMS (ESI) m/z: 218 [M+H]$^+$

Employing the preparation method and steps of Intermediate 12, with the sole replacement of the corresponding raw material intermediate, the following intermediates were obtained:

| Int. No. | Structure | name | m/z (ESI): (M + H)$^+$ |
|---|---|---|---|
| 13 | 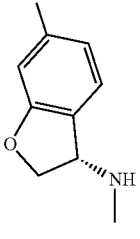 | (S)-6-bromo-N-methyl-2,3-dihydrobenzofuran-3-amine | 228.1 |

| Int. No. | Structure | name | m/z (ESI): (M + H)+ |
|---|---|---|---|
| 14 | 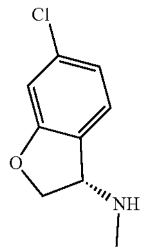 | (S)-6-chloro-N-methyl-2,3-dihydrobenzofuran-3-amine | 184 |
| 15 | 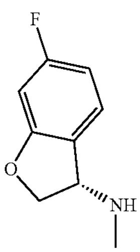 | (S)-6-fluoro-N-methyl-2,3-dihydrobenzofuran-3-amine | 168.2 |
| 16 | 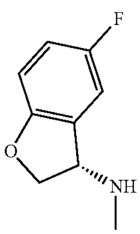 | (S)-5-fluoro-N-methyl-2,3-dihydrobenzofuran-3-amine | 168.2 |
| 17 | 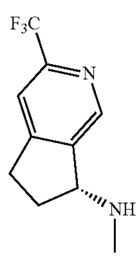 | (R)-N-methyl-3-(trifluoromethyl)-6,7-dihydro-5H-cyclopenta[c]pyridin-7-amine | 217.2 |
| 18 | 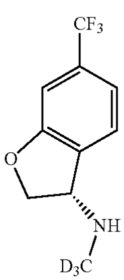 | (S)-N-(methyl-d3)-6-(trifluoromethyl)-2,3-dihydrobenzofuran-3-amine | 221.2 |
| 19 | 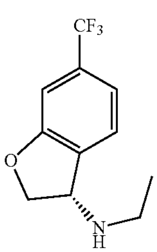 [SMILES: CCN[C@@H]1COc2cc(C(F)(F)F)ccc21] | (S)-N-ethyl-6-(trifluoromethyl)-2,3-dihydrobenzofuran-3-amine | 232.2 |
| 20 | | (R)-N-methyl-6-(trifluoromethyl)-2,3-dihydrobenzofuran-3-amine | 218.2 |
| 21 | | (S)-N-methyl-6-(trifluoromethyl)-2,3-dihydrofuro[3,2-c]pyridin-3-amine | 219.2 |

Int. 22: (S)-3-(methylamino)-2,3-dihydrobenzofuran-6-carbonitrile

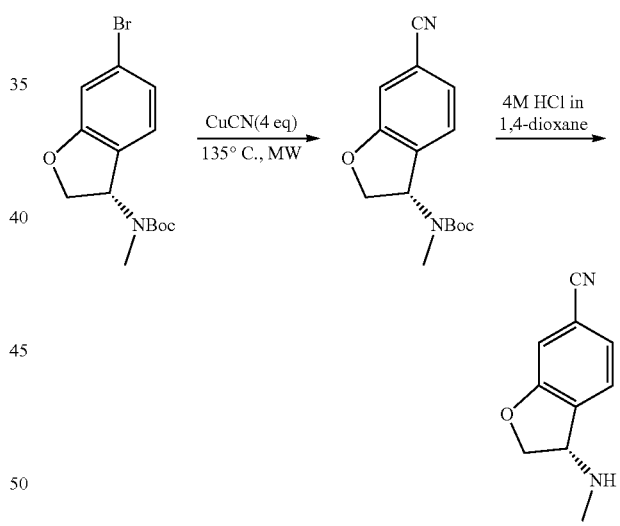

Step 1: Synthesis of tert-butyl (S)-(6-cyano-2,3-dihydrobenzofuran-3-yl)(methyl)carbamate In a microwave reactor, a reaction mixture of tert-butyl (S)-(6-bromo-2,3-dihydrobenzofuran-3-yl)(methyl)carbamate (328 mg, 1 mmol), cuprous cyanide (352 mg, 4 mmol), and N-methylpyrrolidone (4 mL) was heated at 135° C. for 4 hours. After completion of the reaction, the system was cooled to room temperature, then poured into water, and extracted three times with ethyl acetate (30 mL×3). The combined organic phases were washed with saturated brine, dried over anhydrous sodium sulfate, filtered, and the filtrate was concentrated under reduced pressure. The residue was purified by silica gel column chromatography (ethyl acetate:petroleum ether=40:60) to yield tert-butyl (S)-(6-cyano-2,3-dihydrobenzofuran-3-yl)(methyl)carbamate (66 mg, 23.93% yield), a colorless oily substance.

LCMS (ESI): 275 [M+H]+

Step 2: (S)-3-(methylamino)-2,3-dihydrobenzofuran-6-carbonitrile tert-butyl (S)-(6-cyano-2,3-dihydrobenzofuran-3-yl)(methyl)carbamate (66 mg, 0.24 mmol) was added to a solution of hydrogen chloride in 1,4-dioxane (3 mL, 4 mol/L). The mixture was stirred for 2 hours. After completion of the reaction, the resulting mixture was concentrated under reduced pressure to obtain crude (S)-3-(methylamino)-2,3-dihydrobenzofuran-6-carbonitrile (40 mg), a white solid. The crude product was used directly in the next step without purification.

LCMS (ESI): 175 [M+H]+

Int. 23: synthesis of (S)-6-methoxy-N-methyl-2,3-dihydrobenzofuran-3-amine

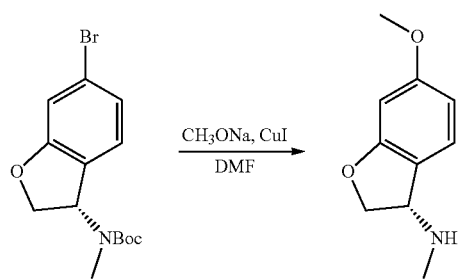

tert-butyl (S)-(6-bromo-2,3-dihydrobenzofuran-3-yl)(methyl)carbamate (328 mg, 1 mmol), CuI (352 mg, 4 mmol), and a solution of sodium methoxide in methanol (180 mg, 40 mmol) in N,N-dimethylformamide (4 mL) were reacted at 120° C. for four hours. After completion of the reaction, the system was cooled to room temperature, and the mixture was extracted three times with ethyl acetate (30 mL each time). The combined organic phases were washed with saturated brine and dried over anhydrous sodium sulfate. After concentration under reduced pressure, (S)-6-methoxy-N-methyl-2,3-dihydrobenzofuran-3-amine (150 mg, 0.8 mmol, 80% yield) was yielded, a colorless oily substance.

LCMS (ESI): 180 [M+H]+

Int. 24 (S)-dimethyl(3-(methylamino)-2,3-dihydrobenzofuran-6-yl)phosphine oxide

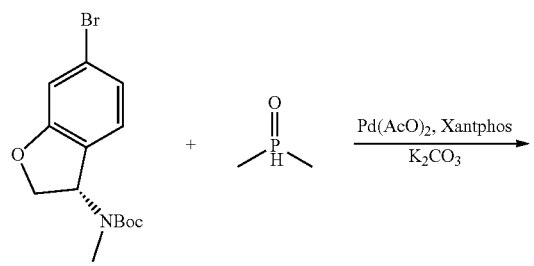

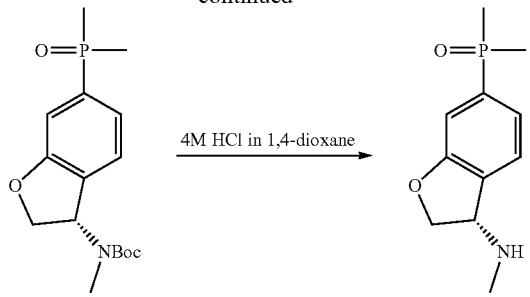

Step 1: tert-butyl (S)-(6-(dimethylphosphoryl)-2,3-dihydrobenzofuran-3-yl)(methyl)carbamate tert-butyl (S)-(6-bromo-2,3-dihydrobenzofuran-3-yl)(methyl)carbamate (200 mg, 0.61 mmol), dimethyl oxophosphorane (57 mg, 0.73 mmol), potassium carbonate (101 mg, 0.73 mmol), palladium acetate (10 mg, 0.06 mmol), 4,5-bis(diphenylphosphino)-9,9-dimethylxanthene (35 mg, 0.06 mmol), and 5 mL of dimethylformamide were reacted in a microwave reactor at 150° C. for 20 minutes. After completion of the reaction, the system was cooled to room temperature, and the mixture was extracted three times with ethyl acetate (30 mL in total, 10 mL each time). The combined organic phases were washed with saturated brine and dried over anhydrous sodium sulfate. After concentration under reduced pressure, tert-butyl (S)-(6-(dimethylphosphoryl)-2,3-dihydrobenzofuran-3-yl)(methyl)carbamate (80 mg, 0.245 mmol, 40.35% yield) was yielded, a white solid.

LCMS (ESI): 326 [M+H]+

Step 2: (S)-dimethyl(3-(methylamino)-2,3-dihydrobenzofuran-6-yl)phosphine oxide tert-butyl (S)-(6-(dimethylphosphoryl)-2,3-dihydrobenzofuran-3-yl)(methyl)carbamate (80 mg, 0.25 mmol) was added to a solution of 4 M hydrochloric acid in 1,4-dioxane (3 mL) and stirred for 2 hours. After completion of the reaction, the resulting mixture was concentrated under reduced pressure. This yielded (S)-dimethyl(3-(methylamino)-2,3-dihydrobenzofuran-6-yl)phosphine oxide (25 mg, 0.11 mmol, 45.14% yield), a white solid.

LCMS (ESI): 226[M+H]+

Int. 25: (S)—N-methyl-6-(methylsulfonyl)-2,3-dihydrobenzofuran-3-amine

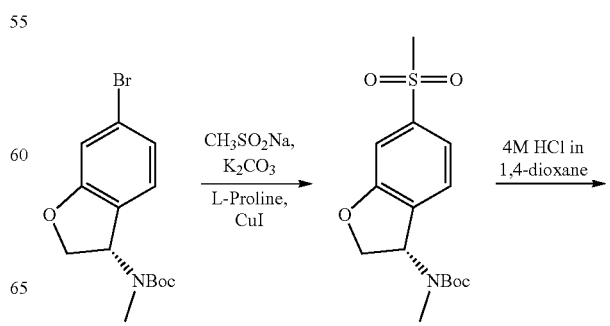

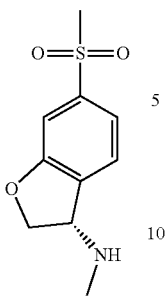

Step 1: synthesis of tert-butyl (S)-methyl(6-(methylsulfonyl)-2,3-dihydrobenzofuran-3-yl)carbamate tert-butyl (S)-(6-bromo-2,3-dihydrobenzofuran-3-yl)(methyl)carbamate (328 mg, 1 mmol), sodium methanesulfinate (122 mg, 1.2 mmol), L-proline (12 mg, 0.1 mmol), potassium carbonate (166 mg, 1.2 mmol), cuprous iodide (19 mg, 0.1 mmol), and N,N-dimethylformamide (5 mL) were reacted in a microwave reactor at 140° C. for 2 hours. After completion of the reaction, the system was cooled to room temperature, and the mixture was extracted three times with ethyl acetate (30 mL in total, 10 mL each time). The combined organic phases were washed with saturated brine and dried over anhydrous sodium sulfate. After concentration under reduced pressure, tert-butyl (S)-methyl(6-(methylsulfonyl)-2,3-dihydrobenzofuran-3-yl)carbamate (60 mg, 0.18 mmol, 18.32% yield) was yielded, a colorless oily substance.

LCMS (ESI): 328 [M+H]⁺

Step 2: synthesis of (S)—N-methyl-6-(methylsulfonyl)-2,3-dihydrobenzofuran-3-amine tert-butyl (S)-methyl(6-(methylsulfonyl)-2,3-dihydrobenzofuran-3-yl)carbamate (60 mg, 0.24 mmol) was added to a solution of 4 M hydrochloric acid in 1,4-dioxane (3 mL) and stirred for 2 hours. After completion of the reaction, the resulting mixture was concentrated under reduced pressure. This yielded synthesis of (S)—N-methyl-6-(methylsulfonyl)-2,3-dihydrobenzofuran-3-amine (30 mg, 0.13 mmol, 72.03% yield), a white solid.

LCMS (ESI): 228[M+H]⁺

Int. 101 Synthesis of (S)-6-(cyclopropylsulfonyl)-N-methyl-2,3-dihydrobenzofuran-3-amine

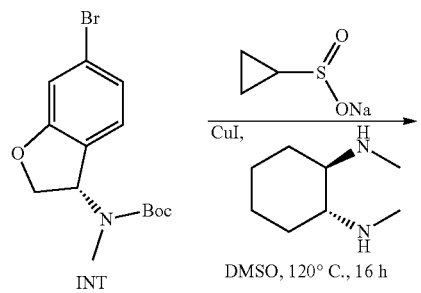

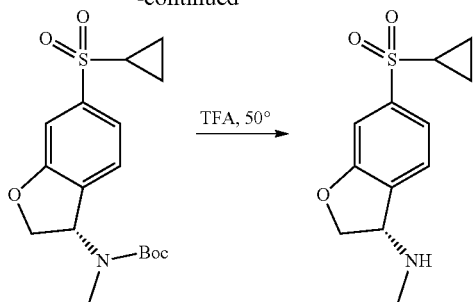

Step 1: Synthesis of tert-butyl (S)-(6-(cyclopropylsulfonyl)-2,3-dihydrobenzofuran-3-yl)(methyl)carbamate tert-butyl (S)-(6-bromo-2,3-dihydrobenzofuran-3-yl)(methyl)carbamate (300 mg, 0.914 mmol) and sodium cyclopropanesulfinate (118 mg, 0.914 mmol) were dissolved in DMSO (10 mL). Copper(I) iodide (35 mg, 0.182 mmol) and (1R,2R)—N1,N2-dimethylcyclohexane-1,2-diamine (52 mg, 0.365 mmol) were added, and the reaction mixture was stirred at 25° C. for 10 hours. After LCMS indicated complete reaction, water (10 mL) was added, followed by extraction with ethyl acetate (20 mL×2). The combined organic phases were washed with anhydrous sodium sulfate, filtered, and concentrated under reduced pressure. Purification by column chromatography (0-10% ethyl acetate/petroleum ether) yielded Synthesis of tert-butyl (S)-(6-(cyclopropylsulfonyl)-2,3-dihydrobenzofuran-3-yl)(methyl)carbamate (150 mg, 46.4% yield).

LCMS (ESI) m/z: 354.1 [M+H]⁺

Step 2: Synthesis of (S)-6-(cyclopropylsulfonyl)-N-methyl-2,3-dihydrobenzofuran-3-amine At room temperature, compound tert-butyl (S)-(6-(cyclopropylsulfonyl)-2,3-dihydrobenzofuran-3-yl)(methyl)carbamate (150 mg, 0.424 mmol) was dissolved in dichloromethane (3 mL), and trifluoroacetic acid (1 mL) was added. The reaction mixture was stirred at room temperature for 16 hours, and the crude product (S)-6-(cyclopropylsulfonyl)-N-methyl-2,3-dihydrobenzofuran-3-amine (150 mg, crude) was obtained by concentration under reduced pressure, without the need for purification, and directly used for the next step.

LCMS (ESI) m/z: 254.1[M+H]⁺

Int. 26 synthesis of (S)—N-methyl-6-(1-(trifluoromethyl)-1H-pyrazol-4-yl)-2,3-dihydrobenzofuran-3-amine

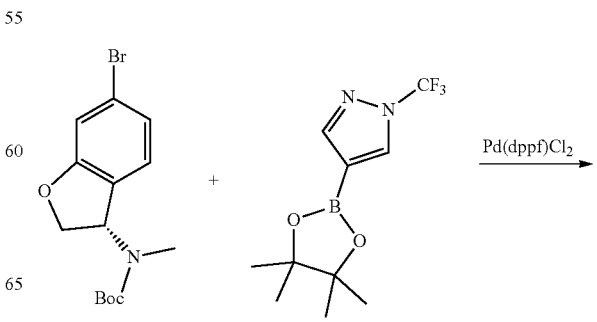

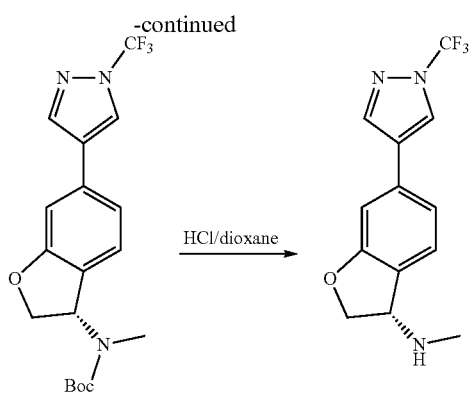

Step 1: Synthesis of tert-butyl (S)-methyl(6-(1-(trifluoromethyl)-1H-pyrazol-4-yl)-2,3-dihydrobenzofuran-3-yl)carbamate Under N₂ atmosphere, tert-butyl (S)-(6-bromo-2,3-dihydrobenzofuran-3-yl)(methyl)carbamate (300 mg, 0.91 mmol) was dissolved in 1,4-dioxane and water (4:1, 10 mL), and 4-(4,4,5,5-tetramethyl-1,3,2-dioxaborolan-2-yl)-1-(trifluoromethyl)-1H-pyrazole (239.0 mg, 1.37 mmol), potassium carbonate (377 mg, 2.73 mmol), and 1,1'-bis(di-tert-butylphosphino)ferrocene palladium dichloride (67.0 mg, 0.09 mmol) were added. The reaction was carried out at 100° C. for 16 hours. The mixture was then poured into water (30 mL), extracted with ethyl acetate (20 mL×3), and the combined organic phase was dried over anhydrous sodium sulfate. After filtration to remove sodium sulfate, the filtrate was rotary evaporated to obtain the crude product. Purification by silica gel column chromatography (petroleum ether:ethyl acetate=10:1) yielded tert-butyl (S)-methyl(6-(1-(trifluoromethyl)-1H-pyrazol-4-yl)-2,3-dihydrobenzofuran-3-yl)carbamate (240.0 mg, 68.8% yield), a white solid.

LCMS (ESI) m/z: 384.1 [M+H]⁺

Step 2: Synthesis of (S)—N-methyl-6-(1-(trifluoromethyl)-1H-pyrazol-4-yl)-2,3-dihydrobenzofuran-3-amine At room temperature, tert-butyl (S)-methyl(6-(1-(trifluoromethyl)-1H-pyrazol-4-yl)-2,3-dihydrobenzofuran-3-yl)carbamate (240 mg, 0.626 mmol) was dissolved in 4 M hydrochloric acid in ethyl acetate (3 mL). After stirring at room temperature for 1 hour, the reaction mixture was concentrated under reduced pressure to obtain the crude product, (S)—N-methyl-6-(1-(trifluoromethyl)-1H-pyrazol-4-yl)-2,3-dihydrobenzofuran-3-amine (25.0 mg, crude product).

LCMS (ESI) m/z: 283.1 [M+H]⁺

Using the methods and steps employed for Intermediate 26, with only the replacement of the corresponding raw materials, the following intermediates were synthesized:

| Int. No. | Structure | name | m/z (ESI): (M + H)⁺ |
|---|---|---|---|
| 27 | 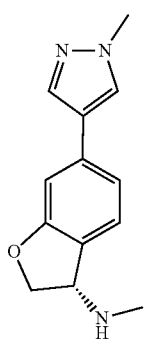 [SMILES: CN[C@@H]1COc2cc(-c3cnn(C)c3)ccc21] | (S)-N-methyl-6-(1-methyl-1H-pyrazol-4-yl)-2,3-dihydrobenzofuran-3-amine | 230.1 |
| 28 | 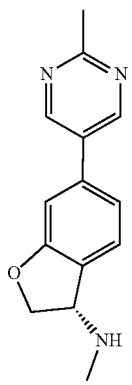 | (S)-N-methyl-6-(2-methylpyrimidin-5-yl)-2,3-dihydrobenzofuran-3-amine | 242.1 |

-continued
| Int. No. | Structure | name | m/z (ESI): (M + H)+ |
|---|---|---|---|
| 29 | 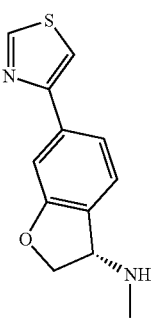 | (S)-N-methyl-6-(thiazol-4-yl)-2,3-dihydrobenzofuran-3-amine | 202.1 |
| 30 | 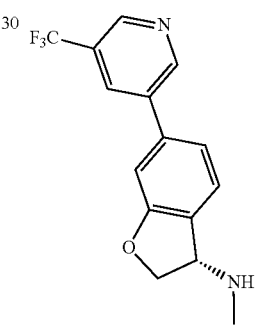 | (S)-N-methyl-6-(5-(trifluoromethyl)pyridin-3-yl)-2,3-dihydrobenzofuran-3-amine | 295.1 |
| 31 | 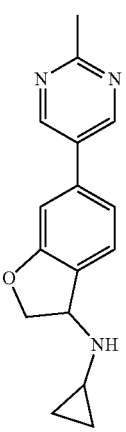 [SMILES: Cc1ncc(-c2ccc3c(c2)OCC3NC2CC2)cn1] | N-cyclopropyl-6-(2-methylpyrimidin-5-yl)-2,3-dihydrobenzofuran-3-amine | 268.1 |
| 32 | 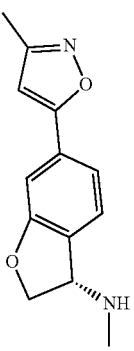 [SMILES: CN[C@@H]1COc2cc(-c3cc(C)no3)ccc21] | (S)-N-methyl-6-(3-methylisoxazol-5-yl)-2,3-dihydrobenzofuran-3-amine | 231.1 |

-continued

| Int. No. | Structure | name | m/z (ESI): (M + H)+ |
|---|---|---|---|
| 33 | 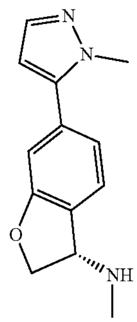 | (S)-N-methyl-6-(1-methyl-1H-pyrazol-5-yl)-2,3-dihydrobenzofuran-3-amine | 230.2 |
| 34 | 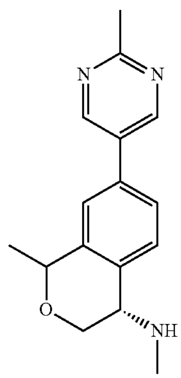 | (4S)-N,1-dimethyl-7-(2-methylpyrimidin-5-yl)isochroman-4-amine | 270.2 |
| 35 | 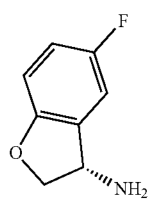 [SMILES: N[C@@H]1COc2ccc(F)cc21] | (4S)-N,1-dimethyl-7-(1-methyl-1H-pyrazol-4-yl)isochroman-4-amine | 258.2 |
| 36 | 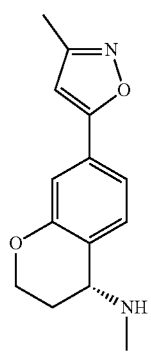 | (R)-N-methyl-7-(3-methylisoxazol-5-yl)chroman-4-amine | 245.2 |
| 37 | 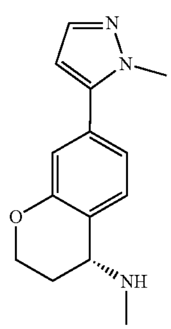 [SMILES: CN[C@@H]1CCOc2cc(-c3ccnn3C)ccc21] | (R)-N-methyl-7-(1-methyl-1H-pyrazol-5-yl)chroman-4-amine | 244.2 |

-continued
| Int. No. | Structure | name | m/z (ESI): (M + H)+ |
|---|---|---|---|
| 38 | 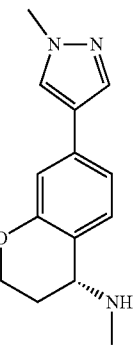 | (R)-N-methyl-7-(1-methyl-1H-pyrazol-4-yl)chroman-4-amine | 244.2 |
| 39 | 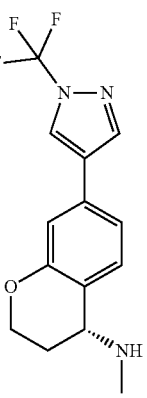 | (R)-N-methyl-7-(1-(trifluoromethyl)-1H-pyrazol-4-yl)chroman-4-amine | 298.2 |
| 40 | 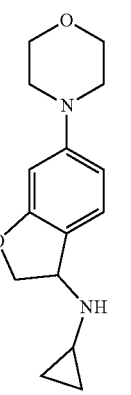 | N-cyclopropyl-6-morpholino-2,3-dihydrobenzofuran-3-amine | 261.2 |
| 103 | 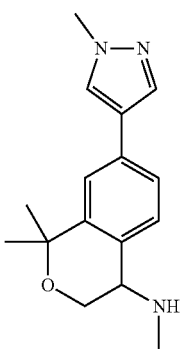 | N,1,1-trimethyl-7-(1-methyl-1H-pyrazol-4-yl)isochroman-4-amine | 272.17 |

| Int. No. | Structure | name | m/z (ESI): (M + H)+ |
|---|---|---|---|
| 104 | ![structure] | N,1,1-trimethyl-7-(1-methyl-1H-pyrazol-5-yl)isochroman-4-amine | 272.17 |

Int. 41 synthesis of 6-(trifluoromethyl)benzo[b]thiophen-3(2H)-one

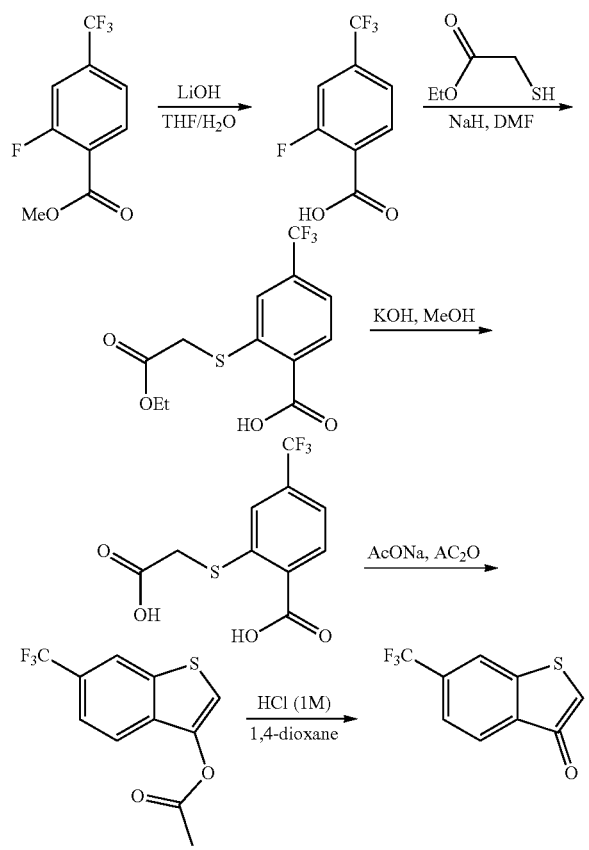

Step 1: Synthesis of 2-fluoro-4-(trifluoromethyl)benzoic acid

At room temperature, lithium hydroxide (9.70 g, 405.15 mmol) was added to a solution of methyl 2-fluoro-4-(trifluoromethyl)benzoate (30.00 g, 135.05 mmol) in tetrahydrofuran:water (300 mL:30 mL). The mixture was stirred at 50° C. for 2 hours. The reaction mixture was poured into water (100 mL), and the pH was adjusted to 4 with formic acid. After extraction with ethyl acetate (100 mL×3), the organic layer was dried over anhydrous sodium sulfate, filtered, and concentrated, the crude product was further purified by rapid silica gel column chromatography (petroleum ether:ethyl acetate=30%) to obtain 2-fluoro-4-(trifluoromethyl)benzoic acid (22.00 g, yield: 78%).

LCMS (ESI) m/z: 209.1 [M+H]+

Step 2: Synthesis of 2-((2-ethoxy-2-oxoethyl)thio)-4-(trifluoromethyl)benzoic acid At 0° C., sodium hydride (8.46 g, 211.43 mmol) was added to a solution of ethyl 2-mercaptoacetate (12.70 g, 105.72 mmol) in N,N-dimethylformamide (200.00 mL). The mixture was stirred at room temperature for 0.5 hours. Then, 2-fluoro-4-(trifluoromethyl)benzoic acid (22.00 g, 105.71 mmol) was added to the solution, and the mixture was stirred for 1 hour at room temperature. The reaction mixture was slowly poured into water (100 mL), extracted with ethyl acetate (200 mL), dried over anhydrous sodium sulfate, filtered, and concentrated. The crude product was purified by rapid silica gel column chromatography (petroleum ether:ethyl acetate=10%) to yield 2-((2-ethoxy-2-oxoethyl)thio)-4-(trifluoromethyl)benzoic acid (13.00 g, yield: 40%).

LCMS (ESI) m/z: 309.2 [M+H]+

Step 3: synthesis of 2-((carboxymethyl)thio)-4-(trifluoromethyl)benzoic acid The mixture of 2-((2-ethoxy-2-oxoethyl)thio)-4-(trifluoromethyl)benzoic acid (13.00 g, 42.17 mmol) and potassium hydroxide (4.72 g, 84.34 mmol) in methanol (130.00 mL) was stirred at room temperature for 2 hours, then concentrated to obtain 2-((carboxymethyl)thio)-4-(trifluoromethyl)benzoic acid (7.00 g, crude).

LCMS (ESI) m/z: 281.2 [M+H]+

Step 4: synthesis of 6-(trifluoromethyl)benzo[b]thiophen-3-yl acetate

At room temperature, sodium acetate trihydrate (10.19 g, 74.94 mmol) was added to a solution of 2-((carboxymethyl)thio)-4-(trifluoromethyl)benzoic acid (7.00 g, 24.98 mmol) in acetic anhydride (70.00 mL). The mixture was stirred at 140° C. for 30 minutes. Afterward, the mixture was poured into water, extracted with ethyl acetate (100 mL), dried over anhydrous sodium sulfate, filtered, and concentrated. Purification by quick column chromatography (petroleum ether: ethyl acetate=50%) yielded 6-(trifluoromethyl)benzo[b]thiophen-3-yl acetate (5.00 g, yield: 77%).
LCMS (ESI) m/z: 261.2 [M+H]⁺

Step 5: synthesis of 6-(trifluoromethyl)benzo[b]thiophen-3(2H)-one

At room temperature, hydrochloric acid solution (10.00 mL, 1 M) was added to a solution of 6-(trifluoromethyl)benzo[b]thiophen-3-yl acetate (1.00 g, 3.84 mmol) in 1,4-dioxane (5.00 mL). The mixture was stirred at 100° C. for 2 hours. After cooling, the reaction mixture was poured into water, and the aqueous layer was extracted with ethyl acetate (2×200 mL). The combined organic layers were washed with saturated brine (300 mL), dried over anhydrous sodium sulfate, concentrated to obtain the crude product. Purification by quick column chromatography (petroleum ether: ethyl acetate=70%) yielded 6-(trifluoromethyl)benzo[b]thiophene-3(2H)-one (0.50 g, yield: 59%), a black solid.
LCMS (ESI) m/z: 219.2 [M+H]⁺

Int. 42 Synthesis of 1-methyl-7-(trifluoromethyl)isochroman-4-one

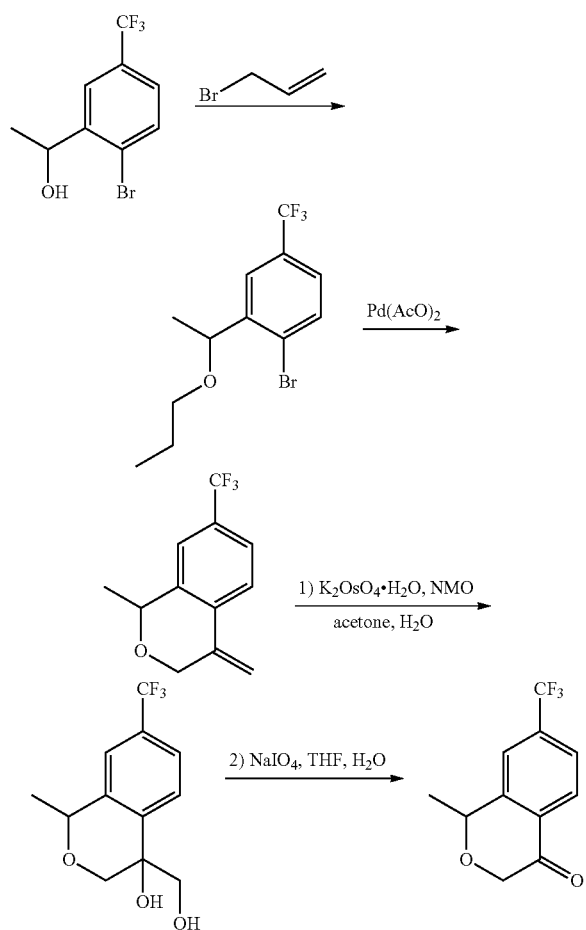

Step 1: Synthesis of 2-(1-(allyloxy)ethyl)-1-bromo-4-(trifluoromethyl)benzene

At room temperature, 1-(2-bromo-5-(trifluoromethyl)phenyl)ethan-1-ol (10 g, 37.16 mmol) was dissolved in tetrahydrofuran (100 mL), followed by the addition of potassium hydroxide (4.2 g, 74.33 mmol), tetrabutylammonium hydrogen sulfate (2.6 g, 7.433 mmol), and 3-bromopropene (5.4 g, 44.60 mmol). The reaction proceeded for 4 hours at 25° C. After completion, the reaction mixture was concentrated under reduced pressure and poured into water (100 mL). The aqueous layer was extracted with ethyl acetate (3×100 mL), and the combined organic phases were dried over anhydrous sodium sulfate, filtered, and concentrated under reduced pressure to obtain the crude product (12 g, crude). No further purification was needed, and it was used directly for the next step.
LCMS (ESI) m/z: 309.2 [M+H]⁺

Step 2: synthesis of 1-methyl-4-methylene-7-(trifluoromethyl)isochromane 2-(1-(allyloxy)ethyl)-1-bromo-4-(trifluoromethyl)benzene (12 g, 38.82 mmol) was dissolved in DMF (100 mL), and cesium carbonate (15.5 g, 46.59 mmol), tri(o-tolyl)phosphine (5.1 g, 19.41 mmol), and palladium acetate (0.89 g, 3.882 mmol) were added. The mixture was stirred at 90° C. under a nitrogen atmosphere for 16 hours. The reaction mixture was poured into 400 mL of water, extracted with ethyl acetate (3×100 mL), the combined organic phases were dried over anhydrous sodium sulfate, concentrated under reduced pressure to obtain the crude product, and further purified by column chromatography (petroleum ether:ethyl acetate=10:1) to yield 1-methyl-4-methylene-7-(trifluoromethyl)isochromane (5.5 g, yield: 62.1%).
LCMS (ESI) m/z: 229.1 [M+H]⁺

Step 3: Synthesis of 4-(hydroxymethyl)-1-methyl-7-(trifluoromethyl)isochroman-4-ol At room temperature, 1-methyl-4-methylene-7-(trifluoromethyl)isochromane (5.5 g, 24.10 mmol) was dissolved in a mixed solvent of acetone (100 mL) and water (20 mL). N-Methylmorpholine N-oxide (9.2 g, 76.68 mmol) and potassium ruthenate (0.91 g, 2.410 mmol) were added. Under a nitrogen atmosphere, the mixture was stirred at 25° C. for 16 hours. After completion of the reaction, sodium sulfite solid (5 g) was added to the reaction mixture and stirred for ten minutes. The solution was concentrated under reduced pressure to remove a certain amount of acetone, poured into water (200 mL), extracted with ethyl acetate (3×100 mL), the combined organic phases were dried over anhydrous Na2SO4, concentrated under reduced pressure to obtain the crude product, and further purified to yield 4-(hydroxymethyl)-1-methyl-7-(trifluoromethyl)isochroman-4-ol (6.0 g, yield: 94.90%).
LCMS (ESI) m/z: 263.0 [M+H]⁺

Step 4: Synthesis of 1-methyl-7-(trifluoromethyl)isochroman-4-one

At room temperature, 4-(hydroxymethyl)-1-methyl-7-(trifluoromethyl)isochroman-4-ol (6.0 g, 22.88 mmol) was dissolved in a mixed solvent of tetrahydrofuran (100 mL) and water (3.5 mL). Sodium periodate (15.0 g, 68.64 mmol) was added under a nitrogen atmosphere, and the mixture was stirred at 25° C. for 4 hours. After completion of the reaction, the reaction mixture was diluted with ethyl acetate, filtered, washed, the combined filtrate was dried over anhydrous sodium sulfate, filtered, and the filtrate was concentrated under reduced pressure to obtain the crude product 1-methyl-7-(trifluoromethyl)isochroman-4-one (5 g, crude product).
LCMS (ESI) m/z: 230.2 [M+H]⁺

Using the methods and steps employed for Intermediate 42, with only the replacement of the corresponding raw materials, the following intermediates were synthesized:

| Int. No. | Structure | Name | m/z (ESI): (M + H)+ |
|---|---|---|---|
| 43 | 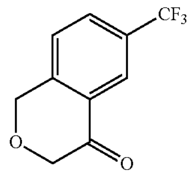 [SMILES: O=C1COCc2ccc(C(F)(F)F)cc21] | 6-(trifluoromethyl)isochroman-4-one | 217.2 |
| 44 | 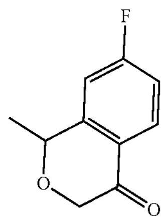 | 7-fluoro-1-methylisochroman-4-one | 180.2 |
| 45 | 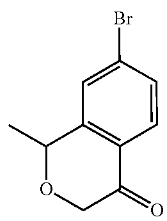 | 7-bromo-1-methylisochroman-4-one | 242.1 |
| 46 | 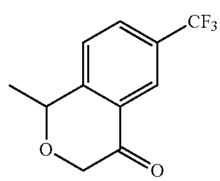 [SMILES: CC1OCC(=O)c2cc(C(F)(F)F)ccc21] | 1-methyl-6-(trifluoromethyl)isochroman-4-one | 230.2 |
| 47 | 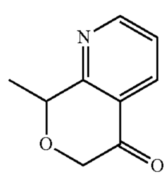 | 8-methyl-6H-pyrano[3,4-b]pyridin-5(8H)-one | 164.2 |
| 48 | 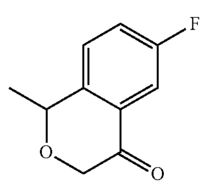 | 6-fluoro-1-methylisochroman-4-one | 181 |
| 49 | 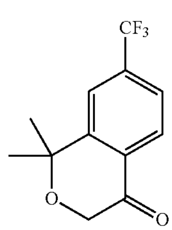 [SMILES: CC1(C)OCC(=O)c2ccc(C(F)(F)F)cc21] | 1,1-dimethyl-7-(trifluoromethyl)isochroman-4-one | 245.2 |

The following ketones were purchased from different suppliers:

| Int. No. | Structure | Name | CAS |
|---|---|---|---|
| 50 | 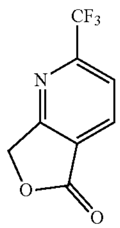 [SMILES: O=C1OCc2nc(C(F)(F)F)ccc21] | 6-(trifluoromethyl)furo[2,3-b]pyridin-3(2H)-one | 1196155-86-8 |
| 51 | 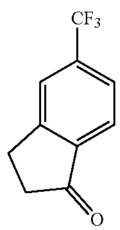 [SMILES: O=C1CCc2cc(C(F)(F)F)ccc21] | 5-(trifluoromethyl)-2,3-dihydro-1H-inden-1-one | 150969-56-5 |
| 52 | 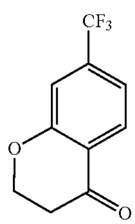 [SMILES: O=C1CCOc2cc(C(F)(F)F)ccc21] | 7-(trifluoromethyl)chroman-4-one | 111141-02-7 |
| 53 | 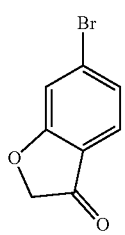 [SMILES: O=C1COc2cc(Br)ccc21] | 6-bromobenzofuran-3(2H)-one | 3260-78-4 |
| 54 | 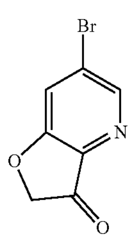 [SMILES: O=C1COc2cc(Br)cnc21] | 7-bromo-2,3-dihydro-4H-pyrano[3,2-b]pyridin-4-one | 1624261-71-7 |
| 102 | 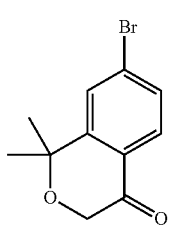 | 7-bromo-1,1-dimethylisochroman-4-one | 2763779-54-8 |

Int. 55
N-methyl-6-(trifluoromethyl)isochroman-4-amine hydrochloride

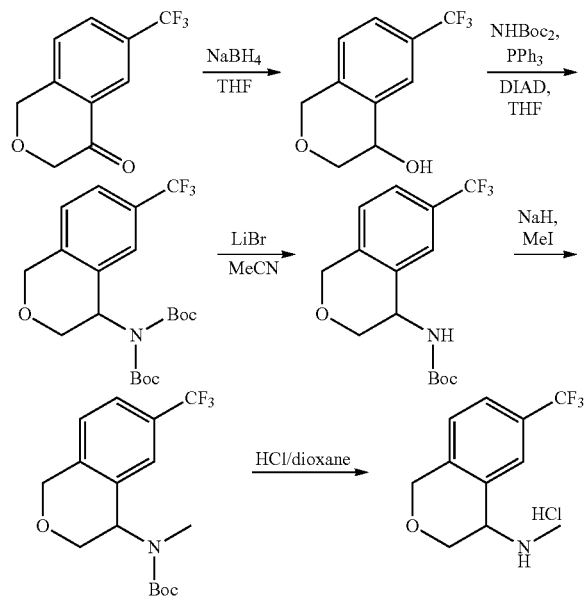

Step 1: Synthesis of 6-(trifluoromethyl)isochroman-4-ol

At room temperature, 6-(trifluoromethyl)isochroman-4-one (1.1 grams, 5.09 mmol) was dissolved in THF (10 mL), followed by the addition of sodium borohydride (251 mg, 6.62 mmol) in an ice bath, and then 2 drops of methanol were slowly added. After complete addition, the reaction was left overnight at room temperature. Upon completion, the reaction was quenched with a solution of 1 M hydrochloric acid (2 mL), extracted with ethyl acetate (10 mL×2), then the organic phases were combined, dried over sodium sulfate, then filtered, and obtained the crude product, which was further purified by column chromatography to yield 6-(trifluoromethyl)isochroman-4-ol (1.16 grams).

Step 2: synthesis of tert-butyl (tert-butoxycarbonyl)(6-(trifluoromethyl)isochroman-4-yl)carbamate At room temperature, 6-(trifluoromethyl)isochroman-4-ol (100.0 mg, 0.459 mmol) was dissolved in THF (5.0 mL), then di-tert-butyl dicarbonate (110 mg, 0.505 mmol) and triphenylphosphine (132 mg, 0.505 mmol) were added successively. The reaction mixture was stirred at 0° C. for 5 minutes, then DIAD (102 mg, 0.505 mmol) was added, and the reaction was stirred at room temperature overnight. After completion, water (10 mL) was added. And the reaction mixture was extracted with ethyl acetate (10 mL×3). Then organic phases were combined, dried over anhydrous sodium sulfate, filtered. And the resulting filtrate was concentrated under reduced pressure to obtain the crude product. Further purification by column chromatography (pure petroleum ether) yielded tert-butyl (tert-butoxycarbonyl)(6-(trifluoromethyl)isochroman-4-yl)carbamate (90.0 mg).

Step 3: Synthesis of tert-butyl (6-(trifluoromethyl)isochroman-4-yl)carbamate

Tert-butyl (tert-butoxycarbonyl)(6-(trifluoromethyl) isoxazol-4-yl)methylamine (60.0 mg, 0.14 mmol) was dissolved in acetonitrile (2.0 mL), then lithium bromide (37.6 mg, 0.432 mmol) was added. The reaction mixture was heated at 60° C. for 20 hours. After completion, saturated sodium bicarbonate (10 mL) was added, and extracted with ethyl acetate (20 mL). Then the organic phase was dried with sodium sulfate, filtered. The resulting filtrate was concentrated under reduced pressure to obtain (6-(trifluoromethyl) isochroman-4-yl)carbamate (30 mg).

Step 4: Synthesis of tert-butyl methyl(6-(trifluoromethyl)isochroman-4-yl)carbamate (6-(trifluoromethyl)isochroman-4-yl)carbamate (360.0 mg, 1.14 mmol) was dissolved in 5.0 mL of DMF and stirred in an ice bath for 2 minutes. Sodium hydride (90.8 mg, 2.27 mmol) was added at this temperature and stirred for 1 hour. Then, methyl iodide (487 mg, 3.41 mmol) was added, and the reaction mixture was stirred overnight at room temperature. After completion, saturated sodium bicarbonate (15 mL) was added, extracted with ethyl acetate (15 mL×3), dried the organic phase with sodium sulfate, then filtered, and the filtrate was concentrated to obtain the crude product tert-butyl methyl(6-(trifluoromethyl)isochroman-4-yl)carbamate (400.0 mg).

Step 5: Synthesis of N-methyl-6-(trifluoromethyl)isochroman-4-amine hydrochloride At room temperature, tert-butyl methyl(6-(trifluoromethyl)isochroman-4-yl)carbamate (400 mg, 1.21 mmol) was dissolved in 2 mL of dichloromethane, followed by addition of a solution of 4 M hydrochloric acid in dioxane (2 mL). The reaction was stirred overnight at room temperature. After completion, the reaction mixture was directly evaporated to obtain N-methyl-6-(trifluoromethyl)isochroman-4-amine hydrochloride (390 mg).

Using the methods and steps employed for Intermediate 55, with only the replacement of the corresponding raw materials, the following intermediates were synthesized:

| Int. No. | Structure | Name | m/z (ESI): (M + H)+ |
|---|---|---|---|
| 56 | ![] | N-methyl-5-(trifluoromethyl)-2,3-dihydro-1H-inden-1-amine | 216.2 |
| 57 | ![] | N-methyl-8-(trifluoromethyl)-1,3,4,5-tetrahydrobenzo[c]oxepin-5-amine | 246.2 |

| Int. No. | Structure | Name | m/z (ESI): (M + H)+ |
|---|---|---|---|
| 58 | 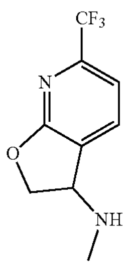 | N-methyl-6-(trifluoromethyl)-2,3-dihydrofuro[2,3-b]pyridin-3-amine | 219.2 |
| 59 | 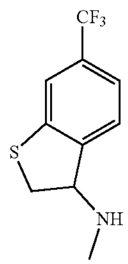 | N-methyl-6-(trifluoromethyl)-2,3-dihydrobenzo[b]thiophen-3-amine | 234.2 |

Int 60 Synthesis of (R)—N-methyl-7-(trifluoromethyl)chroman-4-amine hydrochloride

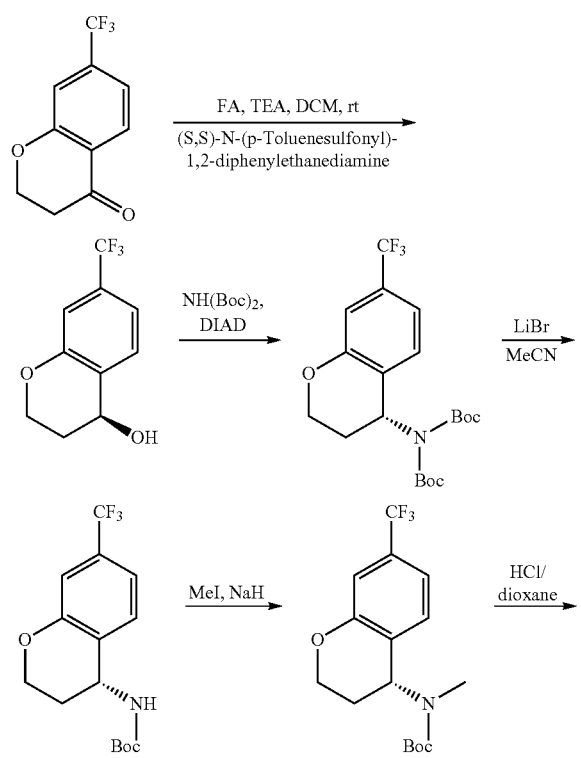

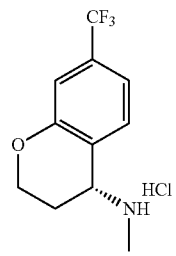

Step 1: Synthesis of (S)-7-(trifluoromethyl)chroman-4-ol

At room temperature, 7-(trifluoromethyl)chroman-4-one (500.0 mg, 2.31 mmol) was dissolved in DCM (10 mL), followed by the addition of (S, S)—N-(p-toluenesulfonyl)-1,2-diphenylethane-1,2-diamine (147.0 mg, 0.23 mmol) cooled by an ice bath. Then, formic acid (372.0 mg, 8.10 mmol) was added dropwise, and finally, triethylamine (701.0 mg, 6.94 mmol) was added dropwise. After completion, the reaction mixture was left overnight at room temperature. Upon completion, saturated sodium bicarbonate solution (10 mL) was added, and the mixture was extracted with ethyl acetate (10 mL×2). After combining the organic phases, drying over sodium sulfate, and filtration, the crude product was obtained. Purification by column chromatography (petroleum ether:ethyl acetate=0-40%) yielded (S)-7-(trifluoromethyl)chroman-4-ol (370 mg, yield: 73%).

Step 2: Synthesis of tert-butyl (R)-(tert-butoxycarbonyl)(7-(trifluoromethyl)chroman-4-yl)carbamate Under a nitrogen atmosphere, (S)-7-(trifluoromethyl)chroman-4-ol (370.0 mg, 1.70 mmol) was first dissolved in THF (5.0 mL), and then di-tert-butyl iminodicarbonate (405 mg, 1.88 mmol) and triphenylphosphine (489 mg, 1.88 mmol) were added. The reaction mixture was stirred for 5 minutes at 0° C., and DIAD (377.0 mg, 1.88 mmol) was added dropwise. After stirring at room temperature overnight, the reaction was complete. Water (10 mL) was added, and the mixture was extracted with ethyl acetate (10 mL×3). After combining the organic phases, drying over anhydrous sodium sulfate, and filtration, the filtrate was concentrated under reduced pressure to obtain the crude product. Further purification by column chromatography (petroleum ether:ethyl acetate=0-5%) resulted in tert-butyl (R)-(tert-butoxycarbonyl)(7-(trifluoromethyl)chroman-4-yl)carbamate (145.0 mg, yield: 20%).

$^1$H NMR (400 MHz, CDCl$_3$) δ 7.25-7.22 (m, 1H), 7.12-7.09 (m, 1H), 7.07 (d, 1H), 5.59-5.54 (m, 1H), 4.46-4.41 (m, 1H), 4.18-4.10 (m, 1H), 2.67-2.60 (m, 1H), 2.16-2.10 (m, 1H), 1.46 (s, 18H).

Step 3: Synthesis of tert-butyl (R)-(7-(trifluoromethyl)chroman-4-yl)carbamate tert-butyl (R)-(tert-butoxycarbonyl)(7-(trifluoromethyl)chroman-4-yl)carbamate (150.0 mg, 0.36 mmol) was dissolved in acetonitrile (5.0 mL), and lithium bromide (94.0 mg, 1.08 mmol) was added. The reaction mixture was heated at 60° C. for 20 hours. After completion of the reaction, saturated sodium bicarbonate solution (10 mL) was added, and the mixture was extracted with ethyl acetate (20 mL). After drying the organic phase over sodium sulfate and filtration, the filtrate was concentrated to obtain the crude product, tert-butyl (R)-(7-(trifluoromethyl)chroman-4-yl)carbamate (83.0 mg, crude product).

Step 4: Synthesis of tert-butyl (R)-methyl(7-(trifluoromethyl)chroman-4-yl)carbamate tert-butyl (R)-(7-(trifluoromethyl)chroman-4-yl)carbamate (83.0 mg, 0.26 mmol) was dissolved in 2.0 mL DMF. The mixture was stirred cooled by an ice bath for 2 minutes, and sodium hydride (26.2 mg, 0.66 mmol) was added in one portion. The reaction mixture was stirred at this temperature for 1 hour, followed by the addition of iodomethane (74.4 mg, 0.52 mmol); the reaction continued overnight at room temperature. After completion of the reaction, saturated sodium bicarbonate solution (10 mL) was added, and the mixture was extracted with ethyl acetate (15 mL). The organic phase was dried over sodium sulfate, filtered, and the filtrate was concentrated to obtain the crude product, tert-butyl (R)-methyl(7-(trifluoromethyl)chroman-4-yl)carbamate (100.0 mg, crude product).

LCMS (ESI) m/z: 276.1[M+H]+

Step 5: Synthesis of (R)—N-methyl-7-(trifluoromethyl)chroman-4-amine hydrochloride tert-butyl (R)-methyl(7-(trifluoromethyl)chroman-4-yl)carbamate (100 mg, 0.3 mmol) was dissolved in 2 mL of dichloromethane, and a solution of 4 M hydrogen chloride in dioxane (2 mL) was added. The reaction was stirred at room temperature overnight. After completion of the reaction, the reaction mixture was directly evaporated to dryness, obtaining the crude product, (R)—N-methyl-7-(trifluoromethyl)chroman-4-amine hydrochloride (90 mg, crude product).

Using the methods and steps employed for Intermediate 60, with only the replacement of the corresponding raw materials, the following intermediates were synthesized:

| Int. No. | Structure | Name | m/z (ESI): (M + H)+ |
|---|---|---|---|
| 61 | 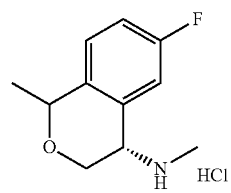 | (4S)-6-fluoro-N,1-dimethylisochroman-4-amine hydrochloride | 196.2 |
| 62 | 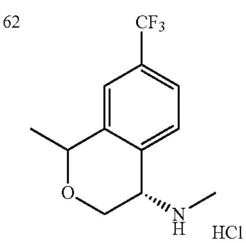 | (4S)-N,1-dimethyl-7-(trifluoromethyl)isochroman-4-amine hydrochloride | 246.2 |
| 63 | 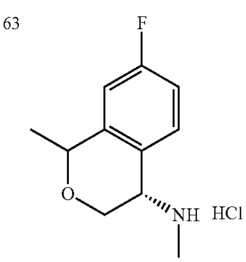 | (4S)-7-fluoro-N,1-dimethylisochroman-4-amine hydrochloride | 196.2 |
| 64 | 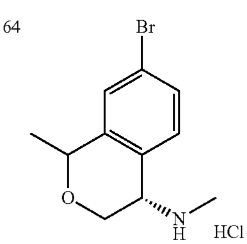 | (4S)-7-bromo-N,1-dimethylisochroman-4-amine hydrochloride | 256.2 |

-continued

| Int. No. | Structure | Name | m/z (ESI): (M + H)+ |
|---|---|---|---|
| 65 | 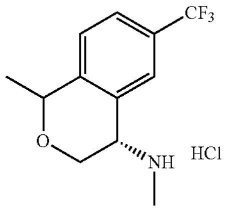 [SMILES: CN[C@@H]1COC(C)c2ccc(C(F)(F)F)cc21 ; Cl] | (4S)-N,1-dimethyl-6-(trifluoromethyl)isochroman-4-amine hydrochloride | 246.2 |
| 66 | 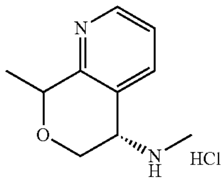 | (5S)-N,8-dimethyl-5,8-dihydro-6H-pyrano[3,4-b]pyridin-5-amine hydrochloride | 179.2 |
| 67 | 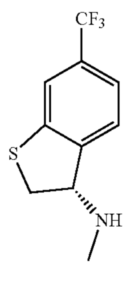 | (S)-N-methyl-6-(trifluoromethyl)-2,3-dihydrobenzo[b]thiophen-3-amine | 234.2 |
| 68 | 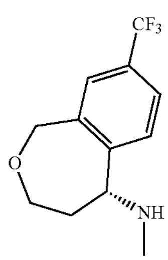 [SMILES: CN[C@@H]1CCOCc2cc(C(F)(F)F)ccc21] | (R)-N-methyl-8-(trifluoromethyl)-1,3,4,5-tetrahydrobenzo[c]oxepin-5-amine | 246.2 |

Int. 100 Synthesis of N,1,1-trimethyl-7-(trifluoromethyl)isochroman-4-amine

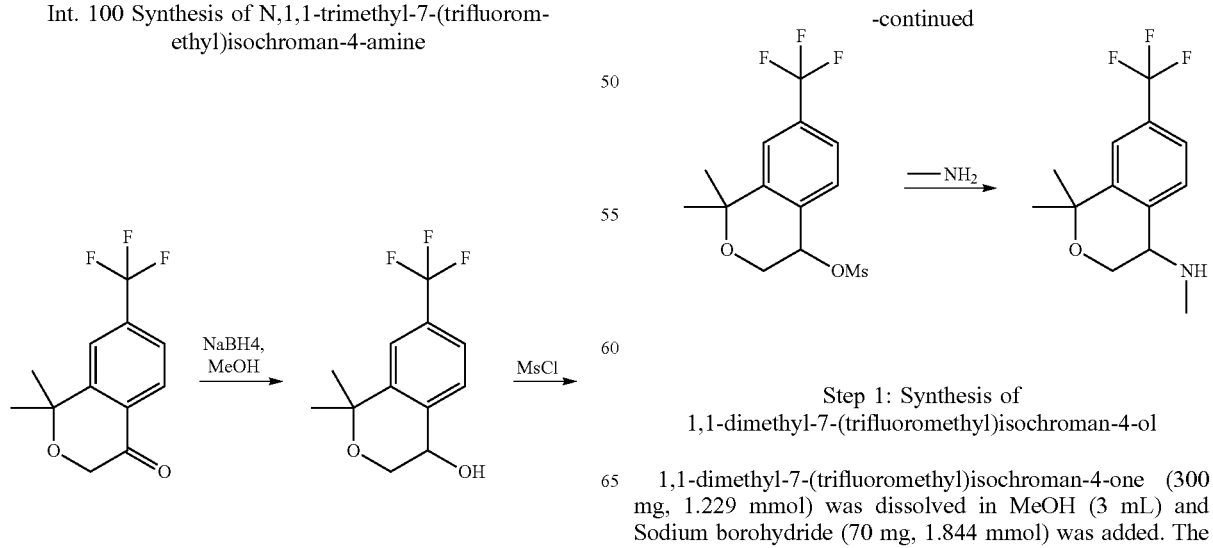

Step 1: Synthesis of 1,1-dimethyl-7-(trifluoromethyl)isochroman-4-ol 1,1-dimethyl-7-(trifluoromethyl)isochroman-4-one (300 mg, 1.229 mmol) was dissolved in MeOH (3 mL) and Sodium borohydride (70 mg, 1.844 mmol) was added. The reaction was stirred at 25° C. for 10 hours. Upon completion indicated by LCMS, NH₄Cl solution (10 mL) was added, and the mixture was extracted with ethyl acetate (20 mL×2). The combined organic phases were dried over anhydrous sodium sulfate, filtered, and the filtrate was concentrated under reduced pressure. Purification by column chromatography (0-10% ethyl acetate/petroleum ether) yielded 1,1-dimethyl-7-(trifluoromethyl)isochroman-4-ol (120 mg, yield: 39.4%).

LCMS (ESI) m/z: 247.1 [M+H]⁺

Step 2: Synthesis of 1,1-dimethyl-7-(trifluoromethyl)isochroman-4-yl methanesulfonate 1,1-dimethyl-7-(trifluoromethyl)isochroman-4-ol (120 mg, 0.487 mmol) and methanesulfonyl chloride (112 mg, 0.974 mmol) were dissolved in DCM (10 mL), and triethylamine (148 mg, 1.461 mmol) was added. The reaction was stirred at 25° C. for 10 hours. Upon completion indicated by LCMS, water (10 mL) was added, and the mixture was extracted with ethyl acetate (20 mL×2). The combined organic phases were dried over anhydrous sodium sulfate, filtered, and the filtrate was concentrated under reduced pressure, yielding crude 1,1-dimethyl-7-(trifluoromethyl)isochroman-4-yl methanesulfonate (130 mg, yield: 13.3%).

LCMS (ESI) m/z: 326.1 [M+H]⁺

Step 3: Synthesis of N,1,1-trimethyl-7-(trifluoromethyl)isochroman-4-amine

At room temperature, compound 1,1-dimethyl-7-(trifluoromethyl)isochroman-4-yl methanesulfonate (130 mg, 0.398 mmol) was dissolved in DMF (3 mL), and a solution of methylamine (0.3 mL, 30%) in MeOH and DIEA (155 mg, 1.194 mmol) was added. The reaction was stirred at room temperature for 16 hours. Upon completion indicated by LCMS, water (10 mL) was added, and the mixture was extracted with ethyl acetate (20 mL×2). The combined organic phases were dried over anhydrous sodium sulfate, filtered, and the filtrate was concentrated under reduced pressure. Purification by column chromatography (50-100% ethyl acetate/petroleum ether) afforded N,1,1-trimethyl-7-(trifluoromethyl)isochroman-4-amine (52 mg, yield: 50.4%).

LCMS (ESI) m/z: 260.1 [M+H]⁺

Using the methods and steps employed for Intermediate 100, with only the replacement of the corresponding raw materials, the following intermediates were synthesized:

| Int. No. | Structure | Name | m/z (ESI): (M + H)⁺ |
|---|---|---|---|
| 105 | (structure) | 7-bromo-N,1,1-trimethylisochroman-4-amine | 270.04 |

Int 69 Synthesis of 6-bromo-N-cyclopropyl-2,3-dihydrobenzofuran-3-amine

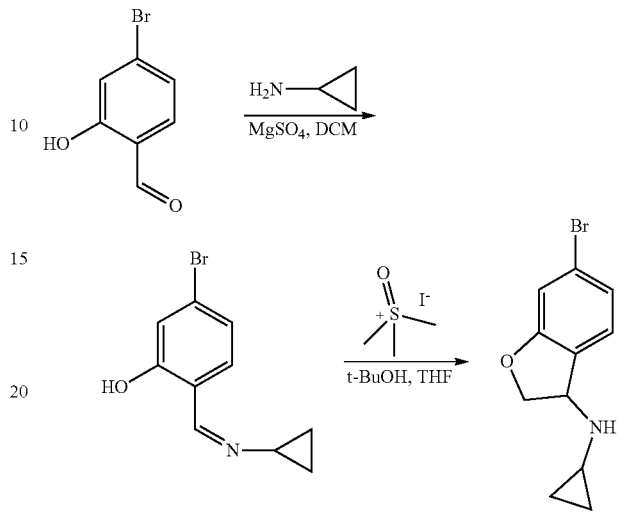

Step 1: Synthesis of 5-bromo-2-((cyclopropylimino)methyl)phenol

At room temperature, 4-bromo-2-hydroxybenzaldehyde (2.0 g, 9.95 mmol) was dissolved in dichloromethane (40 mL), and cyclopropylamine (1.13 g, 19.9 mmol) and anhydrous magnesium sulfate (4.79 g, 39.8 mmol) were added. The mixture was stirred at 25° C. for 20 hours. After completion of the reaction, the reaction mixture was concentrated, and the residue was dissolved in ethyl acetate, filtered, and the filter cake was washed with ethyl acetate. The resulting filtrate was concentrated under reduced pressure to obtain the crude product 5-bromo-2-((cyclopropylimino)methyl)phenol, 1.7 g, crude), as a yellow solid, used directly in the next step without purification.

LCMS (ESI) m/z: 241.1 [M+H]⁺

Step 2: Synthesis of 6-bromo-N-cyclopropyl-2,3-dihydrobenzofuran-3-amine

At room temperature, potassium tert-butoxide (1.99 g, 17.70 mmol) was slowly added to a solution of trimethylsilyl iodide (3.89 g, 17.70 mmol) in THF (5 mL). The mixture was stirred at room temperature for 0.5 hours, and then 5-bromo-2-((cyclopropylimino)methyl)phenol (1.7 g, 7.08 mmol) dissolved in THF was slowly added to the reaction mixture. The resulting suspension was stirred at room temperature for 1 hour and then at 50° C. for 3 hours. The reaction mixture was cooled to room temperature, and 1 equivalent of potassium tert-butoxide (0.79 g, 7.08 mmol) was added. The mixture was stirred at room temperature for 12 hours. The reaction mixture was filtered, and the filtrate was diluted with water and extracted with ethyl acetate. After concentrating the organic layer, purification of the residue was performed by column chromatography (petroleum ether/ethyl acetate=3:1) to obtain an oily substance, 6-bromo-N-cyclopropyl-2,3-dihydrobenzofuran-3-amine (1.0 g, 3.9 3 mmol), as a yellow oily substance.

LCMS (ESI) m/z: 255.1 [M+H]⁺

Using the methods and steps employed for Intermediate 69, with only the replacement of the corresponding raw materials, the following intermediates were synthesized:

| Int. No. | Structure | Name | m/z (ESI): (M + H)+ |
|---|---|---|---|
| 70 | 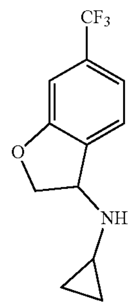 | N-cyclopropyl-6-(trifluoromethyl)-2,3-dihydrobenzofuran-3-amine | 244.2 |

Int. 71 Synthesis of 3-(cyclopropylamino)-2,3-dihydrobenzofuran-6-carbonitrile

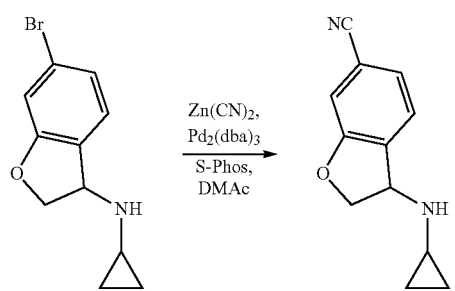 [SMILES: Brc1ccc2c(c1)OCC2NC1CC1 ; "S-Phos,DMAc" ; N#Cc1ccc2c(c1)OCC2NC1CC1]

At room temperature, 6-bromo-N-cyclopropyl-2,3-dihydrobenzofuran-3-amine (100 mg, 0.41 mmol) was added in a 50 mL single-neck flask, and Pd$_2$(dba)$_3$ (18.8 mg, 0.02 mmol), S-Phos (9.8 mg, 0.02 mmol), zinc cyanide (96.5 mg, 0.82 mmol) were added. Then, N,N-dimethylacetamide (1.0 mL) was added, and the reaction mixture was heated to 110° C. under microwave irradiation with stirring for 1 hour. After adding water (10 mL), the mixture was extracted with ethyl acetate (20 mL×2), and the combined organic phase was dried over anhydrous sodium sulfate, filtered, and the organic phase was concentrated to obtain the crude product. After column chromatography purification using ethyl acetate:petroleum ether (0-50%), the final product 3-(cyclopropylamino)-2,3-dihydrobenzofuran-6-carbonitrile (55 mg, yield: 67%) was obtained.

$^1$H NMR (400 MHz, CDCl$_3$) δ 7.44-7.42 (dd, 1H), 7.2-7.19 (dd, 1H), 7.07 (d, 1H), 4.65-4.61 (m, 1H), 4.58-4.55 (m, 1H), 4.47-4.46 (m, 1H), 2.25-2.19 (m, 1H), 0.52-0.49 (m, 2H), 0.43-0.40 (m, 2H).

Int. 72 Synthesis of (S)-6-(fluoromethyl)-N-methyl-2,3-dihydrobenzofuran-3-amine

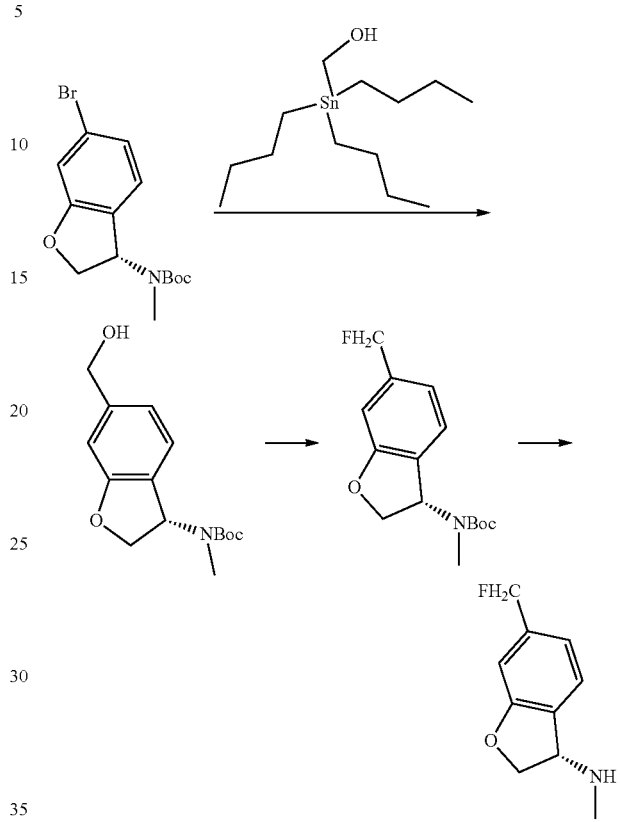

Step 1: Synthesis of tert-butyl (S)-(6-(hydroxymethyl)-2,3-dihydrobenzofuran-3-yl)(methyl)carbamate The mixture of tert-butyl (S)-(6-bromo-2,3-dihydrobenzofuran-3-yl)(methyl)carbamate (400 mg, 1.22 mmol), (tributylstannyl)methanol (391 mg, 1.22 mmol), and 1,1'-bis(diphenylphosphino)ferrocene palladium(II) dichloride (99 mg, 0.12 mmol) in dioxane (5 mL) was reacted at 100° C. for 12 hours. After completion of the reaction, the reaction mixture was poured into water (10 mL), extracted with ethyl acetate (10 mL×2), and the combined organic layers were washed with saturated brine (10 mL), dried over anhydrous sodium sulfate, filtered, and the filtrate was concentrated to obtain the crude product. The crude product was purified by column chromatography (ethyl acetate:petroleum ether=40:60), yielding tert-butyl (S)-(6-(hydroxymethyl)-2,3-dihydrobenzofuran-3-yl)(methyl)carbamate (110 mg, yield: 29%).

LCMS (ESI): 280 [M+H]+

Step 2: Synthesis of tert-butyl (S)-(6-(fluoromethyl)-2,3-dihydrobenzofuran-3-yl)(methyl)carbamate At −78° C., [Bis(2-methoxyethyl)amino]sulfur trifluoride (396 mg, 1.79 mmol) was added to the mixture of tert-butyl (S)-(6-(hydroxymethyl)-2,3-dihydrobenzofuran-3-yl)(methyl)carbamate (100 mg, 0.36 mmol) in dichloromethane (1.00 mL). The mixture was stirred for 1 hour at −78° C. After completion of the reaction, it was quenched with ice water (5 mL), extracted with ethyl acetate (5 mL×2), and the combined organic layers were washed with saturated brine (5 mL), dried over anhydrous sodium sulfate, filtered, and the filtrate was concentrated to obtain the crude product. The crude product was purified by column chromatography (ethyl acetate:petroleum ether=20:80), yielding tert-butyl (S)-(6-(fluoromethyl)-2,3-dihydrobenzofuran-3-yl)(methyl) carbamate (80 mg, yield: 70%).

LCMS (ESI): 282 [M+H]+

Step 3: Synthesis of (S)-6-(fluoromethyl)-N-methyl-2,3-dihydrobenzofuran-3-amine The mixture of tert-butyl (S)-(6-(fluoromethyl)-2,3-dihydrobenzofuran-3-yl)(methyl)carbamate (80 mg, 0.36 mmol) and hydrochloric acid in dioxane (1 mL) was stirred at room temperature for 2 hours. After completion of the reaction, the reaction mixture was directly evaporated to obtain (S)-6-(fluoromethyl)-N-methyl-2,3-dihydrobenzofuran-3-amine (100 mg, crude product).

LCMS (ESI): 182 [M+H]+

Int. 73 Synthesis of (S)-3-(methylamino)-2,3-dihydrobenzofuran-6-carboxamide

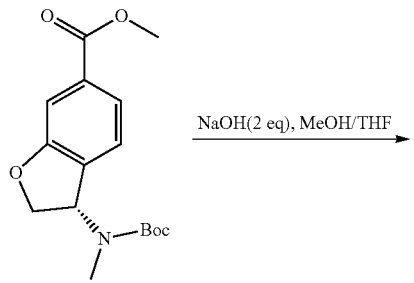

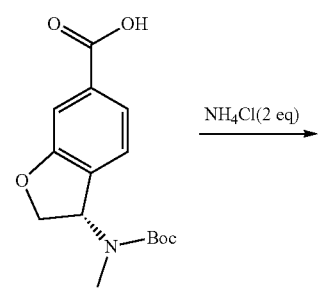

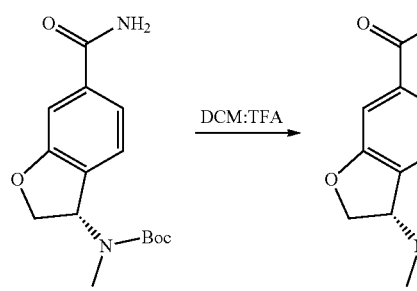

Step 1: Synthesis of (S)-3-((tert-butoxycarbonyl)(methyl)amino)-2,3-dihydrobenzofuran-6-carboxylic Acid At room temperature, the solution of methyl (S)-3-((tert-butoxycarbonyl)(methyl)amino)-2,3-dihydrobenzofuran-6-carboxylate (1 g, 3.25 mmol) in methanol (10.00 mL) and tetrahydrofuran (10.00 mL) was treated with sodium hydroxide (260 mg, 6.5 mmol). The reaction mixture was stirred for 1 hour at room temperature. After completion, the reaction solution was concentrated to yield a white (S)-3-((tert-butoxycarbonyl)(methyl)amino)-2,3-dihydrobenzofuran-6-carboxylic acid (600 mg, crude product).

LCMS (ESI): 294 [M+H]+

Step 2: Synthesis of tert-butyl (S)-(6-carbamoyl-2,3-dihydrobenzofuran-3-yl)(methyl)carbamate At room temperature, (S)-3-((tert-butoxycarbonyl)(methyl)amino)-2,3-dihydrobenzofuran-6-carboxylic acid (600 mg, 2.04 mmol) was dissolved in N,N-dimethylformamide (5.00 mL), followed by the addition of N,N,N',N'-Tetramethylchloroformamidinium-hexafluorophosphate (TCFH) (1.62 g, 4.38 mmol), N,N-diisopropylethylamine (1.38 g, 10.68 mmol), and ammonium chloride (360 mg, 6.78 mmol). The mixture was allowed to react at room temperature for 30 minutes. After completion, the reaction was diluted with ethyl acetate (30 mL) and water (30 mL). The aqueous layer was extracted with ethyl acetate (2×20 mL). The combined organic layers were washed with saturated brine (30 mL), dried over anhydrous sodium sulfate, concentrated, and yielded the crude product. The crude product was purified by flash column chromatography (ethyl acetate/petroleum ether=17%), providing tert-butyl (S)-(6-carbamoyl-2,3-dihydrobenzofuran-3-yl)(methyl)carbamate (240 mg, 40% yield), a yellow liquid.

LCMS (ESI): 293 [M+H]+

Step 3: Synthesis of (S)-3-(methylamino)-2,3-dihydrobenzofuran-6-carboxamide

At room temperature, tert-butyl (S)-(6-carbamoyl-2,3-dihydrobenzofuran-3-yl)(methyl)carbamate (240 mg, 0.82 mmol) was dissolved in dichloromethane (2.00 mL) and trifluoroacetic acid (0.40 mL). The mixture was stirred at room temperature for half an hour. After completion, the reaction solution was concentrated to yield a black solid (S)-3-(methylamino)-2,3-dihydrobenzofuran-6-carboxamide (100 mg, 66.66% yield).

In. 74 Synthesis of (S)—N³-methyl-2,3-dihydrobenzofuran-3,6-diamine

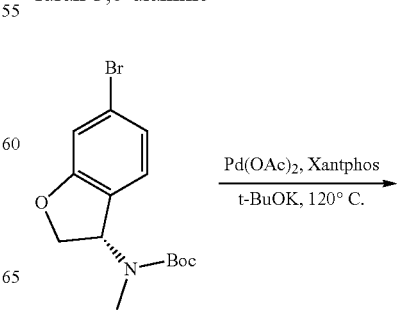

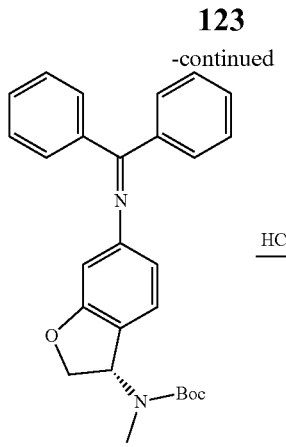
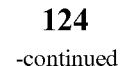

Step 1: Synthesis of tert-butyl (S)-(6-((diphenylmethylene)amino)-2,3-dihydrobenzofuran-3-yl)(methyl)carbamate At room temperature, tert-butyl (S)-(6-bromo-2,3-dihydrobenzofuran-3-yl)(methyl)carbamate (120 mg, 0.35 mmol) was dissolved in 1,4-dioxane (5.00 mL). To the solution, Benzophenone imine (190 mg, 1.06 mmol), potassium tert-butoxide (80 mg, 0.71 mmol), 4,5-Bis(diphenylphosphino)-9,9-diMethylxanthene, Xantphos (40 mg, 0.07 mmol), and palladium acetate (8 mg, 0.03 mmol) were added. The reaction was carried out at 100° C. for 2 hours. After completion, the reaction mixture was poured into water (2 mL), extracted with ethyl acetate (2 mL×2), and the combined organic layers were washed with saturated saline solution (2 mL), dried over anhydrous sodium sulfate, filtered, and the filtrate was concentrated. The crude product was purified by flash column chromatography (petroleum ether:ethyl acetate=10%) to yield the white solid tert-butyl (S)-(6-((diphenylmethylene)amino)-2,3-dihydrobenzofuran-3-yl)(methyl)carbamate (90 mg, 59% yield).

LCMS (ESI): 429 [M+H]+

Step 2: Synthesis of (S)—N³-methyl-2,3-dihydrobenzofuran-3,6-diamine

At room temperature, tert-butyl (S)-(6-((diphenylmethylene)amino)-2,3-dihydrobenzofuran-3-yl)(methyl)carbamate (90 mg, 0.21 mmol) was dissolved in hydrochloric acid-methanol solution (5.00 mL). The mixture was stirred at room temperature for 0.5 hours. After completion, the reaction solution was poured into a dichloromethane solution to precipitate a white solid, yielding (S)—N³-methyl-2,3-dihydrobenzofuran-3,6-diamine (60 mg, 90% yield).

LCMS (ESI): 165 [M+H]+

Int. 75 Synthesis of (S)-1,1,1-trifluoro-N-(3-(methylamino)-2,3-dihydrobenzofuran-6-yl)methanesulfonamide

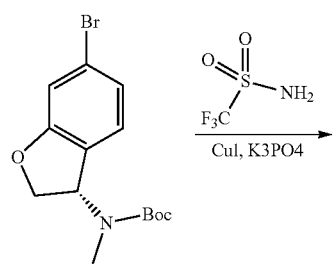

Step 1: Synthesis of tert-butyl (S)-methyl(6-((trifluoromethyl)sulfonamido)-2,3-dihydrobenzofuran-3-yl)carbamate tert-butyl (S)-(6-bromo-2,3-dihydrobenzofuran-3-yl)(methyl)carbamate (200 mg, 0.61 mmol), trifluoromethanesulfonyl amide (136 mg, 0.91 mmol), cuprous iodide (1.16 g, 6.09 mmol), and potassium phosphate (259 mg, 1.22 mmol) were successively dissolved in N,N-dimethylformamide (9 mL) solution. The mixture was stirred at 90° C. for 2 hours. After completion, the system was cooled to room temperature, extracted three times with ethyl acetate (10 mL each). The organic phases were combined, washed with saturated brine (10 mL, 3 times), dried over anhydrous sodium sulfate, and filtered. The filtrate was concentrated under vacuum to obtain tert-butyl (S)-methyl(6-((trifluoromethyl)sulfonamido)-2,3-dihydrobenzofuran-3-yl)carbamate (800 mg, 51.85% yield) as a yellow liquid.

LCMS (ESI): 397.2 [M+H]+

Step 2: Synthesis of (S)-1,1,1-trifluoro-N-(3-(methylamino)-2,3-dihydrobenzofuran-6-yl)methanesulfonamide tert-butyl (S)-methyl(6-((trifluoromethyl)sulfonamido)-2,3-dihydrobenzofuran-3-yl)carbamate (80 mg, 3.246 mmol) was dissolved in a solution of hydrogen chloride in 1,4-dioxane (4.0 M, 5 mL). The mixture was stirred at room temperature for 2 hours. After completion of the reaction, the system was cooled to room temperature, and the reaction mixture was concentrated under vacuum to obtain (S)-1,1,1-trifluoro-N-(3-(methylamino)-2,3-dihydrobenzofuran-6-yl)methanesulfonamide (60 mg, 1.18 mmol, yield: 82.46%).

Int. 76 Synthesis of 4-aminoimidazo[1,5-a]quinoxaline-8-carboxylic Acid

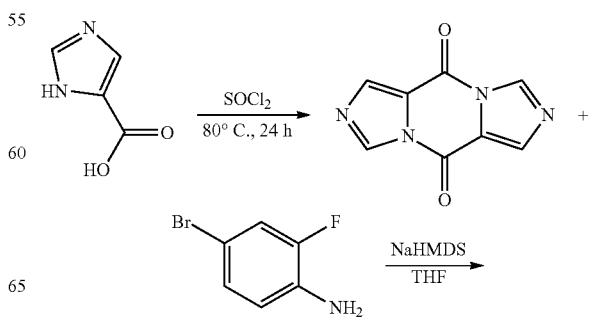

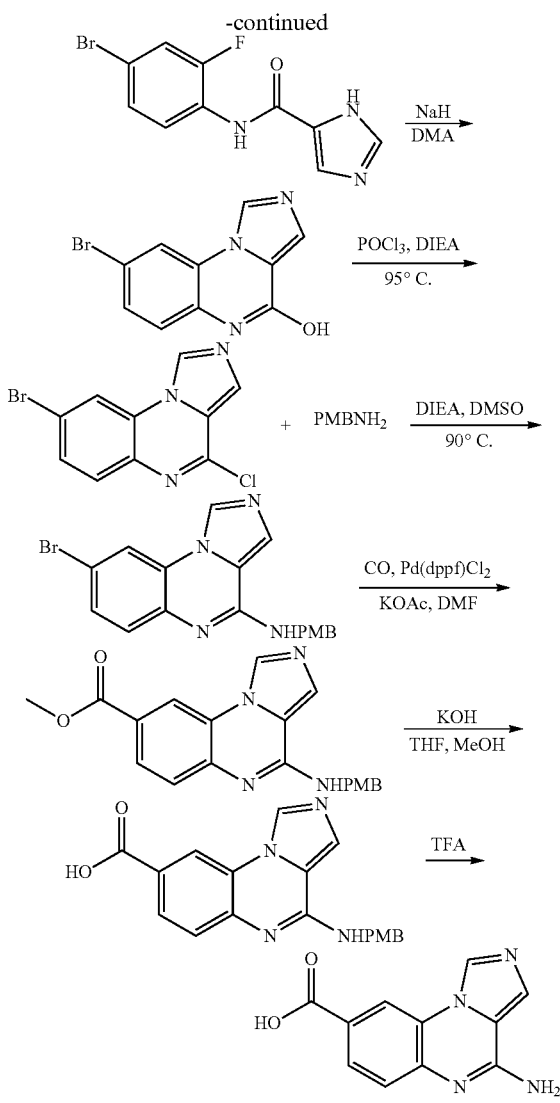

Step 1: Synthesis of 5H,10H-diimidazo[1,5-a:1'5'-d]pyrazine-5,10-dione

Imidazo-5-carboxylic acid (100 g, 892.14 mmol) was added to sulfurous dichloride (500 mL) and stirred at 80° C. for 12 hours. The mixture was concentrated, and the concentrated solution was washed with toluene (500 mL×2), filtered to obtain a solid product. After removing the residual solvent under vacuum, 5H,10H-diimidazo[1,5-a:1',5'-d]pyrazine-5,10-dione (70 g, 0.37 mol, yield: 42%) was obtained as a yellow solid.

LCMS (ESI) m/z: 189[M+H]$^+$

Step 2: Synthesis of N-(4-bromo-2-fluorophenyl)-1H-imidazole-5-carboxamide

At 0° C., a solution of 4-bromo-2-fluorophenylamine (60.60 g, 318.91 mmol) in tetrahydrofuran (600 mL) was slowly added dropwise to a mixture of Sodium bis(trimethylsilyl)amide (318.91 mL, 637.82 mmol, 2 mol/L) over 1 hour. Then, 5H,10H-diimidazo[1,5-a:1',5'-d]pyrazine-5,10-dione (60 g, 318.91 mmol) was added, and the mixture was stirred at room temperature for 12 hours. The reaction mixture was then poured into water, filtered, and the crude product was purified by silica gel column chromatography (petroleum ether:ethyl acetate=40%) to obtain N-(4-bromo-2-fluorophenyl)-1H-imidazole-5-carboxamide (60 g, 0.21 mol, yield: 66%), as a white solid.

LCMS (ESI) m/z: 284.2[M+H]$^+$

Step 3: Synthesis of 8-bromoimidazo[1,5-a]quinoxalin-4-ol

N-(4-bromo-2-fluorophenyl)-1H-imidazole-5-carboxamide (60 g, 211.20 mmol) and sodium hydride (16.88 g, 422.40 mmol, 60% dispersion) were stirred in dimethylacetamide (600 mL) at 140° C. for 12 hours. The mixture was then poured into water, filtered to obtain 8-bromoimidazo[1,5-a]quinoxalin-4-ol (50 g, yield: 90%), as a yellow solid.

LCMS (ESI) m/z: 264.2[M+H]$^+$

Step 4: Synthesis of 8-bromo-4-chloroimidazo[1,5-a]quinoxaline

To the mixture of 8-bromoimidazo[1,5-a]quinoxalin-4-ol (50 g, 189.34 mmol) and N,N-diisopropylethylamine (48.85 g, 378.67 mmol), phosphorous oxychloride (500 mL) was added. The mixture was stirred at 90° C. for 2 hours, then concentrated. The residue was dissolved in acetonitrile, slowly added to ice water, resulting in the precipitation of a solid. Filtration yielded 8-bromo-4-chloroimidazo[1,5-a]quinoxaline (50 g, yield: 93%).

LCMS (ESI) m/z: 282.2[M+H]$^+$.

Step 5: Synthesis of 8-bromo-N-(4-methoxybenzyl)imidazo[1,5-a]quinoxalin-4-amine To the mixture of 8-bromo-4-chloroimidazo[1,5-a]quinoxaline (50 g, 176.98 mmol) and 4-methoxybenzylamine (29.13 g, 212.38 mmol) in dimethyl sulfoxide (500 mL), N,N-diisopropylethylamine (45.66 g, 353.96 mmol) was added. The mixture was stirred at 80° C. for 2 hours, then poured into water. Filtration yielded a yellow oily substance, 8-bromo-N-(4-methoxybenzyl)imidazo[1,5-a]quinoxalin-4-amine (50 g, yield: 74%).

LCMS (ESI) m/z: 383.2[M+H]$^+$

Step 6: synthesis of Methyl 4-((4-methoxybenzyl)amino)imidazo[1,5-a]quinoxaline-8-carboxylate 8-bromo-N-(4-methoxybenzyl)imidazo[1,5-a]quinoxalin-4-amine (50 g, 130.47 mmol), [1,1'-bis(diphenylphosphino)ferrocene]dichloropalladium (10.83 g, 13.05 mmol), and potassium acetate (25.57 g, 260.93 mmol) were successively added to a solution of dimethylformamide (50 mL) and methanol (250 mL). The system was reacted at 100° C. under a carbon monoxide atmosphere (4 MPa) for 12 hours, then poured into water and filtered. Purification by silica gel chromatography (petroleum ether:ethyl acetate=80%) yielded Methyl 4-((4-methoxybenzyl)amino)imidazo[1,5-a]quinoxaline-8-carboxylate (30 g, yield: 63%), as a yellow solid.

LCMS (ESI) m/z: 363.2 [M+H]$^+$

Step 7 Synthesis of 4-((4-methoxybenzyl)amino)imidazo[1,5-a]quinoxaline-8-carboxylic Acid Methyl 4-((4-methoxybenzyl)amino)imidazo[1,5-a]quinoxaline-8-carboxylate (30 g, 82.87 mmol) was added to a mixture of methanol, water, and tetrahydrofuran (1:1:1, 150 mL), along with potassium hydroxide (92.40 g, 165.0 mmol). The reaction proceeded at 60° C. for 12 hours, and after vacuum concentration to remove the organic solvent, the residue was poured into water. Then the pH was adjusted to 7-8 with HCl (2 M), followed by extraction with ethyl acetate (100 mL×3) and vacuum concentration, yielded 4-((4-methoxybenzyl)amino)imidazo[1,5-a]quinoxaline-8-carboxylic acid (25 g, yield: 86%).
LCMS (ESI) m/z: 349.2 [M+H]$^+$
LCMS (ESI) m/z: 229.2 [M+H]$^+$ Step 8: Synthesis of 4-aminoimidazo[1,5-a]quinoxaline-8-carboxylic Acid At room temperature, 4-((4-methoxybenzyl)amino)imidazo[1,5-a]quinoxaline-8-carboxylic acid (100.0 mg, 0.28 mmol) was dissolved in trifluoroacetic acid (2 mL). The mixture was stirred at 100° C. for 2 hours, and the reaction was monitored by LCMS. The reaction mixture was concentrated to yield 4-aminoimidazo[1,5-a]quinoxaline-8-carboxylic acid (60.0 mg, yield: 94%), as a white solid.

Using the methods and steps employed for Intermediate 76, with only the replacement of the corresponding raw materials, the following intermediates were synthesized:

| Int. No. | Structure | Name | m/z (ESI): (M + H)$^+$ |
|---|---|---|---|
| 77 | 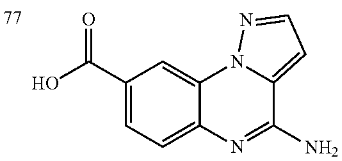 | 4-aminopyrazolo[1,5-a]quinoxaline-8-carboxylic acid | 229.2 |
| 78 | 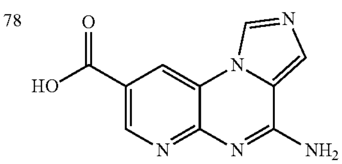 | 4-aminoimidazo[1,5-a]pyrido[2,3-e]pyrazine-8-carboxylic acid | 230.2 |
| 79 | 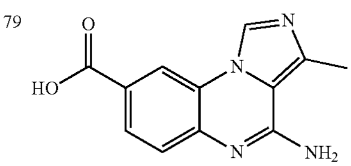 | 4-amino-3-methylimidazo[1,5-a]quinoxaline-8-carboxylic acid | 243.2 |
| 80 | 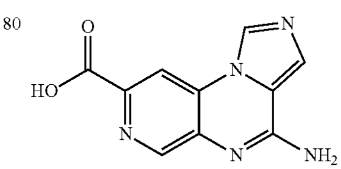 | 4-aminoimidazo[1,5-a]pyrido[3,4-e]pyrazine-8-carboxylic acid | 230.2 |
| 81 | 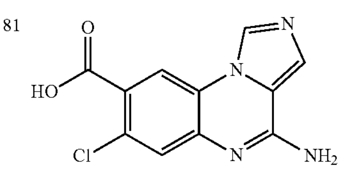 | 4-amino-7-chloroimidazo[1,5-a]quinoxaline-8-carboxylic acid | 263.2 |
| 82 | 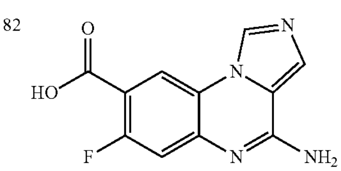 | 4-amino-7-fluoroimidazo[1,5-a]quinoxaline-8-carboxylic acid | 247.2 |
| 83 | 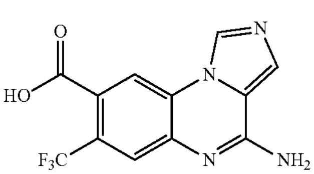 | 4-amino-7-(trifluoromethyl)imidazo[1,5-a]quinoxaline-8-carboxylic acid | 297.2 |

Int. 84 Synthesis of 4-amino-1-methylimidazo[1,5-a]quinoxaline-8-carboxylic Acid

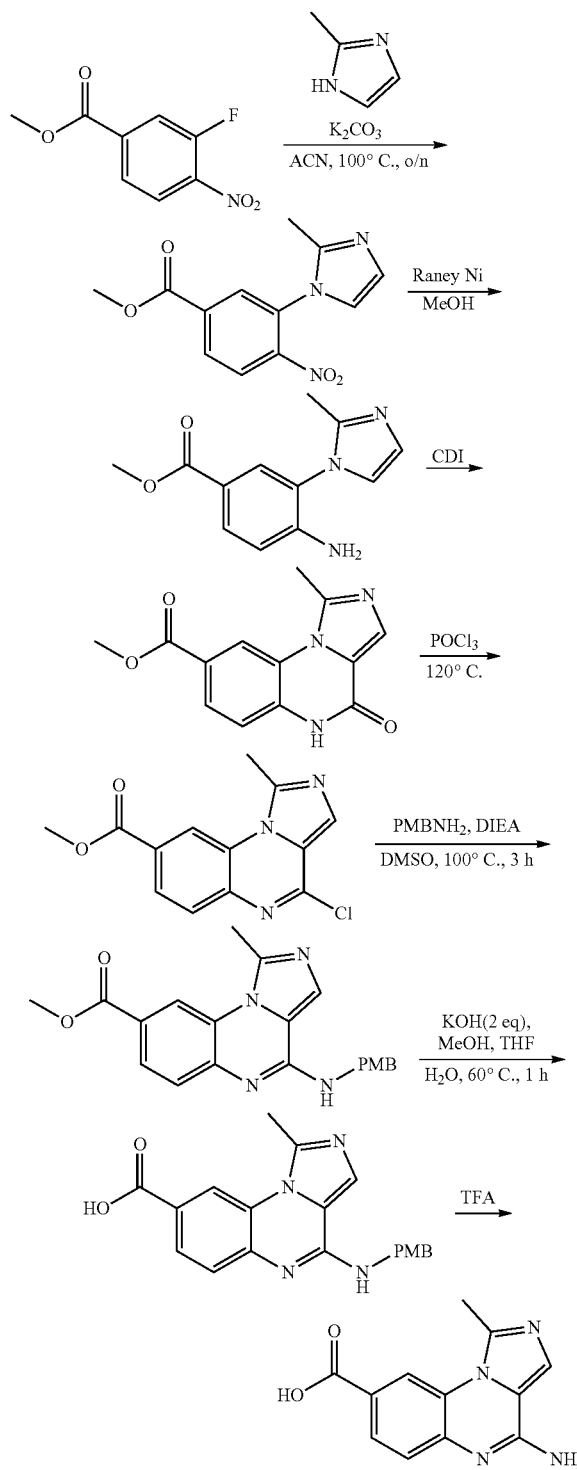

Step 1: Synthesis of methyl 3-(2-methyl-1H-imidazol-1-yl)-4-nitrobenzoate

Methyl 3-fluoro-4-nitrobenzoate (20.0 g, 100 mmol) was dissolved in acetonitrile (100 mL), followed by the addition of 2-methyl-1H-imidazole (8.2 g, 100 mmol) and potassium carbonate (27.6 g, 200 mmol). The mixture was stirred at 100° C. for 12 hours, and the reaction progress was monitored by liquid chromatography-mass spectrometry (LCMS). The reaction mixture was poured into 300 mL water, and then extracted with ethyl acetate (200 mL×3). The combined organic phase was dried over anhydrous sodium sulfate, and the organic phase was concentrated under vacuum and the residues undegone further purification by silica gel column chromatography (petroleum ether:ethyl acetate=10%) to yield the yellow solid Synthesis of methyl 3-(2-methyl-1H-imidazol-1-yl)-4-nitrobenzoate (25.0 g, yield: 95%).

LCMS (ESI) m/z: 262 [M+H]$^+$

Step 2: Synthesis of methyl 4-amino-3-(2-methyl-1H-imidazol-1-yl)benzoate

At room temperature, 3-(2-methyl-1H-imidazol-1-yl)-4-nitrobenzoate (25 g, 95.8 mmol) was dissolved in methanol (300 mL), and then Raney Nickel (2 g) was added. The mixture was stirred for 12 hours under a hydrogen atmosphere at room temperature. The reaction was monitored by LCMS. The residue was filtered, and the filtrate was concentrated and purified by silica gel column chromatography (petroleum ether:ethyl acetate=20%) to yield the yellow solid methyl 4-amino-3-(2-methyl-1H-imidazol-1-yl)benzoate (20.5 g, yield: 93%).

LCMS (ESI) m/z: 232 [M+H]$^+$

Step 3: Synthesis of methyl 1-methyl-4-oxo-4,5-dihydroimidazo[1,5-a]quinoxaline-8-carboxylate At room temperature, methyl 4-amino-3-(2-methyl-1H-imidazol-1-yl)benzoate (2.0 g, 8.7 mmol) was dissolved in o-dichlorobenzene (40 mL), and then carbonyldiimidazole (2.8 g, 17.4 mmol) was added. The mixture was stirred for 12 hours at 180° C. The reaction was monitored by liquid chromatography-mass spectrometry (LCMS). The mixture was filtered to obtain a filter cake, and the filter cake was slurried with ethyl acetate (5 mL) to yield the black solid methyl 1-methyl-4-oxo-4,5-dihydroimidazo[1,5-a]quinoxaline-8-carboxylate (920.0 mg, yield: 41%).

LCMS (ESI) m/z: 258 [M+H]$^+$

Step 4: Synthesis of methyl 4-chloro-1-methylimidazo[1,5-a]quinoxaline-8-carboxylate At room temperature, methyl 1-methyl-4-oxo-4,5-dihydroimidazo[1,5-a]quinoxaline-8-carboxylate (100.0 mg, 0.39 mmol) was dissolved in Phosphorus oxychloride (5 mL), and the mixture was stirred for 4 hours at 120° C. The reaction was monitored by liquid chromatography-mass spectrometry (LCMS). The reaction mixture was concentrated under reduced pressure, diluted with a small amount of acetonitrile, poured into water (5 mL), filtered, and the filter cake was washed with water. The resulting solid, methyl 4-chloro-1-methylimidazo[1,5-a]quinoxaline-8-carboxylate (60.0 mg, yield: 56%), was obtained as a black solid.

LCMS (ESI) m/z: 276 [M+H]$^+$

Step 5: Synthesis of methyl 4-((4-methoxybenzyl)amino)-1-methylimidazo[1,5-a]quinoxaline-8-carboxylate At room temperature, methyl 4-chloro-1-methylimidazo[1,5-a]quinoxaline-8-carboxylate (60 mg, 0.22 mmol) was dissolved in dimethyl sulfoxide (2 mL), followed by the addition of (4-methoxyphenyl)methanamine (60 mg, 0.44 mmol) and N,N-diisopropylethylamine (67 mg, 0.52 mmol). The mixture was stirred for 1 hour at 100° C. The reaction was monitored by liquid chromatography-mass spectrometry (LCMS). The reaction mixture was poured into water (10 mL), extracted with ethyl acetate (10 mL×3). Then the combined organic phase was dried over anhydrous sodium sulfate, and the organic phase was concentrated and purified by silica gel chromatography (petroleum ether:ethyl acetate=40%) to obtain the black solid of methyl 4-((4-methoxybenzyl)amino)-1-methylimidazo[1,5-a]quinoxaline-8-carboxylate (60 mg, yield: 73%).

LCMS (ESI) m/z: 377 [M+H]$^+$

Step 6: Synthesis of 4-((4-methoxybenzyl)amino)-1-methylimidazo[1,5-a]quinoxaline-8-carboxylic acid At room temperature, methyl 4-((4-methoxybenzyl)amino)-1-methylimidazo[1,5-a]quinoxaline-8-carboxylate (60 mg, 0.16 mmol) was dissolved in methanol (1 mL), tetrahydrofuran (1 mL), and water (1 mL), then potassium hydroxide (26 mg, 0.44 mmol) was added. The mixture was stirred for 1 hour at room temperature. The reaction progress was monitored by liquid chromatography-mass spectrometry (LCMS). The reaction mixture was poured into water (10 mL), then carefully adjusted to acidic pH with formic acid, extracted with ethyl acetate (10 mL×3), the combined organic phase was dried over anhydrous sodium sulfate, and the organic phase was concentrated to obtain the white solid of 4-((4-methoxybenzyl)amino)-1-methylimidazo[1,5-a]quinoxaline-8-carboxylic acid (50 mg, yield: 86%).

LCMS (ESI) m/z: 363 [M+H]$^+$
LCMS (ESI) m/z: 243 [M+H]$^+$

Step 7: Synthesis of 4-amino-1-methylimidazo[1,5-a]quinoxaline-8-carboxylic Acid The solution of 4-((4-methoxybenzyl)amino)-1-methylimidazo[1,5-a]quinoxaline-8-carboxylic acid (400 mg, 1.10 mmol) in trifluoroacetic acid (5.00 mL) was stirred at 90° C. for 2 hours. The reaction solution was then vacuum-concentrated to obtain 4-amino-1-methylimidazo[1,5-a]quinoxaline-8-carboxylic acid (250 mg, yield: 94%).

Int. 85 Synthesis of 4-amino-7-cyanoimidazo[1,5-a]quinoxaline-8-carboxylic Acid

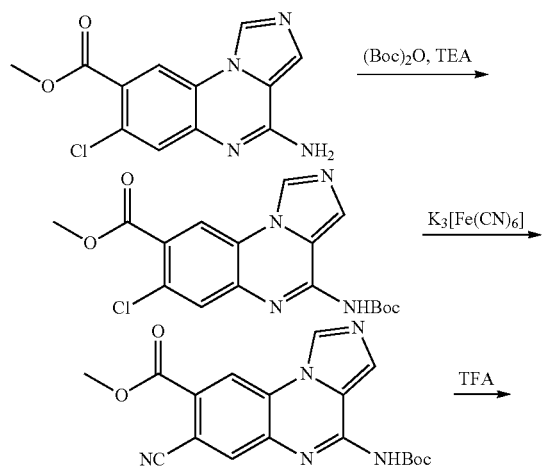

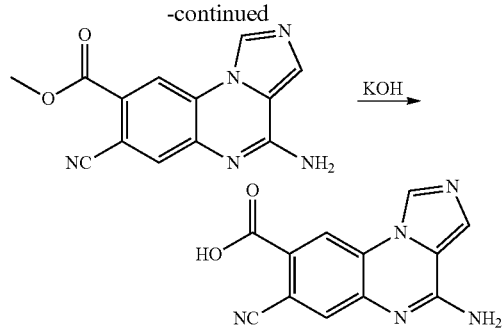

Step 1: Synthesis of Methyl 4-((tert-butoxycarbonyl)amino)-7-chloroimidazo[1,5-a]quinoxaline-8-carboxylate The solution of methyl 4-amino-7-chloroimidazo[1,5-a]quinoxaline-8-carboxylate (1.20 g, 4.34 mmol), di-tert-butyl dicarbonate (1.89 g, 8.67 mmol), and triethylamine (1.30 g, 13.01 mmol) in dichloromethane (10 mL) was stirred at room temperature for 2 hours. After completion of the reaction, the mixture was poured into water (5 mL), extracted with ethyl acetate (5 mL), dried over anhydrous sodium sulfate, and filtered. The solution was then concentrated and purified by column chromatography (petroleum ether:ethyl acetate=70:30) to yield 4-((tert-butoxycarbonyl)amino)-7-chloroimidazo[1,5-a]quinoxaline-8-carboxylate (1.00 g, 61% yield), a white solid.

LCMS (ESI): 376 [M+H]$^+$

Step 2: Synthesis of methyl 4-((tert-butoxycarbonyl)amino)-7-cyanoimidazo[1,5-a]quinoxaline-8-carboxylate Under a nitrogen atmosphere, a mixture of 4-((tert-butoxycarbonyl)amino)-7-chloroimidazo[1,5-a]quinoxaline-8-carboxylate (0.20 g, 0.53 mmol), potassium ferricyanide (0.05 g, 0.16 mmol), 2-Di-tert-butylphosphino-2',4',6'-triisopropylbiphenyl (0.09 g, 0.21 mmol), 2'-(Amino)[1,1'-biphenyl]-2-yl][bis(1,1-dimethylethyl)[2',4',6'-tris(1-methylethyl)[1,1'-biphenyl]-2-yl]phosphine](methanesulfonato) palladium (0.17 g, 0.21 mmol), and potassium acetate (0.01 g, 0.07 mmol) in 1,4-dioxane/water (4.00 mL) was stirred at 100° C. for 2 hours under reflux. The mixture was then concentrated and purified by column chromatography (petroleum ether:ethyl acetate=70:30) to yield methyl 4-((tert-butoxycarbonyl)amino)-7-cyanoimidazo[1,5-a]quinoxaline-8-carboxylate (0.10 g, 51%) as a white solid.

LCMS (ESI): 368[M+H]$^+$

Step 3: Synthesis of methyl 4-amino-7-cyanoimidazo[1,5-a]quinoxaline-8-carboxylate Trifluoroacetic acid (0.10 mL) was added to a solution of 4-((tert-butoxycarbonyl)amino)-7-cyanoimidazo[1,5-a]quinoxaline-8-carboxylate (0.20 g, 0.54 mmol) in dichloromethane (0.50 mL). The reaction mixture was stirred at room temperature for 2 hours, then concentrated to yield methyl 4-amino-7-cyanoimidazo[1,5-a]quinoxaline-8-carboxylate (0.05 g, crude product)

LCMS (ESI): 268[M+H]$^+$

Step 4: Synthesis of 4-amino-7-cyanoimidazo[1,5-a]quinoxaline-8-carboxylic acid A mixture of methyl 4-amino-7-cyanoimidazo[1,5-a]quinoxaline-8-carboxylate (0.20 g, 0.75 mmol), potassium hydroxide (0.07 g, 1.50 mmol) and the mixture of tetrahydrofuran/methanol/water (1 mL/1 mL/1 mL), was stirred at room temperature for 2 hours. After completion of the reaction, the system was concentrated to obtain the crude product, 4-amino-7-cyanoimidazo[1,5-a]quinoxaline-8-carboxylic acid (210 mg, crude product). The crude product is used directly in the next step without purification.

LCMS (ESI): 254[M+H]$^+$

Int. 86 Synthesis of 4-amino-7-methylimidazo[1,5-a]quinoxaline-8-carboxylic Acid

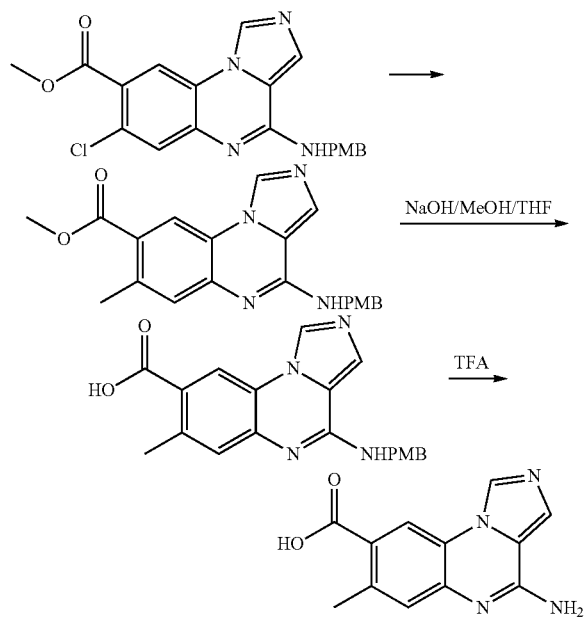

Step 1: Synthesis of methyl 4-((4-methoxybenzyl)amino)-7-methylimidazo[1,5-a]quinoxaline-8-carboxylate A mixture of methyl 7-chloro-4-((4-methoxybenzyl)amino)imidazo[1,5-a]quinoxaline-8-carboxylate (200 mg, 0.5 mmol), potassium carbonate (300 mg, 2 mmol), 1,1'-Bis(di-t-butylphosphino)ferrocene palladium dichloride (0.08 g, 0.1 mmol), and Trimethylboroxine (0.01 g, 0.10 mmol) in 1,2-dimethoxyethane (2.00 mL) was stirred at 100° C. for 12 hours, then poured into water, extracted with ethyl acetate (5 mL), dried over anhydrous sodium sulfate, filtered, and purified by column chromatography (petroleum ether:ethyl acetate=30%) to yield methyl 4-((4-methoxybenzyl)amino)-7-methylimidazo[1,5-a]quinoxaline-8-carboxylate (100 mg, 53%).

LCMS (ESI): 268 [M+H]$^+$

Step 2: Synthesis of 4-((4-methoxybenzyl)amino)-7-methylimidazo[1,5-a]quinoxaline-8-carboxylic Acid Methyl 4-((4-methoxybenzyl)amino)-7-methylimidazo[1,5-a]quinoxaline-8-carboxylate (500 mg, 1.86 mmol) was dissolved in a solvent mixture of methanol:tetrahydrofuran:saturated aqueous potassium hydroxide solution (1 mL: 1 mL: 1 mL). The reaction mixture proceeded at 60° C. for 12 hours, then evaporate to dryness. The pH was adjusted to 3 with formic acid, filtered to obtain 4-((4-methoxybenzyl)amino)-7-methylimidazo[1,5-a]quinoxaline-8-carboxylic acid (52 mg, 12% yield).

LCMS (ESI): 363 [M+H]$^+$

Step 3: Synthesis of 4-amino-7-methylimidazo[1,5-a]quinoxaline-8-carboxylic Acid 4-((4-methoxybenzyl)amino)-7-methylimidazo[1,5-a]quinoxaline-8-carboxylic acid (500 mg, 1.86 mmol) was dissolved in trifluoroacetic acid (5 mL). The reaction mixture was stirred at 100° C. for 12 hours. After completion, the reaction system was evaporated to dryness to obtain 4-amino-7-methylimidazo[1,5-a]quinoxaline-8-carboxylic acid (520 mg, crude product).

LCMS (ESI): 363 [M+H]$^+$

By employing the method used in the third step for Intermediate 86, the following intermediate acids were prepared:

| Int. No. | Structure | Name | m/z (ESI): (M + H)$^+$ |
|---|---|---|---|
| 87 | 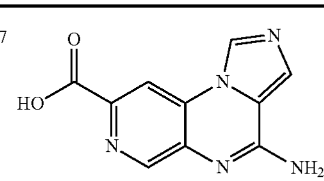 | 4-aminoimidazo[1,5-a]pyrido[3,4-e]pyrazine-8-carboxylic acid | 230.1 |
| 88 | 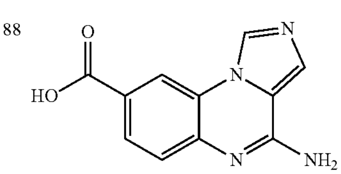 | 4-aminoimidazo[1,5-a]quinoxaline-8-carboxylic acid | 229.1 |

| Int. No. | Structure | Name | m/z (ESI): (M + H)+ |
|---|---|---|---|
| 89 | 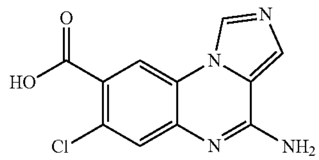 [SMILES: Nc1nc2cc(F)c(C(=O)O)cc2n2cncc12] | 4-amino-7-chloroimidazo[1,5-a]quinoxaline-8-carboxylic acid | 263.1 |
| 90 | 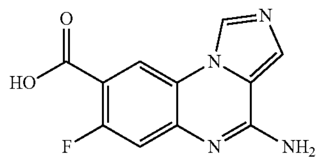 | 4-amino-7-fluoroimidazo[1,5-a]quinoxaline-8-carboxylic acid | 247.1 |
| 91 | 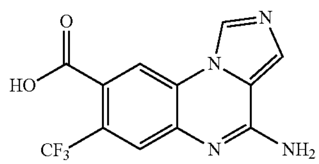 [SMILES: Nc1nc2cc(Cl)c(C(=O)O)cc2n2cncc12] | 4-amino-7-(trifluoromethyl)imidazo[1,5-a]quinoxaline-8-carboxylic acid | 297.1 |
| 92 | 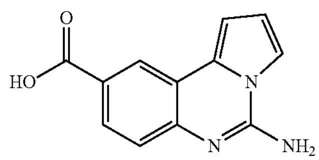 [SMILES: Nc1nc2ccc(C(=O)O)cc2c2cccn12] | 5-aminopyrrolo[1,2-c]quinazoline-9-carboxylic acid | 228.1 |

Int. 93 4-amino-[1,2,4]triazolo[4,3-a]quinoxaline-8-carboxylic Acid

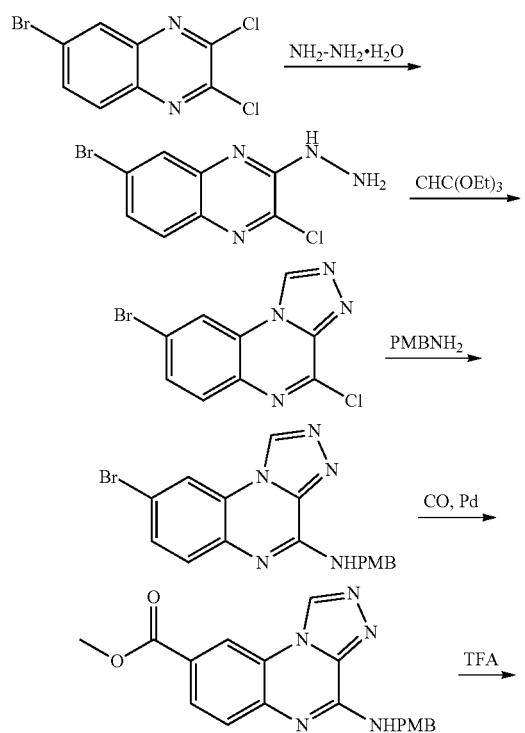

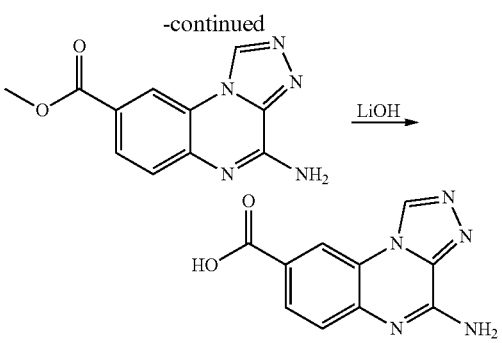

Step 1: Synthesis of 6-bromo-2-chloro-3-hydrazineylquinoxaline

At room temperature, 6-bromo-2,3-dichloroquinoxaline (278.0 mg, 1.0 mmol) was firstly added into a 25 mL single-neck flask. Then hydrazine hydrate (156 mg, 2.5 mmol, 80% wt) was added. After completion, the reaction proceeded overnight at room temperature. After the reaction was complete, the reaction was filtered to obtain a filter cake and the filter cake was washed with water (10 mL×2), washed with ethyl acetate (5 mL×2) to obtain 6-bromo-2-chloro-3-hydrazineylquinoxaline (150 mg).

LCMS (ESI) m/z: 273.0/275.0 [M+H]+

Step 2: Synthesis of 8-bromo-4-chloro-[1,2,4]triazolo[4,3-a]quinoxaline

At room temperature, 6-bromo-2-chloro-3-hydrazineylquinoxaline (116.0 mg, 0.5 mmol) was added into a 25 mL single-neck flask. Then triethyl orthoformate (4.0 mL) was added. Then the reaction was heated to 100° C., and proceeded for 1 hour at this temperature. When reaction was complete indicated by LCMS, the reaction was cooled to room temperature, then filtered to get a filter cake. The filter cake was washed with methanol (3.0 mL×3), then dried to obtain 8-bromo-4-chloro-[1,2,4]triazolo[4,3-a]quinoxaline (110 mg).

$^1$H NMR (400 MHz, CDCl$_3$) δ 10.21 (s, 1H), 8.84 (d, 1H), 7.98 (d, 1H), 7.90 (dd, 1H).

Step 3: Synthesis of 8-bromo-N-(4-methoxybenzyl)-[1,2,4]triazolo[4,3-a]quinoxalin-4-amine 8-bromo-4-chloro-[1,2,4]triazolo[4,3-a]quinoxaline (1.70 g, 6.00 mmol) was dissolved in DMSO (15.0 mL), then benzylamine (1.23 g, 9.00 mmol) and DIEA (2.32 g, 18.00 mmol) were added successively. The reaction system proceeded at 90° C. for 4 hours. After completion, water (60 mL) was added, then extracted with ethyl acetate (40 mL×3), dried with sodium sulfate, filtered, and concentrated to obtain the crude product, 8-bromo-N-(4-methoxybenzyl)-[1,2,4]triazolo[4,3-a]quinoxalin-4-amine (2.20 g).

LCMS (ESI) m/z: 384.1/386.1 [M+H]$^+$

Step 4: Methyl 4-((4-methoxybenzyl)amino)-[1,2,4]triazolo[4,3-a]quinoxaline-8-carboxylate Potassium acetate (1.7 g, 17.2 mmol) and Pd(dppf)Cl2 (420 mg, 0.57 mmol) were successively added to a solution of 8-bromo-N-(4-methoxybenzyl)-[1,2,4]triazolo[4,3-a]quinoxalin-4-amine (2.2 g, 5.74 mmol) in MeOH (30 mL) and DMF (30 mL). Under a CO atmosphere, the mixture was stirred at 100° C. for 12 hours. After removing methanol, 100 mL of water was added, extracted with ethyl acetate (50 mL×3). Then the organic phase was combined, dried over anhydrous Na2SO$_4$, and concentrated to obtain the crude product. The crude product was slurried in ethyl acetate (20 mL) to obtain Methyl 4-((4-methoxybenzyl)amino)-[1,2,4]triazolo[4,3-a]quinoxaline-8-carboxylate (1.1 g, yield: 53%).

LCMS (ESI) m/z: 364.2[M+H]$^+$

Step 5: Synthesis of methyl 4-amino-[1,2,4]triazolo[4,3-a]quinoxaline-8-carboxylate Methyl 4-((4-methoxybenzyl)amino)-[1,2,4]triazolo[4,3-a]quinoxaline-8-carboxylate (300.0 mg, 0.78 mmol) was added into a 25 mL single-neck flask followed by addition of TFA (5.0 mL). The reaction system was heated to 80° C., and stirred for 16 hours at this temperature. After the reaction was complete, the reaction mixture was evaporated to obtain the crude product, methyl 4-amino-[1,2,4]triazolo[4,3-a]quinoxaline-8-carboxylate (190 mg).

LCMS (ESI) m/z: 244.3 [M+H]$^+$

Step 6: Synthesis of 4-amino-[1,2,4]triazolo[4,3-a]quinoxaline-8-carboxylic Acid methyl 4-amino-[1,2,4]triazolo[4,3-a]quinoxaline-8-carboxylate was dissolved in THF (5 ml) and methanol (5.0 ml). The pH was adjusted to 7 using a 3M potassium hydroxide solution followed by addition of lithium hydroxide (65.0 mg, 1.56 mmol). The reaction proceeded at 50° C. for 16 hours. After the reaction was complete, methanol and THF were evaporated from the system, and the pH was adjust to 6.5 with 1M hydrochloric acid. The mixture was filtered to get a filter cake and the filter cake was washed with water (5.0 mL×3), dried to obtain the crude product, 4-amino-[1,2,4]triazolo[4,3-a]quinoxaline-8-carboxylic acid (120 mg).

LCMS (ESI) m/z: 230.1 [M+H]$^+$

Int. 94 Synthesis of 5-aminoimidazo[1,5-c]quinazoline-9-carboxylic Acid

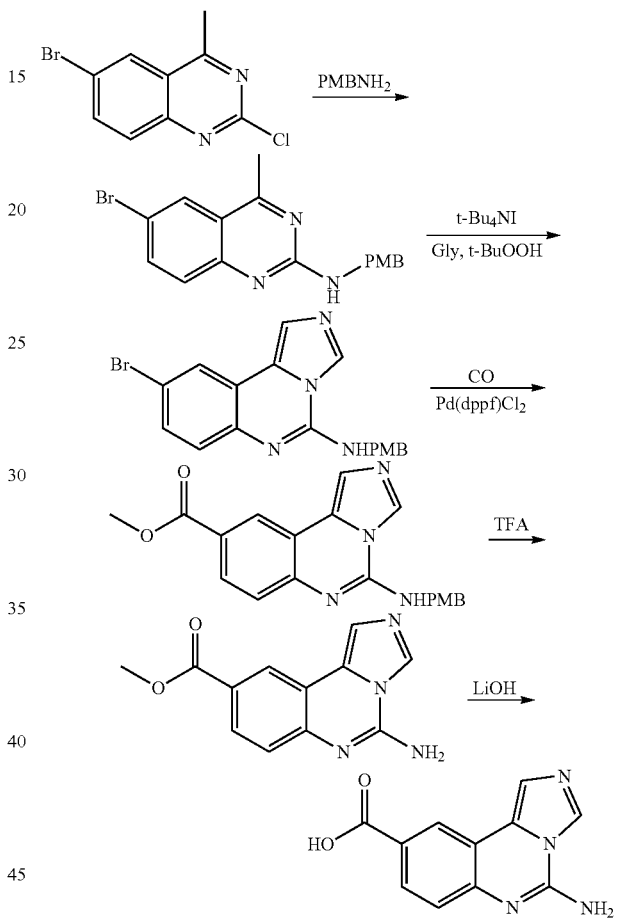

Step 1: Synthesis of 6-bromo-N-(4-methoxybenzyl)-4-methylquinazolin-2-amine

At room temperature, 6-bromo-2-chloro-4-methylquinazoline (0.5 g, 1.942 mmol) was dissolved in DMSO (15 mL) followed by addition of DIEA (768 mg, 5.825 mmol) and 4-methoxybenzylamine (600 mg, 3.883 mmol). The reaction mixture proceeded at room temperature for 16 hours. Then water (50 mL) was added, and extracted with ethyl acetate (20 mL×3). The organic phase was combined and dried over anhydrous sodium sulfate, filtered. The filtrate was concentrated under reduced pressure and the residue was further purified by column chromatography (0-10% methanol/dichloromethane) to obtain 6-bromo-N-(4-methoxybenzyl)-4-methylquinazolin-2-amine (500 mg, yield: 72%).

LCMS (ESI) m/z: 359.2[M+H]$^+$

Step 2: Synthesis of 9-bromo-N-(4-methoxybenzyl) imidazo[1,5-c]quinazolin-5-amine At room temperature, 6-bromo-N-(4-methoxybenzyl)-4-methylquinazolin-2-amine (0.5 g, 1.396 mmol) was dissolved in DMSO (20 mL). Glycine (211 mg, 2.792 mmol), tert-butanol hydrogen peroxide (719 mg, 5.583 mmol), tetrabutylammonium iodide (104 mg, 0.2792 mmol), and acetic acid (251 mg, 4.187 mmol) were added successively. The reaction mixture was stirred at 90° C. under nitrogen protection for 16 hours. After the reaction was complete, water (60 mL) was added, followed by extraction with ethyl acetate (30 mL×3). The organic phases were combined, dried over anhydrous sodium sulfate, filtered, and the filtrate was concentrated under reduced pressure. The product was purified by column chromatography (0-10% methanol/dichloromethane) to yield 9-bromo-N-(4-methoxybenzyl)imidazo[1,5-c]quinazolin-5-amine (300 mg, yield: 56%).

LCMS (ESI) m/z: 384.2 [M+H]$^+$

Step 3 Synthesis of methyl 5-((4-methoxybenzyl)amino)imidazo[1,5-c]quinazoline-9-carboxylate At room temperature, 9-bromo-N-(4-methoxybenzyl)imidazo[1,5-c]quinazolin-5-amine (300 mg, 0.785 mmol) was dissolved in a solution of MeOH (10 mL) and DMF (10 mL). Potassium acetate (230 mg, 2.36 mmol) and Pd(dppf)Cl2 (58 mg, 0.0785 mmol) were added successively. The mixture was stirred at 100° C. for 12 hours under a CO atmosphere. After removing of methanol, water (60 mL) was added, and the solution was extracted with ethyl acetate (30 mL×3). The organic phases were combined, dried over anhydrous sodium sulfate, filtered, and the filtrate was concentrated under reduced pressure. The product was purified by column chromatography (0-10% methanol/dichloromethane) to yield methyl 5-((4-methoxybenzyl)amino)imidazo[1,5-c]quinazoline-9-carboxylate (200 mg, yield: 56%).

LCMS (ESI) m/z: 363.2 [M+H]$^+$

Step 4: Synthesis of Methyl 5-aminoimidazo[1,5-c]quinazoline-9-carboxylate

At room temperature, methyl 5-((4-methoxybenzyl)amino)imidazo[1,5-c]quinazoline-9-carboxylate (200 mg, 0.5519 mmol) was placed into a 20 mL round-bottom flask, and trifluoroacetic acid (2 mL) was added. The mixture was stirred at 78° C. for 3 hours. After removing trifluoroacetic acid, water (5 mL) was added, and the solution was filtered. The filter cake was washed with water, yielding Methyl 5-aminoimidazo[1,5-c]quinazoline-9-carboxylate (200 mg, crude product).

LCMS (ESI) m/z: 243.2 [M+H]$^+$

Step 5: Synthesis of 5-aminoimidazo[1,5-c]quinazoline-9-carboxylic acid

At room temperature, Methyl 5-aminoimidazo[1,5-c]quinazoline-9-carboxylate (200 mg, 0.8257 mmol) was dissolved in a mixed solvent of methanol/tetrahydrofuran/water (9 mL, 4:4:1). Lithium hydroxide (40 mg, 1.651 mmol) was added to the mixture, and the reaction was stirred at 78° C. for 3 hours. After removing trifluoroacetic acid, water (5 mL) was added, and the solution was filtered. The filter cake was washed with water to obtain 5-aminoimidazo[1,5-c]quinazoline-9-carboxylic acid (200 mg, crude product).

LCMS (ESI) m/z: 243.2 [M+H]$^+$

Int. 95 Synthesis of 4-aminotetrazolo[1,5-a]quinoxaline-8-carboxylic acid

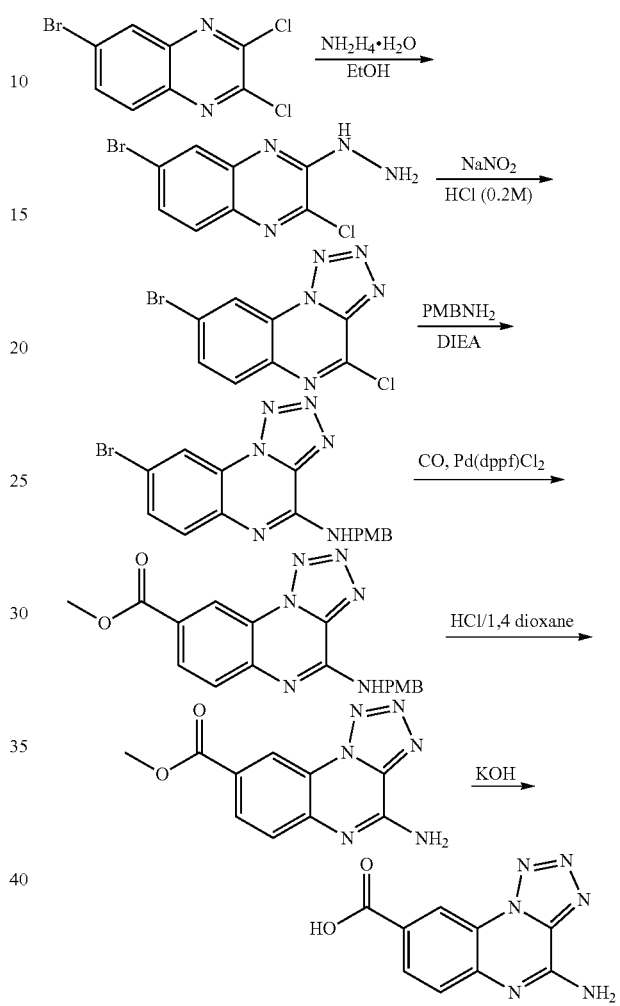

Step 1: Synthesis of 6-bromo-2-chloro-3-hydrazineylquinoxaline

A mixture of 6-bromo-2,3-dichloroquinoxaline (6.00 g, 21.73 mmol) and hydrazine hydrate (1.15 g, 35.98 mmol) in ethanol (50.00 mL) was stirred for 1 hour at 0° C. and then for 2 hours at room temperature. After filtration, washing with ethanol (100 mL) yielded 6-bromo-2-chloro-3-hydrazineylquinoxaline (5.00 g, 18.31 mmol).

LCMS (ESI): 273[M+H]$^+$

Step 2: Synthesis of 8-bromo-4-chlorotetrazolo[1,5-a]quinoxaline

A mixture of 6-bromo-2-chloro-3-hydrazineylquinoxaline (5.00 g, 18.31 mmol) and sodium nitrite (2.52 g, 36.56 mmol) in hydrochloric acid solution (0.2 M, 50.00 mL) was stirred for 2 hours at room temperature. The mixture was extracted with ethyl acetate (100 mL×3), and the organic phase was concentrated under vacuum. Further purification by silica gel column chromatography (petroleum ether:ethyl acetate=70%) yielded 8-bromo-4-chlorotetrazolo[1,5-a]quinoxaline (4.00 g, 18.28 mmol).

LCMS (ESI): 284[M+H]$^+$

Step 3: Synthesis of 8-bromo-N-(4-methoxybenzyl) tetrazolo[1,5-a]quinoxalin-4-amine A mixture of 8-bromo-4-chlorotetrazolo[1,5-a]quinoxaline (4.00 g, 14.13 mmol) with para-methoxybenzylamine (3.87 g, 28.26 mmol) and N,N-diisopropylethylamine (7.30 g, 56.52 mmol) in dichloromethane (50 mL) was stirred for 2 hours at room temperature. After extraction with ethyl acetate (100 mL×3), the organic phase was concentrated under vacuum. Further purification by silica gel column chromatography (petroleum ether:ethyl acetate=30%) yielded 8-bromo-N-(4-methoxybenzyl)tetrazolo[1,5-a]quinoxalin-4-amine (3.00 g, 7.81 mmol).

LCMS (ESI): 385[M+H]$^+$

Step 4: Synthesis of methyl 4-((4-methoxybenzyl) amino)tetrazolo[1,5-a]quinoxaline-8-carboxylate 8-bromo-N-(4-methoxybenzyl)tetrazolo[1,5-a]quinoxalin-4-amine (3.00 g, 7.81 mmol), potassium acetate (1.53 g, 15.61 mmol), and 1,1'-Bis(diphenylphosphino)ferrocene-palladium(II)dichloride dichloromethane complex (0.63 g, 0.77 mmol) were successively dissolved in a mixed solvent of N,N-dimethylformamide and methanol (1:1, 30 mL). The reaction proceeded overnight in a high-pressure vessel under carbon monoxide (4 mPa), at 100° C. After filtration, extraction with water (100 mL) and ethyl acetate (100 mL×3), and vacuum concentration of the organic phase, methyl 4-((4-methoxybenzyl)amino)tetrazolo[1,5-a]quinoxaline-8-carboxylate (3.00 g, 8.24 mmol) was obtained.

LCMS (ESI): 365[M+H]$^+$

Step 5: Synthesis of methyl 4-aminotetrazolo[1,5-a] quinoxaline-8-carboxylate

Methyl 4-((4-methoxybenzyl)amino)tetrazolo[1,5-a]quinoxaline-8-carboxylate (3.00 g, 8.24 mmol) was dissolved in hydrochloric acid/dioxane (4M, 50 mL) solution. The reaction was stirred at room temperature for 2 hours. After extraction with water (100 mL) and ethyl acetate (100 mL×3), the organic phase was concentrated under vacuum. Further purification by silica gel column chromatography (petroleum ether:ethyl acetate=50%) yielded methyl 4-aminotetrazolo[1,5-a]quinoxaline-8-carboxylate (2.00 g, 8.16 mmol).

LCMS (ESI): 245[M+H]$^+$

Step 6: Synthesis of 4-aminotetrazolo[1,5-a]quinoxaline-8-carboxylic acid methyl 4-aminotetrazolo[1,5-a]quinoxaline-8-carboxylate (2.00 g, 8.16 mmol) and potassium hydroxide (0.91 g, 16.32 mmol) were successively dissolved in a mixed solvent: tetrahydrofuran (10 mL), water (10 mL), and methanol (10 mL). The reaction was stirred at 60° C. for 2 hours. After extraction with water (50 mL) and ethyl acetate (50 mL×3), the organic phase was concentrated under vacuum to yield 4-aminotetrazolo[1,5-a]quinoxaline-8-carboxylic acid (1.00 g, 4.34 mmol).

LCMS (ESI): 231[M+H]$^+$

Int. 96 Synthesis of 6-aminoimidazo[1,5-a]pyrido[3,2-e]pyrazine-2-carboxylic Acid

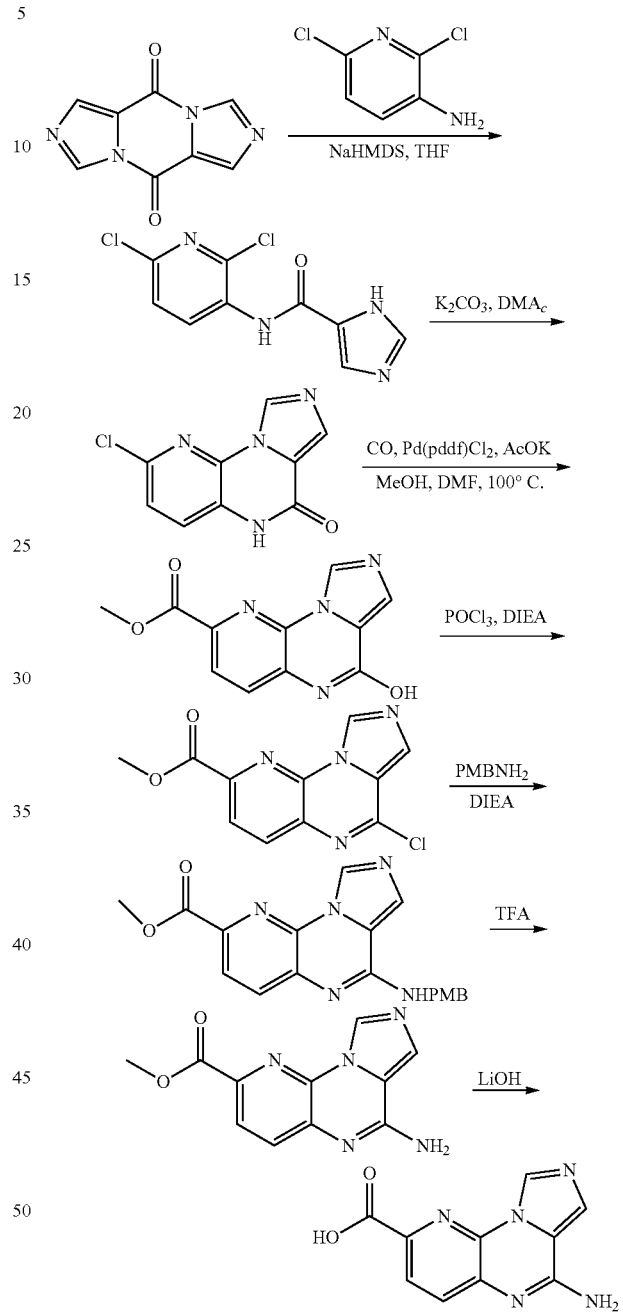

Step 1: Synthesis of N-(2,6-dichloropyridin-3-yl)-1H-imidazole-5-carboxamide 2,6-dichloropyridin-3-amine (163 mg, 1.0 mmol) was dissolved in tetrahydrofuran (5.0 mL). After the reaction system was cooled by an ice bath for 5 minutes, NaHMDS (0.125 mL, 2.0 M, 0.25 mmol) was slowly added to the reaction mixture and stirred for 1 hour. Then, 5H,10H-diimidazo[1,5-a:1',5'-d]pyrazine-5,10-dione (188.0 mg, 1.0 mmol) was added, and the reaction mixture was stirred overnight at room temperature. The reaction progress was monitored by LCMS. After completion, the reaction mixture was poured into water, adjusted to pH=7, resulting in the precipitation of solid. The solid was collected by filtration, dried, yielding crude N-(2,6-dichloropyridin-3-yl)-1H-imidazole-5-carboxamide (175 mg, crude product).

LCMS (ESI) m/z: 257.0[M+H]$^+$

Step 2: Synthesis of 2-chloroimidazo[1,5-a]pyrido[3,2-e]pyrazin-6(5H)-one

N-(2,6-dichloropyridin-3-yl)-1H-imidazole-5-carboxamide (256.0 mg, 1.0 mmol) was dissolved in N,N-dimethylacetamide (2.0 mL). Potassium carbonate (276 mg, 2.0 mmol) was added, and the reaction was heated to 140° C., stirred for 2 hours. After completion indicated by LCMS, the reaction mixture was cooled to room temperature, poured into water, stirred for 30 minutes, leading to the precipitation of solid. The solid was collected by filtration, yielding crude 2-chloroimidazo[1,5-a]pyrido[3,2-e]pyrazin-6(5H)-one (153.0 mg, crude product).

LCMS (ESI) m/z: 221.1[M+H]$^+$

Step 3: Synthesis of methyl 6-hydroxyimidazo[1,5-a]pyrido[3,2-e]pyrazine-2-carboxylate 2-chloroimidazo[1,5-a]pyridine[3,2-e]pyrimidin-6(5H)-one (2.0 g, 9.09 mmol) was dissolved in a solution of MeOH (30.00 mL) and DMF (310.00 mL), followed by the addition of potassium acetate (1.78 g, 18.18 mmol) and Pd(dppf)Cl$_2$ (660 mg, 0.91 mmol). Under a CO atmosphere, the mixture was stirred at 100° C. for 12 hours. After removing of methanol, the reaction mixture was added to 100 mL of water, resulting in the precipitation of solid. The solid was collected by filtration, yielding crude product. The crude product was slurried with ethyl acetate (50 mL×2) to obtain the product, methyl 6-hydroxyimidazo[1,5-a]pyrido[3,2-e]pyrazine-2-carboxylate (1.5 g, yield: 68%), as a brown solid.

LCMS (ESI) m/z: 245.2 [M+H]$^+$

Step 4: Synthesis of Methyl 6-chloroimidazo[1,5-a]pyrido[3,2-e]pyrazine-2-carboxylate Methyl 6-hydroxyimidazo[1,5-a]pyrido[3,2-e]pyrazine-2-carboxylate (200.0 mg, 0.82 mmol) was added to phosphorus oxychloride (2.0 mL), and N,N-diisopropylethylamine (528 mg, 4.09 mmol) was added dropwise. The reaction was heated to 90° C. and maintained for 2.5 hours. After LCMS indicated completion, the mixture was evaporated to remove phosphorus oxychloride. The resulting solution was poured into ice-water, stirred for 15 minutes, filtered, and the filter cake was collected, dried, yielding the crude product of Methyl 6-chloroimidazo[1,5-a]pyrido[3,2-e]pyrazine-2-carboxylate (200.0 mg, crude product).

LCMS (ESI) m/z: 263.0[M+H]$^+$

Step 5: Synthesis of methyl 6-((4-methoxybenzyl)amino)imidazo[1,5-a]pyrido[3,2-e]pyrazine-2-carboxylate Methyl 6-chloroimidazo[1,5-a]pyrido[3,2-e]pyrazine-2-carboxylate (200.0 mg, 0.76 mmol) was dissolved in DMSO (3.0 mL), and para-methoxybenzylamine (125.0 mg, 0.92 mmol) and N,N-diisopropylethylamine (295 mg, 2.29 mmol) were added successively. The reaction was heated to 90° C. and stirred for 16 hours. After completion, the reaction mixture was cooled to room temperature, poured into ice-water, stirred, and then extracted with ethyl acetate (20 mL). The organic phase was dried over anhydrous sodium sulfate, filtered, and the filtrate was concentrated. The crude product was purified by silica gel column chromatography (dichloromethane:methanol=0-5%), yielding methyl 6-((4-methoxybenzyl)amino)imidazo[1,5-a]pyrido[3,2-e]pyrazine-2-carboxylate (250 mg, 91% yield).

LCMS (ESI) m/z: 364.2[M+H]$^+$

Step 6: Synthesis of Methyl 6-aminoimidazo[1,5-a]pyrido[3,2-e]pyrazine-2-carboxylate Methyl 6-((4-methoxybenzyl)amino)imidazo[1,5-a]pyrido[3,2-e]pyrazine-2-carboxylate (250 mg, 0.69 mmol) was dissolved in trifluoroacetic acid (TFA) (5.0 mL), and the reaction was heated to 80° C. for 16 hours. After complete reaction, the mixture was cooled, and TFA was removed by evaporation, resulting in the crude product Methyl 6-aminoimidazo[1,5-a]pyrido[3,2-e]pyrazine-2-carboxylate (160 mg, crude).

LCMS (ESI) m/z: 244.1[M+H]$^+$

Step 7: Synthesis of 6-aminoimidazo[1,5-a]pyrido[3,2-e]pyrazine-2-carboxylic acid Methyl 6-aminoimidazo[1,5-a]pyrido[3,2-e]pyrazine-2-carboxylate (83.0 mg, yield: 55%) was dissolved in a mixture of THF/MeOH (1.2 mL/1.2 mL), and lithium hydroxide solution (0.66 mL, 2.0 M, 1.32 mmol) was added. The reaction was heated to 50° C. and stirred for 16 hours. After complete reaction, the solvent was evaporated, and the pH of the reaction mixture was adjusted to around 7 using 1 N HCl aqueous solution. After stirring for 15 minutes, the mixture was filtered, and the solid product was collected to obtain 6-aminoimidazo[1,5-a]pyrido[3,2-e]pyrazine-2-carboxylic acid (83 mg, yield: 55%)

LCMS (ESI) m/z: 230.1[M+H]$^+$

Int. 97 Synthesis of 4-amino-6-methylimidazo[1,5-a]quinoxaline-8-carboxylic Acid

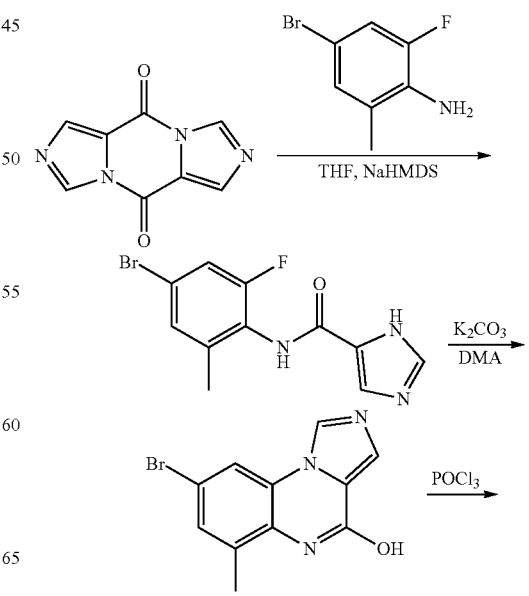

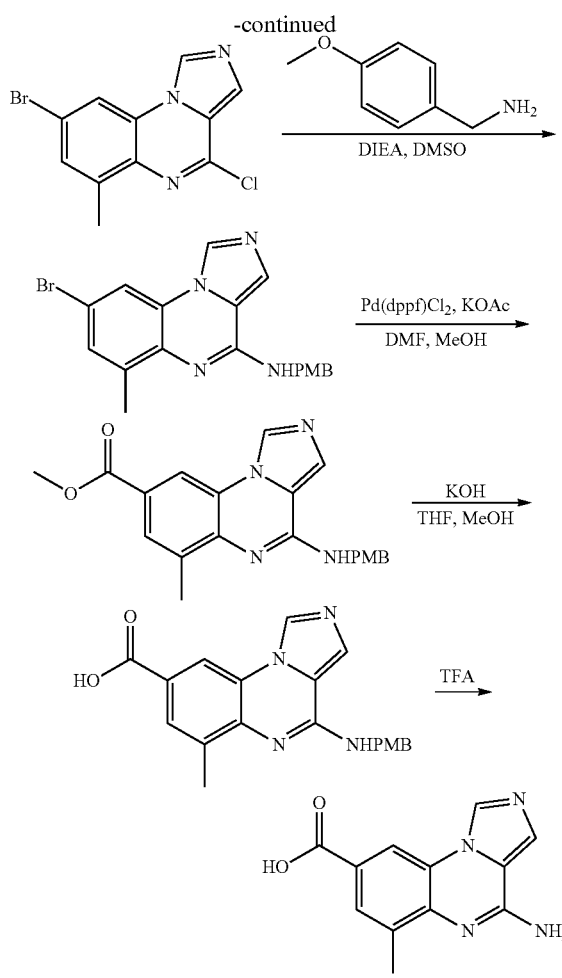

Step 1: Synthesis of N-(4-bromo-2-fluoro-6-methylphenyl)-1H-imidazole-5-carboxamide At room temperature, 4-bromo-2-fluoro-6-methylaniline (15 g, 73.89 mmol) was added to a 500 mL round-bottom flask, followed by the addition of tetrahydrofuran (150 mL). At 0° C., di(trimethylsilyl)amine (74 mL) was added, and after stirring the resulting mixture at 0° C. for half an hour, 5H,10H-diimidazo[1,5-a:1',5'-d]pyrazine-5,10-dione (6.95 g, 36.95 mmol) was added. The mixture proceeded for an additional hour at room temperature. Then the reaction mixture was poured into ice water, filtered to obtain the red solid residue as the product, N-(4-bromo-2-fluoro-6-methylphenyl)-1H-imidazole-5-carboxamide (10 g, yield: 90.9%).

LCMS (ESI) m/z: 298 [M+H]$^+$

Step 2: Synthesis of 8-bromo-6-methylimidazo[1,5-a]quinoxalin-4-ol

At room temperature, N-(4-bromo-2-fluoro-6-methylphenyl)-1H-imidazole-5-carboxamide (10 g, 33.67 mmol) was added to a 250 mL round-bottom flask. Then, N,N-dimethylacetamide (100 mL) was poured into the flask, then potassium carbonate (13.94 g, 101.01 mmol) was added. The resulting mixture was stirred at 140° C. for 2 hours. After the reaction was complete, the reaction mixture was poured into water to adjust the pH to 3-4, filtered, and the black solid residue was collected as the product, obtaining 8-bromo-6-methylimidazo[1,5-a]quinoxalin-4-ol (8 g, yield: 85.74%).

LCMS (ESI) m/z: 278 [M+H]$^+$

Step 3: Synthesis of 8-bromo-4-chloro-6-methylimidazo[1,5-a]quinoxaline

At room temperature, 8-bromo-6-methylimidazo[1,5-a]quinoxalin-4-ol (8 g, 28.88 mmol) was added to a 250 mL round-bottom flask. Then, phosphorus oxychloride (100 mL) was added into the flask, and the resulting mixture was stirred at 120° C. for 12 hours. The reaction solution was concentrated under reduced pressure, poured into ice water, filtered, and the black solid residue was collected as the product, obtaining 8-bromo-4-chloro-6-methylimidazo[1,5-a]quinoxaline (7.5 g, yield: 88.23%).

LCMS (ESI) m/z: 296 [M+H]$^+$

Step 4: Synthesis of 8-bromo-N-(4-methoxybenzyl)-6-methylimidazo[1,5-a]quinoxalin-4-amine At room temperature, 8-bromo-4-chloro-6-methylimidazo[1,5-a]quinoxaline (7.5 g, 25.42 mmol) was added to a 250 mL round-bottom flask. Then, dimethyl sulfoxide (75 mL) was poured into the flask, and (4-methoxyphenyl)methanamine (4.18 g, 30.51 mmol) and N,N-diisopropylethylamine (6.56 g, 50.85 mmol) were added. The resulting mixture was stirred at 90° C. for 2 hours. The reaction solution was concentrated under reduced pressure, poured into ice water, filtered, and the red solid residue was collected as the product, obtaining 8-bromo-N-(4-methoxybenzyl)-6-methylimidazo[1,5-a]quinoxalin-4-amine (6 g, yield: 60%).

LCMS (ESI) m/z: 397[M+H]$^+$

Step 5: Synthesis of methyl 4-((4-methoxybenzyl)amino)-6-methylimidazo[1,5-a]quinoxaline-8-carboxylate At room temperature, 8-bromo-N-(4-methoxybenzyl)-6-methylimidazo[1,5-a]quinoxalin-4-amine (6 g, 15.15 mmol) was added to a 250 mL high-pressure reaction vessel. Then, N,N-dimethylformamide (30 mL) and methanol (60 mL) were poured into the reaction vessel, and potassium acetate (2.97 g, 30.3 mmol) and 1,1'-Bis(diphenylphosphino)ferrocene]dichloropalladium(II) (1.24 g, 1.52 mmol) were added. Carbon monoxide (4 MPa) was introduced, and the resulting mixture was stirred at 100° C. for 12 hours. The reaction solution was concentrated under reduced pressure, poured into water, filtered, and the red solid residue was collected as the product, obtaining methyl 4-((4-methoxybenzyl)amino)-6-methylimidazo[1,5-a]quinoxaline-8-carboxylate (4 g, yield: 70.54%).

LCMS (ESI) m/z: 377[M+H]$^+$

Step 6: Synthesis of 4-((4-methoxybenzyl)amino)-6-methylimidazo[1,5-a]quinoxaline-8-carboxylic Acid At room temperature, methyl 4-((4-methoxybenzyl)amino)-6-methylimidazo[1,5-a]quinoxaline-8-carboxylate (4 g, 10.61 mmol) was added to a 250 mL round-bottom flask. Then, tetrahydrofuran (40 mL) and methanol (40 mL) were poured into the flask, and potassium hydroxide (1.19 g, 21.22 mmol) was added. The reaction mixture was stirred at 60° C. for 1 hour. The reaction solution was concentrated under reduced pressure, poured into water, and the pH was adjusted to around 3 using formic acid, resulting in solid precipitation. The mixture was filtered, and the red solid residue was collected as the product, obtaining 4-((4-methoxybenzyl)amino)-6-methylimidazo[1,5-a]quinoxaline-8-carboxylic acid (2.9 g, yield: 76.31%).

LCMS (ESI) m/z: 363[M+H]$^+$

Step 7: Synthesis of 4-amino-6-methylimidazo[1,5-a]quinoxaline-8-carboxylic acid At room temperature, 4-((4-methoxybenzyl)amino)-6-methylimidazo[1,5-a]quinoxaline-8-carboxylic acid (2.9 g, 7.99 mmol) was added to a 50 mL round-bottom flask. Then, trifluoroacetic acid (30 mL) was poured into the flask, and the resulting mixture was stirred at 100° C. for 3 hours. The reaction solution was concentrated under reduced pressure, yielding a black solid, 4-amino-6-methylimidazo[1,5-a]quinoxaline-8-carboxylic acid (1.5 g, yield: 51.28%).

LCMS (ESI) m/z: 243[M+H]$^+$

Int. 98 Synthesis of 4-amino-1-cyclopropylimidazo[1,5-a]quinoxaline-8-carboxylic Acid

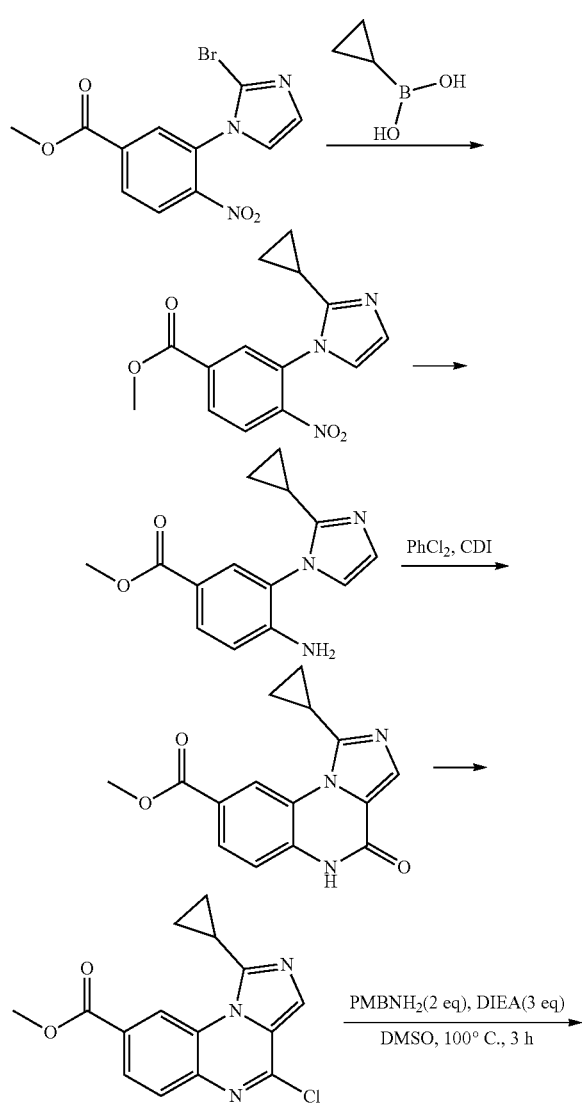

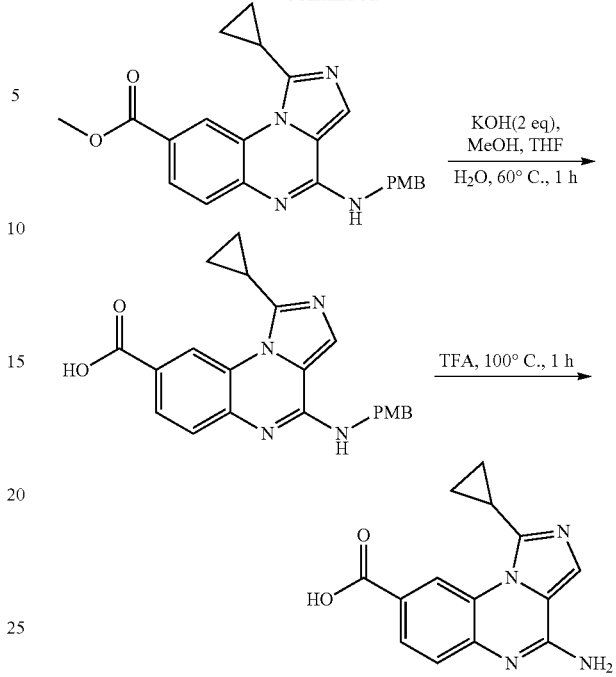

Step 1: Synthesis of methyl 3-(2-cyclopropyl-1H-imidazol-1-yl)-4-nitrobenzoate

A mixture of 3 methyl 3-(2-bromo-1H-imidazol-1-yl)-4-nitrobenzoate (1.00 g, 3.07 mmol), cyclopropylboronic acid (0.26 g, 3.07 mmol), Pd(dppf)Cl2 (0.25 g, 0.31 mmol), and potassium carbonate (0.85 g, 6.13 mmol) in dioxane (10 mL) was stirred at 100° C. for 2 hours. After completion of the reaction, the reaction mixture was poured into water (10 mL), extracted with ethyl acetate (10 mL×2), and the combined organic layers were washed with saturated brine (10 mL), dried over anhydrous sodium sulfate, filtered, and concentrated to obtain the crude product. The crude product was purified by column chromatography (ethyl acetate: petroleum ether=10:90), yielding methyl 3-(2-cyclopropyl-1H-imidazol-1-yl)-4-nitrobenzoate (0.50 g, yield: 57%).

LCMS (ESI): 288 [M+H]$^+$

Step 2: Synthesis of methyl 4-amino-3-(2-cyclopropyl-1H-imidazol-1-yl)benzoate

A mixture of methyl 3-(2-cyclopropyl-1H-imidazol-1-yl)-4-nitrobenzoate (1.00 g, 3.48 mmol), boronic acid (0.94 g, 10.44 mmol), and 4,4'-bipyridine (0.27 g, 1.74 mmol) in N,N-dimethylformamide (10.00 mL) was stirred at room temperature for 2 hours. The reaction mixture was then concentrated, poured into water (10 mL), extracted with ethyl acetate (10 mL×2), and the combined organic layers were washed with saturated brine (10 mL), dried over anhydrous sodium sulfate, filtered, and concentrated to obtain the crude product. The crude product was purified by column chromatography (ethyl acetate:petroleum ether=53%), yielding methyl 4-amino-3-(2-cyclopropyl-1H-imidazol-1-yl)benzoate (0.60 g, yield: 67%).

LCMS (ESI): 257 [M+H]$^+$

Step 3: Synthesis of methyl 1-cyclopropyl-4-oxo-4,5-dihydroimidazo[1,5-a]quinoxaline-8-carboxylate A mixture of methyl 4-amino-3-(2-cyclopropyl-1H-imidazol-1-yl)benzoate (500 mg, 1.94 mmol) and carbonyl imidazole (377 mg, 2.33 mmol) in chlorobenzene (5 mL) was stirred at 140° C. for 12 hours. After concentration, the reaction mixture was poured into water (10 mL), extracted with ethyl acetate (10 mL×2), and the combined organic layers were washed with saturated brine (10 mL), dried over anhydrous sodium sulfate, filtered, and concentrated to obtain the crude product. The crude product was purified by column chromatography (ethyl acetate:petroleum ether=20%), yielding methyl 1-cyclopropyl-4-oxo-4,5-dihydroimidazo[1,5-a]quinoxaline-8-carboxylate (500 mg, yield: 91%).

LCMS (ESI): 283 [M+H]$^+$

Step 4: Synthesis of methyl 4-chloro-1-cyclopropylimidazo[1,5-a]quinoxaline-8-carboxylate A solution of methyl 1-cyclopropyl-4-oxo-4,5-dihydroimidazo[1,5-a]quinoxaline-8-carboxylate (500.00 mg, 1.77 mmol) in phosphorus oxychloride (5.00 mL) was stirred at 120° C. for 12 hours. After concentration, methyl 4-chloro-1-cyclopropylimidazo[1,5-a]quinoxaline-8-carboxylate (300 mg, crude) was obtained.

LCMS (ESI): 301 [M+H]$^+$

Step 5: Synthesis of methyl 1-cyclopropyl-4-((4-methoxybenzyl)amino)imidazo[1,5-a]quinoxaline-8-carboxylate A solution of the mixture of methyl 4-chloro-1-cyclopropylimidazo[1,5-a]quinoxaline-8-carboxylate (300 mg, 0.99 mmol), p-methoxybenzylamine (417 mg, 2.98 mmol), and diisopropylamine (384 mg, 2.98 mmol) in dimethyl sulfoxide (3 mL, 0.00 mmol) was stirred at 120° C. for 2 hours. After concentration, the reaction mixture was poured into water (10 mL), and extracted with ethyl acetate (10 mL×2). The combined organic layers were washed with saturated brine (10 mL), dried over anhydrous sodium sulfate, filtered, and concentrated to obtain the crude product. The crude product was purified by column chromatography (ethyl acetate:petroleum ether=42%) to yield methyl 1-cyclopropyl-4-((4-methoxybenzyl)amino)imidazo[1,5-a]quinoxaline-8-carboxylate (300 mg, yield: 75%).

LCMS (ESI): 402 [M+H]$^+$

Step 6: Synthesis of 1-cyclopropyl-4-((4-methoxybenzyl)amino)imidazo[1,5-a]quinoxaline-8-carboxylic Acid Lithium hydroxide (89.45 mg, 2.24 mmol) was added to a solution of methyl 1-cyclopropyl-4-((4-methoxybenzyl) amino)imidazo[1,5-a]quinoxaline-8-carboxylate (300 mg, 0.75 mmol) in methanol/tetrahydrofuran (5.00 mL/5.00 mL). The reaction mixture was stirred at 60° C. for 2 hours, then concentrated to obtain 1-cyclopropyl-4-((4-methoxybenzyl)amino)imidazo[1,5-a]quinoxaline-8-carboxylic acid (160 mg, yield: 55%).

LCMS (ESI): 388 [M+H]$^+$

Step 7: Synthesis of 4-amino-1-cyclopropylimidazo[1,5-a]quinoxaline-8-carboxylic acid A mixture of 1-cyclopropyl-4-((4-methoxybenzyl)amino) imidazo[1,5-a]quinoxaline-8-carboxylic acid (200 mg, 0.51 mmol) in trifluoroacetic acid (2.00 mL) was heated at 100° C. for 2 hours, then concentrated to obtain 4-amino-1-cyclopropylimidazo[1,5-a]quinoxaline-8-carboxylic acid (100 mg, crude).

LCMS (ESI): 268 [M+H]$^+$

DETAILED DESCRIPTION OF THE EMBODIMENTS

Example 1

4-amino-N-(2,3-dihydrobenzofuran-3-yl)-N-methylimidazo[1,5-a]quinoxaline-8-carboxamide

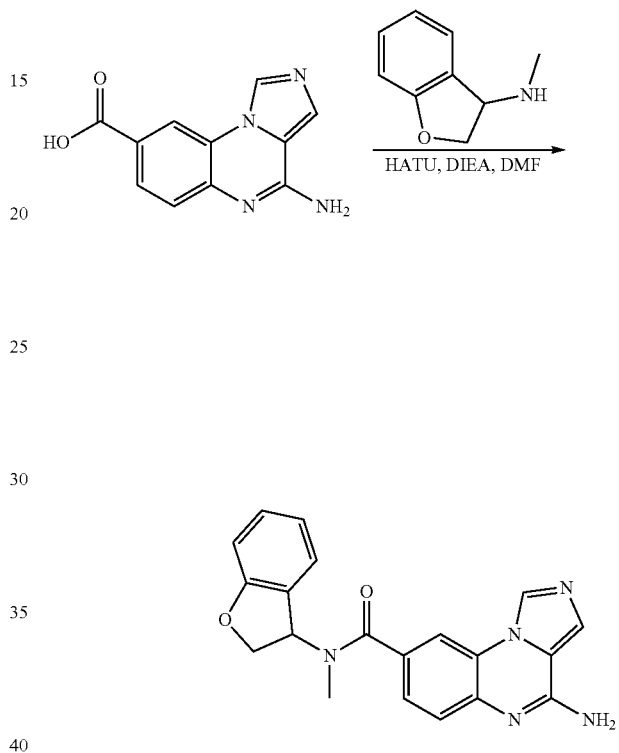

4-aminoimidazo[1,5-a]quinoxaline-8-carboxylic acid (50 mg, 0.21 mmol) was dissolved in DMF (2.5 ml) followed by addition of 2-(7-Azabenzotriazol-1-yl)-N,N,N',N'-tetramethyluronium hexafluorophosphate (125 mg, 0.32 mmol), N,N-diisopropylethylamine (85 mg, 0.65 mmol) and N-methyl-2,3-dihydrobenzofuran-3-amine (33 mg, 0.21 mmol) successively. The reaction mixture was stirred at room temperature for 0.5 h. After completion of the reaction, the reaction solution was concentrated and further purified by HPLC(Column: Xbridge BEH Shield RP18 5 m, 30 mm×150 mm; mobile phase A: water (10 mmol/L ammonium bicarbonate), mobile phase B: acetonitrile, flow rate: 60 ml/min; Gradient: From 20% B to 36% B within 8 minutes; Wavelength: 254 nanometers/220 nanometers.) to obtain 4-amino-N-(2,3-dihydrobenzofuran-3-yl)-N-methylimidazo[1,5-a]quinoxaline-8-carboxamide $^1$H NMR (400 MHz, DMSO-d$_6$) δ 9.19 (s, 1H), 8.33 (s, 1H), 7.92 (s, 1H), 7.48-7.41 (m, 5H), 7.30-7.26 (m, 1H), 7.00-6.99 (m, 1H), 6.91-6.89 (M, 1H), 6.35-5.76 (m, 1H), 4.79-4.56 (m, 2H), 2.68 (s, 3H).

LCMS (ESI): 360.30 [M+H]$^+$

By employing the synthetic steps described in Example 1, with only the replacement of corresponding starting materials, embodiments listed in the table below can be prepared:

| Ex. | Structure | Name | ¹H NMR & ¹⁹F NMR & LCMS |
|---|---|---|---|
| 2 | 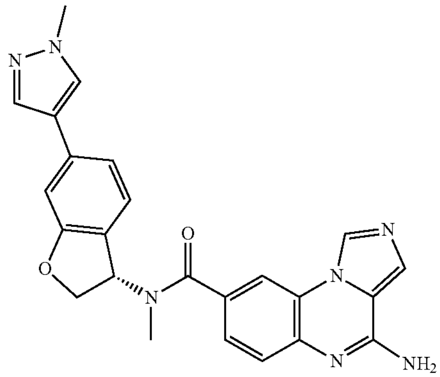 [SMILES: CN(C(=O)c1ccc2nc(N)c3cncn3c2c1)[C@@H]1COc2cc(-c3cnn(C)c3)ccc21] | (S)-4-amino-N-methyl-N-(6-(1-methyl-1H-pyrazol-4-yl)-2,3-dihydrobenzofuran-3-yl)imidazo[1,5-a]quinoxaline-8-carboxamide | ¹H NMR (400 MHz, DMSO-$d_6$): δ ppm 9.11 (s, 1H), 8.25 (s, 1H), 8.0 7 (s, 1H), 7.84-7.79 (m, 2H), 7.40-7.36 (m, 4H), 7.31-7.29 (m, 1H), 7.12-7.10 (m, 1H), 7.02 (s, 1H), 6.21-4.61 (m, 1H), 4.60-4.54 (m, 1H), 3.66 (s, 1H), 2.52 (s, 1H). LCMS (ESI) m/z: 440.35 [M + H]⁺ |
| 3 | 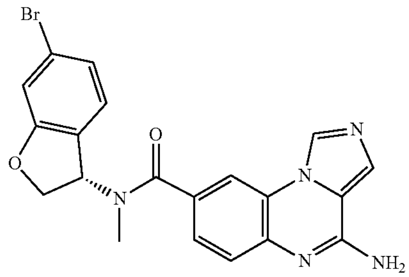 [SMILES: CN(C(=O)c1ccc2nc(N)c3cncn3c2c1)[C@@H]1COc2cc(Br)ccc21] | (S)-4-amino-N-(6-bromo-2,3-dihydrobenzofuran-3-yl)-N-methylimidazo[1,5-a]quinoxaline-8-carboxamide | ¹H NMR (400 MHz, DMSO-$d_6$) δ 9.17 (s, 1H), 8.31 (s, 1H), 7.91 (s, 1H), 7.50-7.45 (m, 4H), 7.38-7.37 (m, 1H), 7.16 (s, 2H), 6.33-5.59 (m, 1H), 4.80-4.55 (m, 2H), 2.71 (s, 3H). LCMS (ESI) m/z: 438.00 [M + H]⁺ |
| 4 | 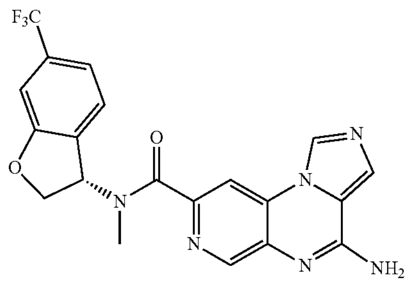 [SMILES: CN(C(=O)c1cc2c(cn1)nc(N)c1cncn12)[C@@H]1COc2cc(C(F)(F)F)ccc21] | (S)-4-amino-N-methyl-N-(6-(trifluoromethyl)-2,3-dihydrobenzofuran-3-yl)imidazo[1,5-a]pyrido[3,4-e]pyrazine-8-carboxamide | ¹H NMR (400 MHz, DMSO-$d_6$) δ 9.31 (d, J = 7.8 Hz, 1H), 8.67 (d, J = 19.6 Hz, 1H), 8.53 (d, J = 19.7 Hz, 1H), 7.99 (d, J = 3.8 Hz, 1H), 7.89-7.65 (m, 2H), 7.57 (d, J = 7.8 Hz, 1H), 7.45-7.19 (m, 2H), 6.51-5.98 (m, 1H), 4.95-4.41 (m, 2H), 2.72 (d, J = 25.9 Hz, 3H). LCMS (ESI) m/z: 429.1 [M + H]⁺ |
| 5 | 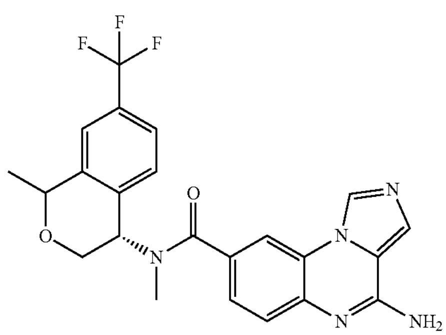 [SMILES: CC1OC[C@@H](N(C)C(=O)c2ccc3nc(N)c4cncn4c3c2)c2ccc(C(F)(F)F)cc21] | 4-amino-N-methyl-N-((4S)-1-methyl-7-(trifluoromethyl)isochroman-4-yl)imidazo[1,5-a]quinoxaline-8-carboxamide | ¹H NMR (400 MHz, DMSO-$d_6$) δ 9.19 (d, J = 18.9 Hz, 1H), 8.37 (d, J = 12.5 Hz, 1H), 7.93 (s, 1H), 7.73-7.41 (m, 7H), 5.78 (d, J = 37.1 Hz, 1H), 4.77 (d, J = 40.0 Hz, 2H), 4.42 3.87 (m, 2H), 2.79 (s, 3H), 1.56 (t, J = 7.8 Hz, 3H). ¹⁹F NMR (376 MHz, DMSO-$d_6$) δ-60.92. LCMS (ESI) m/z: 456 [M + H]⁺ |
| 6 | 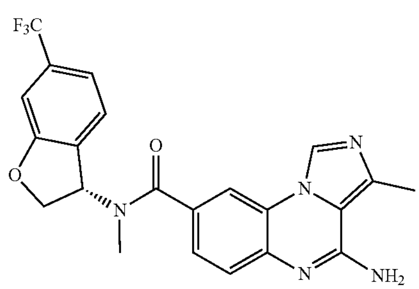 [SMILES: Cc1ncn2c1c(N)nc1ccc(C(=O)N(C)[C@@H]3COc4cc(C(F)(F)F)ccc43)cc12] | (S)-4-amino-N, 3-dimethyl-N-(6-(trifluoromethyl)-2,3-dihydrobenzofuran-3-yl)imidazo[1,5-a]quinoxaline-8-carboxamide | ¹H NMR (400 MHz, DMSO-$d_6$) δ 9.05 (s, 1H), 8.28-8.23 (m, 1H), 7.64 (d, J = 7.8 Hz, 1H), 7.47-7.38 (m, 2H), 7.33 (d, J = 7.9 Hz, 1H), 7.26 (s, 1H), 6.90 (s, 2H), 6.38 (s, 1H), 4.81 (s, 1H), 4.71 (dd, J = 10.3, 4.4 Hz, 1H), 2.67 (s, 3H), 2.63 (s, 3H). ¹⁹F NMR (376 MHz, DMSO-$d_6$) δ-60.80. LCMS (ESI) m/z: 442 [M + H]⁺ |

-continued

| Ex. | Structure | Name | $^1$H NMR & $^{19}$F NMR & LCMS |
|---|---|---|---|
| 7 | 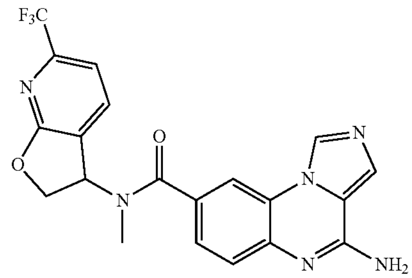 [SMILES: CN(C(=O)c1ccc2nc(N)c3cncn3c2c1)C1COc2nc(C(F)(F)F)ccc21] | 4-amino-N-methyl-N-(6-(trifluoromethyl)-2,3-dihydrofuro[2,3-b]pyridin-3-yl)imidazo[1,5-a]quinoxaline-8-carboxamide | $^1$H NMR (400 MHz, DMSO-d$_6$) δ 9.17 (s, 1H), 8.33 (s, 1H), 8.13 (d, J = 7.4 Hz, 1H), 7.92 (s, 1H), 7.55-7.42 (m, 5H), 6.49-6.03 (m, 1H), 5.01-4.84 (m, 1H), 4.79-4.69 (m, 1H), 2.78 (s, 3H). LCMS (ESI) m/z: 429.20 [M + H]$^+$ |
| 8 | 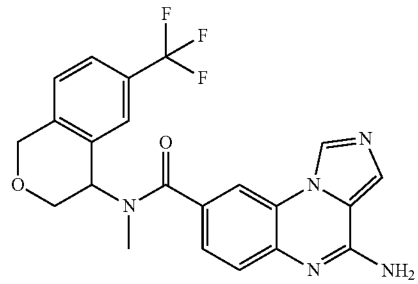 [SMILES: CN(C(=O)c1ccc2nc(N)c3cncn3c2c1)C1COCc2ccc(C(F)(F)F)cc21] | 4-amino-N-methyl-N-(6-(trifluoromethyl)isochroman-4-yl)imidazo[1,5-a]quinoxaline-8-carboxamide | $^1$H NMR (400 MHz, DMSO-d$_6$) δ 9.20 (s, 1H), 8.37 (s, 1H), 7.91 (s, 1H), 7.68-7.66 (m, 2H), 7.51-7.44 (m, 5H), 5.77 (s, 1H), 4.95-4.91 (m, 1H), 4.76-4.72 (m, 1H), 4.22-4.11 (m, 2H), 2.77 (s, 3H). |
| 9 | 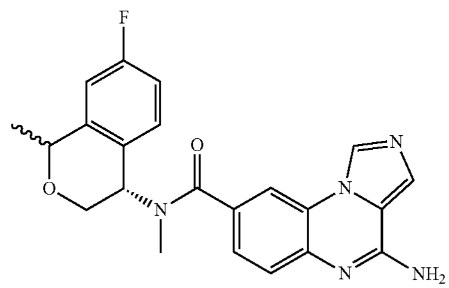 [SMILES: CC1OC[C@@H](N(C)C(=O)c2ccc3nc(N)c4cncn4c3c2)c2ccc(F)cc21] | 4-amino-N-((4S)-7-fluoro-1-methylisochroman-4-yl)-N-methylimidazo[1,5-a]quinoxaline-8-carboxamide | $^1$H NMR (400 MHz, DMSO-d$_6$) δ 9.18 (d, 1H), 8.35 (d, 1H), 7.91 (s, 1H), 7.47-7.42 (m, 5H), 7.18-7.13 (m, 2H), 5.76-5.63 (m, 1H), 4.91-4.61 (m, 2H), 4.34-3.90 (m, 2H), 2.75-2.69 (m, 3H), 1.53-1.33 (m, 3H). LCMS (ESI) m/z: 406.3 [M + H]$^+$ |
| 10 | 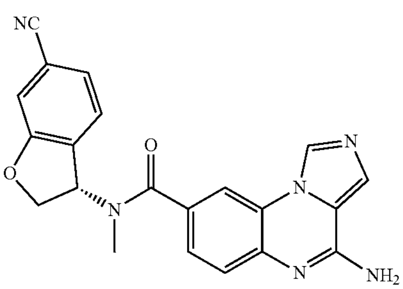 | (S)-4-amino-N-(6-cyano-2,3-dihydrobenzofuran-3-yl)-N-methylimidazo[1,5-a]quinoxaline-8-carboxamide | $^1$H NMR (400 MHz, DMSO-d$_6$) δ 9.17 (s, 1H), 8.34-8.32 (m, 1H), 7.91 (s, 1H), 7.63-7.61 (m, 1H), 7.47-7.42 (m, 6H), 6.52-5.81 (m, 1H), 4.81-4.68 (m, 2H), 2.71 (s, 3H). LCMS (ESI): 385.05 [M + H]$^+$ |
| 11 | 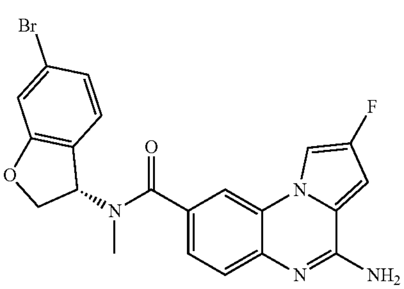 [SMILES: CN(C(=O)c1ccc2nc(N)c3cc(F)cn3c2c1)[C@@H]1COc2cc(Br)ccc21] | (S)-4-amino-N-(6-bromo-2,3-dihydrobenzofuran-3-yl)-2-fluoro-N-methylpyrrolo[1,2-a]quinoxaline-8-carboxamide | $^1$H NMR (400 MHz, DMSO-d$_6$) δ 8.40 (s, 1H), 8.10 (d, J = 1.6 Hz, 1H), 7.45-7.44 (m, 1H), 7.42-7.33 (m, 2H), 7.16 (s, 4H), 6.95 (d, J = 1.8 Hz, 1H), 4.80-4.61 (m, 3H), 2.65 (s, 3H). LCMS (ESI) m/z: 455.20 [M + H]$^+$ |

| Ex. | Structure | Name | ¹H NMR & ¹⁹F NMR & LCMS |
|---|---|---|---|
| 12 | 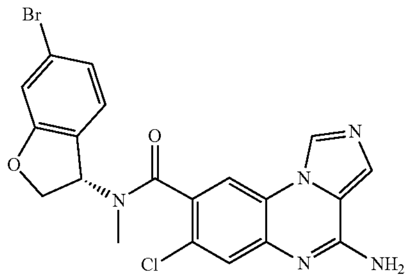 [SMILES: CN(C(=O)c1cc2c(cc1Cl)nc(N)c1cncn12)[C@@H]1COc2cc(Br)ccc21] | (S)-4-amino-N-(6-bromo-2,3-dihydrobenzofuran-3-yl)-7-chloro-N-methylimidazo[1,5-a]quinoxaline-8-carboxamide | ¹H NMR (400 MHz, DMSO-$d_6$) δ 9.20-9.06 (m, 1H), 8.54-8.68 (m, 1H), 7.93-7.92 (m, 1H), 7.64-7.58 (m, 2H), 7.54-7.46 (m, 1H), 7.43-7.25 (m, 1H), 7.20 (s, 1H), 7.16-7.12 (m, 1H), 6.88-6.44 (m, 1H), 5.42-5.30 (m, 1H), 4.85-4.62 (m, 1H), 2.05-1.95 (s, 3H). LCMS (ESI) m/z: 472.15 [M + H]⁺. |
| 14 | 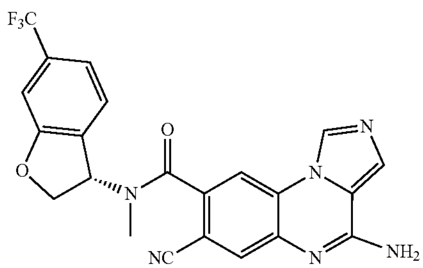 [SMILES: CN(C(=O)c1cc2c(cc1C#N)nc(N)c1cncn12)[C@@H]1COc2cc(C(F)(F)F)ccc21] | (S)-4-amino-7-cyano-N-methyl-N-(6-(trifluoromethyl)-2,3-dihydrobenzofuran-3-yl)imidazo[1,5-a]quinoxaline-8-carboxamide | ¹H NMR (400 MHz, DMSO-$d_6$) δ 9.21 (s, 1H), 8.55-8.44 (m, 1H), 7.97-7.90 (m, 2H), 7.76 (s, 2H), 7.60-7.59 (m, 1H), 7.38-7.36 (m, 1H), 7.30-7.26 (m, 1H), 6.53-5.65 (m, 1H), 4.94-4.68 (m, 2H), 2.73-2.62 (m, 3H). LCMS (ESI): 452.95 [M + H]⁺ |
| 15 | 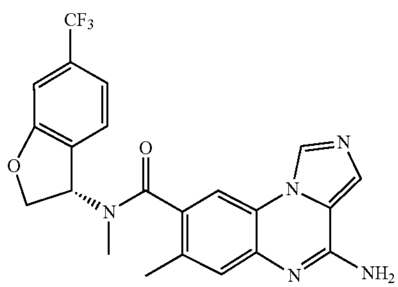 [SMILES: Cc1cc2nc(N)c3cncn3c2cc1C(=O)N(C)[C@@H]1COc2cc(C(F)(F)F)ccc21] | (S)-4-amino-N, 7-dimethyl-N-(6-(trifluoromethyl)-2,3-dihydrobenzofuran-3-yl)imidazo[1,5-a]quinoxaline-8-carboxamide | ¹H NMR (400 MHz, DMSO-$d_6$) δ 9.05 (s, 1H), 8.21 (s, 1H), 7.90 (s, 1H), 7.62 (s, 1H), 7.35-7.32 (m, 2H), 7.22 (s, 1H), 7.16-7.15 (m, 2H), 6.53-5.71 (m, 1H), 4.89-4.70 (m, 2H), 2.71-2.69 (s, 3H), 2.33 (s, 3H). LCMS (ESI): 442.2 [M + H]⁺ |
| 16 | 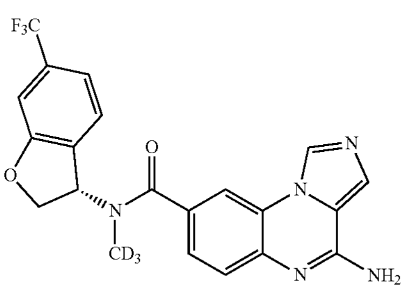 | (S)-4-amino-N-(methyl-d3)-N-(6-(trifluoromethyl)-2,3-dihydrobenzofuran-3-yl)imidazo[1,5-a]quinoxaline-8-carboxamide | ¹H NMR (400 MHz, DMSO-$d_6$) δ 9.19 (s, 1H), 8.34 (t, J = 1.1 Hz, 1H), 7.91 (s, 1H), 7.65-7.63 (d, J = 7.8 Hz, 1H), 7.48-7.44 (m, 4H), 7.34-7.32 (m, 1H), 7.26 (s, 1H), 6.39-5.78 (m, 1H), 4.84-4.69 (m, 2H). LCMS (ESI): 430.95 [M + H]⁺ |
| 17 | 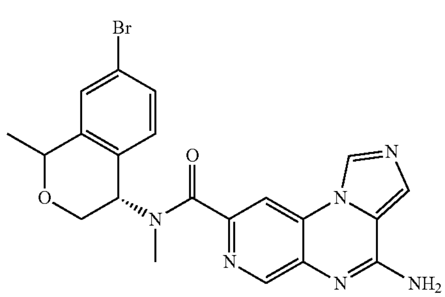 [SMILES: CC1OC[C@@H](N(C)C(=O)c2cc3c(cn2)nc(N)c2cncn23)c2ccc(Br)cc21] | 4-amino-N-((4S)-7-bromo-1-methylisochroman-4-yl)-N-methylimidazo[1,5-a]pyrido[3,4-e]pyrazine-8-carboxamide | ¹H NMR (400 MHz, CDCl₃) δ 9.31-9.28 (m, 1H), 8.67-8.64 (m, 1H), 8.56-8.49 (m, 1H), 7.98 (s, 1H), 7.72-7.66 (m, 2H), 7.56-7.45 (m, 2H), 7.41-7.26 (m, 1H), 5.63-5.62 (m, 0.5H), 5.10-5.09 (m, 0.5H), 4.75-4.64 (m, 1H), 4.24-4.17 (m, 1H), 4.06-4.02 (m, 1H), 3.92-3.88 (m, 1H), 2.85-2.75 (d, 3H), 1.54-1.52 (m, 3H). LCMS (ESI) m/z: 467.1/469.1 [M + H]⁺ |

-continued

| Ex. | Structure | Name | ¹H NMR & ¹⁹F NMR & LCMS |
|---|---|---|---|
| 18 | 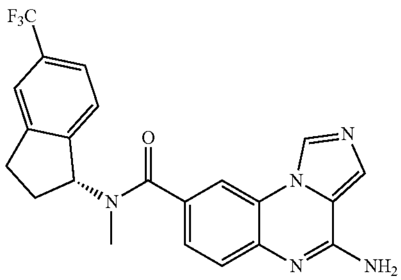 [SMILES: CN(C(=O)c1ccc2nc(N)c3cncn3c2c1)[C@@H]1CCc2cc(C(F)(F)F)ccc21] | (R)-4-amino-N-methyl-N-(5-(trifluoromethyl)-2,3-dihydro-1H-inden-1-yl)imidazo[1,5-a]quinoxaline-8-carboxamide | ¹HNMR (400 MHz, DMSO-d₆) δ 9.19 (d, J = 22.0 Hz, 1H), 8.36 (s, 1H), 7.91 (s, 1H), 7.62 (d, J = 8.0 Hz, 2H), 7.58-7.29 (m, 5H), 5.83 (d, J = 320.9 Hz, 1H), 3.05 (d, J = 33.9 Hz, 2H), 2.71 (s, 3H), 2.28 (d, J = 69.4 Hz, 2H). 19FNMR (376 MHz, DMSO-d₆) δ -60.51 (d, J = 23.8 Hz). LCMS (ESI) m/z: 426.1 [M + H]⁺ |
| 19 | 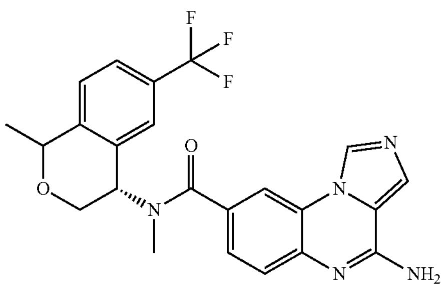 [SMILES: CC1OC[C@@H](N(C)C(=O)c2ccc3nc(N)c4cncn4c3c2)c2cc(C(F)(F)F)ccc21] | 4-amino-N-methyl-N-((4S)-1-methyl-6-(trifluoromethyl)isochroman-4-yl)imidazo[1,5-a]quinoxaline-8-carboxamide | ¹H NMR (400 MHz, DMSO-d₆) δ 9.14 (d, J = 53.8 Hz, 1H), 8.85-8.31 (m, 1H), 7.92 (d, J = 3.4 Hz, 1H), 7.68 (t, J = 10.1 Hz, 2H), 7.62-7.39 (m, 5H), 5.92-5.18 (m, 1H), 5.09-4.73 (m, 1H), 4.46-3.84 (m, 2H), 2.78 (d, J = 21.2 Hz, 3H), 1.77-1.35 (m, 3H). ¹⁹F NMR (376 MHz, DMSO-d₆) δ -60.15--61.37 (m). LCMS (ESI) m/z: 456 [M + H]⁺ |
| 20 | 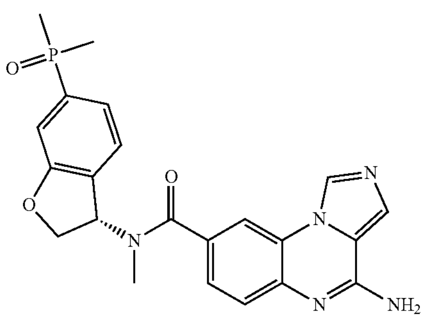 [SMILES: CN(C(=O)c1ccc2nc(N)c3cncn3c2c1)[C@@H]1COc2cc(P(C)(C)=O)ccc21] | (S)-4-amino-N-(6-(dimethylphosphoryl)-2,3-dihydrobenzofuran-3-yl)-N-methylimidazo[1,5-a]quinoxaline-8-carboxamide | ¹H NMR (400 MHz, DMSO-d₆) δ 9.19 (s, 1H), 8.33 (s, 1H), 7.92 (s, 1H), 7.57-7.55 (m, 1H), 7.47-7.46 (m, 4H), 7.41-7.39 (m, 1H), 7.33-7.26 (m, 1H), 6.55-5.71 (m, 1H), 4.79-4.65 (m, 2H), 2.71 (s, 3H), 1.71-1.62 (m, 6H). LCMS (ESI): 436.20 [M + H]⁺ |
| 21 | 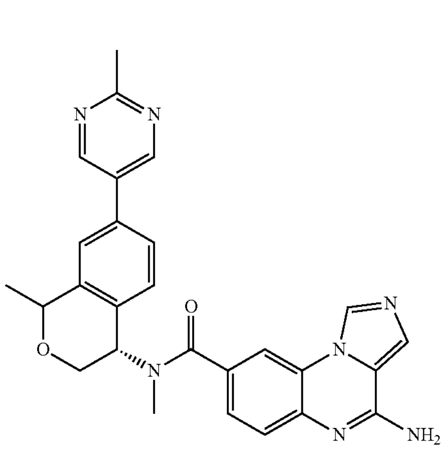 [SMILES: Cc1ncc(-c2ccc3c(c2)C(C)OC[C@H]3N(C)C(=O)c2ccc3nc(N)c4cncn4c3c2)cn1] | 4-amino-N-methyl-N-((4S)-1-methyl-7-(2-methylpyrimidin-5-yl)isochroman-4-yl)imidazo[1,5-a]quinoxaline-8-carboxamide | ¹HNMR (400 MHz, DMSO-d₆) δ 9.22-9.20 (m, 1H), 9.06-9.04 (m, 2H), 8.42-8.36 (m, 1H), 7.92 (s, 1H), 7.74-7.67 (m, 2H), 7.55-7.39 (m, 5H), 5.70-4.90 (m, 1H), 4.71-4.69 (m, 1H), 4.36-4.24 (m, 1H), 4.10-3.94 (m, 1H), 2.82-2.73 (m, 3H), 2.67-2.66 (m, 3H), 1.62-1.40 (m, 3H). LCMS (ESI) m/z: 480.4 [M + H]⁺ |

-continued

| Ex. | Structure | Name | ¹H NMR & ¹⁹F NMR & LCMS |
|---|---|---|---|
| 22 | 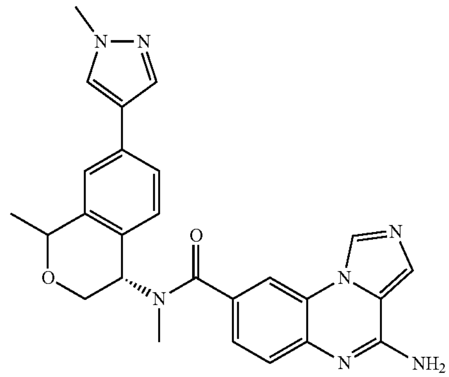 [SMILES: CC1OC[C@@H](N(C)C(=O)c2ccc3nc(N)c4cncn4c3c2)c2ccc(-c3cnn(C)c3)cc21] | 4-amino-N-methyl-N-((4S)-1-methyl-7-(1-methyl-1H-pyrazol-4-yl)isochroman-4-yl)imidazo[1,5-a]quinoxaline-8-carboxamide | ¹H NMR (400 MHz, DMSO-$d_6$) δ 9.22-9.19 (m, 1H), 8.40-8.34 (m, 1H), 8.19-8.17 (m, 1H), 7.92-7.89 (m, 2H), 7.48-7.34 (m, 5H), 7.30-7.23 (m, 2H), 5.62-4.78 (m, 1H), 4.74-4.64 (m, 1H), 4.32-4.27 (m, 1H), 4.06-4.00 (m, 1H), 3.86 (s, 3H), 2.79-2.71 (m, 3H), 1.51-1.38 (m, 3H).<br>LCMS (ESI) m/z: 468.3 [M + H]⁺ |
| 23 | 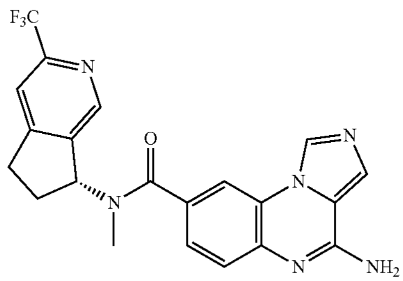 [SMILES: CN(C(=O)c1ccc2nc(N)c3cncn3c2c1)[C@@H]1CCc2cc(C(F)(F)F)ncc21] | (R)-4-amino-N-methyl-N-(3-(trifluoromethyl)-6,7-dihydro-5H-cyclopenta[c]pyridin-7-yl)imidazo[1,5-a]quinoxaline-8-carboxamide | ¹H NMR (400 MHz, DMSO-$d_6$) δ 9.12 (s, 1H), 8.32 (d, J = 6.6 Hz, 1H), 7.93 (d, J = 3.2 Hz, 1H), 7.58 (d, J = 26.7 Hz, 3H), 7.41-7.19 (m, 3H), 6.51-5.61 (m, 1H), 4.96-4.60 (m, 2H), 2.65 (d, J = 31.4 Hz, 3H).<br>¹⁹F NMR (376 MHz, DMSO-$d_6$) δ-65.97.<br>LCMS (ESI) m/z: 427.5 [M + H]⁺ |
| 24 | 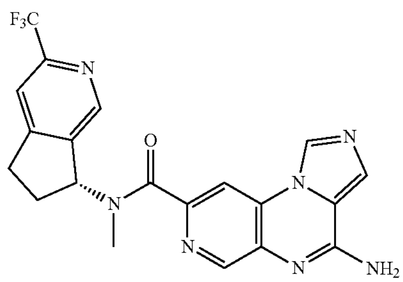 | (R)-4-amino-N-methyl-N-(3-(trifluoromethyl)-6,7-dihydro-5H-cyclopenta[c]pyridin-7-yl)imidazo[1,5-a]pyrido[3,4-e]pyrazine-8-carboxamide | ¹H NMR (400 MHz, DMSO-$d_6$) δ 9.30 (d, J = 7.2 Hz, 1H), 8.81-8.49 (m, 3H), 7.99 (d, J = 2.6 Hz, 1H), 7.89 (d, J = 23.8 Hz, 1H), 7.73 (s, 2H), 6.07 (dt, J = 194.2, 8.2 Hz, 1H), 3.19-3.04 (m, 1H), 2.90 (t, J = 8.7 Hz, 1H), 2.79 (d, J = 18.9 Hz, 3H), 2.46-2.35 (m, 1H), 2.22 (dq, J = 13.3, 8.6 Hz, 1H).<br>¹⁹F NMR (376 MHz, DMSO-$d_6$) δ-65.90.<br>LCMS (ESI) m/z: 428.4 [M + H]⁺ |
| 25 | 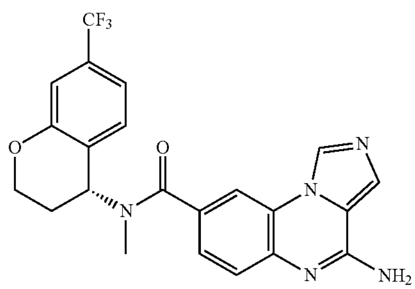 [SMILES: CN(C(=O)c1ccc2nc(N)c3cncn3c2c1)[C@@H]1CCOc2cc(C(F)(F)F)ccc21] | (R)-4-amino-N-methyl-N-(7-(trifluoromethyl)chroman-4-yl)imidazo[1,5-a]quinoxaline-8-carboxamide | ¹H NMR (400 MHz, DMSO-$d_6$) δ 9.24-9.13 (m, 1H), 8.37 (s, 1H), 7.92 (s, 1H), 7.53-7.39 (m, 5H), 7.29-7.24 (m, 1H), 7.15-7.10 (m, 1H), 5.99-5.16 (m, 1H), 4.50-4.10 (m, 2H), 2.73 (d, J = 4.4 Hz, 3H), 2.36-2.15 (m, 2H).<br>LCMS (ESI) m/z: 442.2 [M + H]⁺ |
| 26 | 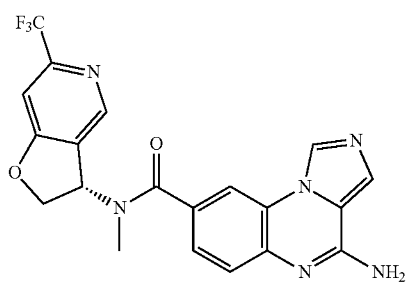 | (S)-4-amino-N-methyl-N-(6-(trifluoromethyl)-2,3-dihydrofuro[3,2-c]pyridin-3-yl)imidazo[1,5-a]quinoxaline-8-carboxamide | ¹H NMR (400 MHz, DMSO-$d_6$) δ 9.19 (s, 1H), 8.79-8.45 (m, 2H), 8.34 (d, J = 1.7 Hz, 1H), 7.93 (s, 1H), 7.65-7.36 (m, 4H), 6.37 (s, 1H), 5.05-4.77 (m, 2H), 2.64 (d, J = 82.3 Hz, 3H).<br>¹⁹F NMR (376 MHz, DMSO-$d_6$) δ-66.36.<br>LCMS (ESI) m/z: 429.4 [M + H]⁺ |

| Ex. | Structure | Name | ¹H NMR & ¹⁹F NMR & LCMS |
|---|---|---|---|
| 27 | 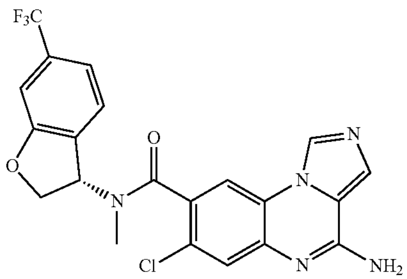 | (S)-4-amino-7-chloro-N-methyl-N-(6-(trifluoromethyl)-2,3-dihydrobenzofuran-3-yl)imidazo[1,5-a]quinoxaline-8-carboxamide | ¹H NMR (400 MHz, DMSO-$d_6$) δ 9.20-9.06 (m, 1H), 8.57-7.92 (m, 2H), 7.68-7.47 (m, 4H), 7.37-7.23 (m, 2H), 6.54-5.50 (m, 1H), 4.91-4.61 (m, 2H), 2.71-2.66 (m, 3H). LCMS (ESI) m/z: 462.10 [M + H]⁺ |
| 28 | 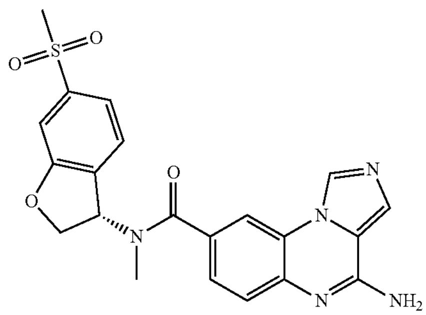 [SMILES: CN(C(=O)c1ccc2nc(N)c3cncn3c2c1)[C@@H]1COc2cc(S(C)(=O)=O)ccc21] | (S)-4-amino-N-methyl-N-(6-(methylsulfonyl)-2,3-dihydrobenzofuran-3-yl)imidazo[1,5-a]quinoxaline-8-carboxamide | ¹HNMR (400 MHz, DMSO-$d_6$) δ 9.18 (s, 1H), 8.34 (s, 1H), 7.92 (s, 1H), 7.69 (d, J = 7.8 Hz, 1H), 7.54 (d, J = 7.9 Hz, 1H), 7.47 (d, J = 10.5 Hz, 4H), 7.41 (s, 1H), 6.40 (s, 1H), 4.84 (s, 1H), 4.74 (dd, J = 10.2, 4.5 Hz, 1H), 3.24 (s, 3H), 2.69 (s, 3H). LCMS (ESI): 438.25 [M + H]⁺ |
| 29 | 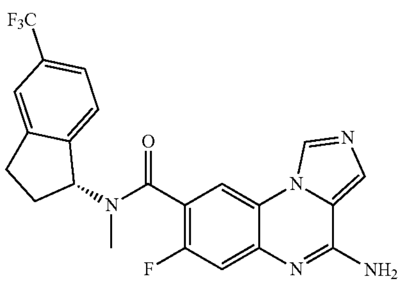 | (S)-4-amino-7-fluoro-N-methyl-N-(6-(trifluoromethyl)-2,3-dihydrobenzofuran-3-yl)imidazo[1,5-a]quinoxaline-8-carboxamide | ¹H NMR (400 MHz, DMSO-$d_6$) δ 9.12 (s, 1H), 8.32 (d, J = 6.6 Hz, 1H), 7.93 (d, J = 3.2 Hz, 1H), 7.58 (d, J = 26.7 Hz, 3H), 7.41-7.19 (m, 3H), 6.51-5.61 (m, 1H), 4.96-4.60 (m, 2H), 2.65 (d, J = 31.4 Hz, 3H). ¹⁹F NMR (376 MHz, DMSO-$d_6$) δ-60.83 (d, J = 10.8 Hz). LCMS (ESI) m/z: 579.2 [M + H]⁺ |
| 30 | 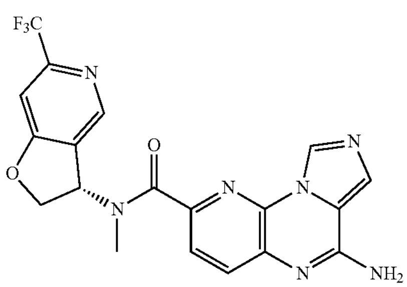 [SMILES: CN(C(=O)c1ccc2nc(N)c3cncn3c2n1)[C@@H]1COc2cc(C(F)(F)F)ncc21] | (S)-6-amino-N-methyl-N-(6-(trifluoromethyl)-2,3-dihydrobenzofuran-3-yl)imidazo[1,5-a]pyrido[3,2-e]pyrazine-2-carboxamide | ¹H NMR (400 MHz, DMSO-$d_6$) δ 8.97 (d, J = 24.2 Hz, 1H), 8.04-7.85 (m, 2H), 7.83-7.58 (m, 4H), 7.31 (dd, J = 36.5, 11.5 Hz, 2H), 6.48-6.08 (m, 1H), 4.78 (dt, J = 30.4, 9.0 Hz, 2H), 2.86-2.69 (s, 3H). LCMS (ESI) m/z: 429.20 [M + H]⁺ |
| 31 | 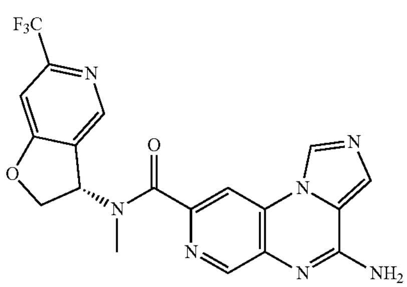 | (S)-4-amino-N-methyl-N-(6-(trifluoromethyl)-2,3-dihydrofuro[3,2-c]pyridin-3-yl)imidazo[1,5-a]pyrido[3,4-e]pyrazine-8-carboxamide | ¹H NMR (400 MHz, DMSO-$d_6$) δ 9.69-9.21 (m, 1H), 8.86-8.41 (m, 3H), 8.12-7.97 (m, 1H), 7.76 (d, J = 12.4 Hz, 2H), 7.58-7.32 (m, 1H), 6.47-6.09 (m, 1H), 4.89-4.84 (m, 1H), 3.17 (d, J = 5.2 Hz, 1H), 2.80 (d, J = 55.3 Hz, 3H). ¹⁹F NMR (376 MHz, DMSO-$d_6$) δ-66.33, −66.34. LCMS (ESI) m/z: 430.4 [M + H]⁺ |

-continued

| Ex. | Structure | Name | ¹H NMR & ¹⁹F NMR & LCMS |
|---|---|---|---|
| 32 | 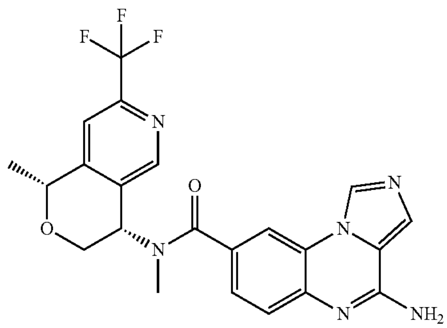 [SMILES: C[C@H]1OC[C@@H](N(C)C(=O)c2ccc3nc(N)c4cncn4c3c2)c2cnc(C(F)(F)F)cc21] | 4-amino-N-methyl-N-((1R,4S)-1-methyl-7-(trifluoromethyl)-3,4-dihydro-1H-pyrano[4,3-c]pyridin-4-yl)imidazo[1,5-a]quinoxaline-8-carboxamide | ¹H NMR (400 MHz, DMSO-d$_6$) δ 9.20 (s, 1H), 8.80 (s, 1H), 8.37 (s, 1H), 8.03-7.76 (m, 2H), 7.67-7.27 (m, 4H), 5.76 (s, 1H), 4.82 (s, 1H), 4.55-3.99 (m, 2H), 2.82 (s, 3H), 1.59 (d, J = 6.6 Hz, 3H). LCMS (ESI): 457.40 [M + H]⁺ |
| 33 | 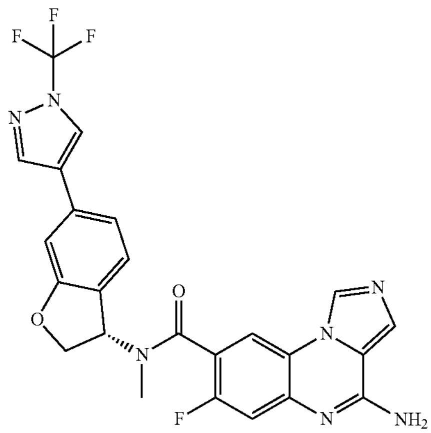 [SMILES: CN(C(=O)c1cc2c(cc1F)nc(N)c1cncn12)[C@@H]1COc2cc(-c3cnn(C(F)(F)F)c3)ccc21] | (S)-4-amino-7-fluoro-N-methyl-N-(6-(1-(trifluoromethyl)-1H-pyrazol-4-yl)-2,3-dihydrobenzofuran-3-yl)imidazo[1,5-a]quinoxaline-8-carboxamide | ¹H NMR (400 MHz, DMSO-d$_6$) δ 9.14 (s, 1H), 9.01 (d, J = 7.1 Hz, 1H), 8.49 (d, J = 8.4 Hz, 1H), 8.33 (d, J = 6.6 Hz, 1H), 7.93 (d, J = 3.6 Hz, 1H), 7.61 (s, 2H), 7.44-7.19 (m, 4H), 6.48-5.53 (m, 1H), 4.88-4.52 (m, 2H), 2.76-2.57 (m, 3H). LCMS (ESI) m/z: 512.2 [M + H]⁺ |
| 34 | 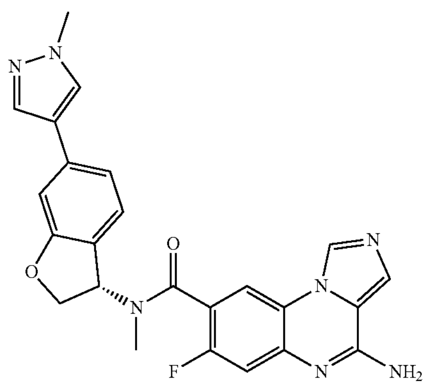 [SMILES: CN(C(=O)c1cc2c(cc1F)nc(N)c1cncn12)[C@@H]1COc2cc(-c3cnn(C)c3)ccc21] | (S)-4-amino-7-fluoro-N-methyl-N-(6-(1-methyl-1H-pyrazol-4-yl)-2,3-dihydrobenzofuran-3-yl)imidazo[1,5-a]quinoxaline-8-carboxamide | ¹H NMR (400 MHz, DMSO-d$_6$) δ 9.14 (s, 1H), 8.33 (d, J = 6.6 Hz, 1H), 8.15 (d, J = 7.2 Hz, 1H), 7.98-7.84 (m, 2H), 7.61 (s, 2H), 7.35-7.05 (m, 4H), 6.44-5.47 (m, 1H), 4.86-4.48 (m, 2H), 3.85 (d, J = 5.3 Hz, 3H), 2.75-2.55 (m, 3H). LCMS (ESI) m/z: 457.2 [M + H]⁺ |
| 35 | 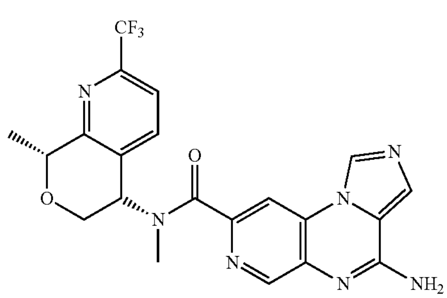 | 4-amino-N-methyl-N-((5S,8R)-8-methyl-2-(trifluoromethyl)-5,8-dihydro-6H-pyrano[3,4-b]pyridin-5-yl)imidazo[1,5-a]pyrido[3,4-e]pyrazine-8-carboxamide | ¹H NMR (400 MHz, DMSO-d$_6$) δ 9.29 (s, 1H), 8.66 (d, J = 6.0 Hz, 1H), 8.55 (d, J = 30.0 Hz, 1H), 8.15 (dd, J = 95.7, 8.1 Hz, 1H), 7.99 (s, 1H), 7.98-7.86 (m, 1H), 7.73 (d, J = 9.9 Hz, 2H), 5.63 (d, J = 169.5 Hz, 1H), 4.80 (dq, J = 40.6, 6.6 Hz, 1H), 4.26 (d, J = 12.3 Hz, 1H), 4.10 (ddd, J = 60.3, 12.6, 4.5Hz, 1H), 2.86 (d, J = 10.3 Hz, 3H), 1.58 (d, J = 6.6 Hz, 3H). LCMS (ESI) m/z: 458.5 [M + H]⁺ |

| Ex. | Structure | Name | ¹H NMR & ¹⁹F NMR & LCMS |
|---|---|---|---|
| 36 | 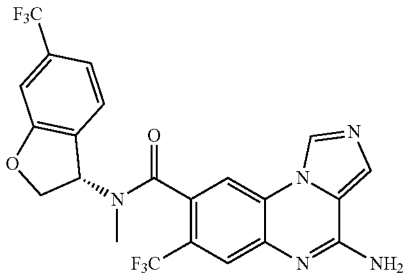 [SMILES: CN(C(=O)c1cc2c(cc1C(F)(F)F)nc(N)c1cncn12)[C@@H]1COc2cc(C(F)(F)F)ccc21] | (S)-4-amino-N-methyl-7-(trifluoromethyl)-N-(6-(trifluoromethyl)-2,3-dihydrobenzofuran-3-yl)imidazo[1,5-a]quinoxaline-8-carboxamide | ¹H NMR (400 MHz, DMSO-d₆) δ 9.23 (d, J = 73.2 Hz, 1H), 8.46 (d, J = 113.8 Hz, 1H), 8.07-7.80 (m, 1H), 7.71 (d, J = 9.0 Hz, 1H), 7.53 (s, 3H), 7.34 (dd, J = 16.4, 7.8 Hz, 1H), 7.21 (d, J = 25.6 Hz, 1H), 6.71-5.28 (m, 1H), 5.09-4.29 (m, 2H), 2.94 (d, J = 178.2 Hz, 3H). LCMS (ESI) m/z: 496.4 [M + H]⁺ |
| 37 | 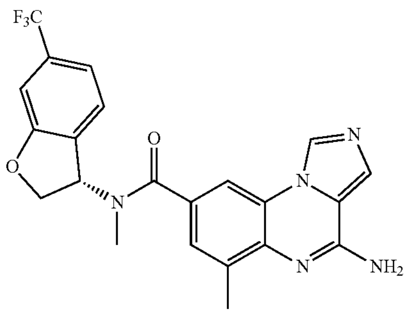 [SMILES: Cc1cc(C(=O)N(C)[C@@H]2COc3cc(C(F)(F)F)ccc32)cc2c1nc(N)c1cncn12] | (S)-4-amino-N, 6-dimethyl-N-(6-(trifluoromethyl)-2,3-dihydrobenzofuran-3-yl)imidazo[1,5-a]quinoxaline-8-carboxamide | ¹H NMR (400 MHz, DMSO-d₆) δ 9.15 (s, 1H), 8.17 (d, J = 2.2 Hz, 1H), 7.91 (s, 1H), 7.65-7.63 (d, J = 7.8 Hz, 1H), 7.43 (s, 2H), 7.39 (s, 1H), 7.35-7.33 (d, J = 7.8 Hz, 1H), 7.26 (s, 1H), 6.53-5.75 (m, 1H), 4.82-4.69 (m, 2H), 2.67 (s, 3H), 2.53 (s, 3H). LCMS (ESI) m/z: 442.10 [M + H]⁺ |
| 38 | 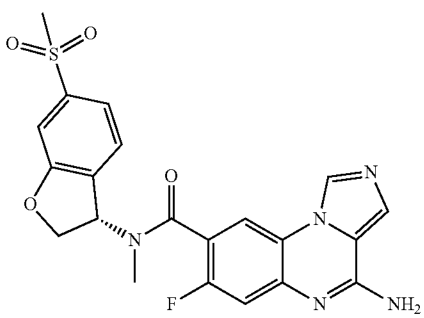 [SMILES: CN(C(=O)c1cc2c(cc1F)nc(N)c1cncn12)[C@@H]1COc2cc(S(C)(=O)=O)ccc21] | (S)-4-amino-7-fluoro-N-methyl-N-(6-(methylsulfonyl)-2,3-dihydrobenzofuran-3-yl)imidazo[1,5-a]quinoxaline-8-carboxamide | ¹H NMR (400 MHz, DMSO-d₆) δ 9.12 (s, 1H), 8.32-8.31 (m, 1H), 7.93-7.92 (m, 1H), 7.65-7.61 (m, 2H), 7.59-7.57 (m, 1H), 7.47-7.39 (m, 1H), 7.28-7.23 (m, 1H), 6.55-6.47 (m, 1H), 4.94 4.85 (m, 1H), 4.69-4.62 (m, 2H), 3.24-3.21 (m, 3H), 2.70-2.53 (m, 3H). LCMS (ESI): 456.10 [M + H]⁺ |
| 39 | 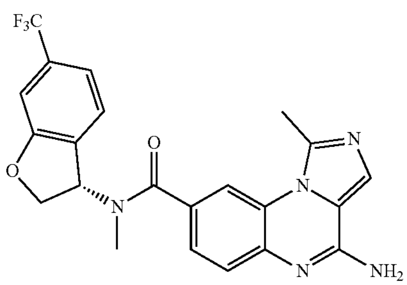 [SMILES: Cc1ncc2c(N)nc3ccc(C(=O)N(C)[C@@H]4COc5cc(C(F)(F)F)ccc54)cc3n12] | (S)-4-amino-N,1-dimethyl-N-(6-(trifluoromethyl)-2,3-dihydrobenzofuran-3-yl)imidazo[1,5-a]quinoxaline-8-carboxamide | ¹H NMR (400 MHz, DMSO-d₆) δ 8.15-8.10 (m, 1H), 7.83 (s, 1H), 7.65-7.61 (m, 1H), 7.55-7.45 (m, 2H), 7.38-7.32 (m, 2H), 7.33 (d, J = 8.0 Hz, 1H), 7.25-7.21 (m, 1H), 6.29-5.95 (m, 1H), 4.86-4.71 (m, 2H), 2.99 (s, 3H), 2.68 (s, 3H). LCMS (ESI) m/z: 442.20 [M + H]⁺ |
| 40 | 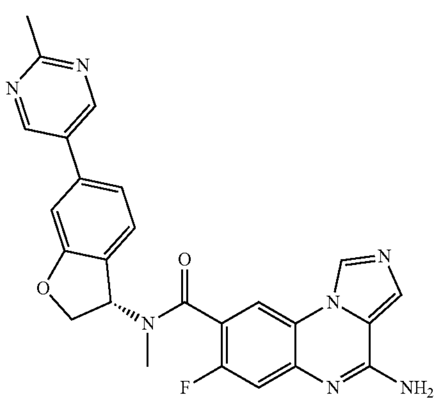 [SMILES: Cc1ncc(-c2ccc3c(c2)OC[C@H]3N(C)C(=O)c2cc3c(cc2F)nc(N)c2cncn23)cn1] | (S)-4-amino-7-fluoro-N-methyl-N-(6-(2-methylpyrimidin-5-yl)-2,3-dihydrobenzofuran-3-yl)imidazo[1,5-a]quinoxaline-8-carboxamide | ¹H NMR (400 MHz, DMSO-d₆) δ 9.15 (d, J = 5.3 Hz, 1H), 9.02 (d, J = 9.9 Hz, 2H), 8.34 (d, J = 6.6 Hz, 1H), 7.94 (d, J = 3.5 Hz, 1H), 7.63 (s, 2H), 7.52-7.13 (m, 4H), 6.56-5.56 (m, 1H), 4.93-4.52 (m, 2H), 2.83-2.57 (m, 6H). LCMS (ESI) m/z: 470.1 [M + H]⁺ |

-continued

| Ex. | Structure | Name | ¹H NMR & ¹⁹F NMR & LCMS |
|---|---|---|---|
| 41 | 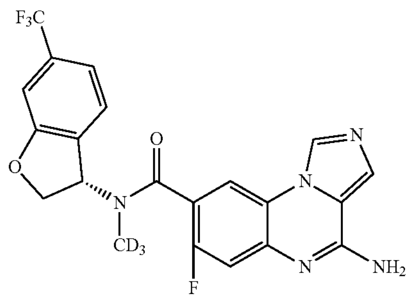 [SMILES: [2H]C([2H])([2H])N(C(=O)c1cc2c(cc1F)nc(N)c1cncn12)[C@@H]1COc2cc(C(F)(F)F)ccc21] | (S)-4-amino-7-fluoro-N-(methyl-d3)-N-(6-(trifluoromethyl)-2,3-dihydrobenzofuran-3-yl)imidazo[1,5-a]quinoxaline-8-carboxamide | ¹H NMR (400 MHz, DMSO-d$_6$) δ 9.14 (s, 1H), 8.34 (d, J = 6.5 Hz, 1H), 7.96 (d, J = 2.3 Hz, 1H), 7.71 (s, 2H), 7.56 (d, J = 7.8 Hz, 1H), 7.42-7.15 (m, 3H), 6.53-5.58 (m, 1H), 4.88 (t, J = 9.8 Hz, 1H), 4.68 (dd, J = 10.3, 4.3 Hz, 1H) LCMS (ESI) m/z: 449.4 [M + H]$^+$ |
| 42 | 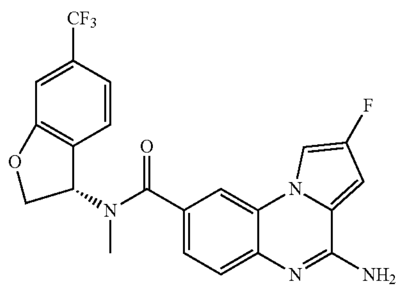 [SMILES: CN(C(=O)c1ccc2nc(N)c3cc(F)cn3c2c1)[C@@H]1COc2cc(C(F)(F)F)ccc21] | (S)-4-amino-2-fluoro-N-methyl-N-(6-(trifluoromethyl)-2,3-dihydrobenzofuran-3-yl)pyrrolo[1,2-a]quinoxaline-8-carboxamide | ¹H NMR (400 MHz, DMSO-d$_6$) δ 8.41 (s, 1H), 8.13 (d, J = 1.6 Hz, 1H), 7.64-7.63 (d, J = 7.8 Hz, 1H), 7.49-7.38 (m, 2H), 7.34-7.32 (m, 1H), 7.25-7.24 (m, 1H), 7.18 (s, 2H), 6.97-6.95 (m, 1H), 6.46-5.62 (m, 1H), 4.82-4.54 (m, 2H), 2.67 (s, 3H). LCMS (ESI): 444.80 [M + H]$^+$ |
| 43 | 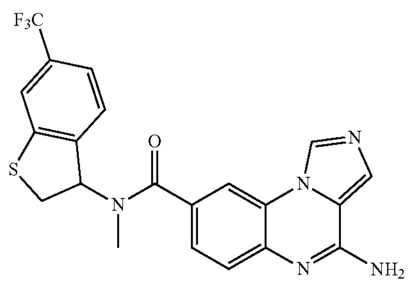 [SMILES: CN(C(=O)c1ccc2nc(N)c3cncn3c2c1)C1CSc2cc(C(F)(F)F)ccc21] | 4-amino-N-methyl-N-(6-(trifluoromethyl)-2,3-dihydrobenzo[b]thiophen-3-yl)imidazo[1,5-a]quinoxaline-8-carboxamide | ¹H NMR (400 MHz, DMSO-d$_6$) δ 9.18 (s, 1H), 8.36 (t, J = 1.2 Hz, 1H), 7.92 (s, 1H), 7.79-7.66 (m, 1H), 7.61-7.37 (m, 6H), 6.13 (d, J = 299.0 Hz, 1H), 3.69 (d, J = 49.5 Hz, 2H), 2.82 (s, 3H). LCMS (ESI): 442.2 [M + H]$^+$ |
| 44 | 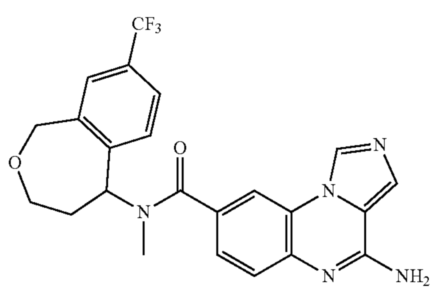 [SMILES: CN(C(=O)c1ccc2nc(N)c3cncn3c2c1)C1CCOCc2cc(C(F)(F)F)ccc21] | 4-amino-N-methyl-N-(8-(trifluoromethyl)-1,3,4,5-tetrahydrobenzo[c]oxepin-5-yl)imidazo[1,5-a]quinoxaline-8-carboxamide | ¹H NMR (400 MHz, DMSO-d$_6$) δ 9.24 (s, 1H), 8.30 (d, J = 69.6 Hz, 1H), 7.94 (s, 1H), 7.70 (s, 2H), 7.62-7.41 (m, 4H), 7.29 (d, J = 10.2 Hz, 1H), 5.97 (d, J = 10.7 Hz, 1H), 4.83 (q, J = 14.1 Hz, 2H), 4.11 (d, J = 57.7 Hz, 2H), 3.02 (s, 3H), 2.23 (dd, J = 48.7, 11.9 Hz, 2H). LCMS (ESI): 455.2 [M + H]$^+$ |
| 45 | 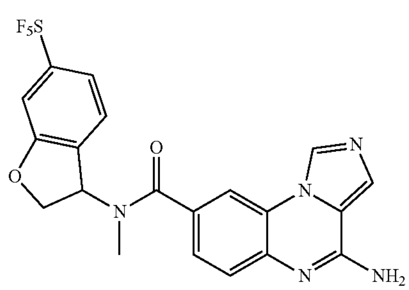 | 4-amino-N-methyl-N-(6-(pentafluoro-λ$^6$-sulfaneyl)-2,3-dihydrobenzofuran-3-yl)imidazo[1,5-a]quinoxaline-8-carboxamide | ¹HNMR (400 MHz, DMSO-d$_6$) δ 9.17 (s, 1H), 8.33 (s, 1H), 7.98 (s, 1H), 7.65-7.63 (m, 1H), 7.52-7.42 (m, 6H), 6.51-5.57 (m, 1H), 4.84-4.69 (m, 2H), 2.70 (s, 3H). LCMS (ESI): 486.1 [M + H]$^+$ |

-continued

| Ex. | Structure | Name | ¹H NMR & ¹⁹F NMR & LCMS |
|---|---|---|---|
| 46 | 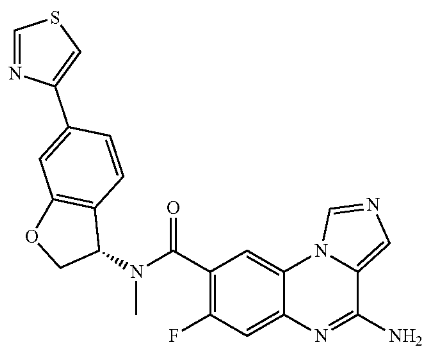 [SMILES: CN(C(=O)c1cc2c(cc1F)nc(N)c1cncn12)[C@@H]1COc2cc(-c3cscn3)ccc21] | (S)-4-amino-7-fluoro-N-methyl-N-(6-(thiazol-4-yl)-2,3-dihydrobenzofuran-3-yl)imidazo[1,5-a]quinoxaline-8-carboxamide | ¹H NMR (400 MHz, DMSO-d₆) δ 9.41-8.97 (m, 2H), 8.63-8.03 (m, 2H), 7.93 (d, J = 4.4 Hz, 1H), 7.77-7.47 (m, 3H), 7.42-7.06 (m, 3H), 6.71-5.34 (m, 1H), 5.00-4.49 (m, 2H), 2.66 (d, J = 41.7 Hz, 3H). LCMS (ESI) m/z: 461.20 [M + H]⁺ |
| 47 | 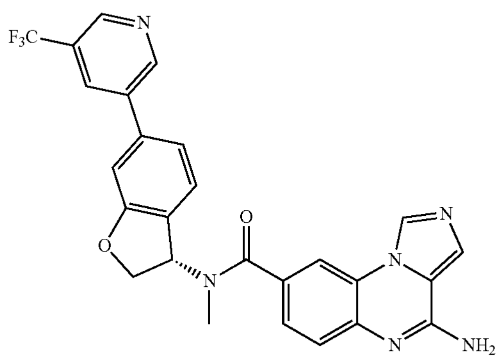 [SMILES: CN(C(=O)c1ccc2nc(N)c3cncn3c2c1)[C@@H]1COc2cc(-c3cncc(C(F)(F)F)c3)ccc21] | (S)-4-amino-N-methyl-N-(6-(5-(trifluoromethyl)pyridin-3-yl)-2,3-dihydrobenzofuran-3-yl)imidazo[1,5-a]quinoxaline-8-carboxamide | ¹H NMR (400 MHz, CDCl₃) δ 9.20 (d, J = 9.1 Hz, 2H), 8.97 (d, J = 1.9 Hz, 1H), 8.47 (s, 1H), 8.35 (s, 1H), 7.92 (s, 1H), 7.57 (d, J = 7.8 Hz, 1H), 7.46 (dd, J = 19.2, 6.8 Hz, 6H), 6.73 5.58 (m, 1H), 4.75 (d, J = 41.0 Hz, 2H), 2.70 (s, 3H). LCMS (ESI) m/z: 505.30 [M + H]⁺ |
| 48 | 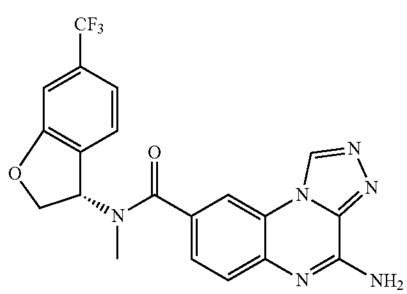 [SMILES: CN(C(=O)c1ccc2nc(N)c3nncn3c2c1)[C@@H]1COc2cc(C(F)(F)F)ccc21] | (S)-4-amino-N-methyl-N-(6-(trifluoromethyl)-2,3-dihydrobenzofuran-3-yl)-[1,2,4]triazolo[4,3-a]quinoxaline-8-carboxamide | ¹H NMR (400 MHz, DMSO-d₆) δ 10.04 (s, 1H), 8.37 (t, J = 1.2 Hz, 1H), 7.88 (s, 2H), 7.68-7.56 (m, 3H), 7.34 (d, J = 7.8 Hz, 1H), 7.27 (s, 1H), 6.09 (d, J = 257.8 Hz, 1H), 5.20-4.40 (m, 2H), 2.69 (s, 3H). LCMS (ESI) m/z: 429.2 [M + H]⁺ |
| 49 | 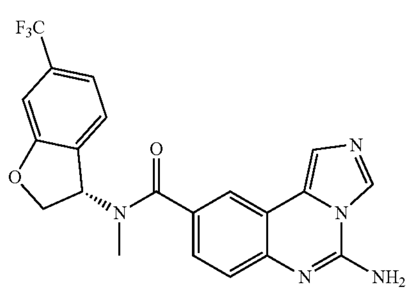 [SMILES: CN(C(=O)c1ccc2nc(N)n3cncc3c2c1)[C@@H]1COc2cc(C(F)(F)F)ccc21] | (S)-5-amino-N-methyl-N-(6-(trifluoromethyl)-2,3-dihydrobenzofuran-3-yl)imidazo[1,5-c]quinazoline-9-carboxamide | ¹H NMR (400 MHz, DMSO-d₆) δ 8.66 (s, 1H), 8.17 (d, J = 2.0 Hz, 1H), 7.99 (s, 1H), 7.81 (s, 2H), 7.66 (d, J = 7.8 Hz, 1H), 7.53 (dd, J = 8.3, 2.0 Hz, 1H), 7.44 (d, J = 8.4 Hz, 1H), 7.34 (d, J = 7.8 Hz, 1H), 7.26 (s, 1H), 6.39 (s, 1H), 4.90-4.60 (m, 2H), 2.68 (s, 3H) LCMS (ESI) m/z: 428.2 [M + H]⁺ |

| Ex. | Structure | Name | ¹H NMR & ¹⁹F NMR & LCMS |
|---|---|---|---|
| 50 | 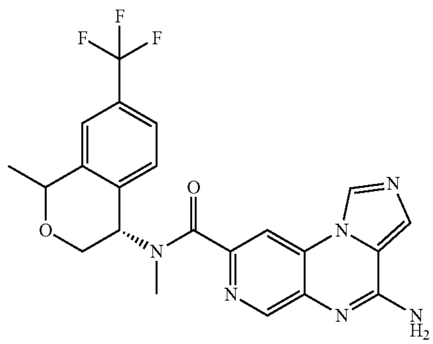 [SMILES: CC1OC[C@@H](N(C)C(=O)c2cc3c(cn2)nc(N)c2cncn23)c2ccc(C(F)(F)F)cc21] | 4-amino-N-methyl-N-((4S)-1-methyl-7-(trifluoromethyl)isochroman-4-yl)imidazo[1,5-a]pyrido[3,4-e]pyrazine-8-carboxamide | $^1$H NMR (400 MHz, DMSO-$d_6$) δ 9.34-9.25 (m, 1H), 8.70-8.62 (m, 1H), 8.62-8.47 (m, 1H), 7.99 (d, J = 2.0 Hz, 1H), 7.78-7.45 (m, 5H), 5.92-5.18 (m, 1H), 4.88 (ddq, J = 74.5, 37.9, 6.4 Hz, 1H), 4.34-4.19 (m, 1H), 4.13-3.88 (m, 1H), 2.83-2.68 (m, 3H), 1.63-1.41 (m, 3H).<br>$^{19}$F NMR (376 MHz, DMSO) δ-60.91.<br>LCMS: LCMS (ESI) m/z: 457 [M + H]$^+$ |
| 51 | 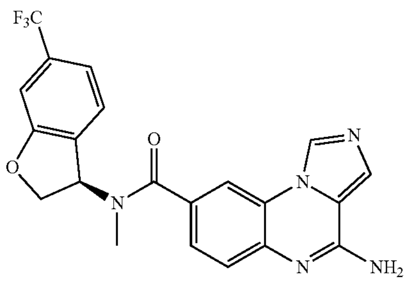 [SMILES: CN(C(=O)c1ccc2nc(N)c3cncn3c2c1)[C@H]1COc2cc(C(F)(F)F)ccc21] | (R)-4-amino-N-methyl-N-(6-(trifluoromethyl)-2,3-dihydrobenzofuran-3-yl)imidazo[1,5-a]quinoxaline-8-carboxamide | $^1$H NMR (400 MHz, DMSO-$d_6$) 9.19 (s, 1H), 8.35 (s, 1H), 7.93 (s, 1H), 7.65 (d, J = 7.8 Hz, 1H), 7.48 (d, J = 8.6 Hz, 4H), 7.40-7.22 (m, 2H), 6.08 (d, J = 254.7 Hz, 1H), 5.00-4.65 (m, 2H), 2.69 (s, 3H).<br>LCMS (ESI) m/z: 428.1 [M + H]$^+$ |
| 52 | 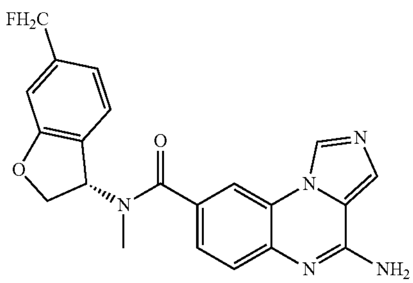 | (S)-4-amino-N-(6-(fluoromethyl)-2,3-dihydrobenzofuran-3-yl)-N-methylimidazo[1,5-a]quinoxaline-8-carboxamide | $^1$H NMR (400 MHz, DMSO-$d_6$) δ 9.08 (s, 1H), 8.26 (s, 1H), 7.94 (s, 1H), 7.58-7.55 (m, 1H), 7.54-7.52 (m, 1H), 7.49-7.30 (m, 1H), 7.05-7.01 (m, 1H), 6.93-6.88 (m, 1H), 6.48-5.75 (m, 1H), 5.44-5.38 (m, 1H), 5.28 (s, 1H), 4.69-4.63 (m, 1H), 3.59-3.54 (m, 1H), 2.80-2.69 (m, 3H)<br>LCMS (ESI): 392.10 [M + H]$^+$ |
| 53 | 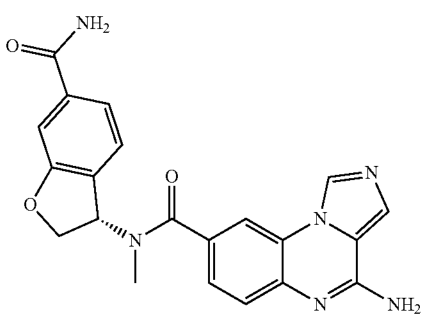 [SMILES: CN(C(=O)c1ccc2nc(N)c3cncn3c2c1)[C@@H]1COc2cc(C(N)=O)ccc21] | (S)-4-amino-N-(6-carbamoyl-2,3-dihydrobenzofuran-3-yl)-N-methylimidazo[1,5-a]quinoxaline-8-carboxamide | $^1$H NMR (400 MHz, DMSO-$d_6$) δ 9.18 (s, 1H), 8.33 (s, 1H), 7.95 (s, 1H), 7.91 (s, 1H), 7.50-7.47 (m, 4H), 7.43 (s, 2H), 7.38-7.35 (m, 2H), 6.42-5.71 (m, 1H), 4.89-4.64 (m, 2H), 2.66-2.65 (m, 3H).<br>LCMS (ESI): 403.10 [M + H]$^+$ |
| 54 | 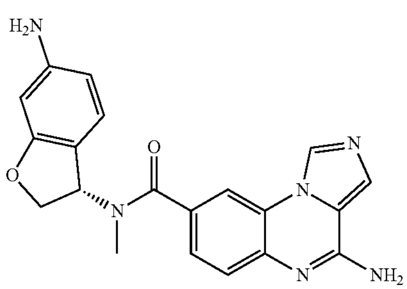 [SMILES: CN(C(=O)c1ccc2nc(N)c3cncn3c2c1)[C@@H]1COc2cc(N)ccc21] | (S)-4-amino-N-(6-amino-2,3-dihydrobenzofuran-3-yl)-N-methylimidazo[1,5-a]quinoxaline-8-carboxamide | $^1$H NMR (400 MHz, DMSO-$d_6$) δ 9.18 (s, 1H), 8.28 (s, 1H), 7.91 (s, 1H), 7.47-7.42 (m, 4H), 7.00 (d, J = 8.0 Hz, 1H), 6.17 (d, J = 8.0 Hz, 1H), 6.05 (s, 1H), 5.40- 5.23 (d, 2H), 4.61-4.48 (s, 2H), 2.77 (s, 1H), 2.61 (s, 3H).<br>LCMS (ESI): 375.10 [M + H]$^+$ |

-continued

| Ex. | Structure | Name | ¹H NMR & ¹⁹F NMR & LCMS |
|---|---|---|---|
| 55 | 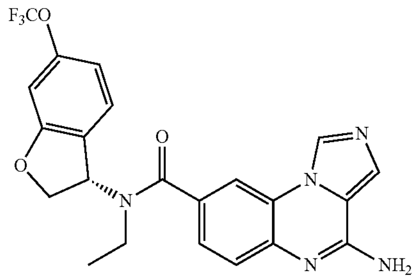 | (S)-4-amino-N-ethyl-N-(6-(trifluoromethyl)-2,3-dihydrobenzofuran-3-yl)imidazo[1,5-a]quinoxaline-8-carboxamide | ¹H NMR (400 MHz, DMSO-d₆) δ 9.17 (s, 1H), 8.28 (d, J = 1.7 Hz, 1H), 7.91 (d, J = 0.7 Hz, 1H), 7.66 (d, J = 7.8 Hz, 1H), 7.47-7.42 (m, 4H), 7.33-7.29 (m, 1H), 7.23 (d, J = 1.5 Hz, 1H), 5.85 (s, 1H), 4.79-4.68 (m, 2H), 3.23-3.20 (m, 2H), 0.93 (s, 3H). LCMS (ESI) m/z: 442.15 [M + H]⁺ |
| 56 | 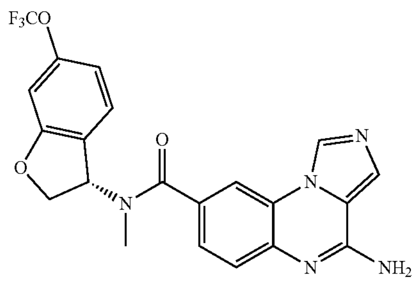 [SMILES: CN(C(=O)c1ccc2nc(N)c3cncn3c2c1)[C@@H]1COc2cc(OC(F)(F)F)ccc21] | (S)-4-amino-N-methyl-N-(6-(trifluoromethoxy)-2,3-dihydrobenzofuran-3-yl)imidazo[1,5-a]quinoxaline-8-carboxamide | ¹H NMR (400 MHz, DMSO-d₆) δ 9.12 (s, 1H), 8.31 (d, J = 6.6 Hz, 1H), 7.93 (d, J = 3.1 Hz, 1H), 7.86-7.03 (m, 5H), 6.94 (s, 2H), 6.42 (dd, J = 9.1, 4.0 Hz, 1H), 4.92-4.55 (m, 2H), 3.06-2.56 (m, 3H). LCMS (ESI): 443.75 [M + H]⁺ |
| 57 | 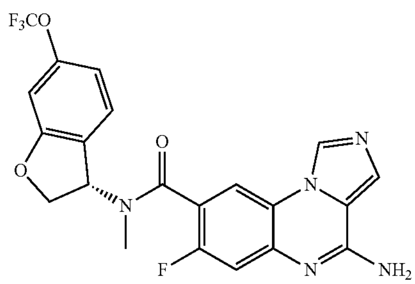 [SMILES: CN(C(=O)c1cc2c(cc1F)nc(N)c1cncn12)[C@@H]1COc2cc(OC(F)(F)F)ccc21] | (S)-4-amino-7-fluoro-N-methyl-N-(6-(trifluoromethoxy)-2,3-dihydrobenzofuran-3-yl)imidazo[1,5-a]quinoxaline-8-carboxamide | ¹H NMR (400 MHz, DMSO-d₆) δ 9.21 (s, 1H), 8.34 (s, 1H), 8.0-7.82 (m, 1H), 7.66-7.39 (m, 1H), 7.36-7.30 (m, 1H), 6.96 (s, 2H), 6.52 (m, 1H), 4.71 (d, J = 4.2 Hz, 2H), 2.67 (s, 3H). LCMS (ESI): 461.75 [M + H]⁺ |
| 107 | 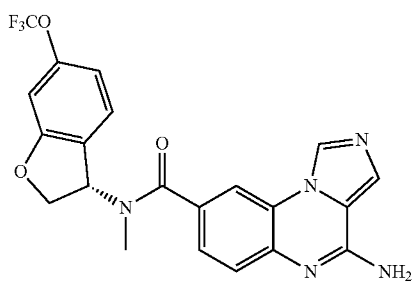 | (S)-4-amino-N-methyl-N-(6-(trifluoromethyl)-2,3-dihydrobenzofuran-3-yl)imidazo[1,5-a]quinoxaline-8-carboxamide | ¹H NMR (400 MHz, DMSO-d₆) δ 9.18 (s, 1H), 8.33 (t, J = 1.1 Hz, 1H), 7.91 (d, J = 0.8 Hz, 1H), 7.64 (d, J = 7.8 Hz, 1H), 7.52-7.41 (m, 4H), 7.33 (d, J = 7.8 Hz, 1H), 7.25 (s, 1H), 6.37 (s, 1H), 5.86 (s, 1H), 4.81 (s, 1H), 4.72 (dd, J = 10.3, 4.4 Hz, 1H), 2.68 (s, 3H). LCMS (ESI) m/z: 428.2 [M + H]⁺ |
| 108 | 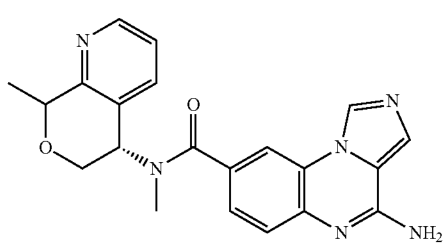 [SMILES: CC1OC[C@@H](N(C)C(=O)c2ccc3nc(N)c4cncn4c3c2)c2cccnc21] | 4-amino-N-methyl-N-((5S)-8-methyl-5,8-dihydro-6H-pyrano[3,4-b]pyridin-5-yl)imidazo[1,5-a]quinoxaline-8-carboxamide | ¹H NMR (400 MHz, DMSO-d₆) δ 9.26-9.12 (m, 1H), 8.52 (d, J = 18.6 Hz, 1H), 8.43-8.32 (m, 1H), 7.92 (s, 1H), 7.79 (dd, J = 23.1, 7.8 Hz, 1H), 7.61-7.32 (m, 5H), 5.79 (d, J = 49.5 Hz, 1H), 5.09-4.53 (m, 2H), 4.43-3.89 (m, 2H), 2.77 (d, J = 31.5 Hz, 3H), 1.67-1.32 (m, 3H). LCMS (ESI) m/z: 389.4 [M + H]⁺ |

| Ex. | Structure | Name | ¹H NMR & ¹⁹F NMR & LCMS |
|---|---|---|---|
| 124 | 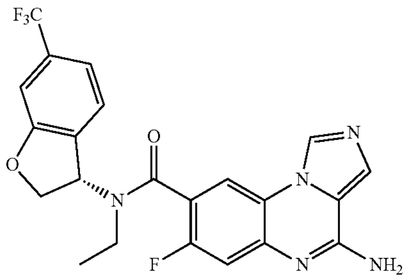 [SMILES: CCN(C(=O)c1cc2c(cc1F)nc(N)c1cncn12)[C@@H]1COc2cc(C(F)(F)F)ccc21] | (S)-4-amino-N-ethyl-7-fluoro-N-(6-(trifluoromethyl)-2,3-dihydrobenzofuran-3-yl)imidazo[1,5-a]quinoxaline-8-carboxamide | ¹H NMR (400 MHz, DMSO-$d_6$) δ 9.10- 9.04 (m, 1H), 8.42-8.21 (m, 1H), 7.86 (s, 1H), 7.53-7.49 (m, 3H), 7.26-7.24 (m, 1H), 7.21-7.15 (m, 2H), 5.94-5.53 (s, 1H), 4.87-4.82 (t, J = 9.7 Hz, 1H), 4.60-4.57 (m, 3H), 0.98-0.79 (m, 3H). LCMS (ESI) m/z: 460.20 [M + H]⁺ |
| 110 | 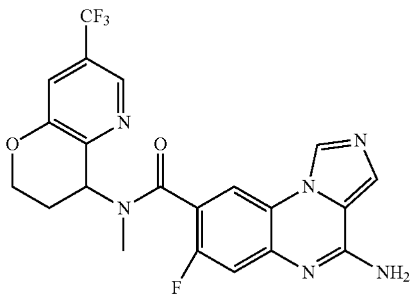 [SMILES: CN(C(=O)c1cc2c(cc1F)nc(N)c1cncn12)C1CCOc2cc(C(F)(F)F)cnc21] | 4-amino-7-fluoro-N-methyl-N-(7-(trifluoromethyl)-3,4-dihydro-2H-pyrano[3,2-b]pyridin-4-yl)imidazo[1,5-a]quinoxaline-8-carboxamide | ¹H NMR (400 MHz, DMSO-$d_6$) δ 9.14 (d, J = 52.0 Hz, 1H), 8.69-8.49 (m, 1H), 8.31 (dd, J = 21.8, 6.5 Hz, 1H), 7.91 (d, J = 11.2 Hz, 1H), 7.63 (dd, J = 23.9, 2.0 Hz, 1H), 7.54 (d, J = 16.2 Hz, 2H), 7.22 (dd, J = 11.0, 7.9 Hz, 1H), 6.03-5.01 (m, 1H), 4.64 4.17 (m, 2H), 2.71 (d, J = 2.0 Hz, 3H), 2.46-2.20 (m, 2H). LCMS (ESI) m/z: 461.20 [M + H]⁺ |
| 125 | 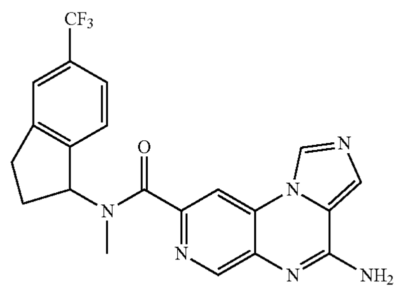 | 4-amino-N-(2,3-dihydro-1H-inden-1-yl)-N-methylimidazo[1,5-a]pyrido[3,4-e]pyrazine-8-carboxamide | ¹H NMR (400 MHz, DMSO-$d_6$) δ 9.43-9.23 (m, 1H), 8.79-8.61 (m, 1H), 8.51 (d, J = 3.7 Hz, 1H), 8.03-7.94 (m, 1H), 7.78-7.59 (m, 2H), 7.37-7.21 (m, 4H), 6.30-5.52 (m, 1H), 3.06-2.84 (m, 2H), 2.72-2.55 (m, 3H), 2.46-2.27 (m, 1H), 2.16-2.01 (m, 1H). LCMS (ESI) m/z: 359.15 [M + H]⁺ |
| 117 | 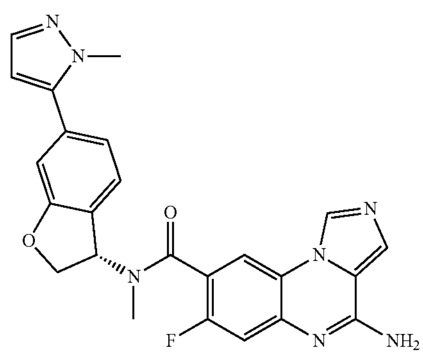 [SMILES: CN(C(=O)c1cc2c(cc1F)nc(N)c1cncn12)[C@@H]1COc2cc(-c3ccnn3C)ccc21] | (S)-4-amino-7-fluoro-N-methyl-N-(6-(1-methyl-1H-pyrazol-5-yl)-2,3-dihydrobenzofuran-3-yl)imidazo[1,5-a]quinoxaline-8-carboxamide | ¹H NMR (400 MHz, DMSO-$d_6$) δ 9.16 (s, 1H), 8.36 (d, J = 6.6 Hz, 1H), 7.95 (d, J = 3.6 Hz, 1H), 7.64 (s, 2H), 7.46 (dt, J = 5.7, 2.9 Hz, 2H), 7.36-6.98 (m, 3H), 6.53-5.46 (m, 2H), 4.92-4.52 (m, 2H), 3.86 (d, J = 14.2 Hz, 3H), 2.69 (d, J = 41.8 Hz, 3H). LCMS (ESI) m/z: 458.1 [M + H]⁺ |
| 119 | 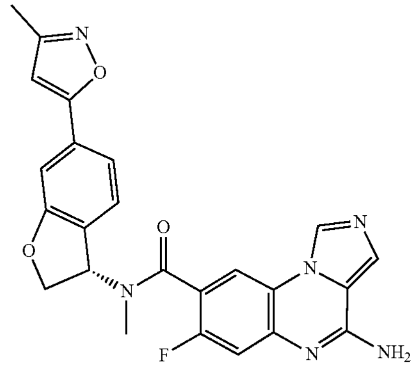 [SMILES: Cc1cc(-c2ccc3c(c2)OC[C@H]3N(C)C(=O)c2cc3c(cc2F)nc(N)c2cncn23)on1] | (S)-4-amino-7-fluoro-N-methyl-N-(6-(3-methylisoxazol-5-yl)-2,3-dihydrobenzofuran-3-yl)imidazo[1,5-a]quinoxaline-8-carboxamide | ¹H NMR (400 MHz, DMSO-$d_6$) δ 9.14 (s, 1H), 8.34 (d, J = 6.6 Hz, 1H), 7.94 (d, J = 3.6 Hz, 1H), 7.62 (s, 2H), 7.48 (d, J = 13.2 Hz, 2H), 7.41-7.20 (m, 2H), 6.93 (d, J = 6.6 Hz, 1H), 6.52-5.60 (m, 1H), 4.93-4.58 (m, 2H), 2.67 (d, J = 37.4 Hz, 3H), 2.29 (d, J = 4.6 Hz, 3H). LCMS (ESI) m/z: 459.1 [M + H]⁺ |

| Ex. | Structure | Name | ¹H NMR & ¹⁹F NMR & LCMS |
|---|---|---|---|
| 116 | 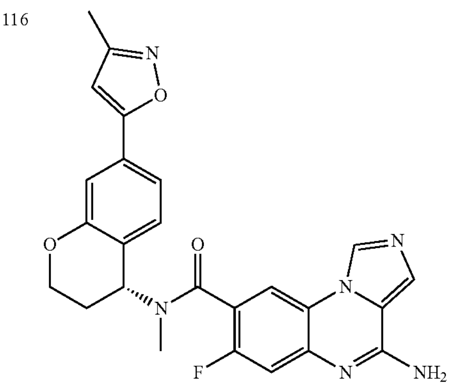 | (R)-4-amino-7-fluoro-N-methyl-N-(7-(3-methylisoxazol-5-yl)chroman-4-yl)imidazo[1,5-a]quinoxaline-8-carboxamide | ¹H NMR (400 MHz, DMSO-d₆) δ 9.27-9.07 (m, 1H), 8.42 (d, J = 6.6 Hz, 1H), 7.94 (d, J = 10.1 Hz, 1H), 7.62 (d, J = 14.7 Hz, 2H), 7.43 (dd, J = 8.1, 1.8 Hz, 1H), 7.33-7.11 (m, 3H), 7.03-6.82 (m, 1H), 6.04 (dd, J = 10.6, 6.3 Hz, 1H), 4.52-4.03 (m, 2H), 2.71 (d, J = 38.4 Hz, 3H), 2.42-2.06 (m, 5H). LCMS (ESI) m/z: 473.1 [M + H]⁺ |
| 130 | 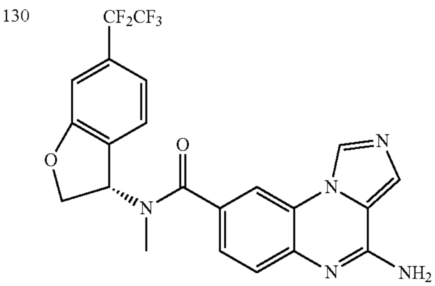 | (S)-4-amino-N-methyl-N-(6-(perfluoroethyl)-2,3-dihydrobenzofuran-3-yl)imidazo[1,5-a]quinoxaline-8-carboxamide | ¹H NMR (400 MHz, CDCl₃) δ 9.19 (s, 1H), 8.34 (d, J = 1.2 Hz, 1H), 7.92 (s, 1H), 7.68 (d, J = 7.8 Hz, 1H), 7.52-7.40 (m, 4H), 7.29 (d, J = 7.9 Hz, 1H), 7.21 (s, 1H), 6.54-5.59 (m, 1H), 5.09-4.48 (m, 2H), 2.69 (s, 3H). LCMS (ESI) m/z: 478.3 [M + H]⁺ |
| 129 | 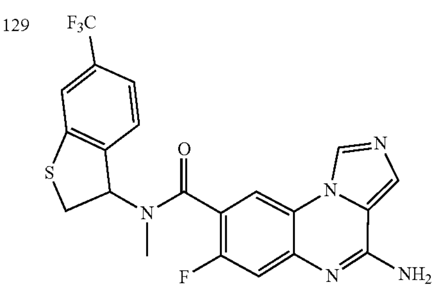 | 4-amino-7-fluoro-N-methyl-N-(6-(trifluoromethyl)-2,3-dihydrobenzo[b]thiophen-3-yl)imidazo[1,5-a]quinoxaline-8-carboxamide | ¹H NMR (400 MHz, DMSO-d₆) δ 9.12 (d, J = 17.1 Hz, 1H), 8.51-8.23 (m, 1H), 7.93 (d, J = 3.1 Hz, 1H), 7.83-7.67 (m, 1H), 7.61 (d, J = 7.1 Hz, 2H), 7.52 (t, J = 9.4 Hz, 1H), 7.40 (d, J = 8.0 Hz, 1H), 7.26 (dd, J = 11.0, 1.7 Hz, 1H), 6.62-5.58 (m, 1H), 3.93-3.38 (m, 2H), 2.79 (d, J = 41.5 Hz, 3H). LCMS (ESI) m/z: 462.2 [M + H]⁺ |

Example 58: (S)-4-amino-N-methyl-N-(6-(trifluoromethyl)-2,3-dihydrobenzofuran-3-yl)tetrazolo[1,5-a]quinoxaline-8-carboxamide

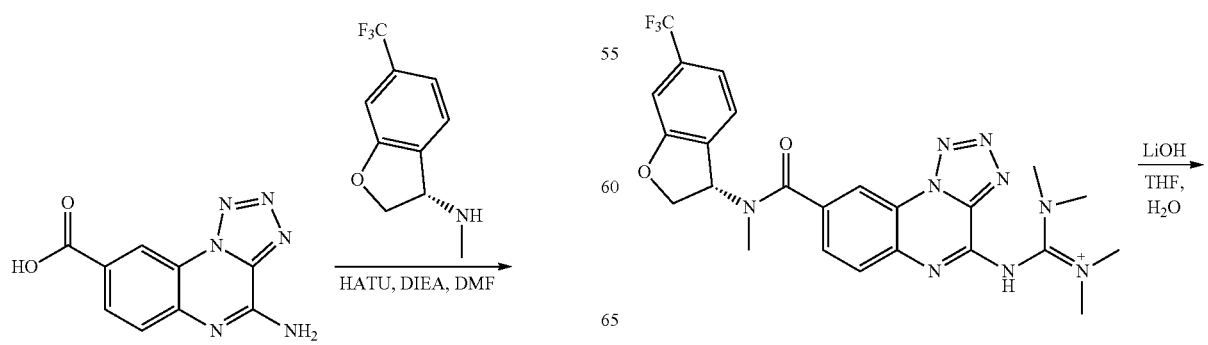

179

-continued

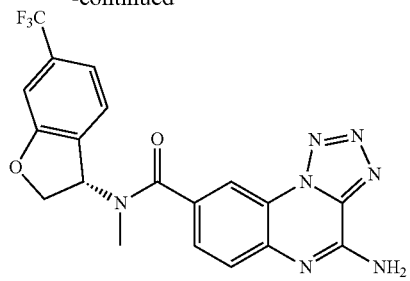

Step 1: Synthesis of (S)—N-((dimethylamino)((8-(methyl(6-(trifluoromethyl)-2,3-dihydrobenzofuran-3-yl)carbamoyl)tetrazolo[1,5-a]quinoxalin-4-yl)amino)methylene)-N-methylmethanaminium 4-aminotetrazolo[1,5-a]quinoxaline-8-carboxylic acid (131 mg, 0.56 mmol) was dissolved in DMF (4.5 mL), followed by addition of 2-(7-Azabenzotriazol-1-yl)-N,N,N',N'-tetramethyluronium hexafluorophosphate (325 mg, 0.85 mmol), N,N-diisopropylethylamine (220 mg, 1.71 mmol) and (S)—N-methyl-6-(trifluoromethyl)-2,3-dihydrobenzofuran-3-amine (144 mg, 0.660 mmol). The reaction proceeded at room temperature for 0.5 h. The reaction mixture was diluted with ethyl acetate (30 mL) and water (30 mL), the water layer was extracted with ethyl acetate (2×20 mL). The organic phase was combined and washed with saturated brine (30 mL), dried over anhydrous sodium sulfate, filtered, the filtrate was concentrated to obtain (S)-4-amino-N-methyl-N-(6-(trifluoromethyl)-2,3-dihydrobenzofuran-3-yl)tetrazolo[1,5-a]quinoxaline-8-carboxamide (100 mg, 0.19 mmol, yield: 33.33%), as white solid.

LCMS (ESI): 528[M+H]$^+$

Step 2: Synthesis of (S)-4-amino-N-methyl-N-(6-(trifluoromethyl)-2,3-dihydrobenzofuran-3-yl)tetrazolo[1,5-a]quinoxaline-8-carboxamide (S)-4-amino-N-methyl-N-(6-(trifluoromethyl)-2,3-dihydrobenzofuran-3-yl)tetrazolo[1,5-a]quinoxaline-8-carboxamide (100 mg, 0.19 mmol) was dissolved in THF (4 mL), followed by addition of water (4 mL) and LiOH (27 mg, 1.12 mmol). After completion of the reaction, the reaction mixture was concentrated and purified by HPLC (column: YMC Triart C$_{18}$ ExRs 5 m, 30 mm×150 mm; mobile phase A: water (10 mmol/L ammonium bicarbonate), mobile phase B: acetonitrile, flow rate: 60 ml/min; Gradient: From 25% B to 50% B within 10 minutes; Wavelength: 254 nanometers/220 nanometers; Rention time: 8.43/9.23 minutes.) to obtain (S)-4-amino-N-methyl-N-(6-(trifluoromethyl)-2,3-dihydrobenzofuran-3-yl)tetrazolo[1,5-a]quinoxaline-8-carboxamide (3.58 mg, 0.01 mmol, yield: 4.41%), as white solid.

$^1$H NMR (400 MHz, DMSO-d$_6$) δ 12.10 (s, 1H), 8.01-7.95 (d, 2H), 7.74-7.71 (d, 2H), 7.41-7.39 (d, 1H), 7.33 (s, 1H), 6.50-5.74 (m, 1H), 4.91-4.73 (m, 2H), 3.94 (s, 3H).

LCMS (ESI) m/z: 430.10[M+H]$^+$

180

Example 59 Synthesis of 4-amino-N-cyclopropyl-7-fluoro-N-(7-(5-(trifluoromethyl)pyridin-3-yl)-3,4-dihydro-2H-pyrano[3,2-b]pyridin-4-yl)imidazo[1,5-a]quinoxaline-8-carboxamide

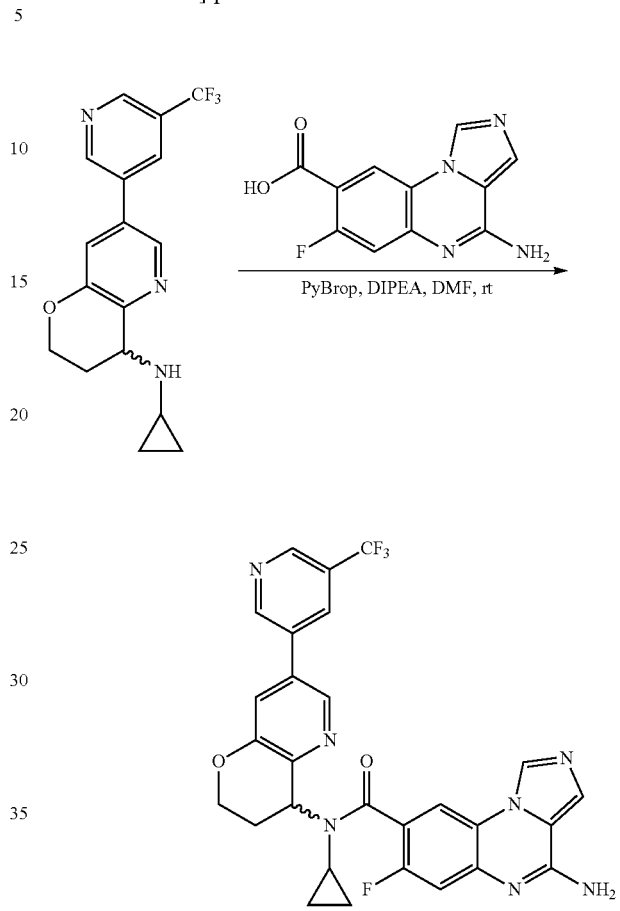

N-cyclopropyl-7-(5-(trifluoromethyl)pyridin-3-yl)-3,4-dihydro-2H-pyrano[3,2-b]pyridin-4-amine (45 mg, 0.13 mmol) was dissolved in DMF (3 mL), followed by addition of 4-amino-7-fluoroimidazo[1,5-a]quinoxaline-8-carboxylic acid (33 mg, 0.13 mmol), PyBrop (79 mg, 0.17 mmol) and DIPEA (50.3 mg, 0.39 mmol). The reaction was stirred at room temperature overnight. Then water (10 mL) was added and extracted with ethyl acetate (20 mL). The combined organic phase was washed with water (2×10 mL), washed with saturated brine (10 mL), dried over anhydrous sodium sulfate, filtered. The filtrate was concentrated to obtain crude product. The crude product was purified by column chromatograpy (MeOH/DCM=0-7%) to obtain 4-amino-N-cyclopropyl-7-fluoro-N-(7-(5-(trifluoromethyl)pyridin-3-yl)-3,4-dihydro-2H-pyrano[3,2-b]pyridin-4-yl)imidazo[1,5-a]quinoxaline-8-carboxamide (18 mg, yield: 25%).

$^1$H NMR (400 MHz, DMSO-d$_6$) δ 9.31 (s, 1H), 9.18 (s, 1H), 9.02 (s, 1H), 8.63 (d, J=29.1 Hz, 2H), 8.24 (s, 1H), 7.93 (s, 1H), 7.77 (s, 1H), 7.56 (s, 2H), 7.22 (d, J=11.4 Hz, 1H), 5.39 (s, 1H), 4.46 (d, J=53.9 Hz, 2H), 3.05 (s, 1H), 2.35 (s, 2H), 0.70 (s, 4H).

LCMS (ESI) m/z: 564.30[M+H]$^+$

By using the synthetic procedures described in Example 59, and replacing the corresponding starting materials, the embodiments listed in the table below can be prepared:

| Ex. | Structure | name | ¹H NMR & ¹⁹F NMR & LCMS |
|---|---|---|---|
| 60 | 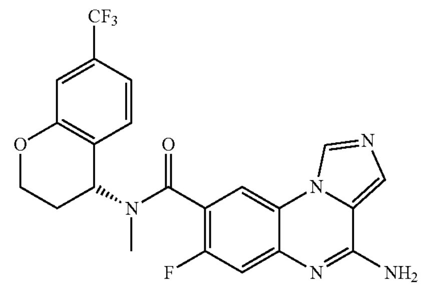 | (R)-4-amino-7-fluoro-N-methyl-N-(7-(trifluoromethyl)chroman-4-yl)imidazo[1,5-a]quinoxaline-8-carboxamide | ¹H NMR (400 MHz, DMSO-d₆) δ 9.14 (d, J = 28.3 Hz, 1H), 8.40 (d, J = 6.6 Hz, 1H), 8.02-7.84 (m, 1H), 7.59 (d, J = 14.5 Hz, 2H), 7.45-7.22 (m, 2H), 7.14 (d, J = 27.6 Hz, 1H), 5.56 (ddd, J = 387.9, 10.8, 6.3 Hz, 1H), 4.69-3.91 (m, 2H), 2.94-2.59 (m, 3H), 2.36-2.09 (m, 2H). LCMS (ESI) m/z: 460.20 [M + H]⁺ |
| 61 | 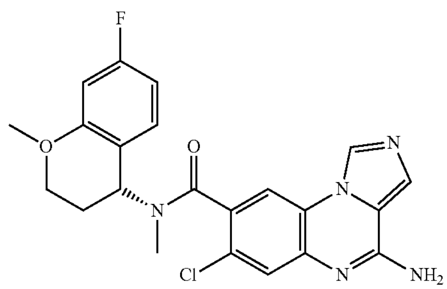 | 4-amino-7-chloro-N-((4S)-7-fluoro-1-methylisochroman-4-yl)-N-methylimidazo[1,5-a]quinoxaline-8-carboxamide | ¹HNMR (400 MHz, DMSO-d₆) δ 9.26-9.13 (m, 1H), 8.41-8.34 (m, 1H), 7.93-7.91 (m, 1H), 7.59-7.58 (m, 2H), 7.56-7.47 (m, 1H), 7.47-7.37 (m, 1H), 7.23-7.08 (m, 2H), 5.68-4.93 (m, 1H), 4.85-4.61 (m, 1H), 4.27-3.88 (m, 2H), 2.78-2.51 (m, 3H), 1.52-1.48 (m, 3H). LCMS (ESI) m/z: 440.2 [M + H]⁺ |
| 62 | 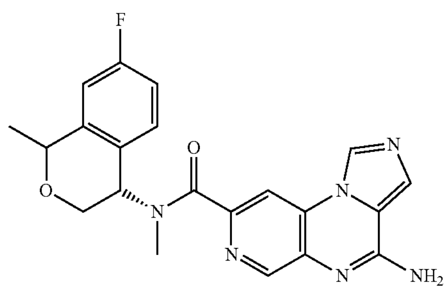 | 4-amino-N-((4S)-7-fluoro-1-methylisochroman-4-yl)-N-methylimidazo[1,5-a]pyrido[3,4-e]pyrazine-8-carboxamide | ¹HNMR (400 MHz, DMSO-d₆) δ 9.31-9.27 (m, 1H), 8.67-8.65 (m, 1H), 8.55-8.48 (m, 1H), 7.98 (d, 1H), 7.72-7.70 (m, 2H), 7.49-7.39 (m, 1H), 7.21-7.10 (m, 2H), 5.64-5.08 (m, 1H), 4.86-4.62 (m, 1H), 4.25-3.87 (m, 2H), 2.78-2.69 (m, 3H), 1.54-1.37 (m, 3H). LCMS (ESI) m/z: 407.2[M + H]⁺ |
| 63 | 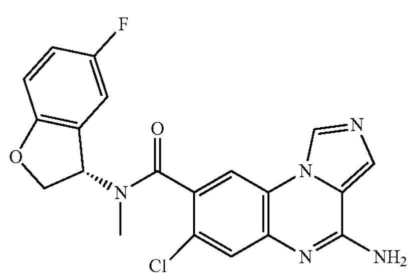 [SMILES: CN(C(=O)c1cc2c(cc1Cl)nc(N)c1cncn12)[C@@H]1COc2ccc(F)cc21] | (S)-4-amino-7-chloro-N-(5-fluoro-2,3-dihydrobenzofuran-3-yl)-N-methylimidazo[1,5-a]quinoxaline-8-carboxamide | ¹H NMR (400 MHz, DMSO-d₆) δ 9.03 (s, 1H), 8.45-8.21 (m, 1H), 8.22 (s, 1H), 7.91 (s, 1H), 7.46 (s, 1H), 7.31 (s, 2H), 7.15-7.06 (m, 2H), 6.90- 6.86 (m, 1H), 6.42-5.39 (m, 1H), 4.78-4.54 (m, 2H), 2.72-2.48 (m, 3H). LCMS (ESI) m/z: 412.1[M + H]⁺ |
| 64 | 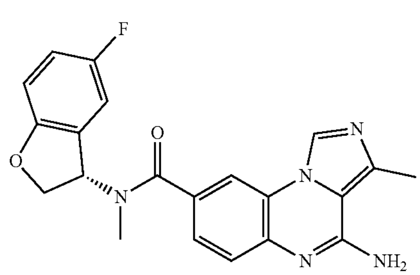 [SMILES: Cc1ncn2c1c(N)nc1ccc(C(=O)N(C)[C@@H]3COc4ccc(F)cc43)cc12] | (S)-4-amino-N-(5-fluoro-2,3-dihydrobenzofuran-3-yl)-N, 3-dimethylimidazo[1,5-a]quinoxaline-8-carboxamide | ¹H NMR (400 MHz, DMSO-d₆) δ 9.05 (s, 1H), 8.25 (s, 1H), 744-7.40 (m, 2H), 7.30-7.28 (m, 1H), 7.11-7.09 (m, 1H), 6.70-6.88 (m, 3H), 4.72-4.62 (m, 2H), 4.62-4.60 (m, 1H), 2.67 (s, 3H), 2.63 (s, 3H). LCMS (ESI) m/z: 392.2 [M + H]⁺ |

| Ex. | Structure | name | ¹H NMR & ¹⁹F NMR & LCMS |
|---|---|---|---|
| 65 | 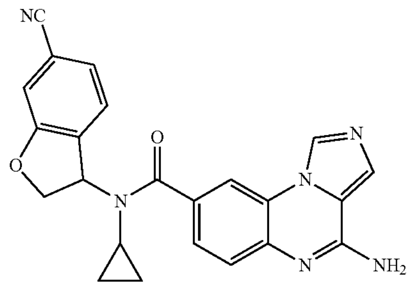 [SMILES: N#Cc1ccc2c(c1)OCC2N(C(=O)c1ccc2nc(N)c3cncn3c2c1)C1CC1] | 4-amino-N-(6-cyano-2,3-dihydrobenzofuran-3-yl)-N-cyclopropylimidazo[1,5-a]quinoxaline-8-carboxamide | ¹H NMR (400 MHz, DMSO-$d_6$) δ 9.17 (s, 1H), 8.38 (s, 1H), 7.92 (s, 1H), 7.73 (d, 1H), 7.62 (m, 1H), 7.47-7.41 (m, 3H), 7.37 (s, 1H), 5.95-5.91 (m, 1H), 4.89-4.84 (m, 1H), 4.70-4.67 (m, 1H), 3.0 (m, 1H), 0.46-0.09 (m, 4H). LCMS (ESI) m/z: 411.30 [M + H]⁺. |
| 66 | 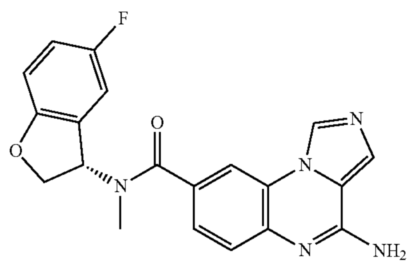 [SMILES: CN(C(=O)c1ccc2nc(N)c3cncn3c2c1)[C@@H]1COc2ccc(F)cc21] | (S)-4-amino-N-(5-fluoro-2,3-dihydrobenzofuran-3-yl)-N-methylimidazo[1,5-a]quinoxaline-8-carboxamide | ¹H NMR (400 MHz, DMSO-$d_6$) δ 9.18 (s, 1H), 8.32 (s, 1H), 7.91 (s, 1H), 7.46 (d, 4H), 7.31-7.28 (m, 1H), 7.13-7.08 (td, 1H), 6.91-6.88 (m, 1H), 4.81-4.65 (m, 2H), 4.63-4.60 (m, 1H), 2.67 (s, 3H). LCMS (ESI) m/z: 378.1 [M + H]⁺ |
| 67 | 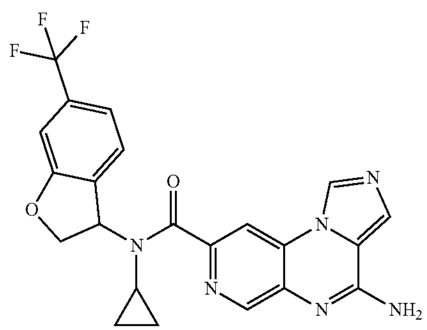 [SMILES: Nc1nc2cnc(C(=O)N(C3CC3)C3COc4cc(C(F)(F)F)ccc43)cc2n2cncc12] | 4-amino-N-cyclopropyl-N-(6-(trifluoromethyl)-2,3-dihydrobenzofuran-3-yl)imidazo[1,5-a]pyrido[3,4-e]pyrazine-8-carboxamide | ¹H NMR (400 MHz, DMSO-$d_6$) δ 9.27 (s, 1H), 8.65 (d, J = 1.9 Hz, 1H), 8.44 (s, 1H), 7.98 (d, J = 1.9 Hz, 1H), 7.72 (s, 2H), 7.63 (d, J = 7.8 Hz, 1H), 7.30 (d, J = 7.8 Hz, 1H), 7.21 (s, 1H), 5.97 (s, 1H), 4.87 (d, J = 10.3 Hz, 1H), 4.78-4.68 (m, 1H), 2.95 (s, 1H), 0.37 (s, 2H), 0.22 (s, 1H), 0.11 (s, 1H). LCMS (ESI) m/z: 455 [M + H]⁺ |
| 68 | 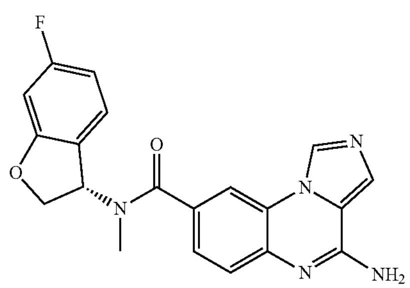 | (S)-4-amino-N-(6-fluoro-2,3-dihydrobenzofuran-3-yl)-N-methylimidazo[1,5-a]quinoxaline-8-carboxamide | ¹H NMR (400 MHz, DMSO-$d_6$) δ 9.20 (s, 1H), 8.33 (d, J = 1.2 Hz, 1H), 7.95 (s, 1H), 7.58 (s, 2H), 7.48 (s, 2H), 7.42 (dd, J = 7.8, 5.8 Hz, 1H), 6.80 (t, J = 9.1 Hz, 2H), 6.29 (s, 1H), 4.90-4.57 (m, 2H), 2.65 (s, 3H). LCMS (ESI) m/z: 378 [M + H]⁺ |
| 9 | 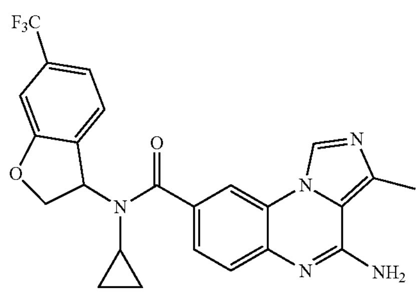 [SMILES: Cc1ncn2c1c(N)nc1ccc(C(=O)N(C3CC3)C3COc4cc(C(F)(F)F)ccc43)cc12] | 4-amino-N-cyclopropyl-3-methyl-N-(6-(trifluoromethyl)-2,3-dihydrobenzofuran-3-yl)imidazo[1,5-a]quinoxaline-8-carboxamide | ¹H NMR (400 MHz, DMSO-$d_6$) δ 9.05 (s, 1H), 8.32 (d, J = 1.8 Hz, 1H), 7.73 (d, J = 7.8 Hz, 1H), 7.60-7.52 (m, 1H), 7.38 (d, J = 8.4 Hz, 1H), 7.30 (d, J = 7.8 Hz, 1H), 7.20 (s, 1H), 6.91 (s, 2H), 5.94 (dd, J = 9.7, 4.5 Hz, 1H), 4.87 (t, J = 9.8 Hz, 1H), 4.70 (dd, J = 10.3, 4.6 Hz, 1H), 3.01-2.94 (m, 1H), 2.63 (s, 3H), 0.49-0.38 (m, 1H), 0.34 (h, J = 5.0 Hz, 1H), 0.20 (dq, J = 12.7, 6.4 Hz, 1H), 0.10 (dt, J = 10.6, 5.2 Hz, 1H). LCMS (ESI) m/z: 468 [M + H]⁺ |

-continued

| Ex. | Structure | name | ¹H NMR & ¹⁹F NMR & LCMS |
|---|---|---|---|
| 70 | 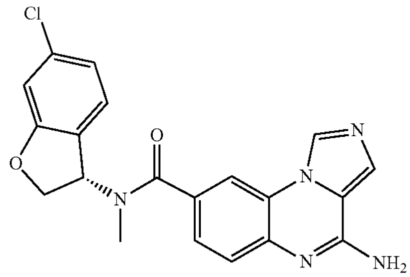 [SMILES: CN(C(=O)c1ccc2nc(N)c3cncn3c2c1)[C@@H]1COc2cc(Cl)ccc21] | (S)-4-amino-N-(6-chloro-2,3-dihydrobenzofuran-3-yl)-N-methylimidazo[1,5-a]quinoxaline-8-carboxamide | ¹H NMR (400 MHz, DMSO-d₆) δ 9.19 (s, 1H), 8.32 (d, J = 1.4 Hz, 1H), 7.94 (s, 1H), 7.54 (h, J = 4.9, 4.4 Hz, 1H), 7.48 (s, 2H), 7.43 (d, J = 8.4 Hz, 1H), 7.09-6.97 (m, 2H), 4.86-4.59 (m, 2H), 2.66 (s, 3H). LCMS (ESI) m/z: 395 [M + H]⁺ |
| 72 | 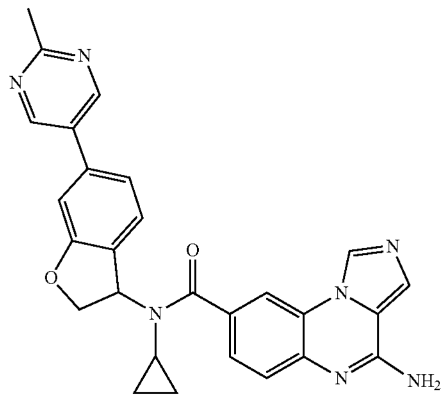 [SMILES: Cc1ncc(-c2ccc3c(c2)OCC3N(C(=O)c2ccc3nc(N)c4cncn4c3c2)C2CC2)cn1] | 4-amino-N-cyclopropyl-N-(6-(2-methylpyrimidin-5-yl)-2,3-dihydrobenzofuran-3-yl)imidazo[1,5-a]quinoxaline-8-carboxamide | ¹H NMR (400 MHz, DMSO-d₆) δ 9.23 (s, 1H), 9.04 (s, 2H), .42 (d, J = 1.8 Hz, 1H), 7.98 (s, 1H), 7.81~7.55 (m, 4H), .46 (d, J = 8.4 Hz, 1H), 7.41~7.22 (m, 2H), 5.96 (dd, J = .2, 4.2 Hz, 1H), 4.83 (t, J = 9.7 Hz, 1H), 4.68 (m, 1H), 2.95 (s, 1H), 2.67 (s, 3H), 0.38 (ddt, J = 20.6, 5.9, 6.1 Hz, 2H), 0.26~0.08 (m, 2H). LCMS (ESI) m/z: 478.2 [M + H]⁺ |
| 73 | 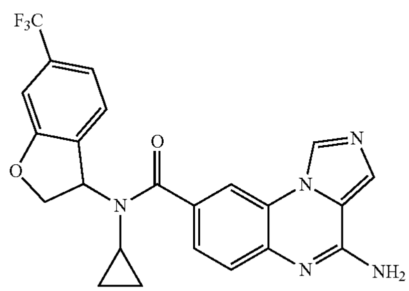 [SMILES: Nc1nc2ccc(C(=O)N(C3CC3)C3COc4cc(C(F)(F)F)ccc43)cc2n2cncc12] | 4-amino-N-cyclopropyl-N-(6-(trifluoromethyl)-2,3-dihydrobenzofuran-3-yl)imidazo[1,5-a]quinoxaline-8-carboxamide | ¹H NMR (400 MHz, DMSO-d₆) δ 9.18 (s, 1H), 8.39 (d, J = 1.9 Hz, 1H), 7.92 (s, 1H), 7.74 (d, J = 7.8 Hz, 1H), 7.61 (dd, J = 8.4, 1.9 Hz, 1H), 7.51~7.38 (m, 3H), 7.31 (d, J = 7.8 Hz, 1H), 7.21 (s, 1H), 5.95 (dd, J = 9.8, 4.5 Hz, 1H), 4.87 (t, J = 9.8 Hz, 1H), 4.71 (dd, J = 10.1, 4.6 Hz, 1H), 2.98 (dt, J = 11.3, 5.1 Hz, 1H), 0.38 (ddt, J = 36.4, 10.8, 5.7 Hz, 2H), 0.26~0.04 (m, 2H). LCMS (ESI) m/z: 454.3 [M + H]⁺ |
| 74 | 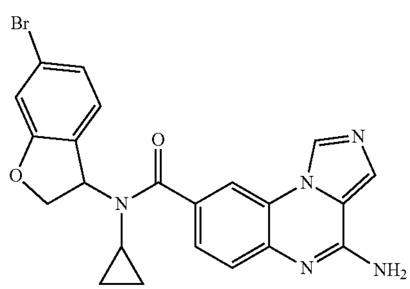 [SMILES: Nc1nc2ccc(C(=O)N(C3CC3)C3COc4cc(Br)ccc43)cc2n2cncc12] | 4-amino-N-(6-bromo-2,3-dihydrobenzofuran-3-yl)-N-cyclopropylimidazo[1,5-a]quinoxaline-8-carboxamide | ¹H NMR (400 MHz, DMSO-d₆) δ 9.18 (s, 1H), 8.37 (d, J = 1.9 Hz, 1H), 7.92 (s, 1H), 7.59 (dd, J = 8.4, 1.8 Hz, 1H), 7.55-7.37 (m, 4H), 7.24-7.03 (m, 2H), 5.86 (dd, J = 9.3, 4.2 Hz, 1H), 4.81 (t, J = 9.7 Hz, 1H), 4.65 (dd, J = 10.2, 4.2 Hz, 1H), 2.92 (d, J = 17.5 Hz, 1H), 0.50-0.27 (m, 2H), 0.27-0.04 (m, 2H). LCMS (ESI) m/z: 465.3 [M + H]⁺ |
| 126 | 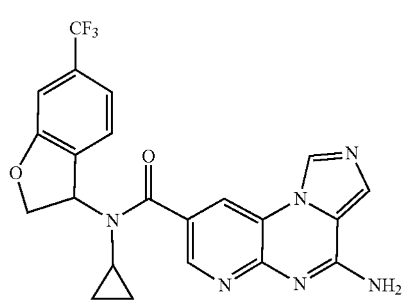 [SMILES: Nc1nc2ncc(C(=O)N(C3CC3)C3COc4cc(C(F)(F)F)ccc43)cc2n2cncc12] | 4-amino-N-cyclopropyl-N-(6-(trifluoromethyl)-2,3-dihydrobenzofuran-3-yl)imidazo[1,5-a]pyrido[2,3-e]pyrazine-8-carboxamide | ¹H NMR (400 MHz, DMSO-d₆) δ 9.29 (s, 1H), 8.84 (d, 1H), 8.75 (d, 1H), 8.5-8.5 (m, 2H), 8.10 (s, 1H), 7.74 (d, 1H), 7.31 (d, 1H), 7.22 (s, 1H), 5.99-5.95 (m, 1H), 4.91-4.86 (m, 1H), 4.73-4.70 (m, 1H), 3.63-3.59 (m, 1H), 0.51-0.13 (m, 4H). LCMS (ESI) m/z: 455.3[M + H]⁺ |

| Ex. | Structure | name | ¹H NMR & ¹⁹F NMR & LCMS |
|---|---|---|---|
| 121 | 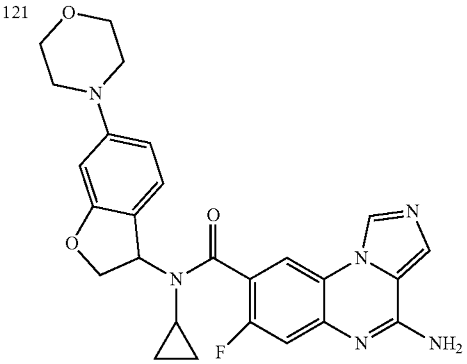 | 4-amino-N-cyclopropyl-7-fluoro-N-(6-morpholino-2,3-dihydrobenzofuran-3-yl)imidazo[1,5-a]quinoxaline-8-carboxamide | ¹H NMR (400 MHz, DMSO-$d_6$) δ 9.11 (s, 1H), 8.30 (d, J = 6.6 Hz, 1H), 7.92 (s, 1H), 7.58 (s, 2H), 7.21 (t, J = 9.3 Hz, 2H), 6.60-6.38 (m, 2H), 5.97 (s, 1H), 4.71 (s, 1H), 4.54 (dd, J = 10.5, 3.5 Hz, 1H), 3.72 (t, J = 4.7 Hz, 4H), 3.10 (t, J = 4.8 Hz, 4H), 2.62-2.54 (m, 1H), 0.22 (d, J = 76.8 Hz, 4H). LCMS (ESI) m/z: 489.1 [M + H]⁺ |

Example 75 Synthesis of (S)-4-amino-N-(methyl-d3)-N-(6-(trifluoromethyl)-2,3-dihydrobenzofuran-3-yl)imidazo[1,5-a]pyrido[3,4-e]pyrazine-8-carboxamide

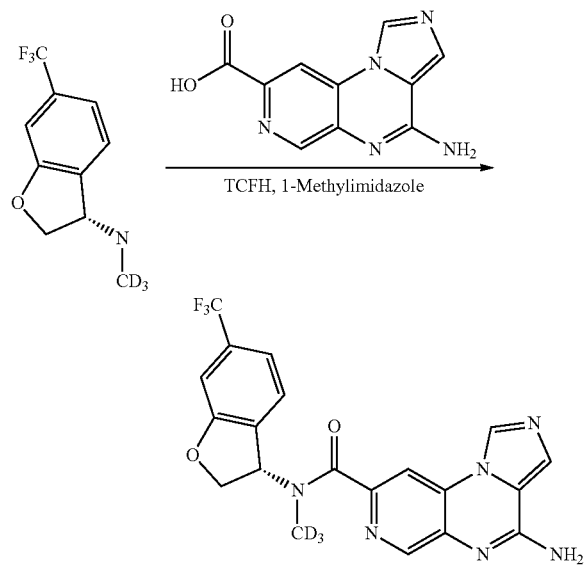

(S)—N-(methyl-d3)-6-(trifluoromethyl)-2,3-dihydrobenzofuran-3-amine (0.1 g, 0.45 mmol), 4-aminoimidazo[1,5-a]pyrido[3,4-e]pyrazine-8-carboxylic acid (0.1 g, 0.45 mmol), N,N,N',N'-Tetramethylchloroformamidinium hexafluorophosphate (0.19 g, 0.68 mmol) and 1-Methylimidazole (0.11 g, 1.36 mmol) were added in DMF (1 mL) and the reaction mixture was stirred for 1 hour. After the reaction was complete, the reaction system was cooled to room temperature. Then the reaction mixture was extracted with ethyl acetate (10 mL×3). The combined organic phase was washed with saturated brine (10 mL×3), dried over anhydrous sodium sulfate, concentrated to dryness. The residue was further purified by HPLC (column: YMC Triart $C_{18}$ ExRs 5 m, 30 mm×150 mm; mobile phase A: water (10 mmol/L ammonium bicarbonate), mobile phase B: acetonitrile, flow rate: 60 ml/min; Gradient: From 25% B to 55% B within 8 minutes; Wavelength: 254 nanometers/220 nanometers. Retention time (minimum value): 7.22 minutes.) to obtain (S)-4-amino-N-(methyl-d3)-N-(6-(trifluoromethyl)-2,3-dihydrobenzofuran-3-yl)imidazo[1,5-a]pyrido[3,4-e]pyrazine-8-carboxamide (11.94 mg, yield: 6.09%).

¹H NMR (400 MHz, DMSO-$d_6$) δ 9.31-9.30 (m, 1H), 8.70-8.65 (m, 1H), 8.56-8.51 (m, 1H), 7.99 (d, J=4.0 Hz, 1H), 7.79-7.56 (m, 3H), 7.36-7.34 (m, 1H), 7.27-7.25 (m, 1H), 6.44-6.02 (m, 1H), 4.89-4.71 (m, 2H).

LCMS (ESI): 431.85 [M+H]⁺

By using the synthetic procedures described in Example 75, and replacing the corresponding starting materials, the embodiments listed in the table below can be prepared:

| Ex. | Structure | name | ¹H NMR & ¹⁹F NMR & LCMS |
|---|---|---|---|
| 76 | 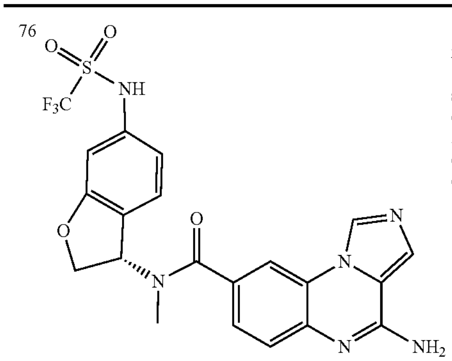 | (S)-4-amino-N-methyl-N-(6-((trifluoromethyl)sulfonamido)-2,3-dihydrobenzofuran-3-yl)imidazo[1,5-a]quinoxaline-8-carboxamide | ¹H NMR (400 MHz, DMSO-$d_6$) δ 9.19 (s, 1H), 8.30 (s, 1H), 7.91 (s, 1H), 7.80-7.16 (m, 4H), 7.08 (s, 1H), 6.52-6.46 (m, 3H), 5.73-5.41 (m, 1H), 4.62-4.49 (m, 2H), 2.98-2.50 (m, 3H). LCMS (ESI): 507.1 [M + H]⁺ |

-continued

| Ex. | Structure | name | $^1$H NMR & $^{19}$F NMR & LCMS |
|---|---|---|---|
| 118 | 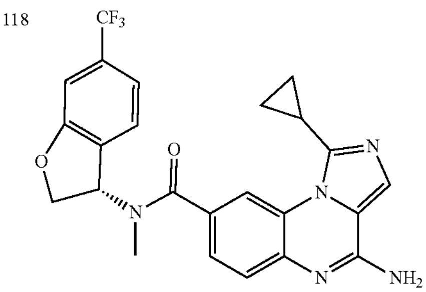 | (S)-4-amino-1-cyclopropyl-N-methyl-N-(6-(trifluoromethyl)-2,3-dihydrobenzofuran-3-yl)imidazo[1,5-a]quinoxaline-8-carboxamide | $^1$H NMR (400 MHz, DMSO-d$_6$) δ 8.66 (s, 1H), 7.79 (s, 1H), 7.62-7.60 (m, 1H), 7.54-7.45 (m, 2H), 7.32-7.31 (m, 3H), 7.25 (s, 1H), 6.34-6.11 (m, 1H), 4.84-4.70 (m, 2H), 2.67 (d, J = 3.0 Hz, 3H), 2.58-2.51 (m, 1H), 1.30-0.95 (m, 4H). LCMS (ESI): 467.75 [M + H]$^+$ |

Example 77: Synthesis of 4-amino-N-((4S)-6-fluoro-1-methylisochroman-4-yl)-N-methylimidazo[1,5-a]quinoxaline-8-carboxamide

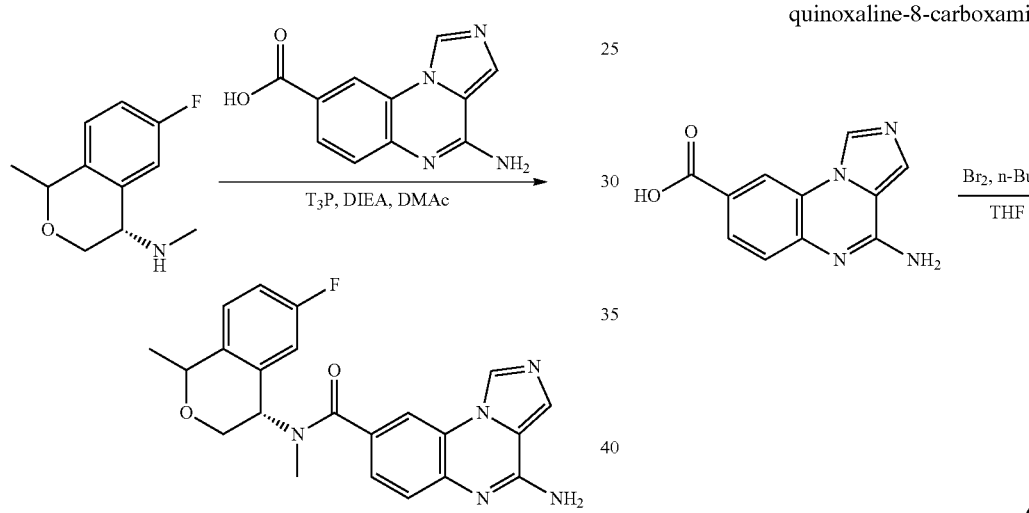

(4S)-6-fluoro-N,1-dimethylisochroman-4-amine hydrochloride (100 mg, 0.5122 mmol) was dissolved in DMA (4 mL), followed by addition of 4-aminoimidazo[1,5-a]quinoxaline-8-carboxylic acid (140 mg, 0.6146 mmol), T3P (489 mg, 0.7683 mmol) and N,N-diisopropylethylamine (338 mg, 3.561 mmol). After the reaction mixture was stirred for 2 hours, the reaction solution was poured into water (40 mL), extracted with ethyl acetate (20 mL×3). The combined organic phase was dried over anhydrous sodium sulfate, filtered. The filtrate was concentrated to obtain crude product and was further purified by silica column chromatography (DCM:MeOH=10:1) to obtain 4-amino-N-((4S)-6-fluoro-1-methylisochroman-4-yl)-N-methylimidazo[1,5-a]quinoxaline-8-carboxamide (70 mg, yield: 33.7%).

$^1$H NMR (400 MHz, DMSO-d$_6$) δ 9.27-9.11 (m, 1H), 8.38 (d, J=17.2 Hz, 1H), 7.92 (s, 1H), 7.60-6.98 (m, 7H), 5.62 (s, 1H), 4.94-4.67 (m, 1H), 4.38-3.79 (m, 2H), 2.87-2.66 (m, 3H), 1.49 (dd, J=13.0, 6.2 Hz, 3H).

$^{19}$F NMR (376 MHz, DMSO-d$_6$) δ −115.37, −115.39.

LCMS (ESI) m/z: 406 [M+H]$^+$

Example 78 (S)-4-amino-N-methyl-N-(6-(trifluoromethyl)-2,3-dihydrobenzofuran-3-yl)imidazo[1,5-a]quinoxaline-8-carboxamide-1-d & Example 111 (S)-4-amino-1-bromo-N-methyl-N-(6-(trifluoromethyl)-2,3-dihydrobenzofuran-3-yl)imidazo[1,5-a]quinoxaline-8-carboxamide

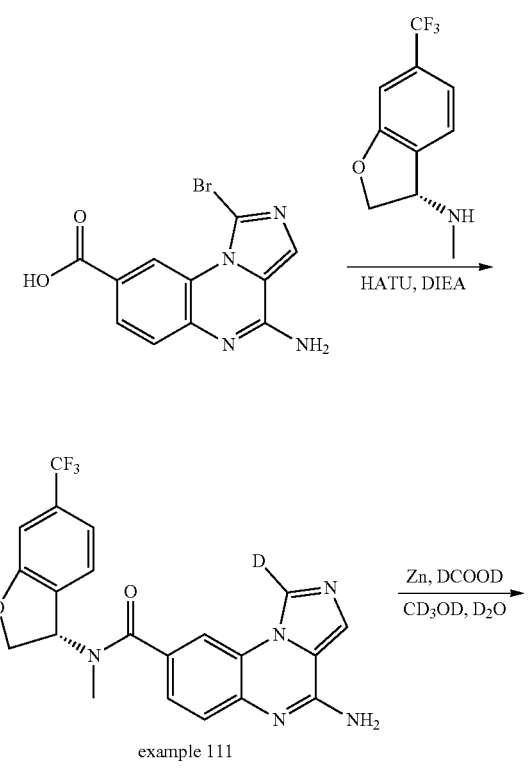

example 111

-continued

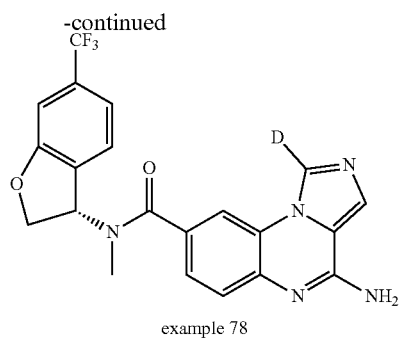

example 78

Step 1: Synthesis of 4-amino-1-bromoimidazo[1,5-a]quinoxaline-8-carboxylic acid 4-aminoimidazo[1,5-a]quinoxaline-8-carboxylic acid (500 mg, 2.19 mmol) was dissolved THF (15 mL). Then the reaction system was cooled to −40° C., and n-butyllithium (5 ml. 15.34 mmol) was added dropwise keeping −40° C. The mixture reacted for 10 minutes at 40° C., then reacted for 10 minutes at room temperature. After the reaction was complete, the reaction mixture was concentrated under vacuum to dryness. After DCM was added, the mixture was filtered then further purified by silica column chromatography (Formic acid:acetonitrile=1:1) to obtain 4-amino-1-bromoimidazo[1,5-a]quinoxaline-8-carboxylic acid (30 mg, yield: 4.46%), as a white solid.

LCMS (ESI) m/z: 307 [M+H]+

Step 2: Synthesis of Example 111 (S)-4-amino-1-bromo-N-methyl-N-(6-(trifluoromethyl)-2,3-dihydrobenzofuran-3-yl)imidazo[1,5-a]quinoxaline-8-carboxamide 4-amino-1-bromoimidazo[1,5-a]quinoxaline-8-carboxylic acid (10 mg, 0.03 mmol), 2-(7-Azabenzotriazol-1-yl)-N,N,N',N'-tetramethyluronium hexafluorophosphate (19 mg, 0.05 mmol), N,N-diisopropylethylamine (8 mg, 0.05 mmol) and (S)—N-methyl-6-(trifluoromethyl)-2,3-dihydrobenzofuran-3-amine (7 mg, 0.03 mmol) were successively dissolved in DMF (1 mL). After completion, the reaction mixture was stirred at room temperature for 2 hours. After completion, the reaction mixture was extracted with ethyl acetate (10 mL×3). The combined organic phase was washed with saturated brine (10 mL×3), dried over anhydrous sodium sulfate and filtered. The filtrate was concentrated under vacuum to obtain Example 111 (S)-4-amino-1-bromo-N-methyl-N-(6-(trifluoromethyl)-2,3-dihydrobenzofuran-3-yl)imidazo[1,5-a]quinoxaline-8-carboxamide (30 mg, 0.03 mmol, yield: 80%), as yellow liquid.

$^1$H NMR (400 MHz, DMSO-d$_6$) δ 9.09 (s, 1H), 7.98 (s, 1H), 7.65-7.55 (m, 2H), 7.52 (d, J=7.9 Hz, 3H), 7.32 (d, J=7.7 Hz, 1H), 7.25 (s, 1H), 6.42 (s, 1H), 4.79-4.72 (m, 2H), 2.75-2.62 (m, 3H).

LCMS (ESI) m/z: 506 [M+H]+

Step 3 Synthesis of Example 78 (S)-4-amino-N-methyl-N-(6-(trifluoromethyl)-2,3-dihydrobenzofuran-3-yl)imidazo[1,5-a]quinoxaline-8-carboxamide-1-d (S)-4-amino-1-bromo-N-methyl-N-(6-(trifluoromethyl)-2,3-dihydrobenzofuran-3-yl)imidazo[1,5-a]quinoxaline-8-carboxamide (20 mg, 0.16 mmol), Zinc powder (26 mg, 1.58 mmol), and deuterated formic acid (19 mg, 1.58 mmol) were dissolved in the solution of deuterated methanol (1 mL) and D$_2$O (1 mL). The reaction mixture was stirred at room temperature for 1 hour. After the reaction was complete, the mixture was extracted with ethyl acetate (10 mL×3). The combined organic phase was washed with saturated brine (10 mL×3), dried over anhydrouse sodium sulfate, concentrated under reduced pressure. The residue was purified by HPLC (column: Kinetex 5 m EVO C$_{18}$, 30 mm×150 mm; mobile phase A: water (10 mmol/L ammonium bicarbonate), mobile phase B: acetonitrile, flow rate: 60 ml/min; Gradient: From 20% B to 47% B within 10 minutes; Wavelength: 254 nanometers/220 nanometers. Retention time: 9.35 minutes.) to obtain Example 78 (S)-4-amino-N-methyl-N-(6-(trifluoromethyl)-2,3-dihydrobenzofuran-3-yl)imidazo[1,5-a]quinoxaline-8-carboxamide-1-d (3.34 mg, 0.16 mmol, yield: 8.45%), as white solid.

$^1$H NMR (400 MHz, DMSO-d$_6$) δ 8.34 (s, 1H), 7.92 (d, J=7.3 Hz, 1H), 7.64-7.62 (d, J=7.6 Hz, 1H), 7.49 (s, 4H), 7.33-7.32 (m, 1H), 7.26 (s, 1H), 6.48 (m, 1H), 4.73-4.72 (m, 2H), 2.68 (s, 3H).

LCMS (ESI) m/z: 428 [M+H]+

By using the synthetic procedures described in Example 78, and replacing the corresponding starting materials, the embodiments listed in the table below can be prepared:

| Ex. | Structure | name | $^1$H NMR & $^{19}$F NMR & LCMS |
|---|---|---|---|
| 79 | (structure with CF$_3$, benzofuran, carboxamide, imidazoquinoxaline, D, NH$_2$) | (S)-4-amino-N-methyl-N-(6-(trifluoromethyl)-2,3-dihydrobenzofuran-3-yl)imidazo[1,5-a]quinoxaline-8-carboxamide-3-d | $^1$H NMR (400 MHz, DMSO-d$_6$) δ 9.18 (s, 1H), 8.33 (t, J = 1.1 Hz, 1H), 7.64 (d, J = 7.8 Hz, 1H), 7.52-7.37 (m, 4H), 7.33 (d, J = 7.9 Hz, 1H), 7.26 (s, 1H), 6.52 (s, 1H), 4.72 (dd, J = 10.1, 4.5 Hz, 2H), 2.67 (d, J = 2.8 Hz, 3H). LCMS (ESI) m/z: 428 [M + H]+ |

| Ex. | Structure | name | ¹H NMR & ¹⁹F NMR & LCMS |
|---|---|---|---|
| 127 | (structure shown) | (S)-4-amino-3-bromo-N-methyl-N-(6-(trifluoromethyl)-2,3-dihydrobenzofuran-3-yl)imidazo[1,5-a]quinoxaline-8-carboxamide | ¹H NMR (400 MHz, DMSO-d₆) δ 9.25 (s, 1H), 8.33 (s, 1H), 7.63 (d, J = 7.8 Hz, 1H), 7.56-7.47 (m, 2H), 7.34-7.32 (m, 1H), 7.26 (s, 1H), 7.05 (s, 2H), 6.52-5.65 (m, 1H), 4.89-4.65 (m, 2H), 2.67 (s, 3H). LCMS (ESI): 506 [M + H]⁺ |

Example 109 Synthesis of ethyl 4-amino-8-(methyl(6-(trifluoromethyl)-2,3-dihydrobenzofuran-3-yl)carbamoyl)imidazo[1,5-a]quinoxaline-3-carboxylate 4-amino-3-bromo-N-methyl-N-(6-(trifluoromethyl)-2,3-dihydrobenzofuran-3-yl)imidazo[1,5-a]quinoxaline-8-carboxamide (30 mg, 0.006 mmol), potassium acetate (17 mg, 0.18 mmol) and 1,1'-Bis(diphenylphosphino)ferrocene-palladium(II)dichloride dichloromethane complex (4 mg, 0.01 mmol) were added to the mixed solvent of DMF (5 mL) and EtOH (5 mL). The reaction proceeded overnight in a high-pressure vessel under carbon monoxide (4 MPa), at 110° C. After the reaction was complete, the reaction was diluted with ethyl acetate (10 mL) and water (5 mL). The water layer was extracted with ethyl acetate (2×10 mL). The combined organic phase was washed with saturated brine (10 mL), dried over anhydrous sodium sulfate and concentrated to obtain crude product. The crude product was purified by HPLC(Column: Sunfire C₁₈ 5 m, 30 mm×150 mm; Mobile Phase A: Water (0.1% FA), Mobile Phase B: ACN; Flow rate: 60 ml/min mL/min; Gradient: 37% B to 64% B in 10 min; Wave Length: 254 nm/220 nm; RT1(min): 5.97) to obtain Ethyl 4-amino-8-(methyl(6-(trifluoromethyl)-2,3-dihydrobenzofuran-3-yl)carbamoyl)imidazo[1,5-a]quinoxaline-3-carboxylate (4.22 mg, 14%).

¹H NMR (400 MHz, DMSO-d₆) δ 9.36 (s, 1H), 9.30-8.61 (m, 1H), 8.46 (s, 1H), 8.10-7.92 (m, 1H), 7.70-7.64 (m, 1H), 7.61-7.50 (m, 2H), 7.34-7.30 (m, 1H), 7.26 (s, 1H), 6.38-5.76 (m, 1H), 4.84-4.70 (m, 2H), 4.32-4.37 (m, 2H), 2.68-2.66 (m, 3H), 1.37 (t, J=7.1 Hz, 3H).

LCMS (ESI): 500.10[M+H]⁺

Example 80 Synthesis of (S)-4-amino-7-fluoro-N-(6-methoxy-2,3-dihydrobenzofuran-3-yl)-N-methyl-imidazo[1,5-a]quinoxaline-8-carboxamide

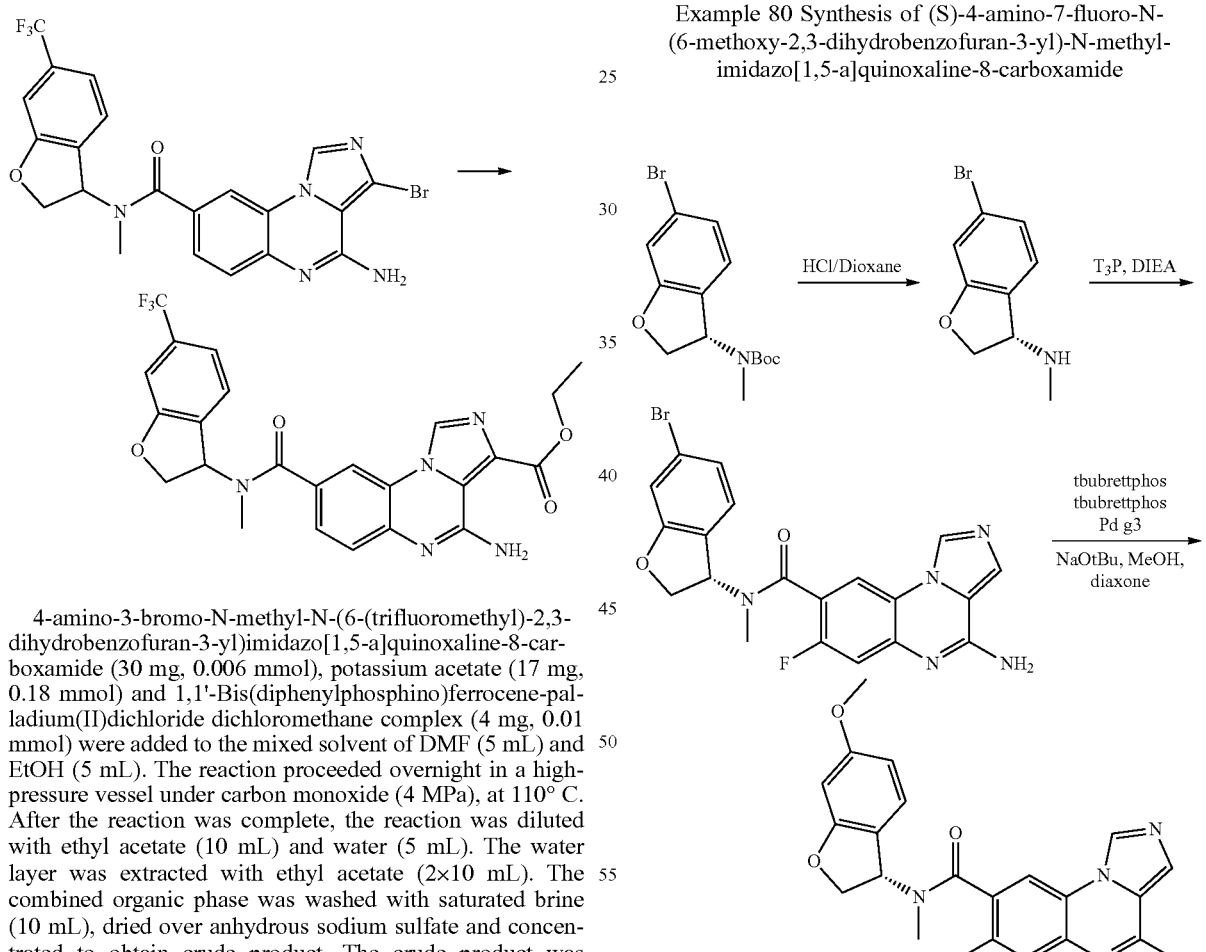

Step 1: Synthesis of (S)-6-bromo-N-methyl-2,3-dihydrobenzofuran-3-amine tert-butyl (S)-(6-bromo-2,3-dihydrobenzofuran-3-yl)(methyl)carbamate (200 mg, 0.6 mmol) was dissolved in the solution of hydrochloride acid in 1.4-dioxane and was stirred at room temperature. After the reaction was complete, the reaction solution was concentrated to obtain crude product (S)-6-bromo-N-methyl-2,3-dihydrobenzofuran-3-amine (85 mg, yield 61%)

LCMS (ESI) m/z: 228 [M+H]+

Step 2: Synthesis of (S)-4-amino-N-(6-bromo-2,3-dihydrobenzofuran-3-yl)-7-fluoro-N-methylimidazo[1,5-a]quinoxaline-8-carboxamide 4-amino-7-fluoroimidazo[1,5-a]quinoxaline-8-carboxylic acid was dissolved in DMA (2 mL), followed by addition of Propylphosphonic anhydride (172 mg, 0.74 mmol), N,N-diisopropylethylamine (144 mg, 1.12 mmol) and (S)-6-bromo-N-methyl-2,3-dihydrobenzofuran-3-amine (85 mg, 0.37 mmol) successively. The reaction system was then stirred overnight at room temperature. After the reaction was complete, the solution was extracted with ethyl acetate (10 mL×3). The combined organic phase was washed with saturated brine, dried over anhydrous sodium sulfate, concentrated then purified by silical column chromatography (DCM: MeOH=10%) to obtain (S)-4-amino-N-(6-bromo-2,3-dihydrobenzofuran-3-yl)-7-fluoro-N-methylimidazo[1,5-a]quinoxaline-8-carboxamide (35 mg, 20%).

LCMS (ESI) m/z: 456 [M+H]+

Step 3: Synthesis of (S)-4-amino-7-fluoro-N-(6-methoxy-2,3-dihydrobenzofuran-3-yl)-N-methylimidazo[1,5-a]quinoxaline-8-carboxamide (S)-4-amino-N-(6-bromo-2,3-dihydrobenzofuran-3-yl)-7-fluoro-N-methylimidazo[1,5-a]quinoxaline-8-carboxamide (35 mg, 0.08 mmol) was dissolved in dioxane (1 mL), followed by addition of [(2-Di-tert-butylphosphino-3,6-dimethoxy-2',4',6'-triisopropyl-1,1'-biphenyl)-2-(2'-amino-1,1'-biphenyl)]palladium(II) methanesulfonate (65 mg, 0.07 mmol), MeOH (86 mg, 2.68 mmol) under N2 atmosphere. After completion, the reaction system was stirred for 10 hours at room temperature. After the reaction was complete, the solution was extracted with ethyl acetate (10 mL×3). The combined organic phase was washed with saturated brine, dried over anhydrous sodium sulfate and concentrated. The residue was further purified by preparative HPLC Column: XBridge BEH Shield RP18 5 m, 30 mm×150 mm; Mobile Phase A: Water (10 mmol/L NH4HCO3), Mobile Phase B: ACN; Flow rate: 60 ml/min mL/min; Gradient: 28% B to 50% B in 8 min; Wave Length: 254 nm/220 nm; RT1(min): 7.88) to obtain (S)-4-amino-7-fluoro-N-(6-methoxy-2,3-dihydrobenzofuran-3-yl)-N-methylimidazo[1,5-a]quinoxaline-8-carboxamide (14.25 mg, yield: 44.6%).

$^1$H NMR (400 MHz, DMSO-d$_6$) δ 9.12 (s, 1H), 8.46-8.29 (m, 1H), 7.92 (d, J=3.6 Hz, 1H), 7.59 (s, 2H), 7.28-7.20 (m, 2H), 6.58-6.31 (m, 2H), 5.42-4.79 (m, 1H), 4.74-4.53 (m, 2H), 3.74 (d, J=10.0 Hz, 3H), 2.70-2.58 (m, 3H).

LCMS (ESI) m/z: 408.10 [M+H]+

Example 122: Synthesis of methyl (S)-3-(4-amino-N-methylimidazo[1,5-a]quinoxaline-8-carboxamido)-2,3-dihydrobenzofuran-6-carboxylate

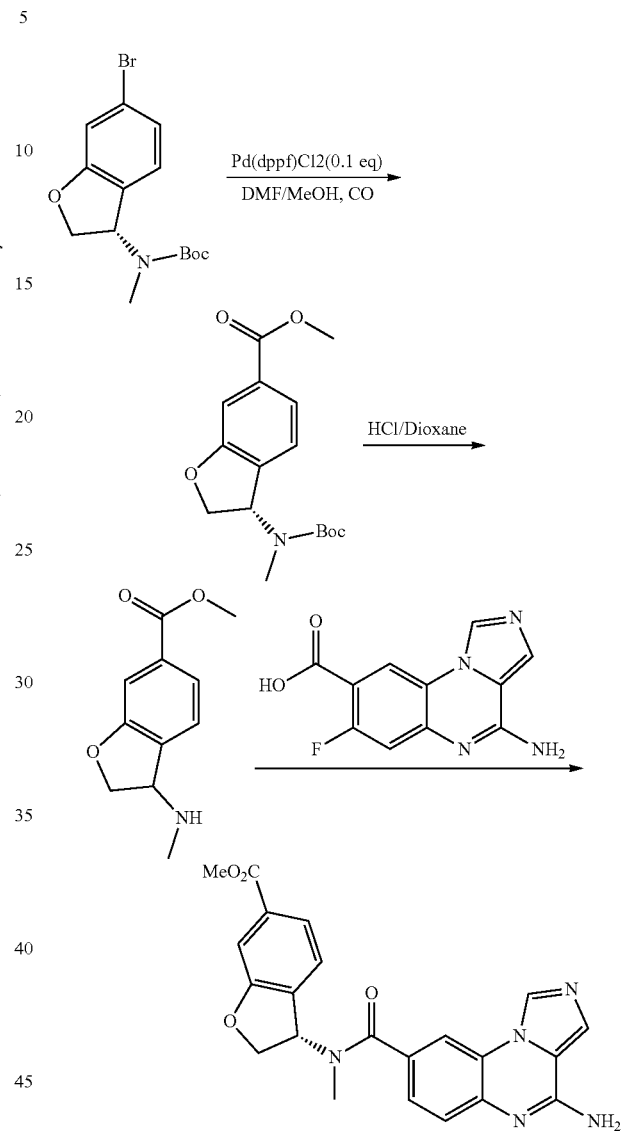

Step 1: Synthesis of methyl (S)-3-((tert-butoxycarbonyl)(methyl)amino)-2,3-dihydrobenzofuran-6-carboxylate At room temperature, tert-butyl (S)-(6-bromo-2,3-dihydrobenzofuran-3-yl)(methyl)carbamate (100 mg, 0.31 mmol) was dissolved in the solution of MeOH (5 mL) and DMF (10 mL). Then [1,1'-Bis(diphenylphosphino)ferrocene]dichloropalladium(II) (56 mg, 0.07 mmol) and potassium acetate (68 mg, 0.69 mmol) were added successively. The reaction system proceeded overnight at 100° C. under CO atmosphere (4 MPa). After the reaction was complete, the solution was concentrated, poured into water and filtered. The filtered cake was slurried in petroleum ether to obtain methyl (S)-3-((tert-butoxycarbonyl)(methyl)amino)-2,3-dihydrobenzofuran-6-carboxylate (70 mg, yield: 77.78%), as red solid.

LCMS (ESI): 308 [M+H]+

Step 2: Synthesis of methyl (S)-3-(methylamino)-2,3-dihydrobenzofuran-6-carboxylate (S)-3-((tert-butoxycarbonyl)(methyl)amino)-2,3-dihydrobenzofuran-6-carboxylate (70 mg, 0.23 mmol) was dissolved in the solution of HCl in 1,4-dioxane (2 mL, 4M). The reaction mixture proceeded for 0.5 h at room temperature. After the reaction was complete, the solution was concentrated to obtain methyl (S)-3-(methylamino)-2,3-dihydrobenzofuran-6-carboxylate (46 mg, yield 97%), as black solid.

LCMS (ESI): 208 [M+H]$^+$

Step 3 Synthesis of methyl (S)-3-(4-amino-N-methylimidazo[1,5-a]quinoxaline-8-carboxamido)-2,3-dihydrobenzofuran-6-carboxylate 4-aminoimidazo[1,5-a]quinoxaline-8-carboxylic acid was dissolved in DMF (4 mL), followed by addition of 2-(7-Azabenzotriazol-1-yl)-N,N,N',N'-tetramethyluronium hexafluorophosphate (128 mg, 0.34 mmol), N,N-diisopropylethylamine (87 mg, 0.67 mmol) and (S)-3-(methylamino)-2,3-dihydrobenzofuran-6-carboxylate (46 mg, 0.22 mmol) successively. The reaction mixture was stirred for 3 hours at room temperature. After the reaction was complete, the mixture was diluted with ethyl acetate (10 mL) and water (5 mL). Then the water phase was separated and extracted with ethyl acetate (2×10 mL). The combined organic phase was washed with saturated brine (10 mL), dried over anhydrous sodium sulfate, filtered and the filtrate was concentrated to obtain crude product. The crude product was further purified by HPLC (column: Sunfire C$_{18}$ 5 m, 30 mm×150 mm; mobile phase A: water (0.1% formic acid), mobile phase B: acetonitrile; flow rate: 60 ml/min; gradient from 5% B to 30% B within 8 mins; wavelength: 254 nm/220 nm) to obtain methyl (S)-3-(4-amino-N-methylimidazo[1,5-a]quinoxaline-8-carboxamido)-2,3-dihydrobenzofuran-6-carboxylate (21 mg, yield: 1%), as white solid.

$^1$H NMR (400 MHz, DMSO-d$_6$) δ9.21 (s, 1H), 8.35 (s, 1H), 8.13 (s, 1H), 8.01-7.92 (s, 1H), 7.62-7.60 (m, 1H), 7.56-7.54 (m, 1H), 7.50-7.49 (m, 2H), 7.40-7.36 (m, 1H), 6.39-5.66 (s, 1H), 4.87-4.68 (m, 2H), 3.85-3.84 (m, 3H), 2.67-2.64 (m, 3H), 0.98-0.79 (m, 3H)

LCMS (ESI): 418.20 [M+H]$^+$

Example 112: Synthesis of (S)-4-amino-N-(6-(difluoromethyl)-2,3-dihydrobenzofuran-3-yl)-N-methylimidazo[1,5-a]quinoxaline-8-carboxamide

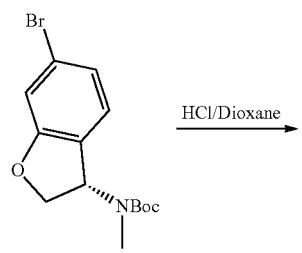

HCl/Dioxane

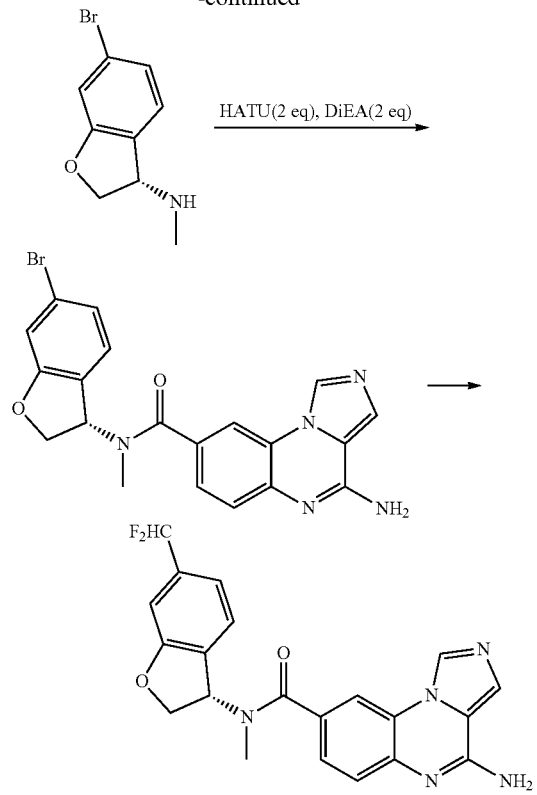

Step 1 Synthesis of (S)-6-bromo-N-methyl-2,3-dihydrobenzofuran-3-amine tert-butyl (S)-(6-bromo-2,3-dihydrobenzofuran-3-yl)(methyl)carbamate was dissolved in the solution of HCl in 1,4-dioxane (4.0M, 10 mL). Then the reaction mixture was stirred at room temperature for 2 hours. After the reaction was complete, the solution was concentrated under vacuum to obtain (S)-6-bromo-N-methyl-2,3-dihydrobenzofuran-3-amine (80 mg, 0.30 mmol, yield: 95.46%), as yellow liquid.

LCMS (ESI): 228 [M+H]$^+$

Step 2: Synthesis of (S)-4-amino-N-(6-bromo-2,3-dihydrobenzofuran-3-yl)-N-methylimidazo[1,5-a]quinoxaline-8-carboxamide 4-aminoimidazo[1,5-a]quinoxaline-8-carboxylic acid (80 mg, 0.35 mmol), 2-(7-Azabenzotriazol-1-yl)-N,N,N',N'-tetramethyluronium hexafluorophosphate (200 mg, 0.53 mmol) and N,N-diisopropylethylamine (136 mg, 1.05 mmol) were dissolved in DMA (3 mL) followed by addition of (S)-6-bromo-N-methyl-2,3-dihydrobenzofuran-3-amine (80 mg, 0.35 mmol). The reaction mixture was stirred for 2 hours at room temperature. After the reaction was complete, the solution was extracted with ethyl acetate (10 mL×3). The combined organic phase was washed with saturated brine (10 mL×3), dried over anhydrous sodium sulfate and concentrated to obtain crude product. The crude product was further purified by silica column chromatography (petroleum ether:ethyl acetate=80:20) to obtain (S)-4-amino-N-(6-bromo-2,3-dihydrobenzofuran-3-yl)-N-methylimidazo[1,5-a]quinoxaline-8-carboxamide (70 mg, 0.35 mmol, yield: 45.54%).

LCMS (ESI): 438 [M+H]$^+$

Step 3: Synthesis of (S)-4-amino-N-(6-(difluoromethyl)-2,3-dihydrobenzofuran-3-yl)-N-methylimidazo[1,5-a]quinoxaline-8-carboxamide (S)-4-amino-N-(6-bromo-2,3-dihydrobenzofuran-3-yl)-N-methylimidazo[1,5-a]quinoxaline-8-carboxamide (30 mg, 0.07 mmol) was dissolved in THF (2 mL), followed by successively addition of [Ir(dF(CF$_3$)ppy)$_2$(dpy)]PF$_6$ (8 mg, 0.007 mmol), nickel(II) bromide ethylene glycol dimethyl ether complex (1 mg, 0.003 mmol), PPh3(CF$_2$H)$_2$ (17 mg, 0.14 mmol), diphenyl phenanthroline (2 mg, 0.007 mmol). The reaction proceeded overnight at room temperature under wavelength of 465 nm. After the reaction was complete, the solution was extracted with ethyl acetate (10 mL×3). The combined organic phase was washed with saturated brine (10 mL×3), dried over anhydrous sodium sulfate, concentrated to obtain crude product. The crude product was further purified by HPLC (column: Kinetex 5 m EVO C$_{18}$, 30 mm×150 mm; mobile phase A: water (10 mmol/L ammonium bicarbonate), mobile phase B: Acetonitrile; flow rate: 60 ml/minutes; Gradient from 20% B to 47% B with 10 minutes; wavelength: 254/220 nm; retention time (minimum value): 9.35) to obtain (S)-4-amino-N-(6-(difluoromethyl)-2,3-dihydrobenzofuran-3-yl)-N-methylimidazo[1,5-a]quinoxaline-8-carboxamide (0.84 mg, 0.07 mmol, yield: 2.96%).

$^1$H NMR (400 MHz, Methanol-d$_4$) δ 9.11 (s, 1H), 8.29 (s, 1H), 7.98 (s, 1H), 7.57-7.54 (m, 3H), 7.17-7.16 (s, 1H), 7.03 (s, 1H), 4.73-4.62 (s, 2H), 4.60-4.52 (m, 1H), 2.78 (s, 3H).

LCMS (ESI): 409 [M+H]$^+$

Example 115: Synthesis of (R)-4-amino-7-fluoro-N-methyl-N-(7-(1-methyl-1H-pyrazol-5-yl)chroman-4-yl)imidazo[1,5-a]quinoxaline-8-carboxamide

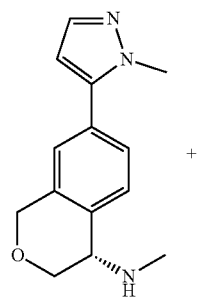

+

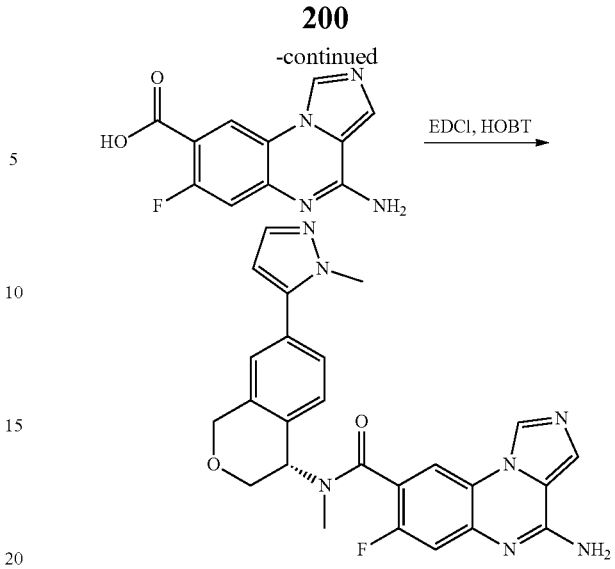

At room temperature, 4-amino-7-fluoroimidazo[1,5-a]quinoxaline-8-carboxylic acid (200 mg, 0.813 mmol) was dissolved in DMAc (3 mL), followed by addition of 1-(3-Dimethylaminopropyl)-3-ethylcarbodiimide (187 mg, 0.976 mmol) and 1-Hydroxybenzotriazole (133 mg, 0.976 mmol) then DIEA (421 mg, 3.264 mmol). The reaction system proceeded at room temperature for 0.5 h. Then (R)—N-methyl-7-(1-methyl-1H-pyrazol-5-yl)chroman-4-amine (1 g, 4.184 mmol) was added. The reaction mixture preceded at room temperature for 16 hours. After completion of the reaction indicated by LCMS, water (30 mL) was added, and extracted with ethyl acetate (10 mL×3). The combined organic phase was washed with saturated brine (30 mL), dried over anhydrous sodium sulfate, filtered. And the filtrate was concentrated to obtain crude product. And the crude product was further purified by silica column chromatography (0-5% MeOH/DCM) to obtain (R)-4-amino-7-fluoro-N-methyl-N-(7-(1-methyl-1H-pyrazol-5-yl)chroman-4-yl)imidazo[1,5-a]quinoxaline-8-carboxamide (45 mg, yield: 11.750%)

$^1$H NMR (400 MHz, DMSO-d$_6$) δ 9.17 (d, J=22.9 Hz, 1H), 8.42 (d, J=6.6 Hz, 1H), 7.94 (d, J=8.6 Hz, 1H), 7.61 (d, J=12.8 Hz, 2H), 7.46 (dd, J=6.2, 1.9 Hz, 1H), 7.27 (td, J=11.3, 7.6 Hz, 2H), 7.14 (dd, J=7.9, 1.8 Hz, 1H), 6.98 (dd, J=27.5, 1.8 Hz, 1H), 6.41 (dd, J=9.7, 1.9 Hz, 1H), 6.10-5.04 (m, 1H), 4.49-4.05 (m, 2H), 3.86 (d, J=15.6 Hz, 3H), 2.82-2.62 (m, 3H), 2.32 (dd, J=17.9, 7.3 Hz, 1H), 2.13 (dd, J=7.1, 3.6 Hz, 1H).

LCMS (ESI) m/z: 472.1 [M+H]$^+$

By using the synthetic procedures described in Example 115, and replacing the corresponding starting materials, the embodiments listed in the table below can be prepared:

| Ex. | Structure | name | $^1$H NMR & $^{19}$F NMR & LCMS |
|---|---|---|---|
| 13 | (structure shown) | 4-amino-N-(1,1-dimethyl-7-(trifluoromethyl)isochroman-4-yl)-7-fluoro-N-methylimidazo[1,5-a]quinoxaline-8-carboxamide | $^1$H NMR (400 MHz, DMSO-d$_6$) δ 9.13 (s, 1H), 8.81 (s, 1H), 8.34 (d, J = 6.6 Hz, 1H), 8.08 (d, J = 8.0 Hz, 1H), 7.96 (d, J = 16.4 Hz, 2H), 7.60 (s, 2H), 7.24 (d, J = 11.2 Hz, 1H), 4.90 (s, 2H), 2.81 (s, 1H), 0.53 (d, J = 12.7 Hz, 4H). LCMS (ESI) m/z: 488.2 [M + H]$^+$ |

| Ex. | Structure | name | ¹H NMR & ¹⁹F NMR & LCMS |
|---|---|---|---|
| 113 | 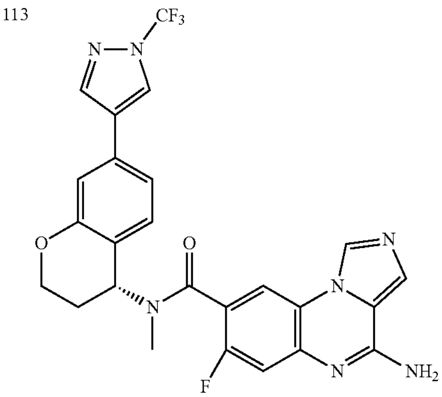 | (R)-4-amino-7-fluoro-N-methyl-N-(7-(1-(trifluoromethyl)-1H-pyrazol-4-yl)chroman-4-yl)imidazo[1,5-a]quinoxaline-8-carboxamide | ¹H NMR (400 MHz, DMSO-d₆) δ 9.16 (d, J = 22.8 Hz, 1H), 8.98 (d, J = 3.8 Hz, 1H), 8.44 (dd, J = 20.3, 7.1 Hz, 2H), 7.93 (d, J = 9.8 Hz, 1H), 7.58 (t, J = 13.0 Hz, 2H), 7.39-7.13 (m, 4H), 5.52 (ddd, J = 405.6, 10.5, 6.5 Hz, 1H), 4.49-3.96 (m, 2H), 2.81-2.58 (m, 3H), 2.28 (qd, J = 12.2, 10.9, 6.8 Hz, 1H), 2.19-2.02 (m, 1H). LCMS (ESI) m/z: 472.1 [M + H]⁺ |
| 114 | 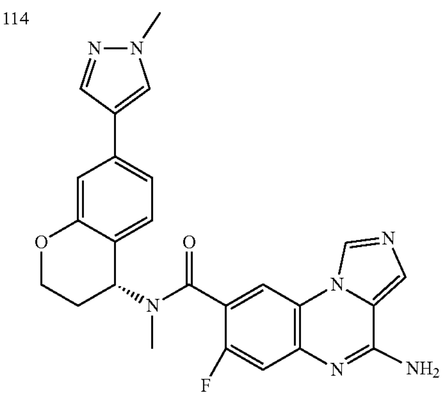 | (R)-4-amino-7-fluoro-N-methyl-N-(7-(1-methyl-1H-pyrazol-4-yl)chroman-4-yl)imidazo[1,5-a]quinoxaline-8-carboxamide | ¹H NMR (400 MHz, DMSO-d₆) δ 9.19 9.13 (m, 1H), 8.43-8.19 (m, 1H), 8.12 (d, J = 5.2 Hz, 1H), 7.93 (d, J = 9.2 Hz, 1H), 7.84 (d, J = 7.5 Hz, 1H), 7.60-7.53 (m, 2H), 7.29-6.96 (m, 4H), 5.48 (ddd, J = 409.0, 10.4, 6.4 Hz, 1H), 4.43-3.98 (m, 2H), 3.85 (d, J = 6.1 Hz, 3H), 2.82-2.59 (m, 3H), 2.36-2.19 (m, 1H), 2.08 (t, J = 5.9 Hz, 1H). LCMS (ESI) m/z: 472.1 [M + H]⁺ |
| 120 | 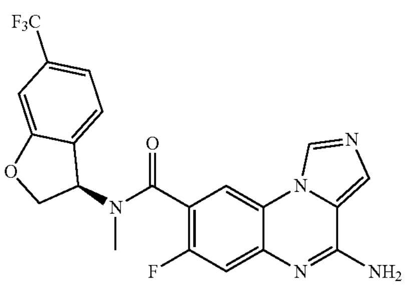 [SMILES: CN(C(=O)c1cc2c(cc1F)nc(N)c1cncn12)[C@H]1COc2cc(C(F)(F)F)ccc21] | (R)-4-amino-7-fluoro-N-methyl-N-(6-(trifluoromethyl)-2,3-dihydrobenzofuran-3-yl)imidazo[1,5-a]quinoxaline-8-carboxamide | ¹H NMR (400 MHz, DMSO-d₆) δ 9.13 (s, 1H), 8.44- 8.24 (m, 1H), 7.93 (d, J = 3.1 Hz, 1H), 7.58 (d, J = 28.1 Hz, 3H), 7.43-7.15 (m, 3H), 6.53-5.60 (m, 1H), 4.96-4.58 (m, 2H), 2.65 (d, J = 31.4 Hz, 3H). LCMS (ESI) m/z: 446.1 [M + H]⁺ |
| 133 | 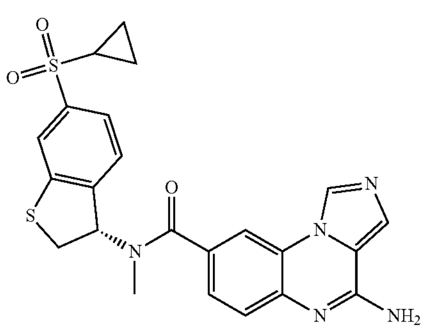 | (S)-4-amino-N-(6-(cyclopropylsulfonyl)-2,3-dihydrobenzo[b]thiophen-3-yl)-N-methylimidazo[1,5-a]quinoxaline-8-carboxamide | ¹H NMR (400 MHz, DMSO-d₆) δ 9.19 (s, 1H), 8.34 (s, 1H), 7.92 (s, 1H), 7.69 (d, J = 7.8 Hz, 1H), 7.60-7.29 (m, 6H), 6.55-5.83 (m, 1H), 4.97-4.58 (m, 2H), 2.98-2.84 (m, 1H), 2.70 (s, 3H), 1.19-0.94 (m, 4H). LCMS (ESI) m/z: 464.2 [M + H]⁺ |

| Ex. | Structure | name | ¹H NMR & ¹⁹F NMR & LCMS |
|---|---|---|---|
| 136 | 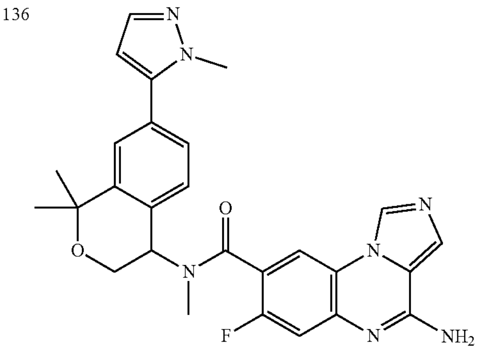 | 4-amino-N-(1,1-dimethyl-7-(1-methyl-1H-pyrazol-5-yl)isochroman-4-yl)-7-fluoro-N-methylimidazo[1,5-a]quinoxaline-8-carboxamide | LCMS (ESI) m/z: 500.2 [M + H]⁺ |
| 137 | 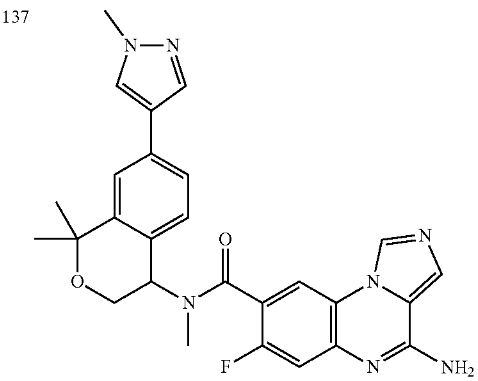 | 4-amino-N-(1,1-dimethyl-7-(1-methyl-1H-pyrazol-4-yl)isochroman-4-yl)-7-fluoro-N-methylimidazo[1,5-a]quinoxaline-8-carboxamide | LCMS (ESI) m/z: 500.2 [M + H]⁺ |

Example 128 Synthesis of (S)-4-amino-3-(hydroxymethyl)-N-methyl-N-(6-(trifluoromethyl)-2,3-dihydrobenzofuran-3-yl)imidazo[1,5-a]quinoxaline-8-carboxamide

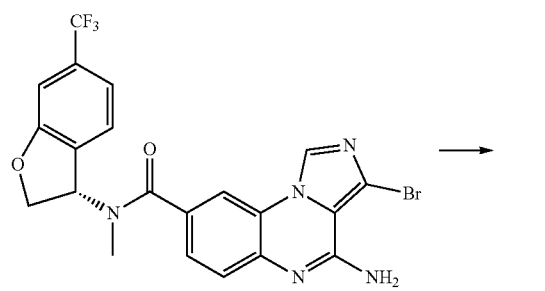

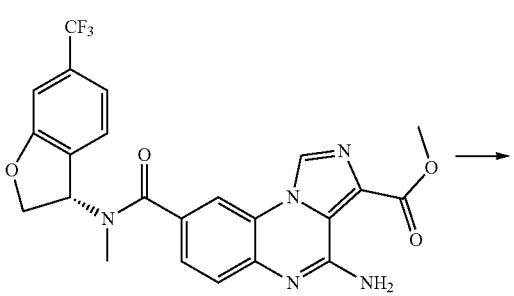

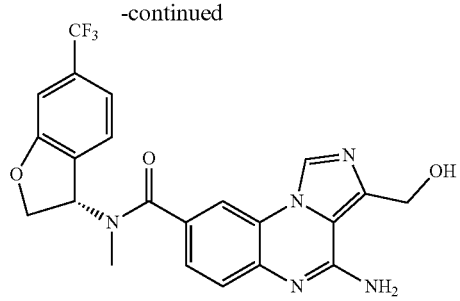

Step 1: Synthesis of methyl (S)-4-amino-8-(methyl (6-(trifluoromethyl)-2,3-dihydrobenzofuran-3-yl) carbamoyl)imidazo[1,5-a]quinoxaline-3-carboxylate (S)-4-amino-3-bromo-N-methyl-N-(6-(trifluoromethyl)-2,3-dihydrobenzofuran-3-yl)imidazo[1,5-a]quinoxaline-8-carboxamide (60 mg, 0.12 mmol) was dissolved in the solution of DMF (2 mL) and MeOH (2 mL), followed by addition of [1,1'-Bis(diphenylphosphino)ferrocene]dichloropalladium(II) (3 mL, 0.04 mmol) and potassium acetate (23 mg, 0.24 mmol). The reaction proceeded for 16 hours at 100° C. under CO atmosphere (4 MPa) in high pressure vessel. After the reaction was complete, the solution was extracted with ethyl acetate (10 mL×3). The combined organic phase was washed with saturated brine (10 mL×3), dried over anhydrous sodium sulfate and concentrated under vacuum and further purified by silica column chromatography (basic water:acetonitrile=1:1) to obtain methyl (S)-4-amino-8-(methyl(6-(trifluoromethyl)-2,3-dihydrobenzofuran-3-yl)carbamoyl)imidazo[1,5-a]quinoxaline-3-carboxylate (40 mg, yield: 69.53%), as brown solid.

LCMS (ESI): 485.42 [M+H]+

Step 2: Synthesis of (S)-4-amino-3-(hydroxymethyl)-N-methyl-N-(6-(trifluoromethyl)-2,3-dihydrobenzofuran-3-yl)imidazo[1,5-a]quinoxaline-8-carboxamide methyl (S)-4-amino-8-(methyl(6-(trifluoromethyl)-2,3-dihydrobenzofuran-3-yl)carbamoyl)imidazo[1,5-a]quinoxaline-3-carboxylate (30 mg, 0.06 mmol) was dissolved in methanol (2 mL), followed by Sodium borohydride (5 mg, 0.12 mmol). The reaction mixture was stirred for 2 hours at room temperature. After completion of the reaction, the solution was extracted with ethyl acetate (10 mL×3). The combined organic phase was washed with saturated brine (10 mL×3), dried over anhydrous sodium sulfate and concentrated under vacuum to obtain crude product. The crude product was purified by HPLC (column: Kinetex 5 m EVO C$_{18}$, 30 mm×150 mm; mobile phase A: water (10 mmol/L ammonium bicarbonate), mobile phase B: Acetonitrile; flow rate: 60 ml/min; Gradient from 20% B to 47% B within 10 minutes; wavelength: 254/220 nm; retention time (minimum value): 9.35) to obtain (S)-4-amino-3-(hydroxymethyl)-N-methyl-N-(6-(trifluoromethyl)-2,3-dihydrobenzofuran-3-yl)imidazo[1,5-a]quinoxaline-8-carboxamide (3.17 mg, yield: 11.13%), as white solid.

$^1$H NMR (400 MHz, DMSO-d$_6$) δ 9.11 (s, 1H), 8.31 (s, 1H), 7.64 (d, J=7.8 Hz, 1H), 7.59 (s, 2H), 7.47 (d, J=5.5 Hz, 2H), 7.34 (d, J=7.8 Hz, 1H), 7.27-7.23 (m, 1H), 6.36 (t, J=5.2 Hz, 1H), 4.85 (d, J=5.1 Hz, 3H), 4.73 (d, J=4.6 Hz, 1H), 3.31 (s, 1H), 2.67 (S, 3H).

LCMS (ESI): 457.41 [M+H]+

Example 132: Synthesis of (S)-4-amino-N8-methyl-N8-(6-(trifluoromethyl)-2,3-dihydrobenzofuran-3-yl)imidazo[1,5-a]quinoxaline-3,8-dicarboxamide

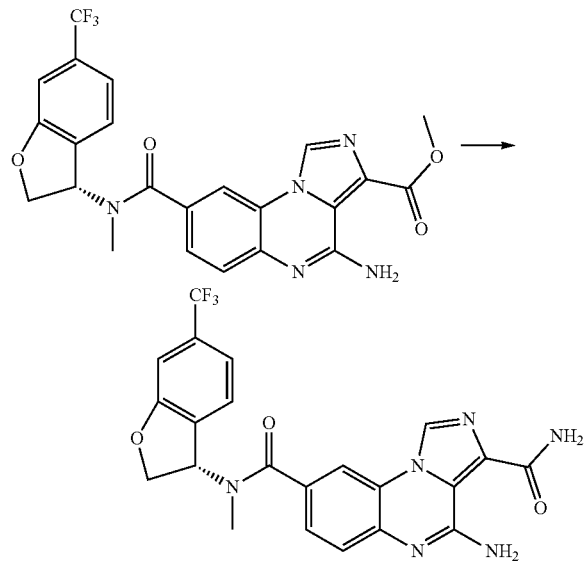

methyl (S)-4-amino-8-(methyl(6-(trifluoromethyl)-2,3-dihydrobenzofuran-3-yl)carbamoyl)imidazo[1,5-a]quinoxaline-3-carboxylate (30 mg, 0.06 mmol) was dissolved in MeOH(0.5 mL)/THF (0.50 mL)/ammonia solution (0.5 mL) and proceeded at 60° C. for 2 hours. After the reaction was complete, the reaction solution was poured into water (5 mL), extracted with ethyl acetate and concentrated to obtain crude product. The crude product was further purified by high pressure preparative HPLC to obtain (S)-4-amino-N$^8$-methyl-N$^8$-(6-(trifluoromethyl)-2,3-dihydrobenzofuran-3-yl)imidazo[1,5-a]quinoxaline-3,8-dicarboxamide (1.06 mg, 4%), as white solid.

$^1$H NMR (400 MHz, DMSO-d$_6$) δ 10.01 (s, 1H), 9.32 (s, 1H), 8.42 (s, 1H), 8.21 (s, 1H), 7.92 (s, 1H), 7.78 (s, 1H), 7.64 (d, J=7.9 Hz, 1H), 7.54 (d, J=8.2 Hz, 1H), 7.48 (d, J=11.1 Hz, 1H), 7.34 (d, J=7.8 Hz, 1H), 7.27 (s, 1H), 6.43 (s, 1H), 4.73 (s, 2H), 2.76-2.63 (m, 3H).

LCMS (ESI): 470.80 [M+H]+

Example 131 Synthesis of (S)-4-amino-3-cyano-N-methyl-N-(6-(trifluoromethyl)-2,3-dihydrobenzofuran-3-yl)imidazo[1,5-a]quinoxaline-8-carboxamide

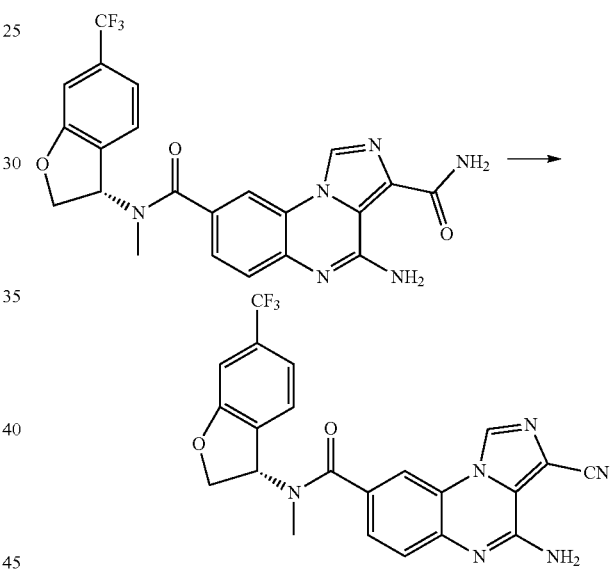

To a stirred solution of (S)-4-amino-N$^8$-methyl-N$^8$-(6-(trifluoromethyl)-2,3-dihydrobenzofuran-3-yl)imidazo[1,5-a]quinoxaline-3,8-dicarboxamide in DCM (2 mL), pyridine (10.09 mg, 0.13 mmol), Trifluoroacetic anhydride (26.79 mg, 0.26 mmol) was added. The reaction proceeded at room temperature for 12 hours. After completion of the reaction, the solution was poured into water (5 mL), extracted with ethyl acetate. The combined organic phase was concentrated to obtain crude product and the crude product was further purified by high pressure preparative HPLC(Column: C18; mobile phase A: water, mobile phase B: Acetonitrile; Gradient from 10% to 50% within 10 minutes.) to obtain (S)-4-amino-3-cyano-N-methyl-N-(6-(trifluoromethyl)-2,3-dihydrobenzofuran-3-yl)imidazo[1,5-a]quinoxaline-8-carboxamide (1.61 mg, yield: 5%), as white solid.

$^1$H NMR (400 MHz, DMSO-d$_6$) δ 9.46 (s, 1H), 8.48 (s, 1H), 7.64 (d, J=8.7 Hz, 3H), 7.33 (s, 1H), 7.26 (s, 1H), 7.12 (s, 2H), 6.40 (s, 1H), 4.72 (d, J=10.5 Hz, 1H), 4.71 (s, 1H), 2.67 (d, J=2.8 Hz, 3H).

LCMS (ESI): 452.80 [M+H]+

Example 81&82

Example 81 (R)-4-amino-N-(6-bromo-2,3-dihydrobenzofuran-3-yl)-N-cyclopropylimidazo[1,5-a]quinoxaline-8-carboxamide & Example 82 (S)-4-amino-N-(6-bromo-2,3-dihydrobenzofuran-3-yl)-N-cyclopropylimidazo[1,5-a]quinoxaline-8-carboxamide

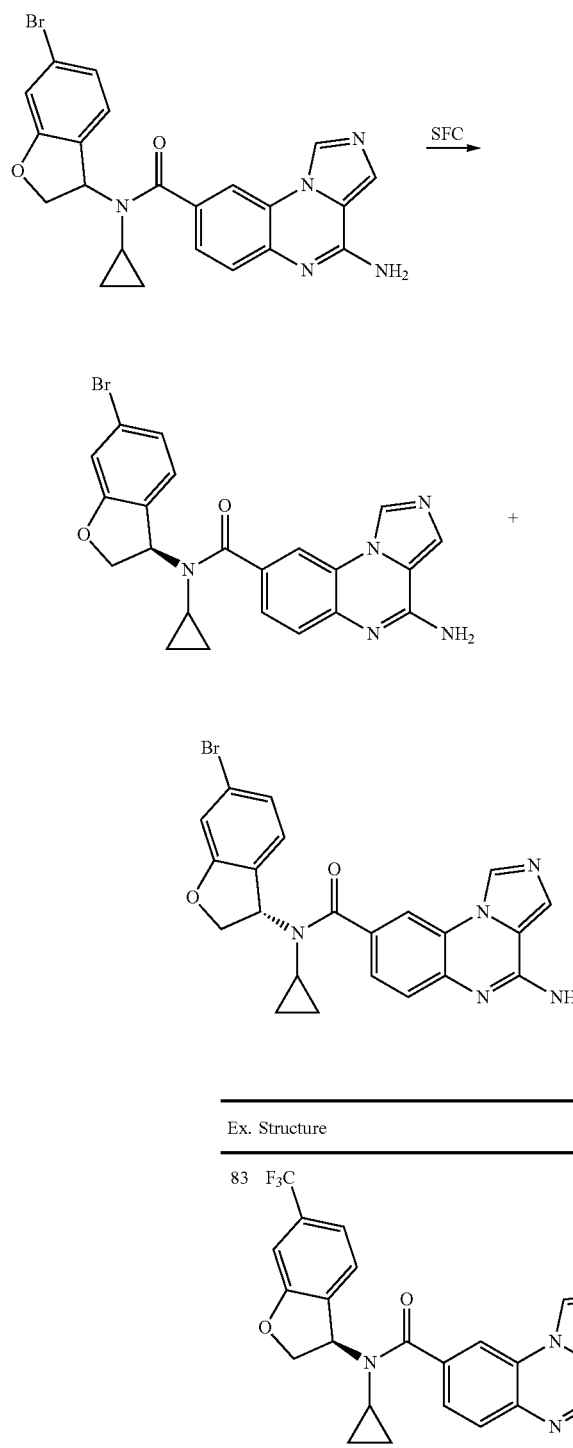

Compound 4-amino-N-(6-bromo-2,3-dihydrobenzofuran-3-yl)-N-cyclopropylimidazo[1,5-a]quinoxaline-8-carboxamide (90 mg) was purified by SFC(Column: DAICEL CHIRALCEL OJ (250 mm×30 mm, 10 um; condition: $CO_2$-i-PrOH (0.1% $NH_3·H_2O$), 50%/50%, flow rate: 80 ml/min) to obtain (R)-4-amino-N-(6-bromo-2,3-dihydrobenzofuran-3-yl)-N-cyclopropylimidazo[1,5-a]quinoxaline-8-carboxamide (34.61 mg) & (S)-4-amino-N-(6-bromo-2,3-dihydrobenzofuran-3-yl)-N-cyclopropylimidazo[1,5-a]quinoxaline-8-carboxamide (28.15 mg)

Example 81 (R)-4-amino-N-(6-bromo-2,3-dihydrobenzofuran-3-yl)-N-cyclopropylimidazo[1,5-a]quinoxaline-8-carboxamide LCMS (ESI) m/z: 465.3 [M+H]$^+$ $^1$H NMR (400 MHz, DMSO-$d_6$) δ 9.18 (s, 1H), 8.37 (d, J=1.8 Hz, 1H), 7.91 (s, 1H), 7.59 (dd, J=8.4, 1.8 Hz, 1H), 7.55-7.39 (m, 4H), 7.18-7.09 (m, 2H), 5.86 (dd, J=9.3, 4.1 Hz, 1H), 4.81 (t, J=9.7 Hz, 1H), 4.65 (dd, J=10.2, 4.2 Hz, 1H), 2.90 (p, J=3.2 Hz, 1H), 0.45-0.26 (m, 2H), 0.24-0.03 (in, 2H).

Example 82 (S)-4-amino-N-(6-bromo-2,3-dihydrobenzofuran-3-yl)-N-cyclopropylimidazo[1,5-a]quinoxaline-8-carboxamide LCMS (ESI) m/z: 465.3 [M+H]$^+$ $^1$H NMR (400 MHz, DMSO-$d_6$) δ 9.24 (d, J=3.6 Hz, 1H), 8.40 (d, J=3.5 Hz, 1H), 8.03 (s, 1H), 7.85 (s, 2H), 7.62 (dd, J=8.4, 3.3 Hz, 1H), 7.47 (dd, J=8.2, 3.3 Hz, 2H), 7.13 (dd, J=8.7, 3.3 Hz, 2H), 5.86 (dt, J=8.6, 4.0 Hz, 1H), 4.80 (td, J=9.7, 3.6 Hz, 1H), 4.65 (dt, J=9.2, 4.1 Hz, 1H), 2.90 (d, J=6.7 Hz, 1H), 0.44-0.26 (m, 2H), 0.13 (ddd, J=45.3, 10.6, 4.8 Hz, 2H).

By performing the procedures outlined in Examples 81 and 82, along with the respective chiral SFC separation conditions, the embodiments listed in the table below can be prepared:

| Ex. | Structure | name | SFC condition |
|---|---|---|---|
| 83 | (structure shown with $F_3C$ group) | (R)-4-amino-N-cyclopropyl-N-(6-(trifluoromethyl)-2,3-dihydrobenzofuran-3-yl)imidazo[1,5-a]quinoxaline-8-carboxamide | Peak1: SFC (column: DAICEL CHIRALCEL OJ (250 × 30 mm, 10 μm), condition: A for $CO_2$ and B for MeOH (0.1% $NH_3H_2O$), 40%/40%, flow rate: 80 ml/min) |

| Ex. | Structure | name | SFC condition |
|---|---|---|---|
| 84 | 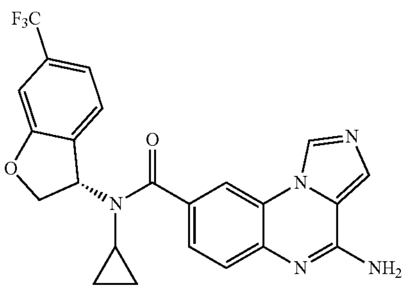 [SMILES: Nc1nc2ccc(C(=O)N(C3CC3)[C@@H]3COc4cc(C(F)(F)F)ccc43)cc2n2cncc12] | (S)-4-amino-N-cyclopropyl-N-(6-(trifluoromethyl)-2,3-dihydrobenzofuran-3-yl)imidazo[1,5-a]quinoxaline-8-carboxamide | Peak2: SFC (column: DAICEL CHIRALCEL OJ (250 × 30 mm, 10 μm), condition: A for $CO_2$ and B for MeOH (0.1% $NH_3H_2O$), 40%/40%, flow rate: 80 ml/min) |
| 85 | 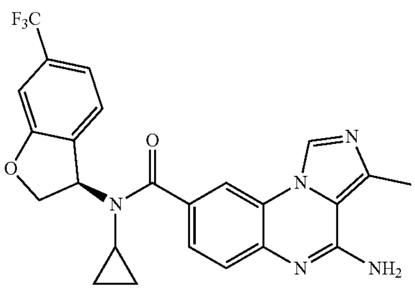 [SMILES: Cc1ncn2c1c(N)nc1ccc(C(=O)N(C3CC3)[C@H]3COc4cc(C(F)(F)F)ccc43)cc12] | (R)-4-amino-N-cyclopropyl-3-methyl-N-(6-(trifluoromethyl)-2,3-dihydrobenzofuran-3-yl)imidazo[1,5-a]quinoxaline-8-carboxamide | Peak1: SFC (column: Phenomenex-Cellulose-2, (250 mm × 30 mm, 10 μm), conditions: A for $CO_2$ and B for EtOH (0.1% $NH_3H_2O$), 45%/45%, flow rate: 80 ml/min) |
| 86 | 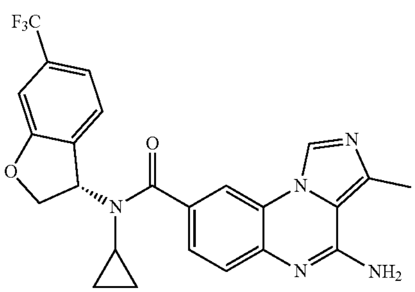 [SMILES: Cc1ncn2c1c(N)nc1ccc(C(=O)N(C3CC3)[C@@H]3COc4cc(C(F)(F)F)ccc43)cc12] | (S)-4-amino-N-cyclopropyl-3-methyl-N-(6-(trifluoromethyl)-2,3-dihydrobenzofuran-3-yl)imidazo[1,5-a]quinoxaline-8-carboxamide | Peak2: SFC (column: Phenomenex-Cellulose-2, (250 mm × 30 mm, 10 μm), conditions: A for $CO_2$ and B for EtOH (0.1% $NH_3H_2O$), 45%/45%, flow rate: 80 ml/min) |
| 87 | 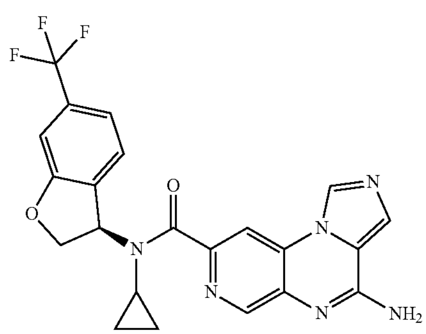 [SMILES: Nc1nc2cnc(C(=O)N(C3CC3)[C@H]3COc4cc(C(F)(F)F)ccc43)cc2n2cncc12] | (R)-4-amino-N-cyclopropyl-N-(6-(trifluoromethyl)-2,3-dihydrobenzofuran-3-yl)imidazo[1,5-a]pyrido[3,4-e]pyrazine-8-carboxamide | Peak 1: SFC (column: DAICEL CHIRALCEL OJ, (250 mm × 30 mm, 10 μm), conditions: A for $CO_2$ and B for EtOH (0.1% $NH_3H_2O$), 35%/35%, flow rate: 80 ml/min) |
| 88 | 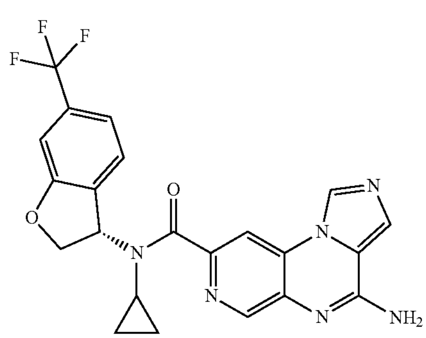 | (S)-4-amino-N-cyclopropyl-N-(6-(trifluoromethyl)-2,3-dihydrobenzofuran-3-yl)imidazo[1,5-a]pyrido[3,4-e]pyrazine-8-carboxamide | Peak 2: SFC (column: DAICEL CHIRALCEL OJ, (250 mm × 30 mm, 10 μm), conditions: A for $CO_2$ and B for EtOH (0.1% $NH_3H_2O$), 35%/35%, flow rate: 80 ml/min) |

| Ex. | Structure | name | SFC condition |
|---|---|---|---|
| 89 | 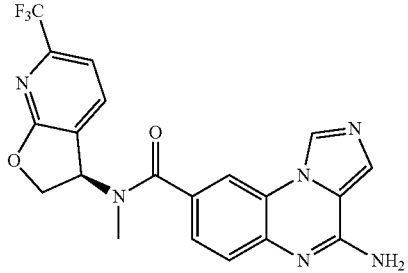 [SMILES: CN(C(=O)c1ccc2nc(N)c3cncn3c2c1)[C@H]1COc2nc(C(F)(F)F)ccc21] | (R)-4-amino-N-methyl-N-(6-(trifluoromethyl)-2,3-dihydrofuro[2,3-b]pyridin-3-yl)imidazo[1,5-a]quinoxaline-8-carboxamide | Peak 1: SFC (column: DAICEL CHIRALCEL AD, (250 mm × 30 mm, 10 μm), conditions: A for CO$_2$ and B for EtOH (0.1% NH$_3$H$_2$O), 45%/45%, flow rate: 150 ml/min) |
| 90 | 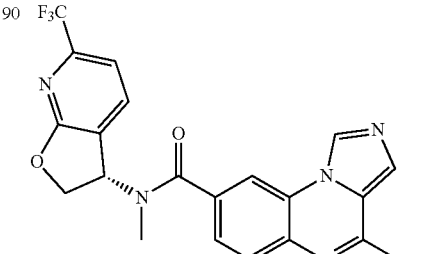 | (S)-4-amino-N-methyl-N-(6-(trifluoromethyl)-2,3-dihydrofuro[2,3-b]pyridin-3-yl)imidazo[1,5-a]quinoxaline-8-carboxamide | Peak 2: SFC (column: DAICEL CHIRALCEL AD, (250 mm × 30 mm, 10 μm), conditions: A for CO$_2$ and B for EtOH (0.1% NH$_3$H$_2$O), 45%/45%, flow rate: 150 ml/min) |
| 91 | 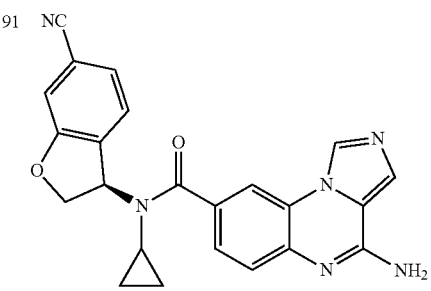 | (R)-4-amino-N-(6-cyano-2,3-dihydrobenzofuran-3-yl)-N-cyclopropylimidazo[1,5-a]quinoxaline-8-carboxamide | Peak 1: SFC (column: DAICELCHIRALPAK AS, (250 mm × 30 mm, 10 μm), conditions: A for CO$_2$ and B for EtOH (0.1% NH$_3$H$_2$O), 45%/45%, flow rate: 100 ml/min) |
| 92 | 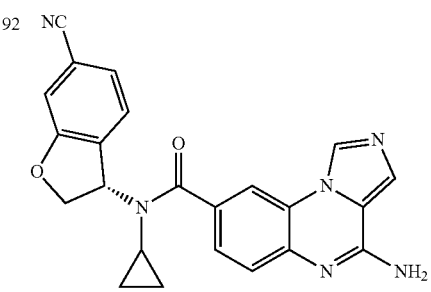 | (S)-4-amino-N-(6-cyano-2,3-dihydrobenzofuran-3-yl)-N-cyclopropylimidazo[1,5-a]quinoxaline-8-carboxamide | Peak 2: SFC (column: DAICEL CHIRALPAK AS, (250 mm × 30 mm, 10 μm), conditions: A for CO$_2$ and B for EtOH (0.1% NH$_3$H$_2$O), 45%/45%, flow rate: 100 ml/min) |
| 93 | 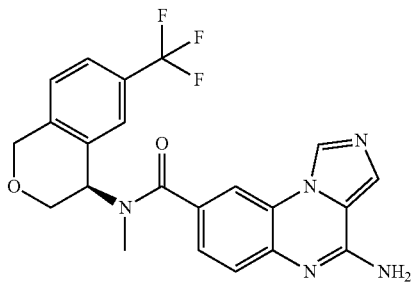 [SMILES: CN(C(=O)c1ccc2nc(N)c3cncn3c2c1)[C@H]1COCc2ccc(C(F)(F)F)cc21] | (R)-4-amino-N-methyl-N-(6-(trifluoromethyl) isochroman-4-yl)imidazo[1,5-a] quinoxaline-8-carboxamide | Peak 1: SFC (column: ChiralCel OJ, (250 × 40 mm I.D., 10 μm), condition: A for CO$_2$ and B for MeOH (0.1% NH$_3$H$_2$O), 40%/40%, flow rate: 120 ml/min) |

| Ex. | Structure | name | SFC condition |
|---|---|---|---|
| 94 | 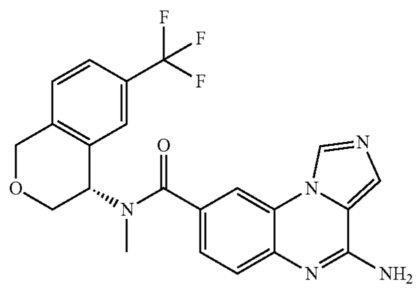 [SMILES: CN(C(=O)c1ccc2nc(N)c3cncn3c2c1)[C@@H]1COCc2ccc(C(F)(F)F)cc21] | (S-4-amino-N-methyl-N-(6-(trifluoromethyl)isochroman-4-yl)imidazo[1,5-a]quinoxaline-8-carboxamide | Peak 2: SFC (column: ChiralCel OJ, (250 × 40 mm I.D., 10 μm), condition: A for $CO_2$ and B for MeOH (0.1% $NH_3H_2O$), 40%/40%, flow rate: 120 ml/min) |
| 95 | 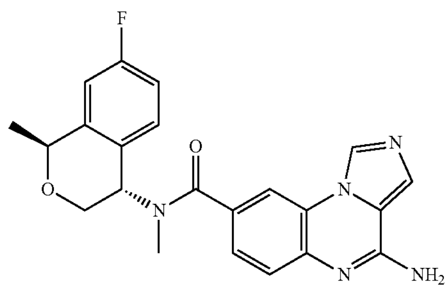 [SMILES: C[C@@H]1OC[C@@H](N(C)C(=O)c2ccc3nc(N)c4cncn4c3c2)c2ccc(F)cc21] | 4-amino-N-((1S,4S)-7-fluoro-1-methylisochroman-4-yl)-N-methylimidazo[1,5-a]quinoxaline-8-carboxamide | Peak1: SFC (column: ChiralCel OJ, (250 × 40 mm I.D., 10 μm), condition: for $CO_2$ and B for MeOH (0.1% $NH_3H_2O$), 40%/40%, flow rate: 120 ml/min) |
| 96 | 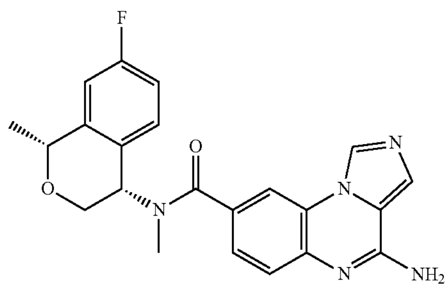 [SMILES: C[C@H]1OC[C@@H](N(C)C(=O)c2ccc3nc(N)c4cncn4c3c2)c2ccc(F)cc21] | 4-amino-N-((1R,4S)-7-fluoro-1-methylisochroman-4-yl)-N-methylimidazo[1,5-a]quinoxaline-8-carboxamide | Peak2: SFC (column: ChiralCel OJ, (250 × 40 mm I.D., 10 μm), condition: for $CO_2$ and B for MeOH (0.1% $NH_3H_2O$), 40%/40%, flow rate: 120 ml/min) |
| 97 | 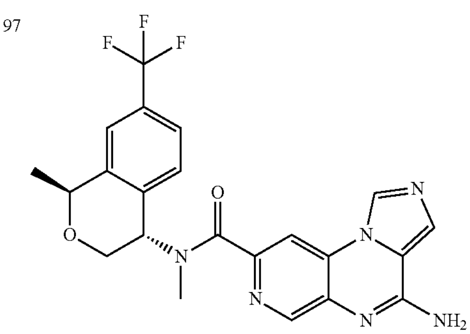 | 4-amino-N-methyl-N-((1S,4S)-1-methyl-7-(trifluoromethyl)isochroman-4-yl)imidazo[1,5-a]pyrido[3,4-e]pyrazine-8-carboxamide | Peak1: SFC (column: ChiralCel OJ, (250 × 40 mm I.D., 10 μm), condition: A for $CO_2$ and B for MeOH (0.1% $NH_3H_2O$), 50%/50%, flow rate: 120 ml/min) |
| 98 | 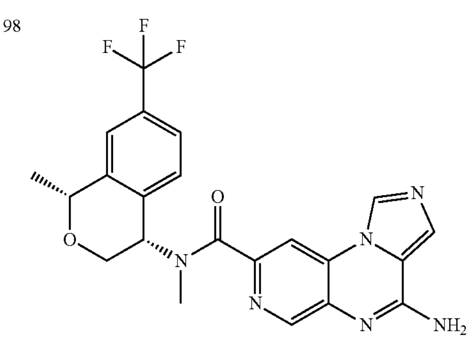 | 4-amino-N-methyl-N-((1R,4S)-1-methyl-7-(trifluoromethyl)isochroman-4-yl)imidazo[1,5-a]pyrido[3,4-e]pyrazine-8-carboxamide | Peak2: SFC (column: ChiralCel OJ, (250 × 40 mm I.D., 10 μm), condition: A for $CO_2$ and B for MeOH (0.1% $NH_3H_2O$), 50%/50%, flow rate: 120 ml/min) |

| Ex. | Structure | name | SFC condition |
|---|---|---|---|
| 99 | 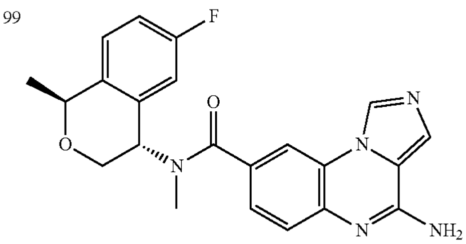 | 4-amino-N-((1S,4S)-6-fluoro-1-methylisochroman-4-yl)-N-methylimidazo[1,5-a]quinoxaline-8-carboxamide | Peak1: SFC (column: ChiralCel OJ, (250 × 40 mm I.D., 10 μm), condition: A for $CO_2$ and B for MeOH (0.1% $NH_3H_2O$), 40%/40%, flow rate: 120 ml/min) |
| 100 | 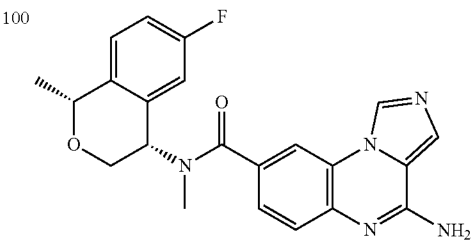 | 4-amino-N-((1R,4S)-6-fluoro-1-methylisochroman-4-yl)-N-methylimidazo[1,5-a]quinoxaline-8-carboxamide | Peak2: SFC (column: ChiralCel OJ, (250 × 40 mm I.D., 10 μm), condition: A for $CO_2$ and B for MeOH (0.1% $NH_3H_2O$), 40%/40%, flow rate: 120 ml/min) |
| 101 | 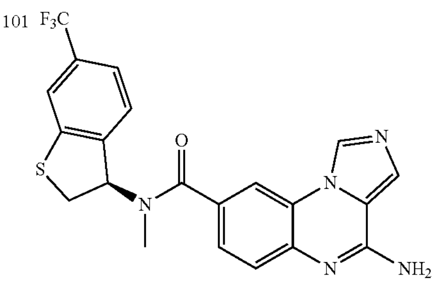 | (R)-4-amino-N-methyl-N-(6-(trifluoromethyl)-2,3-dihydrobenzo[b]thiophen-3-yl)imidazo[1,5-a]quinoxaline-8-carboxamide | Peak1: SFC (column:ChiralPak IJ, (250 × 40 mm I.D., 10 μm), condition: A for $CO_2$ and B for MeOH (0.1% $NH_3H_2O$), 45%/45%, flow rate: 130 ml/min) |
| 102 | 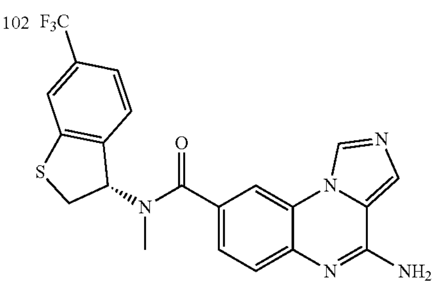 | (S)-4-amino-N-methyl-N-(6-(trifluoromethyl)-2,3-dihydrobenzo[b]thiophen-3-yl)imidazo[1,5-a]quinoxaline-8-carboxamide | Peak2: SFC (column:ChiralPak IJ, (250 × 40 mm I.D., 10 μm), condition: A for $CO_2$ and B for MeOH (0.1% $NH_3H_2O$), 45%/45%, flow rate: 130 ml/min) |
| 103 | 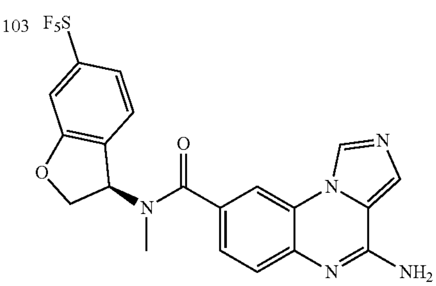 | (R)-4-amino-N-methyl-N-(6-(pentafluoro-16-sulfaneyl)-2,3-dihydrobenzofuran-3-yl)imidazo[1,5-a]quinoxaline-8-carboxamide | Peak1: SFC (column: Daicel ChiralPak IG, (250 × 40 mm I.D., 10 μm), condition: A for $CO_2$ and B for MeOH (0.1% $NH_3H_2O$), 50%/50%, flow rate: 140 ml/min) |

| Ex. | Structure | name | SFC condition |
|---|---|---|---|
| 104 | 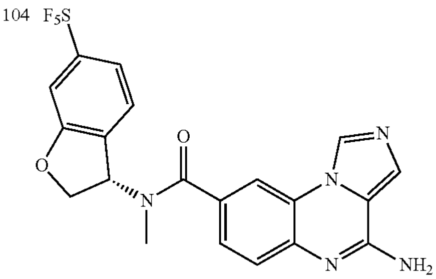 | (S)-4-amino-N-methyl-N-(6-(pentafluoro-16-sulfaneyl)-2,3-dihydrobenzofuran-3-yl)imidazo[1,5-a]quinoxaline-8-carboxamide | Peak2: SFC (column: Daicel ChiralPak IG, (250 × 40 mm I.D., 10 μm), condition: A for CO$_2$ and B for MeOH (0.1% NH$_3$H$_2$O), 50%/50%, flow rate: 140 ml/min) |
| 105 | 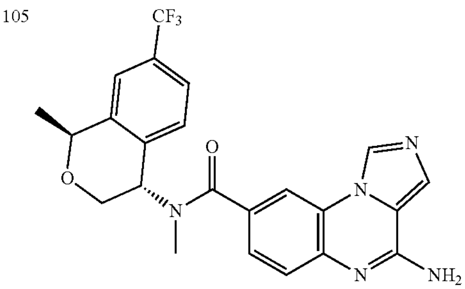 | 4-amino-N-methyl-N-((1S,4S)-1-methyl-7-(trifluoromethyl)isochroman-4-yl)imidazo[1,5-a]quinoxaline-8-carboxamide | Peak1: SFC (column: ChiralCel OJ, (250 × 40mm I.D., 10 μm), condition: A for CO$_2$ and B for MeOH (0.1% NH$_3$H$_2$O), 50%/50%, flow rate: 120 ml/min) |
| 106 | 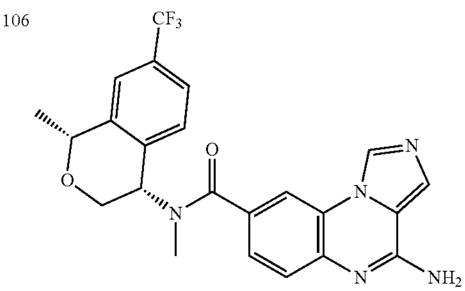 | 4-amino-N-methyl-N-((1R,4S)-1-methyl-7-(trifluoromethyl)isochroman-4-yl)imidazo[1,5-a]quinoxaline-8-carboxamide | Peak2: SFC (column: ChiralCel OJ, (250 × 40 mm I.D., 10 μm), condition: A for CO$_2$ and B for MeOH (0.1% NH$_3$H$_2$O), 50%/50%, flow rate: 120 ml/min) |
| 134 | 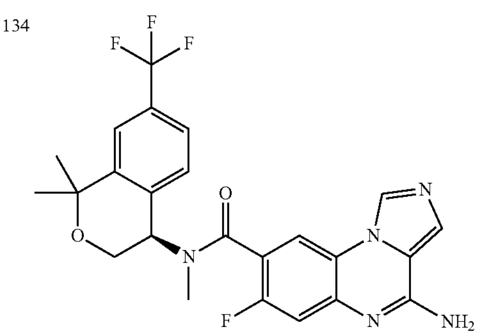 | (R)-4-amino-N-(1,1-dimethyl-7-(trifluoromethyl)isochroman-4-yl)-7-fluoro-N-methylimidazo[1,5-a]quinoxaline-8-carboxamide | Peak1: SFC (column: ChiralPak IC, (40 mm I.D. × 250 mm, 10 μm), condition: A for CO$_2$ and B for MeOH (0.1% NH$_3$H$_2$O), 50%/50%, flow rate: 140 ml/min) |
| 135 | 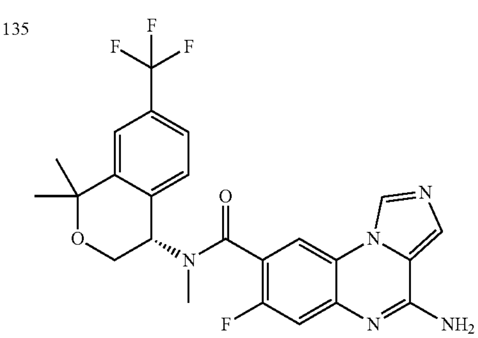 | (S)-4-amino-N-(1,1-dimethyl-7-(trifluoromethyl)isochroman-4-yl)-7-fluoro-N-methylimidazo[1,5-a]quinoxaline-8-carboxamide | Peak2: SFC (column: ChiralPak IC, (40 mm I.D. × 250 mm, 10 μm), condition: A for CO$_2$ and B for MeOH (0.1% NH$_3$H$_2$O), 50%/50%, flow rate: 140 ml/min) |

Biology Activity Testing

I. Tumor Cell Growth Inhibition Assay

Test 1: Compound's inhibitory activity on proliferation of HCT-116 MTAP(−/−) deficient cells. P Materials and Cells: HCT-116 MTAP(−/−) deficient cells obtained from Kyinno Bio (China); RPMI-1640 medium, fetal bovine serum, and penicillin-streptomycin purchased from Thermo Fisher Scientific (America); 384-well plates from PerkinElmer (America); Cell-Titer Glo assay kit from Promega (America).

Cell Culture: HCT116 MTAP(−/−) deficient cells were cultured in RPMI 1640 medium containing 10% fetal bovine serum and 1% penicillin-streptomycin at 37° C., 5% $CO_2$. Only cells in logarithmic growth phase were used for experiments.

Cell Proliferation Inhibition Assay: The compound's inhibitory activity on HCT-116 MTAP(−/−) deficient cells was assessed using the Cell-Titer Glo assay kit. Adjusting cell concentration, 40 μL was seeded into a 384-well plate and cultured overnight at 37° C., 5% $CO_2$. Each well received 40 nL of the compound, achieving concentrations from 0 to 10,000 nM (starting concentration 10,000 nM, 3-fold dilution, 10 points), with 0.1% DMSO. The cell plate was incubated for 8 days at 37° C., 5% $CO_2$. Cell-Titer Glo reagent (40 μL) was added to measure cell viability. Results are shown in Table 1.

Test 2: Compound's inhibitory activity on proliferation of HCT-116 MTAP wild-type cells.

Materials and Cells: HCT-116 MTAP wild-type cells obtained from Kyinno Bio (China); RPMI-1640 medium, fetal bovine serum, and penicillin-streptomycin purchased from Thermo Fisher Scientific (America); 384-well plates from PerkinElmer (America); Cell-Titer Glo assay kit from Promega (America).

Cell Culture: HCT116 MTAP wild-type cells were cultured in RPMI 1640 medium containing 10% fetal bovine serum and 1% penicillin-streptomycin at 37° C., 5% $CO_2$. Only cells in logarithmic growth phase were used for experiments.

Cell Proliferation Inhibition Assay: The compound's inhibitory activity on HCT-116 MTAP wild-type cells was assessed using the Cell-Titer Glo assay kit. Adjusting cell concentration, 40 μL was seeded into a 384-well plate and cultured overnight at 37° C., 5% $CO_2$. Each well received 40 nL of the compound, achieving concentrations from 0 to 10,000 nM (starting concentration 10,000 nM, 3-fold dilution, 10 points), with 0.1% DMSO. The cell plate was incubated for 8 days at 37° C., 5% $CO_2$. Cell-Titer Glo reagent (40 μL) was added to measure cell viability. Results are shown in Table 1.

The following Table 1 presents the inhibitory activity of various compound embodiments on the proliferation of HCT116 MTAP(−/−) deficient cells and HCT116 wild-type cells.

TABLE 1

| | $IC_{50}$ (nM) | |
|---|---|---|
| Ex. | HCT-116 MTAP(−/−) deficient | HCT-116 wild-type |
| 1 | 2306 | >10000 |
| 2 | 61 | 6667.6 |
| 3 | 23.4 | 2251 |
| 4 | 9.9 | 1711 |
| 5 | 4 | 280 |
| 6 | 10.6 | 993 |
| 7 | 141 | >10000 |
| 8 | 106 | 6478.3 |
| 9 | 41.1 | 2144.5 |
| 10 | 31.2 | 3111.3 |
| 11 | 1767.4 | 6410 |
| 12 | 6.1 | 1112.4 |
| 13 | 15.7 | 2511.8 |
| 14 | 14.7 | 1283.1 |
| 15 | 3.5 | 282.3 |
| 16 | 5.6 | 1081 |
| 17 | 4.2 | 243 |
| 18 | 14.5 | 4327.5 |
| 19 | 23.2 | 2233.8 |
| 20 | >3000 | >10000 |
| 21 | 14.8 | 2129.6 |
| 22 | 5.1 | 1688.6 |
| 23 | 119.5 | >10000 |
| 24 | 147.5 | >10000 |
| 25 | 176.9 | >10000 |
| 26 | 67.7 | >10000 |
| 27 | 4.4 | 842.1 |
| 28 | 321.2 | >10000 |
| 29 | 7.1 | 934.8 |
| 30 | 2086.4 | >10000 |
| 31 | 296.6 | >10000 |
| 32 | 25.7 | 1411.8 |
| 33 | 15.1 | 2665 |
| 34 | 29.6 | 6572.3 |
| 35 | 23.2 | 2233.8 |
| 36 | 36 | 5126.7 |
| 37 | >3000 | >10000 |
| 38 | 30 | 4063 |
| 39 | 15.9 | 2041.3 |
| 40 | 32.1 | 9203.5 |
| 41 | 11 | 1144 |
| 42 | 659.7 | 5456.9 |
| 43 | 22.4 | 2988 |
| 44 | 310 | >10000 |
| 45 | 10.3 | 947.4 |
| 46 | 52.2 | >10000 |
| 47 | 17.7 | 4096 |
| 48 | >3000 | >3000 |
| 49 | 588.7 | >10000 |
| 50 | 4.2 | 196 |
| 51 | 212.6 | 5864 |
| 52 | 123.4 | >10000 |
| 53 | >3000 | >10000 |
| 54 | 2495 | >10000 |
| 55 | 11.8 | 1221.7 |
| 56 | 15.9 | 1532.1 |
| 57 | 10.5 | 1869.6 |
| 58 | >3000 | >10000 |
| 59 | 710.6 | >10000 |
| 60 | 66.8 | 7074.5 |
| 61 | 7.7 | 882.4 |
| 62 | 19.7 | 3705.7 |
| 63 | 46.8 | 3256.4 |
| 64 | 278.2 | >20000 |
| 65 | 95.3 | 5946.3 |
| 66 | 2257 | >20000 |
| 67 | 35.6 | 3639.1 |
| 68 | 381.5 | 8570 |
| 69 | 87.1 | 5019.1 |
| 70 | 54 | 3889 |
| 72 | 117.2 | >20000 |
| 73 | 55.5 | 4622.8 |
| 74 | 148.1 | 5991.4 |
| 75 | 7.3 | 1167.4 |
| 76 | >3000 | >10000 |
| 77 | 101.4 | 4260.8 |
| 78 | 7.1 | 2071.4 |
| 79 | 5.6 | 1302.6 |
| 80 | 39.3 | 9168.6 |
| 81 | 1791.2 | 2359 |
| 82 | 52.9 | 1920.5 |
| 83 | 2635.5 | 4704 |
| 84 | 21.9 | 1470.1 |

TABLE 1-continued

| Ex. | IC$_{50}$ (nM) | |
|---|---|---|
| | HCT-116 MTAP(-/-) deficient | HCT-116 wild-type |
| 85 | 790.6 | 780.7 |
| 86 | 61.1 | 1329.3 |
| 87 | 9029.4 | 10755 |
| 88 | 24.1 | 1846.5 |
| 89 | >3000 | >10000 |
| 90 | 36.4 | >10000 |
| 91 | 2179.2 | >20000 |
| 92 | 46.6 | 4753.5 |
| 93 | >3000 | >10000 |
| 94 | 80.8 | 5169.3 |
| 95 | 211.4 | >10000 |
| 96 | 6.6 | 1255.1 |
| 97 | 29.8 | 1547.7 |
| 98 | 1.4 | 114 |
| 99 | 927.7 | 7131 |
| 100 | 68.3 | 3581 |
| 101 | 2187.6 | >10000 |
| 102 | 7.9 | 1993 |
| 103 | 930.6 | 6256.4 |
| 104 | 4.6 | 591.2 |
| 105 | 66.1 | 2193.5 |
| 106 | 3.5 | 145.2 |
| 107 | 7.4 | 1727.2 |
| 108 | 120.8 | >10000 |
| 109 | >3000 | 9086 |
| 110 | >3000 | >10000 |
| 111 | 500 | >10000 |
| 112 | 338.1 | >10000 |
| 113 | 88.1 | >10000 |
| 114 | 146.4 | >10000 |
| 115 | 84.3 | >10000 |
| 116 | 109.1 | >10000 |
| 117 | 6.6 | 617.3 |
| 118 | 2933 | >10000 |
| 119 | 13.5 | 1307.8 |
| 120 | 900 | >10000 |
| 121 | 73.7 | >10000 |
| 122 | 50.6 | >10000 |
| 123 | 428.7 | >10000 |
| 124 | 6.5 | 634.4 |
| 125 | 2447.2 | >10000 |
| 126 | 592.1 | >20000 |
| 127 | 100.1 | 9905 |
| 128 | 26 | >10000 |
| 129 | 14.5 | 2676.6 |
| 130 | 5.8 | 1291.6 |
| 131 | >3000 | >10000 |
| 132 | >3000 | >10000 |
| 133 | 71.4 | >10000 |
| 134 | 623 | 5891 |
| 135 | 9.3 | 1959 |

II. Mouse Pharmacokinetic Experiment

1. Test Compounds

The compounds used in this experiment are specific embodiments of the present invention, with reference to compound AMG473 as an example from Amgen's patent WO 2022/169948A1, identified as example 473.

2. Test Animals

ICR male mice, N=3/group; sourced from Zhejiang Vital River Laboratory Animal Technology Co., Ltd.

3. Drug Preparation and Administration

Single oral (PO) administration to ICR mice: Compounds were dissolved in dimethyl sulfoxide, added to polyethylene glycol 400 and sterile water, and then adjusted to a clear solution with a small amount of 1 mol/L hydrochloric acid. After overnight fasting, the mice were orally gavaged with a dose of 10 mg/kg.

Single intravenous (IV) administration to ICR mice: Compounds were dissolved in dimethyl sulfoxide, added to polyethylene glycol 400 and sterile water, and then adjusted to a clear solution with a small amount of 1 mol/L hydrochloric acid. After overnight fasting, the mice received tail vein injections with a dose of 3 mg/kg.

4. Sample Collection

Approximately 30 μL/time point blood samples were collected via the tail vein. Potassium ethylenediaminetetraacetate was used as an anticoagulant, and samples were centrifuged at 4000 g/min for 5 minutes at 4° C. within 1 hour. Blood sampling time points were 0.0833 (IV), 0.25, 0.5, 1, 2, 4, 6, 8, 24 hours. Samples were stored in a −20° C. freezer.

Plasma samples (30 μL, 10 μL sample+20 μL blank plasma) were mixed with 200 μL ice-cold acetonitrile containing internal standards. After vortexing for 30 seconds, samples were centrifuged at 4000 g/min for 20 minutes. One hundred microliters of the supernatant were transferred to a 96-well plate, followed by the addition of 200 μL ultrapure water. After vortexing for 30 seconds, 5 μL or 10 μL were injected into LC-MS/MS for analysis.

TABLE 2

Pharmacokinetic Data

| Ex | Administration Route (Dosage) | AUCl$_{ast}$ (hr*ng/ml) | T$_{1/2}$(h) | Bioavailability F (%) |
|---|---|---|---|---|
| 4 | IV(3 mg/kg) | 8094 | 4.06 | NA |
| | PO(10 mg/kg) | 21020 | 2.67 | 77 |
| 29 | IV(3 mg/kg) | 12925 | 4.38 | NA |
| | PO(10 mg/kg) | 43906 | 4.16 | 102 |
| 16 | IV(3 mg/kg) | 9710 | 3.65 | NA |
| | PO(10 mg/kg) | 42546 | 3.31 | 131 |
| 107 | IV(3 mg/kg) | 11237 | 4.53 | NA |
| | PO(10 mg/kg) | 44065 | 4.56 | 119 |
| 104 | IV(3 mg/kg) | 10548 | 6.1 | NA |
| | PO(10 mg/kg) | 26536 | 5.02 | 74 |
| 130 | IV(3 mg/kg) | 10782 | 4.5 | NA |
| | PO(10 mg/kg) | 28276 | 3.34 | 77.5 |
| 41 | IV(3 mg/kg) | 5421 | 4.3 | NA |
| | PO(10 mg/kg) | 46322 | 4.12 | 257 |
| AMG473 | PO(10 mg/kg) | 16174 | 4.2 | NA |

"NA": absent.

By comparing pharmacokinetic parameters, it can be observed that, compared to AMG473, at equivalent doses and under the same administration route, the embodiments of the present invention consistently exhibit higher plasma exposure. This could reduce the effective dose of the compound, expanding the safety margin.

III. hERG Ion Channel Inhibition Experiment

1. Tested Compounds

The compounds used in this experiment are specific embodiments of the present invention, with reference to compound AMG473 as an example from Amgen's patent WO 2022/169948A1, identified as example 473.

2. Cell Line and Cell Culture

Stably expressing hERG ion channel HEK293 cell line (Catalog: K1236) was purchased from Invitrogen. This cell line was cultured in a medium containing 85% DMEM, 10% dialyzed fetal bovine serum, 0.1 mM non-essential amino acid solution, 100 U/mL penicillin-streptomycin solution, 25 mM HEPES, 5 μg/mL blasticidin, and 400 μg/mL geneticin. When the cell density reached 40%~80% of the culture dish area, digestion was performed using trypsin, and cells were passaged three times per week. Before the experiment, cells were cultured at a density of 5×10' in 3.5 cm culture dishes, induced with 1 g/mL Doxycycline for 48 hours. Subsequently, cells were digested and seeded onto slides for subsequent manual patch clamp experiments.)

3. Experimental Procedure
1) Place glass slides containing HEK293 cells in the perfusion chamber of the micro-manipulation station.
2) Under an Olympus IX71 or IX73 inverted microscope, position suitable cells in the central field of view using a ×10 objective. Locate the tip of the glass electrode in the central field. Use the micromanipulator to lower the electrode while adjusting the coarse focus spiral to slowly approach the cell.
3) When approaching the cell rapidly, switch to a ×40 objective for observation. Fine-tune the electrode approach using the micromanipulator to gradually reach the cell's surface.
4) Apply negative pressure to establish 1GΩ seal between the electrode tip and the cell membrane.
5) Compensate for the transient capacitance current $C_{fast}$ under voltage clamp mode. Then, repeat the brief negative pressure application for membrane rupture, ultimately reaching the whole-cell recording mode.
6) Under voltage clamp at −60 mV, compensate for slow capacitance current $C_{slow}$, cell membrane capacitance (Cm), and input membrane resistance (Ra).
7) Once the cell is stable, change the clamping voltage to −90 mV, set the sampling frequency to 20 kHz, and the filtering frequency to 10 kHz. Leak current detection conditions involve changing the clamping voltage to −80 mV for a duration of 500 ms.
8) The hERG current testing method is as follows: Apply a 4.8-second depolarization command voltage to depolarize the membrane potential from −80 mV to +30 mV, then instantly apply a 5.2-second repolarization voltage to reduce the membrane potential to −50 mV to remove channel inactivation, allowing observation of the hERG tail current. The peak of the tail current represents the size of the hERG current.
9) The hERG current induced by the test compound is continuously recorded for 120 seconds before administration to assess the stability of the tested cells in producing hERG currents. Only stable cells within an acceptable range are eligible for subsequent compound testing.
10) Testing the inhibitory effect of the test compound on hERG current: First, determine the baseline of hERG current obtained in extracellular fluid containing 0.1% DMSO. After maintaining stable hERG current for at least 5 minutes, sequentially perfuse the solution containing the test compound around the cells from low to high concentrations. After each perfusion, wait for about 5 minutes to allow the compound to act on the cells and simultaneously record hERG currents. Record the last 5 hERG current values after the recorded current stabilizes, and take their average as the final current value at a specific concentration. After testing the compound, add 450 nM dofetilide to the same cell to completely inhibit its current, serving as a positive control for that cell. Meanwhile, positive compound dofetilide is synchronously detected before and after the end of the test drug experiment using the same patch clamp system to ensure the reliability and sensitivity of the entire detection system. The above test steps will be repeated on two separate test cells (n=2).

4. Data Analysis
Data meeting the above criteria will be analyzed using the following steps. Note: Data is output by PatchMaster software.
1) After perfusing blank solvent or compound gradient solution, obtain 5 consecutive stable current values, calculate the average, and use them as "Tail Current Blank" and "Tail Current Compound," respectively.

The percentage of current inhibition is calculated using the following formula:

Tail current inhibition percentage=(1−(Tail Current Compound−Tail Current positive control)/(Tail Current Blank−Tail Current positive control))× 100%

2) Dose-response curves were fitted, and $IC_{50}$ values were calculated using GraphPad Prism 8.0 software. 3) The standard deviation range for the three sets of data is less than 15 (SD<15); 4) Widely accepted criteria for assessing the inhibitory potency of compounds in hERG channel detection are as follows:
1) Low inhibitory potency: $IC_{50}$>10 μM
2) Moderate inhibitory potency: 1 μM<$IC_{50}$<10 μM
3) High inhibitory potency: $IC_{50}$<1 μM Data Quality Control Standards
Only data meeting the following criteria will be subject to further analysis: 1) Initial gigohm seal resistance greater than 1 GΩ; 2) Series resistance less than 15 MΩ and series resistance voltage error less than 5 mV; 3) Leakage current at the detection voltage is less than 50% of the current value under this condition; 4) Tail current greater than the plateau current size before the pre-pulse, with an initial tail current value greater than 250 pA; 5) Rupture resistance Ra less than 15 MΩ; 6) Decay rate of tail current per minute less than 2.5%.

5. The hERG $IC_{50}$ (μM) Data are Shown in Table 3:

TABLE 3

| hERG $IC_{50}$ data | |
|---|---|
| Ex. | hERG $IC_{50}$(μM) |
| 4 | 5.29 |
| 29 | 11.4 |
| 16 | 2.3 |
| 107 | 4.5 |
| 104 | 1.51 |
| 130 | 1.36 |
| 41 | 8.16 |
| AMG473 | <0.37 |

By comparing hERG $IC_{50}$ data, in comparison to AMG473, the embodiments of the present invention demonstrate a lower risk of cardiac toxicity, indicating a larger safety margin.

While preferred embodiments have been described above, it is evident that modifications can be made by those skilled in the art without departing from the scope of the invention. Such modifications are considered possible variants within the scope of the present invention.

What is claimed is:
1. A compound of Formula (II), a pharmaceutical salt thereof, an ester thereof, a prodrug thereof, a stereoisomer thereof or isotopic derivative thereof:

Formula (II)

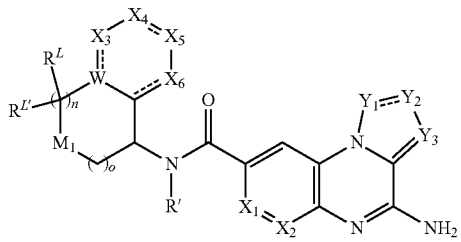

wherein,
W is C;
$X_3$ is $CR^{X3}$;
$X_4$ is $CR^{X4}$;
$X_5$ is $CR^{X5}$;
$X_6$ is $CR^{X6}$;
wherein, $R^{X3}$ is hydrogen, deuterium, $C_1$-$C_6$ alkyl;
wherein, $R^{X4}$ is hydrogen, $C_1$-$C_6$ alkyl, halogen, —SF$_5$, $C_1$-$C_6$ haloalkyl;
wherein, $R^{X5}$ is hydrogen;
wherein, $R^{X6}$ is hydrogen;
wherein, R' is $C_1$-$C_6$ alkyl, which are independently optionally substituted with 0-3 groups selected from deuterium, halogen;
wherein, $M_1$ is O or S;
wherein, $R^L$ and $R^{L'}$ are independently hydrogen, deuterium, $C_1$-$C_6$ alkyl;
wherein, n and o are independently 0, 1;
wherein, $X_1$ is N or $CR^{X1}$;
wherein, $X_2$ is $CR^{X2}$;
wherein, $Y_1$ is $CR^{Y1}$;
wherein, $Y_2$ is N;
wherein, $Y_3$ is $CR^{Y3}$;
wherein, $R^{X1}$ is independently hydrogen, halogen or CN;
wherein, $R^{X2}$ is hydrogen;
wherein, $R^{Y1}$ is hydrogen or deuterium; $R^{Y3}$ is hydrogen or deuterium;
Wherein, ═══ is double bond.

2. The compound according to claim 1, the pharmaceutical salt thereof, the ester thereof, the prodrug thereof, the stereoisomer thereof or isotopic derivative thereof, wherein, $X_1$ is CH or CF.

3. The compound according to claim 1, the pharmaceutical salt thereof, the ester thereof, the prodrug thereof, the stereoisomer thereof or isotopic derivative thereof, wherein, $X_2$ is CH.

4. The compound according to claim 1, the pharmaceutical salt thereof, the ester thereof, the prodrug thereof, the stereoisomer thereof or isotopic derivative thereof, wherein, $X_3$ is CH.

5. The compound according to claim 1, the pharmaceutical salt thereof, the ester thereof, the prodrug thereof, the stereoisomer thereof or isotopic derivative thereof, wherein, $X_4$ is $CR^{X4}$; wherein, $R^{X4}$ is $C_1$-$C_6$ haloalkyl, —SF$_5$.

6. The compound according to claim 1, the pharmaceutical salt thereof, the ester thereof, the prodrug thereof, the stereoisomer thereof or isotopic derivative thereof, wherein, $X_4$ is $CR^{X4}$; wherein, $R^{X4}$ is $C_1$-$C_6$ haloalkyl.

7. The compound according to claim 1, the pharmaceutical salt thereof, the ester thereof, the prodrug thereof, the stereoisomer thereof or isotopic derivative thereof, wherein, $X_5$ is CH.

8. The compound according to claim 1, the pharmaceutical salt thereof, the ester thereof, the prodrug thereof, the stereoisomer thereof or isotopic derivative thereof, wherein, $X_6$ is CH.

9. The compound according to claim 1, the pharmaceutical salt thereof, the ester thereof, the prodrug thereof, the stereoisomer thereof or isotopic derivative thereof, wherein, $Y_1$ is CH.

10. The compound according to claim 1, the pharmaceutical salt thereof, the ester thereof, the prodrug thereof, the stereoisomer thereof or isotopic derivative thereof, wherein, $Y_2$ is N.

11. The compound according to claim 1, the pharmaceutical salt thereof, the ester thereof, the prodrug thereof, the stereoisomer thereof or isotopic derivative thereof, wherein, $Y_3$ is CH.

12. The compound according to claim 1, the pharmaceutical salt thereof, the ester thereof, the prodrug thereof, the stereoisomer thereof or isotopic derivative thereof, wherein, R' is $CH_3$ or $CD_3$.

13. The compound according to claim 1, the pharmaceutical salt thereof, the ester thereof, the prodrug thereof, the stereoisomer thereof or isotopic derivative thereof, wherein, $M_1$ is O.

14. The compound according to claim 1, the pharmaceutical salt thereof, the ester thereof, the prodrug thereof, the stereoisomer thereof or isotopic derivative thereof, wherein, o is 1.

15. The compound according to claim 1, the pharmaceutical salt thereof, the ester thereof, the prodrug thereof, the stereoisomer thereof or isotopic derivative thereof, wherein, n is 0.

16. The compound, the pharmaceutical salt thereof, the ester thereof, the prodrug thereof, the stereoisomer thereof or isotopic derivative thereof, wherein the compound is selected from the following compounds:

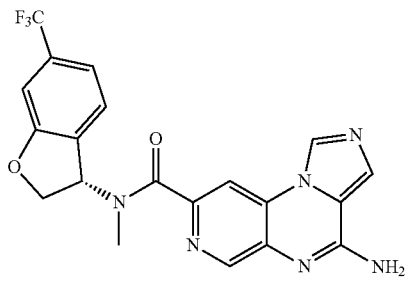

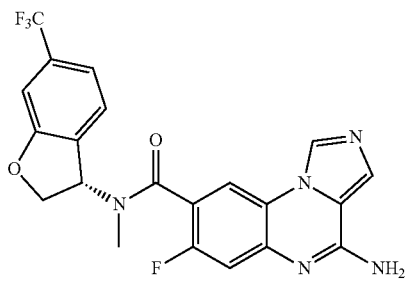

227
-continued
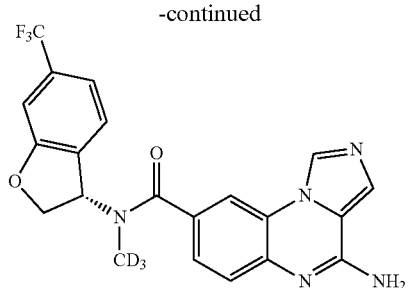
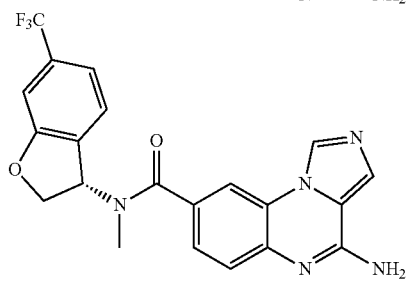
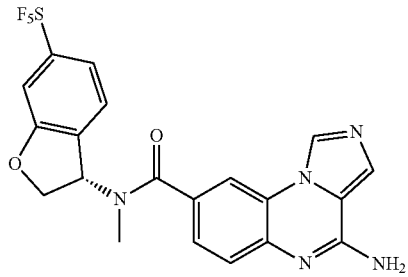
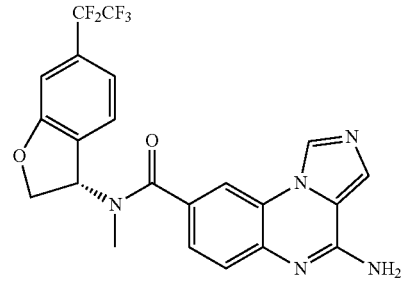
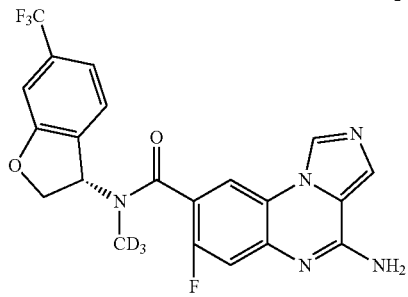
228
-continued
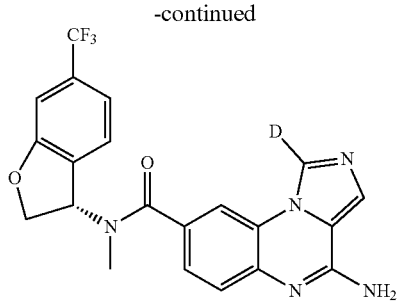
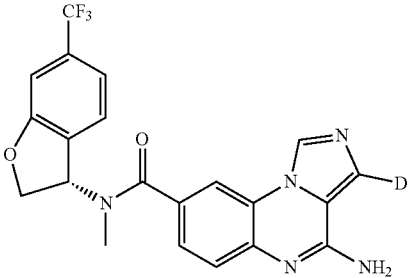
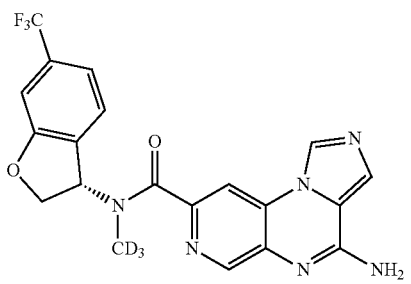
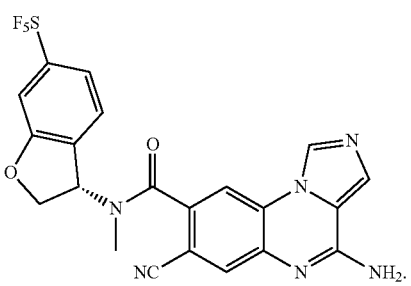
* * * * *

UNITED STATES PATENT AND TRADEMARK OFFICE
CERTIFICATE OF CORRECTION

| | | |
|---|---|---|
| PATENT NO. | : 12,173,002 B2 | Page 1 of 1 |
| APPLICATION NO. | : 18/437335 | |
| DATED | : December 24, 2024 | |
| INVENTOR(S) | : Bing Yao and Xiaohui Gu | |

It is certified that error appears in the above-identified patent and that said Letters Patent is hereby corrected as shown below:

In the Specification

Column 215, for Ex. '103' the second complete parenthetical in the name should read -pentafluoro-$\lambda^6$-sulfanely-.

Column 217, for Ex. '104' the second complete parenthetical in the name should read -pentafluoro-$\lambda^6$-sulfanely-.

Signed and Sealed this
Thirtieth Day of September, 2025

John A. Squires
*Director of the United States Patent and Trademark Office*